United States Patent
Slusher et al.

(10) Patent No.: US 10,568,868 B2
(45) Date of Patent: Feb. 25, 2020

(54) METHODS AND COMPOSITIONS FOR TREATING METABOLIC REPROGRAMMING DISORDERS

(71) Applicant: THE JOHNS HOPKINS UNIVERSITY, Baltimore, MD (US)

(72) Inventors: Barbara Slusher, Kingsville, MD (US); Jonathan Powell, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/885,147

(22) Filed: Jan. 31, 2018

(65) Prior Publication Data

US 2018/0221337 A1   Aug. 9, 2018

Related U.S. Application Data

(63) Continuation-in-part of application No. PCT/US2016/044810, filed on Jul. 29, 2016.
(Continued)

(51) Int. Cl.
*A61K 31/223* (2006.01)
*A61K 31/4045* (2006.01)
(Continued)

(52) U.S. Cl.
CPC .......... *A61K 31/4045* (2013.01); *A61K 31/22* (2013.01); *A61K 31/223* (2013.01);
(Continued)

(58) Field of Classification Search
CPC ..... A61K 31/223; A61K 38/05; A61K 39/395
(Continued)

(56) References Cited

U.S. PATENT DOCUMENTS 3,773,919 A    11/1973   Boswell et al.
4,485,045 A    11/1984   Regen
(Continued)

FOREIGN PATENT DOCUMENTS

EP    0058481 A1    8/1982
EP    0102324 A2    3/1984
(Continued)

OTHER PUBLICATIONS

Copending U.S. Appl. No. 15/885,258, filed Jan. 31, 2018. (Year: 2018).*
(Continued)

*Primary Examiner* — Craig D Ricci
*Assistant Examiner* — Janet L. Coppins
(74) *Attorney, Agent, or Firm* — Sterne, Kessler, Goldstein & Fox P.L.L.C.

(57) ABSTRACT

The disclosure provides methods of treating a condition, disease, or disorder in a subject that involves metabolically reprogrammed cells whose activation, function, growth, proliferation, or survival depends on increased activity of at least one metabolic pathway selected from the group consisting of glutamine metabolism, glycolysis, and fatty acid synthesis, comprising administering to the subject a compound having formula (I):

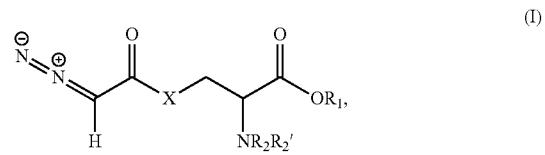

and the pharmaceutically acceptable salts thereof, wherein $R_1$, $R_2$, $R_2'$, and X are as defined as set forth in the
(Continued)

specification. Compounds having formula (I) are prodrugs that release glutamine analogs, e.g., 6-diazo-5-oxo-L-norleucine (DON).

19 Claims, 64 Drawing Sheets

Related U.S. Application Data

(60) Provisional application No. 62/199,381, filed on Jul. 31, 2015, provisional application No. 62/199,566, filed on Jul. 31, 2015.

(51) Int. Cl.
  *A61K 38/05* (2006.01)
  *A61K 31/655* (2006.01)
  *A61K 39/395* (2006.01)
  *A61K 31/22* (2006.01)
  *A61K 31/225* (2006.01)

(52) U.S. Cl.
  CPC .......... *A61K 31/225* (2013.01); *A61K 31/655* (2013.01); *A61K 38/05* (2013.01); *A61K 39/39541* (2013.01)

(58) Field of Classification Search
  USPC ........................................................ 514/547
  See application file for complete search history.

(56) References Cited

U.S. PATENT DOCUMENTS

| | | | |
|---|---|---|---|
| 4,544,545 A | 10/1985 | Ryan et al. | |
| 5,328,470 A | 7/1994 | Nabel et al. | |
| 6,362,226 B2 | 3/2002 | Phillips, III et al. | |
| 7,723,307 B2 * | 5/2010 | Griffin ................ | C07K 5/06026 514/19.3 |
| 2004/0029801 A1 | 2/2004 | Zhong et al. | |
| 2006/0035838 A1 | 2/2006 | Khosla et al. | |
| 2006/0276438 A1 * | 12/2006 | Sethuraman ......... | A61K 31/198 514/114 |
| 2008/0107624 A1 | 5/2008 | D'Andrea et al. | |
| 2008/0146526 A1 | 6/2008 | Gallop et al. | |
| 2008/0160024 A1 | 7/2008 | Ware | |
| 2009/0042806 A1 | 2/2009 | Khosla et al. | |
| 2009/0062223 A1 | 3/2009 | Keicher et al. | |
| 2009/0169537 A1 | 7/2009 | Bausch et al. | |
| 2014/0004081 A1 | 1/2014 | Cobbold et al. | |
| 2014/0065100 A1 | 3/2014 | Rossignol et al. | |
| 2015/0202291 A1 | 7/2015 | Bosch et al. | |
| 2015/0258082 A1 | 9/2015 | Parlati et al. | |
| 2016/0022674 A1 | 1/2016 | Steggerda et al. | |
| 2016/0193239 A1 | 7/2016 | Baylin et al. | |
| 2016/0310453 A1 | 10/2016 | Mathios et al. | |
| 2017/0190657 A1 | 7/2017 | Gallop et al. | |
| 2018/0193362 A1 | 7/2018 | Slusher et al. | |
| 2018/0221395 A1 | 8/2018 | Slusher et al. | |
| 2018/0222930 A1 | 8/2018 | Slusher et al. | |

FOREIGN PATENT DOCUMENTS

| | | | |
|---|---|---|---|
| EP | 0123170 A2 | 10/1984 | |
| EP | 0133988 A2 | 3/1985 | |
| WO | WO-2004113363 A2 | 12/2004 | |
| WO | WO-2005068455 A1 | 7/2005 | |
| WO | WO-2005097108 A1 | 10/2005 | |
| WO | WO-2013019058 A2 | 2/2013 | |
| WO | WO-2014138391 A1 | 9/2014 | |
| WO | WO-2014160071 A1 | 10/2014 | |
| WO | WO-2015101957 A2 * | 7/2015 | ........... C07D 417/06 |
| WO | WO-2017023774 A1 | 2/2017 | |
| WO | WO-2017023787 A1 | 2/2017 | |
| WO | WO-2017023791 A1 | 2/2017 | |
| WO | WO-2017023793 A2 | 2/2017 | |

OTHER PUBLICATIONS

Copending U.S. Appl. No. 15/885,275, filed Jan. 31, 2018. (Year: 2018).*
Ostroukhova et al, J. Allergy and Clinical Immunology, vol. 125 (Issue 2, Supplement 1) p. AB39, abstract 155. (Year: 2010).*
Office Action dated Nov. 13, 2018, for co-pending U.S. Appl. No. 15/885,258, filed Jan. 31, 2018, U.S. Patent and Trademark Office, Alexandria, Virginia.
Office Action dated Feb. 26, 2019, for co-pending U.S. Appl. No. 15/885,258, filed Jan. 31, 2018, U.S. Patent and Trademark Office, Alexandria, Virginia.
Office Action dated Nov. 2, 2018, for co-pending U.S. Appl. No. 15/885,275, filed Jan. 31, 2018, U.S. Patent and Trademark Office, Alexandria, Virgina.
Leone et al., "A2aR antagonists: Next generation checkpoint blockade for cancer immunotherapy," Computational and Structural Biotechnology, Journal 13:265-272, Elsevier B. V., (2015).
Liwschitz et al., "Diazo-ketone with Potential Tumor-inhibitory properties derived from L-Aspartic and L-Glutamic acids," J. Chem. Soc. (C) 223-225, The Chemical Society: London, (1971).
Noonan et al., "Phase I/II Study of Marrow Infiltrating Lymphocytes (MILs) Generates Measurable Myeloma-Specific immunity in the Autologous Stem Cell Transplant (SCT) Setting," Blood 118:997, The American Society of Hematology, (2011).
Simplicio et al., "Prodrug for Amines," Molecules, 13:519-547, MDPI, (2008).
Sznol, M. and Chen, L., "Antagonist Antibodies to PD-1 and B7-H1 (PD-L1) in the Treatment of Advanced Human Cancer," Clinical Cancer Research, 19:1021-1034, American Association for Cancer Research, (2013).
Extended European Search Report, European Appl. No. 16833623.8, dated Feb. 12, 2019.
Abo-Ghalia, M, et al., "Synthesis of inhibitors of the meso-diaminopimelate-adding enzyme from *Escherichia coli*", Int. J. Peptide Protein Res. 32:208-222, Munksgaard International Publishers, Copenhagen, (1988).
Jancarik, A. "Novel lymphoid targeted prodrugs of the glutamine antagonist DON for the treatment of hematological malignancies", The FASEB Journal, Abstract No. lb472, Published Online: Apr. 1, 2016.
Englert, J. et al., "Abstract 1035: Targeting glutamine metabolism with the novel inhibitor JHU-083 inhibits tumor growth and alters the tumor immune microenvironment", Proceedings: AACR 107th Annual Meeting, New Orleans, LA, American Association for Cancer Research, Apr. 16-20, 2016.
Extended European Search Report, European Appl. No. 16833623.7, dated Feb. 12, 2019.
Griffiths, M. et al., "The Role of Glutamine and Glucose Analogues in Metabolic Inhibition of Human Myeloid Leukaemia In Vitro", Int. J. Biochem., 25:1749-1755, Pergamon Press Ltd, (1993).
Kelly, B. et al., "Metabolic reprogramming in macrophages and dendritic cells in innate immunity", Cell Research, 25:771-784, Creative Commons (2015).
Levesley, J. et al., "ABT-263 Enhances Sensitivity to Metformin and 2-Deoxyglucose in Pediatric Glioma by Promoting Apoptotic Cell Death", PloS One, 8(5), e64051, Creative Commons (2013).
Abdelmalek, M.F., et.al., "Sirolimus Conversion Regimen Versus Continued Calcineurin Inhibitors in Liver Allograft Recipients: a Randomized Trial.," American Journal of Transplantation : Official Journal of the American Society of Transplantation and the American Society of Transplant Surgeons 12(3):694-705, Wiley-blackwell on Behalf of the American Society of Transplant Surgeons and the American Society of Transplantation, United States (Jan. 2012).
Acevedo., et.al., "Synthesis and Analysis of the Sterically Constrained L-glutamine Analogues (3s,4r)-3,4-dimethyl-l-glutamine and (3s,4r)-3,4-dimethyl-l-pyroglutamic Acid," Tetrahedron 57 (30):6353-6359, Elsevier Science Ltd (Jul. 2001).

(56) References Cited

OTHER PUBLICATIONS

Ahluwalia.,G.S., et.al., "Metabolism and Action of Amino Acid Analog Anti-cancer Agents.," Pharmacology & Therapeutics 46(2):243-271, Pergamon Press, England (1990).

Alt,J., et.al., "Bioanalysis of 6-diazo-5-oxo-l-norleucine in Plasma and Brain by Ultra-performance Liquid Chromatography Mass Spectrometry.," Analytical Biochemistry 474:28-34, Elsevier, United States (Jan. 2010).

Altschul, S.F., et al., "Basic Local Alignment Search Tool," Journal of Molecular Biology 215(3):403-410, Elsevier, England (Oct. 1990).

Altschul, S.F., et al., "Gapped BLAST and PSI-BLAST: A New Generation of Protein Database Search Programs," Nucleic Acids Research 25(17):3389-3402, Oxford University Press, England (Sep. 1997).

Antinori, A., et.al., "Updated Research Nosology for HIV-associated Neurocognitive Disorders.," Neurology 69(18):1789-1799, Lippincott Williams & Wilkins, United States (Oct. 2007).

Arnold, R., et.al., "Association Between Calcineurin inhibitor Treatment and Peripheral Nerve Dysfunction in Renal Transplant Recipients.," American Journal of Transplantation : Official Journal of the American Society of Transplantation and the American Society of Transplant Surgeons 13(9):2426-2432, Wiley-blackwell on Behalf of the American Society of Transplant Surgeons and the American Society of Transplantation, United States (Jul. 2010).

Barclay, R.K., et.al., "Effects of 6-diazo-5-oxol-norleucine and Other Tumor Inhibitors on the Biosynthesis of Nicotinamide Adenine Dinucleotide in Mice.," Cancer research 26(2):282-286, American Association for Cancer Research, United States (Feb. 1966).

Berge, S.M., et al., "Pharmaceutical Salts," Journal of Pharmaceutical Sciences 66(1):1-19, Wiley, United States (Jan. 1977).

Bestard, O., et.al., "Costimulatory Blockade With Mtor Inhibition Abrogates Effector T-cell Responses Allowing Regulatory T-cell Survival in Renal Transplantation.," Transplant International : Official Journal of the European Society for Organ Transplantation 24(5):451-460, Blackwell Pub, England (May 2011).

Borjabad, A., et.al, "Significant Effects of Antiretroviral Therapy on Global Gene Expression in Brain Tissues of Patients With Hiv-1-associated Neurocognitive Disorders.," Plos Pathogens 7(9):e1002213, Public Library of Science, United States (Sep. 2011).

Buzzai, M., et.al., "Systemic Treatment With the Antidiabetic Drug Metformin Selectively Impairs P53-deficient Tumor Cell Growth.," Cancer Research 67(14):6745-6752, American Association for Cancer Research, United States (Jul. 2007).

Cao, X., et.al., "Astrocyte-derived Atp Modulates Depressive-like Behaviors.," Nature Medicine 19(6):773-777, Nature Publishing Company, United States (Jun. 2013).

Carr, E.L., et.al., "Glutamine Uptake and Metabolism Are Coordinately Regulated by Erk/mapk During T Lymphocyte Activation.," Journal of Immunology (Baltimore, Md. : 1950) 185(2):1037-1044, American Association of Immunologists, United States (Jul. 2010).

Cervantes-Madrid, D., et al., "Reviving Lonidamine and 6-Diazo-5-oxo-L-norleucine to be used in Combination for Metabolic Cancer Therapy," BioMed Research International 2015:690492, Hindawi Pub. Co, United States (2015).

Cham, C.M and Gajewski, T.F, "Glucose Availability Regulates IFN-gamma Production and p70S6 Kinase Activation in CD8+ Effector T Cells," Journal of Immunology (Baltimore, Md. : 1950) 174(8):4670-4677, American Association of Immunologists, United States (Apr. 2005).

Cham, C.M., et.al., "Glucose Deprivation Inhibits Multiple Key Gene Expression Events and Effector Functions in Cd8+ T Cells.," European Journal of Immunology 38(9):2438-2450, Wiley-vch, Germany (Sep. 2008).

Chambers, J.W., et al., "Glutamine Metabolism is Essential for Human Cytomegalovirus Infection," Journal of Virology 84(4):1867-1873, American Society for Microbiology, United States (Feb. 2010).

Chang, L., et al., "Persistent Brain Abnormalities in Antiretroviral-naive HIV Patients 3 Months after HAART," Antiviral Therapy 8(1):17-26, International Medical Press, England (Feb. 2003).

Chapman, A.P., "PEGylated Antibodies and Antibody Fragments for Improved Therapy: a Review," Advanced Drug Delivery Reviews 54(4):531-545, Elsevier Science Publishers, Netherlands (Jun. 2002).

Chen, S.H., et al., "Gene Therapy for Brain Tumors: Regression of Experimental Gliomas by Adenovirus-mediated Gene Transfer in Vivo," Proceedings of the National Academy of Sciences 91(8):3054-3057, National Academy of Sciences, United States (Apr. 1994 ).

Cheng, G., et al., "Mitochondria-targeted Drugs Synergize with 2-deoxyglucose to Trigger Breast Cancer Cell Death," Cancer Research 72(10):2634-2644, American Association for Cancer Research, United States (May 2012).

Cheng, G., et al., "Profiling and Targeting of Cellular Bioenergetics: Inhibition of Pancreatic Cancer Cell Proliferation," British Journal of Cancer 111(1):85-93, Nature Publishing Group on behalf of Cancer Research UK, England (Jul. 2014).

Cheong, J.H., et al., "Dual inhibition of tumor energy pathway by 2-Deoxyglucose and Metformin is Effective against a Broad Spectrum of Preclinical Cancer Models," Molecular Cancer Therapeutics 10(12):2350-2362, American Association for Cancer Research, United States (Dec. 2011).

Cinatl, J., et al., "Antiviral Effects of 6-diazo-5-oxo-L-norleucin on Replication of Herpes Simplex Virus Type 1," Antiviral Research 33(3):165-175, Elsevier, Netherlands (Feb. 1997).

Coffey, G.L., et al., "6-diazo-5-oxo-L-norleucine, a New Tumor-inhibitory Substance. I. Biologic Studies," Antibiotics & Chemotherapy 6(8):487-497, Washington Institute of Medicine, United States (Aug. 1956).

Coggin, Jr., J.H. and Martin, W. R., "6-Diazo-5-Oxo-I-Norleucine Inhibition of *Escherichia coli*," Journal of Bacteriology 89(5):1348-1353, American Society for Microbiology, United States (May 1965).

Corry, R.J., et al., "Primarily Vascularized Allografts of Hearts in Mice. The Role of H-2D, H-2K, and Non-H-2 Antigens in Rejection," Transplantation 16(4):343-350, Lippincott Williams & Wilkins, United States (Oct. 1973).

Csibi, A., et al.. "The mTORC1 Pathway Stimulates Glutamine Metabolism and Cell Proliferation by Repressing SIRT4," Cell 153(4):840-854, Cell Press, United States (May 2013).

Cui, F., et al., "Overexpression of Cathepsin L is Associated with Gefitinib Resistance in Non-small Cell Lung Cancer," Clinical & Translational Oncology 18(7):722-727, Springer Italia, Italy (Jul. 2016).

Cunningham-Rundles, C., et al., "Biological Activities of Polyethylene-glycol Immunoglobulin Conjugates. Resistance to Enzymatic Degradation," Journal of Immunological Methods 152(2):177-190, Elsevier, Netherlands (Aug. 1992).

Crutchlow, M.F. and Bloom, R.D., "Transplant-Associated Hyperglycemia: A New Look at an Old Problem," Clinical Journal of the American Society of Nephrology 2(2):343-355, American Society of Nephrology, United States (Mar. 2007).

Dickens, A.M., et al., "Cerebrospinal Fluid Metabolomics Implicate Bioenergetic Adaptation as a Neural Mechanism Regulating Shifts in Cognitive States of HIV-infected Patients," AIDS 29(5):559-569, Lippincott Williams & Wilkins, England (Mar. 2015).

Darmaun, D., et al., "Phenylbutyrate-induced Glutamine Depletion in Humans: Effect on Leucine Metabolism," The American Journal of Physiology 274(5pt1):E801-E807, American Physiological Society, United States (May 1998).

Deberardinis, R.J. and Cheng, T., "Q's Next: the Diverse Functions of Glutamine in Metabolism, Cell Biology and Cancer," Oncogene 29(3):313-324, Nature Publishing Group, England (Jan. 2010).

Delgoffe, G.M., et al., "The Kinase mTOR Regulates the Differentiation of Helper T Cells Through the Selective Activation of Signaling by mTORC1 and mTORC2," Nature Immunology 12(4):295-303, Nature America Inc, United States (Apr. 2011).

Delgoffe, G.M., et al., "The mTOR Kinase Differentially Regulates Effector and Regulatory T Cell Lineage Commitment," Immunity 30(6):832-844, Cell Press, United States (Jun. 2009).

(56) References Cited

OTHER PUBLICATIONS

Dewald, H.A.and Alexander M.M., "6-diazo-5-oxo-L-norleucine, a New Tumor-inhibitory Substance. Preparation of L-, D- and Di-forms," Journal of the American Chemical Society 80(15):3941-3945, (Aug. 1958).

Dion, H.W., et al., "6-Diazo-5-oxo-L-norleucine, A New Tumor-inhibitory Substance. II. Isolation and Characterization," Journal of the American Chemical Society 78(13):3075-3077, (Jul. 1956).

Dolan, D.E. and Gupta, S., "PD-1 Pathway Inhibitors: Changing the Landscape of Cancer Immunotherapy," Cancer Control 21(3):231-237, SAGE Publishing, United States (Jul. 2014).

Dranoff, G., et al., "Combination Chemotherapy in Vitro Exploiting Glutamine Metabolism of Human Glioma and Medulloblastoma," Cancer Research 45(9):4082-4086, American Association for Cancer Research, United States (Sep. 1985).

Dranoff, G., et al., "Influence of Glutamine on the Growth of Human Glioma and Medulloblastoma in Culture," Cancer Research 45(9):4077-4081, American Association for Cancer Research, United States (Sep. 1985).

Eagan, R.T., et al., "Phase II Study on DON in Patients with Previously Treated Advanced Lung Cancer," Cancer Treatment Reports 66(8):1665-1666, National Cancer Institute, United States (Aug. 1982).

Earhart, R.H., et al., "Phase I Trial of 6-diazo-5-oxo-L-norleucine (DON) Administered by 5-day Courses," Cancer Treatment Reports 66(5):1215-1217, National Cancer Institute, United States (May 1982).

Earhart, R.H., et al., "Phase II Trial of 6-diazo-5-oxo-L-norleucine Versus Aclacinomycin-a in Advanced Sarcomas and Mesotheliomas," Investigational New Drugs 8(1):113-119, Springer, United States (Feb. 1990).

Ellis, R., et al., "HIV and Antiretroviral Therapy in the Brain: Neuronal Injury and Repair," Nature Reviews. Neuroscience 8(1):33-44, Nature Pub. Group, England (Jan. 2007).

El-Mir, M.Y., et al., "Dimethylbiguanide Inhibits Cell Respiration via an Indirect Effect Targeted on the Respiratory Chain Complex I," The Journal of Biological Chemistry 275(1):223-228, American Society for Biochemistry and Molecular Biology, United States (Jan. 2000).

Engels, E.A., et al., "Spectrum of Cancer Risk among U.S. Solid Organ Transplant Recipients: the Transplant Cancer Match Study," JAMA 306(17):1891-1901, American Medical Association, United States (Nov. 2011).

Eppstein, D.A., et al., "Biological activity of liposome-encapsulated murine interferon gamma is mediated by a cell membrane receptor," Proceedings of the National Academy of Sciences 82(11):3688-3692, National Academy of Sciences, United States (1985).

Erickson, J.W. and Cerione R.A., "Glutaminase: A Hot Spot for Regulation of Cancer Cell Metabolism?," Oncotarget 1(8):734-740, Impact Journals, United States (Dec. 2010).

Eshleman, J.S., et al., "Inhibition of the Mammalian Target of Rapamycin Sensitizes U87 Xenografts to Fractionated Radiation Therapy," Cancer Research 62(24):7291-7297, American Association for Cancer Research, United States (Dec. 2002).

Everall, I., et al., "Cliniconeuropathologic Correlates of Human Immunodeficiency Virus in the Era of Antiretroviral Therapy," Journal of Neurovirology 15(5-6):360-370, Springer, United States (Sep. 2009).

Franciosi, M., et al., "Metformin Therapy and Risk of Cancer in Patients with Type 2 Diabetes: Systematic Review," PloS one 8(8):e71583, Public Library of Science, United States (Aug. 2013).

Kull, F.C., et al., "Mixtures of Quaternary Ammonium Compounds and Long-chain Fatty Acids as Antifungal Agents," Applied Microbiology 9(6):538-541, American Society for Microbiology, United States (Nov. 1961).

Fogal, V., et al., "Mitochondrial p32 is Upregulated in Myc Expressing Brain Cancers and Mediates Glutamine Addiction," Oncotarget 6(2):1157-1170, Impact Journals, United States (Jan. 2015).

Gelman, B.B., et al., "The National NeuroAIDS Tissue Consortium Brain Gene Array: Two Types of HIV-associated Neurocognitive Impairment," PLoS One 7(9):e46178, Public Library of Science, United States (2012).

Grayzel, A.I., et al., "Suppression of Uric Acid Synthesis in the Gouty Human by the Use of 6-diazo-5-oxo-L-norleucine.," The Journal of Clinical Investigation 39:447-454, American Society for Clinical Investigation, United States (Mar. 1960).

Gross, M.I., et al., "Antitumor Activity of the Glutaminase Inhibitor CB-839 in Triple-Negative Breast Cancer," Molecular Cancer Therapeutics 13(4):890-901, American Association for Cancer Research, United States (Apr. 2014).

Grupp, S.A., et al., "Chimeric Antigen Receptor-Modified T Cells for Acute Lymphoid Leukemia," The New England Journal of Medicine 368(16):1509-1518, Massachusetts Medical Society, United States (Apr. 2013).

Guba, M., et al., "Pro- and Anti-cancer Effects of Immunosuppressive Agents used in Organ Transplantation," Transplantation 77(12):1777-1782, Lippincott Williams & Wilkins, United States (Jun. 2004).

Harding, J.J., et al., "Safety and Tolerability of Increasing Doses of CB-839, a First-in-class, Orally Administered Small Molecule Inhibitor of Glutaminase, in Solid Tumors," Journal of Clinical Oncology 33(15_suppl ):2512, (May 2015).

Harezlak, J., et al., "Persistence of HIV-associated Cognitive Impairment, Inflammation, and Neuronal Injury in Era of Highly Active Antiretroviral Treatment," AIDS 25(5):625-633, Lippincott Williams & Wilkins, England (Mar. 2011).

Hart, R.G., et al., "Neuroprotection Trials in Parkinson's Disease: Systematic Review," Movement Disorders 24(5):647-654, Wiley-Liss, United States (Apr. 2009).

Hausch, F., et al., "Design, Synthesis, and Evaluation of Gluten Peptide Analogs as Selective Inhibitors of Human Tissue Transglutaminase," Chemistry & Biology 10(3):225-231, Elsevier, United States (Mar. 2003).

Heaton, R.K., et al., "HIV-associated Neurocognitive Disorders Before and During the Era of Combination Antiretroviral Therapy: Differences in Rates, Nature, and Predictors," Journal of Neurovirology 17(1):3-16, Springer, United States (Feb. 2011).

Heaton, R.K., et al., "HIV-associated Neurocognitive Disorders Persist in the Era of Potent Antiretroviral Therapy: Charter Study," Neurology 75(23):2087-2096, Lippincott Williams & Wilkins, United States (Dec. 2010).

Henderson, J.M., et al., "Hepatocellular Carcinoma: Mouse Models and the Potential Roles of Proteases," Cancer Letters 387:106-113, Elsevier Science Ireland, Ireland (Feb. 2017).

Hensley, C.T., et al., "Glutamine and Cancer: Cell Biology, Physiology, and Clinical Opportunities," The Journal of Clinical Investigation 123(9):3678-3684, American Society for Clinical Investigation, United States (Sep. 2013).

Hodes, G.E., et al., "Individual Differences in the Peripheral Immune System Promote Resilience Versus Susceptibility to Social Stress," Proceedings of the National Academy of Sciences of the United States of America 111(45):16136-16141, National Academy of Sciences, United States (Nov. 2014).

Hofer, A., et al., "Trypanosorna Brucei CTP Synthetase: a Target for the Treatment of African Sleeping Sickness," Proceedings of the National Academy of Sciences of the United States of America 98(11):6412-6416, National Academy of Sciences, United States (May 2001).

Hollinger, K.R., et al., "Dose-dependent Inhibition of GCPII to Prevent and Treat Cognitive Impairment in the EAE Model of Multiple Sclerosis," Brain Research 1635:105-112, North-Holland Biomedical Press, Netherlands (Mar. 2016).

Hoorn, E.J., et al., "Pathogenesis of Calcineurin Inhibitor-induced Hypertension," Journal of Nephrology 25(3):269-275; Springer, Italy (May-Jun. 2012).

Hu, X., et al., "Genetic Alterations and Oncogenic Pathways Associated with Breast Cancer Subtypes," Molecular Cancer Research 7(4):511-522, American Association for Cancer Research, United States (Apr. 2009).

(56) References Cited

OTHER PUBLICATIONS

Hutchinson, J.A., et al., "Peptide Hormones and Lipopeptides: from Self-assembly to Therapeutic Applications," Journal of Peptide Science 23(2):82-94, John Wiley & Sons, England (Feb. 2017).

Hwang, K.J., et al., "Hepatic uptake and degradation of unilamellar sphingomyelin/cholesterol liposomes: a kinetic study," Proceedings of the National Academy of Sciences 77(7):4030-4034, National Academy of Sciences, United States (1980).

International Search Report and Written Opinion for International Application No. PCT/US2016/044767; European Patent Office, Netherlands, dated Oct. 31, 2016, 9 pages.

International Search Report and Written Opinion for International Application No. PCT/US2016/044810, European Patent Office, Netherlands, dated Dec. 5, 2016, 10 pages.

International Search Report and Written Opinion for International Application No. PCT/US2016/044825, European Patent Office, Netherlands, dated Dec. 5, 2016, 10 pages.

Jacobs, S.R., et al., "Glucose Uptake is Limiting in T Cell Activation and Requires CD28-Mediated Akt-Dependent and Independent Pathways," Journal of Immunology 180(7):4476-4486, American Association of Immunologists, United States (Apr. 2008).

Jones, R.G. and Thompson, C.B., "Revving the Engine: Signal Transduction Fuels T Cell Activation," Immunity 27(2):173-178, Cell Press, United States (Aug. 2007).

Karlin, S. and Altschul, S.E., "Methods for Assessing the Statistical Significance of Molecular Sequence Features by using General Scoring Schemes," Proceedings of the National Academy of Sciences USA 87(6):2264-2268, National Academy of Sciences, United States (Mar. 1990).

Karlin, S, and Altschul, S.F., "Applications and Statistics for Multiple High-scoring Segments in Molecular Sequences," Proceedings of the National Academy of Sciences USA 90(12):5873-5877, National Academy of Sciences, United States (Jun. 1993).

Kaul, M., et al., "HIV-1 Infection and AIDS: Consequences for the Central Nervous System," Cell Death and Differentiation 12 Suppl 1:878-892, Nature Publishing Group, England (Aug. 2005).

Konopleva., et al., "Phase 1 study: Safety and tolerability of increasing doses of cb-839, an orally-administered small molecule inhibitor of glutaminase," In Acute Leukemia, Haematologica (2015).

Kovach, J.S., et al., "Phase I and Pharmacokinetic Studies of DON," Cancer Treatment Reports 65(11-12):1031-1036, National Cancer Institute, United States (Nov.-Dec. 1981).

Krishnan, V., et al., "Molecular Adaptations Underlying Susceptibility and Resistance to Social Defeat in Brain Reward Regions," Cell 131(2):391-404, Cell Press, United States (Oct. 2007).

Lagodzinski, Z., et al., "Effect of FK506 and Cyclosporine on Primary and Secondary Skin Allograft Survival in Mice," Immunology 71(1):148-150, Blackwell Scientific Publications, England (Sep. 1990).

Langer, R., et al., "Biocompatibility of Polymeric Delivery Systems for Macromolecules," Journal of Biomedical Materials Research 15(2):267-277, John Wiley & Sons, Inc., United States (1981).

Le, A., et al., "Glucose-independent Glutamine Metabolism via TCA Cycling for Proliferation and Survival in B Cells," Cell Metabolism 15(1):110-121, Cell Press, United States (Jan. 2012).

Le Maux, P., et al., "Chemical Reactivity of 6-diazo-5-oxo-L-norleucine (DON) Catalyzed by Metalloporphyrins (Fe,Ru)," Tetrahedron 66(25):4462-4468, Elsevier (Jun. 2010).

Lee, M.D., et al., "New Antitumor Antibiotic, LL-D05139 Beta. Fermentation, Isolation, Structure Determination and Biological Activities," The Journal of Antibiotics 40(12):1657-1663, Nature Publishing Group, Japan (Dec. 1987).

Lee, C.F., et al., "Preventing Allograft Rejection by Targeting Immune Metabolism," Cell Reports 13(4):760-770, Cell Press, United States (Oct. 2015).

Lee, Y.Z., et al., "Discovery of Selective Inhibitors of Glutaminase-2, which Inhibit mTORC1, Activate Autophagy and Inhibit Proliferation in Cancer Cells," Oncotarget 5(15):6087-6101, Impact Journals, United States (Aug. 2014).

Lentz, M.R., et al., "Changes in MRS Neuronal Markers and T Cell Phenotypes Observed During Early HIV Infection," Neurology 72(17):1465-1472, Lippincott Williams & Wilkins, United States (Apr. 2009).

Li, Q., et al., "A Central Role for mTOR Kinase in Homeostatic Proliferation Induced CD8+ T Cell Memory and Tumor Immunity," Immunity 34(4):541-553, Cell Press, United States (Apr. 2011).

Li, Y., et al., "Learning and Reconsolidation Implicate Different Synaptic Mechanisms," Proceedings of the National Academy of Sciences of the United States of America 110(12):4798-4803, National Academy of Sciences, United States (Mar. 2013).

Liddy, N., et al., "Monoclonal TCR-redirected Tumor Cell Killing," Nature Medicine 18(6):980-987, Nature Publishing Company, United States (Jun. 2012).

Lim, J.H., et al., "Targeting Mitochondrial Oxidative Metabolism in Melanoma Causes Metabolic Compensation through Glucose and Glutamine Utilization," Cancer Research 74(13):3535-3545, American Association for Cancer Research, United States (Jul. 2014).

Liu, W., et al., "Reprogramming of Proline and Glutamine Metabolism Contributes to the Proliferative and Metabolic Responses Regulated by Oncogenic Transcription Factor c-MYC," Proceedings of the National Academy of Sciences of the United States of America 109(23):8983-8988, National Academy of Sciences, United States (Jun. 2012).

Lo, Y.C., et al., "Insight into the Role of mTOR and Metabolism in T Cells Reveals New Potential Approaches to Preventing Graft Rejection," Current Opinion in Organ Transplantation 19(4):363-371, Lippincott Williams & Wilkins, United States (Aug. 2014).

Stupp, R., et al., "Effects of Radiotherapy with Concomitant and Adjuvant Temozolomide Versus Radiotherapy Alone on Survival in Glioblastoma in a Randomised Phase III Study: 5-year Analysis of the EORTC-NCIC Trial," The Lancet. Oncology 10(5):459-466, Lancet Pub. Group, England (May 2009).

Lynch, G., et al., "Phase II Evaluation of DON (6-diazo-5-oxo-L-norleucine) in Patients with Advanced Colorectal Carcinoma," American Journal of Clinical Oncology 5(5):541-543, Lippincott Williams & Wilkins, United States (Oct. 1982).

MacIntyre, A.N., et al., "The Glucose Transporter Glut1 is Selectively Essential for CD4 T Cell Activation and Effector Function," Cell Metabolism 20(1):61-72, Cell Press, United States (Jul. 2014).

MacIver, N.J., et al., "Metabolic Regulation of T Lymphocytes," Annual Review of Immunology 31:259-283, Annual Reviews Inc, United States (2013).

Magill, G.B. and Myers, W.P., "Alterations in Calcium Metabolism in Cancer Patients Treated with 6-diazo-5-oxo-L-norleucine," Proceedings of the Society for Experimental Biology and Medicine 93(2):314-318, Blackwell Science, United States (Nov. 1956).

Magill, G.B., et al., "Pharmacological and Initial Therapeutic Observations on 6-diazo-5-oxo-1-norleucine (DON) in Human Neoplastic Disease," Cancer 10(6):1138-1150, Wiley, United States (Nov.-Dec. 1957).

McArthur, J.C., et al., "Human Immunodeficiency Virus-associated Neurocognitive Disorders: Mind the Gap," Annals of Neurology 67(6):699-714, Wiley-Liss, United States (Jun. 2010).

McDermott, L.A., et al., "Design and Evaluation of Novel Glutaminase Inhibitors," Bioorganic & Medicinal Chemistry 24(8):1819-1839, Elsevier Science, England (Apr. 2016).

McGaugh, J.L., "Memory—a Century of Consolidation," Science 287(5451):248-251, American Association for the Advancement of Science, United States (Jan. 2000).

Medina, M.A., et al., "Relevance of Glutamine Metabolism to Tumor Cell Growth," Molecular and Cellular Biochemistry 113(1):1-15, Springer, Netherlands (Jul. 1992).

Michalek, R.D., et al., "Cutting Edge: Distinct Glycolytic and Lipid Oxidative Metabolic Programs are Essential for Effector and Regulatory CD4+ T Cell Subsets," Journal of Immunology 186(6):3299-3303, American Association of Immunologists, United States (Mar. 2011).

Nakaya, M., et al., "Inflammatory T Cell Responses Rely on Amino Acid Transporter ASCT2 Facilitation of Glutamine Uptake and mTORC1 Kinase Activation," Immunity 40(5):692-705, Cell Press, United States (May 2014).

(56) References Cited

OTHER PUBLICATIONS

Nedelcovych, M.T., et al. "N-(Pivaloyloxy)alkoxy-carbonyl Prodrugs of the Glutamine Antagonist 6-Diazo-5-oxo-L-norleucine (DON) as a Potential Treatment for HIV Associated Neurocognitive Disorders," Journal of Medicinal Chemistry 60(16):7186-7198, American Chemical Society, United States (Aug. 2017).

Ngiow, S.F., et al., "Prospects for TIM3-Targeted Antitumor Immunotherapy," Cancer Research 71(21):6567-6571, American Association for Cancer Research, United States (Nov. 2011).

Nishio, M., et al., "Antiviral Effect of 6-diazo-5-oxo-L-norleucine, Antagonist of Gamma-glutamyl Transpeptidase, on Replication of Human Parainfluenza Virus Type 2," The Journal of General Virology 71( Pt 1):61-67, Microbiology Society, England (Jan. 1990).

Oberhuber, R., et al., "Murine Cervical Heart Transplantation Model using a Modified Cuff Technique," Journal of Visualized Experiments 92:e50753, MYJoVE Corporation, United States (Oct. 2014).

Oderup, C., et al., "Costimulation Blockade-Induced Cardiac Allograft Tolerance: Inhibition of T Cell Expansion and Accumulation of Intragraft cD4+Foxp3+ T Cells," Transplantation 82(11):1493-1500, Lippincott Williams & Wilkins, United States (Dec. 2006).

Online Mendelian Inheritance in Man, OMIM as of [retrieved on May 1, 2010-May 1]. World Wide Web Retrieved from the Internet: (URL: http://www.ncbi.nlm.nih.gov/omim/and m OnlineMendelianInheritance in Animals (OMIA) at http://omia.angis.org.au/contact.shtml).

Ostrom, Q.T., et al., "CBTRUS Statistical Report: Primary Brain and Central Nervous System Tumors Diagnosed in the United States in 2008-2012," Neuro-oncology 17(Suppl 4):iv1-iv62, Oxford University Press, England (Oct. 2015).

Ovejera, A.A., et al., "Efficacy of 6-diazo-5-oxo-L-norleucine and N-[N-gamma-glutamyl-6-diazo-5-oxo-norleucinyl]-6-diazo-5-oxo-norleucine against Experimental Tumors in Conventional and Nude Mice," Cancer Research 39(8):3220-3224, American Association for Cancer Research, United States (Aug. 1979).

Pawlik, T.M., et al., "Hepatic Glutamine Transporter Activation in Burn Injury: Role of Amino Acids and Phosphatidylinositol-3-kinase," American Journal of Physiology. Gastrointestinal and Liver Physiology 278(4):G532-G541, American Physiological Society, United States (Apr. 2000).

Pearce, E.L., et al., "Fueling Immunity: Insights into Metabolism and Lymphocyte Function," Science 342(6155):1242454, American Association for the Advancement of Science, United States (Oct. 2013).

Pilon, C.B., et al., "Administration of Low Doses of IL-2 Combined to Rapamycin Promotes Allogeneic Skin Graft Survival in Mice," American Journal of Transplantation 14(12):2874-2882, Wiley-Blackwell, United States (Dec. 2014).

Pollizzi, K.N. and Powell, J.D., "Integrating Canonical and Metabolic Signalling Programmes in the Regulation of T Cell Responses," Nature Reviews. Immunology 14(7):435-446, Nature Pub. Group, England (Jul. 2014).

Potter, M.C., et al., "Neurological Sequelae Induced by Alphavirus Infection of the CNS are Attenuated by Treatment with the Glutamine Antagonist 6-diazo-5-oxo-l-norleucine," Journal of Neurovirology 21(2):159-173, Stockton Press, United States (Apr. 2015).

Potter, M.C., et al., "Targeting the Glutamatergic System for the Treatment of HIV-associated Neurocognitive Disorders," Journal of Neuroimmune Pharmacology 8(3):594-607, Springer Science, United States (Jun. 2013).

Powell, J.D. and Zheng, Y., "Dissecting the Mechanism of T-cell Anergy with Immunophilin Ligands," Current Opinion in Investigational Drugs 7(11):1002-1007, Thomson Reuters, England (Nov. 2006).

Powell, J.D., et al., "A Modified Model of T-Cell Differentiation Based on mTOR Activity and Metabolism," Cold Spring Harbor Symposia on Quantitative Biology 78(1):125-130, Cold Spring Harbor Laboratory Press, United States (2013).

Powell, J.D., et al., "A2ar Antagonists: Next Generation Checkpoint Blockade for Cancer Immunotherapy," Computational and Structural Biotechnology Journal 13:265-272, Elsevier B.V, Netherlands (Apr. 2015).

Pugh, C.R., et al., "Selective Effects of Peripheral Lipopolysaccharide Administration on Contextual and Auditory-cue Fear Conditioning," Brain, Behavior, and Immunity 12(3):212-229, Elsevier, Netherlands (Sep. 1998).

Raez, L.E., et al., "A Phase I Dose-escalation Trial of 2-deoxy-d-glucose Alone or Combined with Docetaxel in Patients with Advanced Solid Tumors," Cancer Chemotherapy and Pharmacology 71(2):523-530, Springer Verlag, Germany (Feb. 2013).

Rahman, A., et al., "Phase I Study and Clinical Pharmacology of 6-diazo-5-oxo-L-norleucine (DON)," Investigational New Drugs 3(4):369-374, Springer, United States (1985).

Rahn, K.A., et al., "Inhibition of Glutamate Carboxypeptidase II (GCPII) Activity as a Treatment for Cognitive Impairment in Multiple Sclerosis," Proceedings of the National Academy of Sciences of the United States of America 109(49):20101-20106, National Academy of Sciences, United States (Dec. 2012).

Rais, R., et al., "Discovery of 6-diazo-5-oxo-L-norleucine (DON) Prodrugs with Enhanced CSF Delivery in Monkeys: a Potential Treatment for Glioblastoma," Journal of Medicinal Chemistry 59(18):8621-8633, American Chemical Society, United States (Sep. 2016).

Rautio, J., et al., "Prodrugs: Design and Clinical Applications," Nature Reviews. Drug Discovery 7(3):255-270, Nature Publishing Group, England (Mar. 2008).

Reitzer, L.J., et al., "Evidence that Glutamine, not Sugar, is the Major Energy Source for Cultured HeLa Cells," The Journal of Biological Chemistry 254(8):2669-2676, American Society for Biochemistry and Molecular Biology, United States (Apr. 1979).

Robertson, K.R., et al., "The Prevalence and Incidence of Neurocognitive Impairment in the HAART Era," AIDS 21(14):1915-1921, Lippincott Williams & Wilkins, England (Sep. 2007).

Roodnat, J.I., et al., "15-year Follow-up of a Multicenter, Randomized, Calcineurin Inhibitor withdrawal Study in Kidney Transplantation," Transplantation 98(1):47-53, Lippincott Williams & Wilkins, United States (Jul. 2014).

Rowe, I., et al., "Defective Glucose Metabolism in Polycystic Kidney Disease Identifies a New Therapeutic Strategy," Nature Medicine 19(4):488-493, Nature Publishing Company, United States (Apr. 2013).

Roybal, K., et al., "Mania-like Behavior Induced by Disruption of CLOCK," Proceedings of the National Academy of Sciences of the United States of America 104(15):6406-6411, National Academy of Sciences, United States (Apr. 2007).

Ru, P., et al., "Tumor Metabolism of Malignant Gliomas," Cancers 5(4):1469-1484, MDPI, Switzerland (Dec. 2013).

Rubin, J., et al., "A Phase II Study of 6-diazo-5-oxo-L-norleucine (DON, NSC-7365) in Advanced Large Bowel Carcinoma," American Journal of Clinical Oncology 6(3):325-326, Lippincott Williams & Wilkins, United States (Jun. 1983).

Sailasuta, N., et al., "Change in Brain Magnetic Resonance Spectroscopy Alter Treatment During Acute HIV Infection," PLoS One 7(11):e49272, Public Library of Science, United States (2012).

Satake, A., et al., "Inhibition of Calcineurin Abrogates while Inhibition of mTOR Promotes Regulatory T Cell Expansion and Graft-versus-host Disease Protection by IL-2 in Allogeneic Bone Marrow Transplantation," PLoS One 9(3):e92888, Public Library of Science, United States (Mar. 2014).

Sayegh, M.H., and Carpente, C.B., "Transplantation 50 Years Later—progress, Challenges, and Promises," The New England Journal of Medicine 351(26):2761-2766, Massachusetts Medical Society, United States (Dec. 2004).

Sengupta, S., et al., "Regulation of the mTOR Complex 1 Pathway by Nutrients, Growth Factors, and Stress," Molecular Cell 40(2):310-322, Cell Press, United States (Oct. 2010).

Shah, U., and Hodgson, R., "Recent Progress in the Discovery of Adenosine A(2A) Receptor Antagonists for the Treatment of Parkinson's Disease," Current Opinion in Drug Discovery & Development 13(4):466-480, Thomson Reuters, England (Jul. 2010).

(56) References Cited

OTHER PUBLICATIONS

Shi, L.Z., et al., "HIF1alpha-dependent Glycolytic Pathway Orchestrates a Metabolic Checkpoint for the Differentiation of TH17 and Treg Cells," The Journal of Experimental Medicine 208(7):1367-1376, Rockefeller University Press, United States (Jul. 2011).

Shijie, J., et al., "Blockade of Glutamate Release from Microglia Attenuates Experimental Autoimmune Encephalomyelitis in Mice," The Tohoku Journal of Experimental Medicine 217(2):87-92, Tohoku University Medical Library, Japan (Feb. 2009).

Schulze, A. and Harris, A.L., "How Cancer Metabolism is Tuned for Proliferation and Vulnerable to Disruption," Nature 491(7424):364-373, Nature Publishing Group, England (Nov. 2012).

Shelton, L.M., et al., "Glutamine Targeting Inhibits Systemic Metastasis in the VM-M3 Murine Tumor Model," International Journal of Cancer 127(10):2478-2485, International Union Against Cancer, United States (Nov. 2010).

Shukla, K., et al., "Design, Synthesis, and Pharmacological Evaluation of Bis-2-(5-phenylacetamido-1,2,4-thiadiazol-2-yl)ethyl Sulfide 3 (BPTES) Analogs as Glutaminase Inhibitors," Journal of Medicinal Chemistry 55(23):10551-10563, American Chemical Society, United States (Dec. 2012).

Sidman, et al., "Controlled Release of Macromolecules and Pharmaceuticals from Synthetic Polypeptides Based on Glutamic Acid," Biopolymers 22:547-556, John Wiley & Sons, Inc., United States (Jan. 1983).

Simioni, S., et al., "Cognitive Dysfunction in HIV Patients Despite Long-standing Suppression of Viremia," AIDS 24(9):1243-1250, Lippincott Williams & Wilkins, England (Jun. 2010).

Sklaroff, R.B., et al., "Phase I Study of 6-diazo-5-oxo-L-norleucine (DON)," Cancer Treatment Reports 64(12):1247-1251, National Cancer Institute, United States (1980).

Srikanth, K., et al., "Synthesis, Screening and Quantitative Structure-activity Relationship (QSAR) Studies of Some Glutamine Analogues for Possible Anticancer Activity," Bioorganic & Medicinal Chemistry 10(7):2119-2131, Elsevier Science, England (Jul. 2002).

Stupp, R., et al., "Radiotherapy Plus Concomitant and Adjuvant Temozolomide for Glioblastoma," The New England Journal of Medicine 352(10):987-996, Massachusetts Medical Society, United States (Mar. 2005).

Sullivan, M.P., et al., "A Comparison of the Effectiveness of Standard Dose 6-mercaptopurine, Combination 6-mercaptopurine and DON, and High-loading 6-mercaptopurine Therapies in Treatment of the Acute Leukemias of Childhood: Results of a Coperative Study," Cancer Chemotherapy Reports 18:83-95, National Cancer Institute, United States (May 1962).

Sullivan, M.P., et al., "Pharmacokinetic and Phase I Study of Intravenous DON (6-diazo-5-oxo-L-norleucine) in Children," Cancer Chemotherapy Reports 21(1):78-84, Springer Verlag, Germany (1988).

Suzuki, A., et al., "Memory Reconsolidation and Extinction have Distinct Temporal and Biochemical Signatures," The Journal of Neuroscience 24(20):4787-4795, Society for Neuroscience, United States (May 2004).

Tanaka, K., et al., "Compensatory Glutamine Metabolism Promotes Glioblastoma Resistance to mTOR Inhibitor Treatment," The Journal of Clinical Investigation 125(4):1591-1602, American Society for Clinical Investigation, United States (Apr. 2015).

Tarnowski, G.S., and Stock, C.C., "Effects of Combinations of Azaserine and of 6-diazo-5-oxo-L-norleucine with Purine Analogs and Other Antimetabolites on the Growth of Two Mouse Mammary Carcinomas," Cancer Research 17(10):1033-1039, American Association for Cancer Research, United States (Nov. 1957).

Thangavelu, K., et al., "Structural Basis for the Active Site Inhibition Mechanism of Human Kidney-type Glutaminase (KGA)," Scientific Reports 4:3827, Nature Publishing Group, England (Jan. 2014).

Thomas, A.G., et al., "Kinetic Characterization of Ebselen, Chelerythrine and Apomorphine as Glutaminase Inhibitors," Biochemical and Biophysical Research Communications 438(2):243-248, Elsevier, United States (Aug. 2013).

Thomas, A.G., et al., "Small Molecule Glutaminase Inhibitors Block Glutamate Release from Stimulated Microglia," Biochemical and Biophysical Research Communications 443(1):32-36, Elsevier, United States (Jan. 2014).

Thomson, L.M., and Sutherland, R.J., "Systemic Administration of Lipopolysaccharide and Interleukin-1beta have Different Effects on Memory Consolidation," Brain Research Bulletin 67(1-2):24-29, Elsevier Science, United States (Sep. 2005).

Tran, T.Q., et al., "Glutamine Deficiency Induces DNA Alkylation Damage and Sensitizes Cancer Cells to Alkylating Agents through Inhibition of ALKBH Enzymes," PLoS Biology 15(11):e2002810, Public Library of Science, United States (Nov. 2017).

Tsilidis, K.K., et al., "Metformin does not Affect Cancer Risk: A Cohort Study in the U.K. Clinical Practice Research Datalink Analyzed like an Intention-to-Treat Trial," Diabetes Care 37(9):2522-2532, American Diabetes Association, United States (Sep. 2014).

Ueki, N., et al, "Synthesis and Preclinical Evaluation of a Highly Improved Anticancer Prodrug Activated by Histone Deacetylases and Cathepsin L," Theranostics 6(6):808-816, Ivyspring International Publisher, Australia (Mar. 2016).

Upadhyay, R.K., "Drug Delivery Systems, CNS Protection, and the Blood Brain Barrier," BioMed Research International 2014:869269, Hindawi Pub. Co, United States (2014).

Vander Heiden, M.G., et al., "Understanding the Warburg Effect: The Metabolic Requirements of Cell Proliferation," Science 324(5930):1029-1033, American Association for the Advancement of Science, United States (May 2009).

Varoqui, H., et al., "Cloning and Functional Identification of a Neuronal Glutamine Transporter," The Journal of Biological Chemistry 275(6):4049-4054, American Society for Biochemistry and Molecular Biology, United States (Feb. 2000).

Waickman, A.T., and Powell, J.D., "mTOR, Metabolism, and the Regulation of T-cell Differentiation and Function," Immunological Reviews 249(1):43-58, Blackwell, England (Sep. 2012).

Wang, R., et al., "The Transcription Factor Myc Controls Metabolic Reprogramming upon T Lymphocyte Activation," Immunity 35(6):871-882, Cell Press, United States (Dec. 2011).

Warburg, O., "On Respiratory Impairment in Cancer Cells," Science 124(3215):269-270, American Association for the Advancement of Science, United States (Aug. 1956).

Weller, M., et al., "EANO Guideline for the Diagnosis and Treatment of Anaplastic Gliomas and Glioblastoma.," The Lancet. Oncology 15(9):e395-403, Lancet Pub. Group, England (Aug. 2014).

Willems, L., et al., "Inhibiting Glutamine Uptake Represents an Attractive New Strategy for Treating Acute Myeloid Leukemia," Blood 122(20):3521-3532, American Society of Hematology, United States (Nov. 2013).

Willis, R.C. and Seegmiller, J.E., "The Inhibition by 6-diazo-5-oxo-L-norleucine of Glutamine Catabolism of the Cultured Human Lymphoblast," Journal of Cellular Physiology 93(3):375-382, Wiley-Liss, United States (Dec. 1977).

Windmueller, H,G. and Spaeth, A.E., "Uptake and Metabolism of Plasma Glutamine by the Small Intestine," The Journal of Biological Chemistry 249(16):5070-5079, American Society for Biochemistry and Molecular Biology, United States (Aug. 1974).

Wise, D.R. and Thompson, C.B., "Glutamine Addiction: a New Therapeutic Target in Cancer," Trends in Biochemical Sciences 35(8):427-433, Elsevier Trends Journals, England (Aug. 2010).

Wise, D.R., et al., "Myc Regulates a Transcriptional Program that Stimulates Mitochondrial Glutaminolysis and Leads to Glutamine Addiction," Proceedings of the National Academy of Sciences of the United States of America 105(48):18782-18787, National Academy of Sciences, United States (Dec. 2008).

Wook Koo, J., et al., "Essential Role of Mesolimbic Brain-Derived Neurotrophic Factor in Chronic Social Stress-InducedDepressive Behaviors," Biological Psychiatry 80(6):469-478, Elsevier, United States (Sep. 2016).

Wu, T., et al., "Immunosuppressive Drugs on Inducing Ag-specific CD4(+)CD25(+)Foxp3(+) Treg Cells During Immune Response in Vivo," Transplant Immunology 27(1):30-38, Elsevier, Netherlands (Aug. 2012).

(56) References Cited

OTHER PUBLICATIONS

Yamasaki, T., et al., "Exploring a Glycolytic Inhibitor for the Treatment of an FH-deficient Type-2 Papillary RCC," Nature Reviews. Urology 8(3):165-171, Nature Pub. Group, England (Mar. 2011).

Yang, K. and Chi, H., "mTOR and Metabolic Pathways in T Cell Quiescence and Functional Activation," Seminars in Immunology 24(6):421-428, Academic Press, England (Dec. 2012).

Zgodka, D., et al., "A Diffusible Analogue of N3-(4-methoxyfumaroyl)-l-2,3-diaminopropanoic Acid With Antifungal Activity," Microbiology 147(Pt 7):1955-1959, (Jul. 2001).

Zhang, W., et al., "Overexpression of Cysteine Cathepsin L Is a Marker of Invasion and Metastasis in Ovarian Cancer," Oncology Reports 31(3):1334-1342, D.A. Spandidos, Greece (Mar. 2014).

Zheng, Y., et al., "Anergic T Cells Are Metabolically Anergic," Journal of Immunology 183(10):6095-6101, American Association of Immunologists, United States (Nov. 2009).

Zimmermann, S.C., et al., "N-substituted Prodrugs of Mebendazole Provide Improved Aqueous Solubility and Oral Bioavailability in Mice and Dogs," Journal of Medicinal Chemistry 61(9):3918-3929, American Chemical Society, United States (May 2018).

Zink, M.C, "Translational Research Models and Novel Adjunctive Therapies for NeuroAIDS," Journal of Neuroimmune Pharmacology 2(1):14-19, Springer Science + Business Media, United States (Mar. 2007).

Office Action dated Feb. 8, 2019, for co-pending U.S. Appl. No. 15/884,974, filed Jan. 31, 2018, U.S. Patent and Trademark Office, Alexandria, Virginia.

Office Action dated Sep. 20, 2019, for co-pending U.S. Appl. No. 15/884,974, filed Jan. 31, 2018, U.S. Patent and Trademark Office, Alexandria, Virginia.

\* cited by examiner

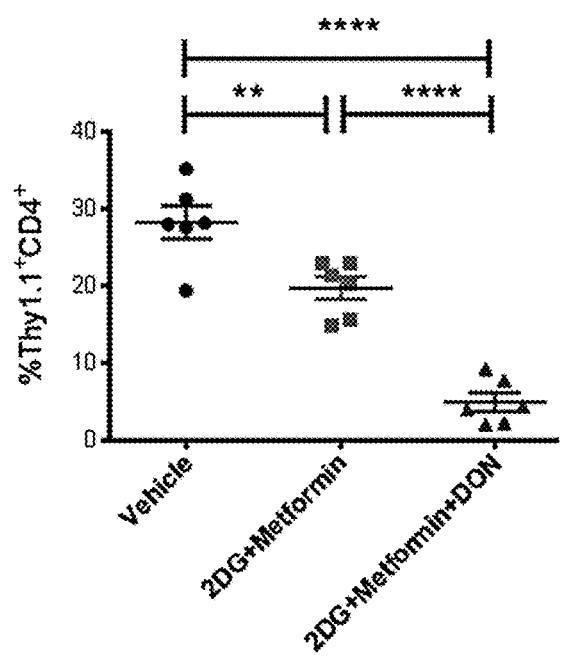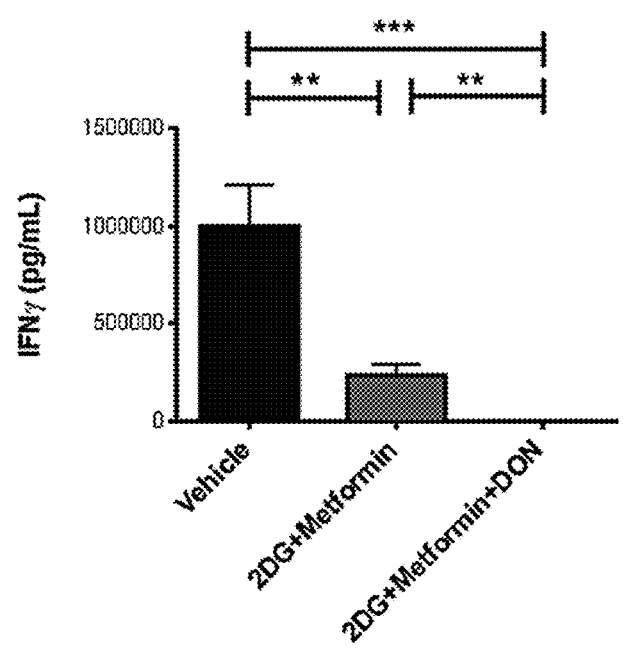
*FIG. 13B*  *FIG. 13C*

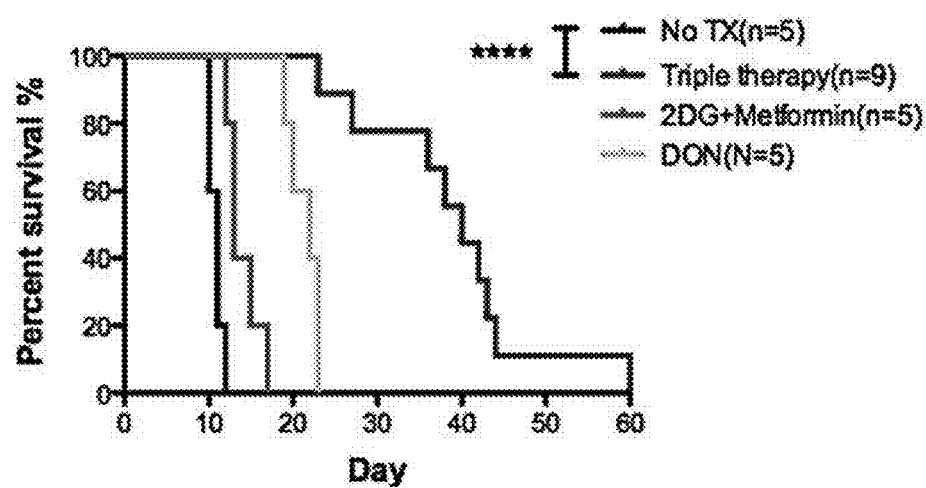
*FIG. 15A*
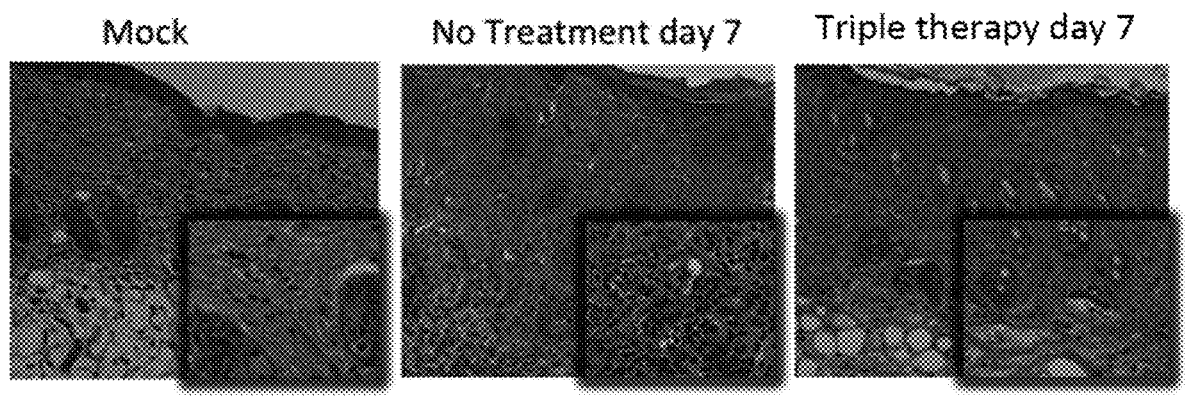
*FIG. 15B*  *FIG. 15C*  *FIG.15D*

Triple therapy day 40

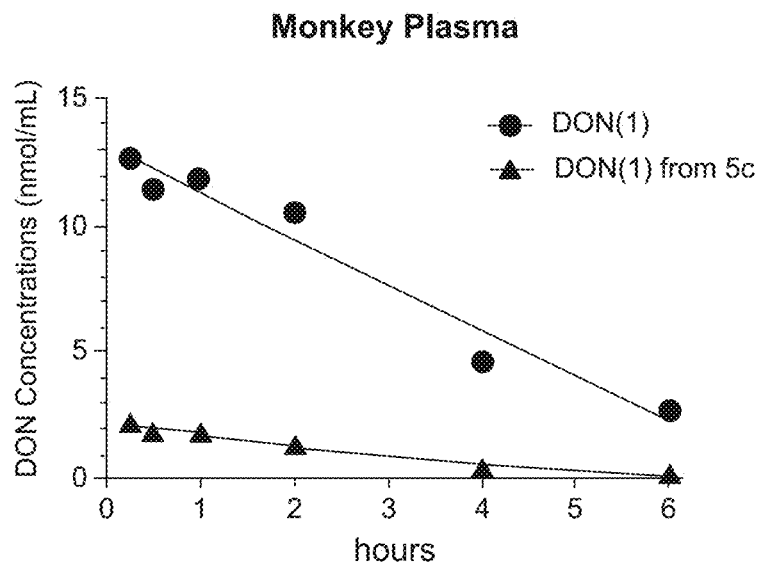
FIG. 23A
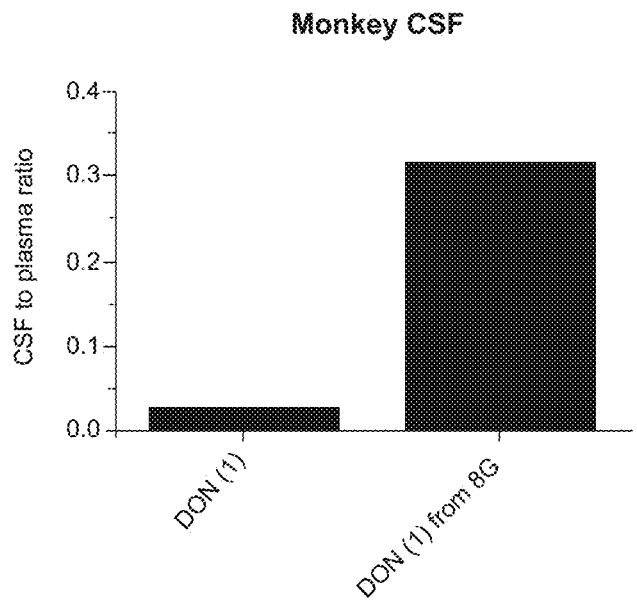
FIG. 23B
| Compound Dosed | Dose (mg/kg equiv) | DON $C_{max}$ (nmol/mL) | DON $T_{max}$ (hr) | DON $AUC_{0-t}$ (hr*nmol/mL) |
|---|---|---|---|---|
| 1 | 1.6 | 12.6 | 0.25 | 42.7 |
| 5c | 1.6 | 2.23 | 0.25 | 5.71 |
FIG. 23C

METHODS AND COMPOSITIONS FOR TREATING METABOLIC REPROGRAMMING DISORDERS

CROSS-REFERENCE TO RELATED APPLICATIONS

This application is a continuation-in-part of PCT/US2016/044810, filed Jul. 29, 2016, that claims the benefit of U.S. Provisional Application Nos. 62/199,381 and 62/199,566, both filed Jul. 31, 2015, the contents of each are incorporated herein by reference in their entirety.

BACKGROUND

Cells under certain conditions may undergo a metabolic switch from a metabolic profile that requires less activity of certain metabolic pathways to meet the cell's energy demands to a metabolic profile that requires greater activity of those metabolic pathways or increased activity of other metabolic pathways to meet its energy demands. For example, cells under certain conditions may undergo a switch toward increased glycolysis and away from oxidative phosphorylation (OXPHOS). While glycolysis provides less adenosine triphosphate (ATP) than oxidative phosphorylation, it has been proposed that aerobic glycolysis permits the generation of the substrates necessary for the generation of amino acids, nucleic acids and lipids, all of which are crucial for proliferation (Vander Heiden et al. (2009) *Science* 324(5930):1029-1033). This use of glycolysis in the presence of oxygen was first described by Otto Warburg in cancer cells (Warburg (1956) *Science* 124 (3215):269-270) and was subsequently found to be important in activated T cells (Warburg et al. (1958) [Metabolism of leukocytes]. *Zeitschrift fur Naturforschung. Teil B: Chemie, Biochemie, Biophysik, Biologie* 13B (8):515-516). These metabolically reprogrammed cells depend on the increased activity of certain metabolic pathways, such as pathways involved in glutamine metabolism, glycolysis, and fatty acid synthesis. However, specific inhibitors of individual enzymes in these metabolic pathways alone have not proven effective because multiple points within each metabolic pathway are modulated as a cell's metabolism is reprogrammed to meet the extraordinarily large energy demands of the abnormal, harmful, or unhealthy state.

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning. A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml.

In an aspect, the presently disclosed subject matter provides a method for treating a subject having a condition, disease, or disorder that involves metabolically reprogrammed cells whose activation, function, growth, proliferation, and/or survival depends on increased activity of at least one metabolic pathway selected from the group consisting of glutamine metabolism, glycolysis, and fatty acid synthesis, the method comprising administering to the subject at least one metabolic reprogramming agent that decreases activity of at least one metabolic pathway selected from the group consisting of glutamine metabolism, glycolysis, and fatty acid synthesis in an amount effective to treat the condition, disease, or disorder.

In an aspect, the presently disclosed subject matter provides a method for treating a subject having a condition, disease, or disorder that involves at least one of aberrant and/or excessive glutamine metabolism, aberrant and/or excessive glycolysis, or aberrant and/or excessive fatty acid synthesis, the method comprising administering to the subject at least one metabolic reprogramming agent that decreases activity of at least one metabolic pathway selected from the group consisting of glutamine metabolism, glycolysis, and fatty acid synthesis in an amount effective to treat the condition, disease, or disorder.

In an aspect, the presently disclosed subject matter involves the use of at least one metabolic reprogramming agent that decreases activity of at least one metabolic pathway selected from the group consisting of glutamine metabolism, glycolysis, and fatty acid synthesis for treating a condition, disease, or disorder that involves (i) metabolically reprogrammed cells whose activation, function, growth, proliferation, and/or survival depends on increased activity of at least one metabolic pathway selected from the group consisting of glutamine metabolism, glycolysis, and fatty acid synthesis or (ii) at least one of aberrant and/or excessive glutamine metabolism, aberrant and/or excessive glycolysis, or aberrant and/or excessive fatty acid synthesis.

In an aspect, the presently disclosed subject matter provides a pharmaceutical composition comprising an effective amount of at least one, at least two, or at least three metabolic reprogramming agents that decrease the activity of at least one metabolic pathway selected from the group consisting of glutamine metabolism, glycolysis, and fatty acid synthesis, and a pharmaceutically acceptable carrier, diluent, or excipient. In particular embodiments, the pharmaceutical composition further includes at least one additional therapeutic agent selected from the group consisting of cytotoxic agents, immunotherapeutic agents, immunosuppressant agents, radiotherapeutic agents, anti-inflammatory agents, and neuroprotective agents.

In particular embodiments, the method or use comprises administering to the subject at least two metabolic reprogramming agents that decrease the activity of at least two metabolic pathways selected from the group consisting of glutamine metabolism, glycolysis, and fatty acid synthesis in an amount effective to treat the condition, disease, or disorder.

In particular embodiments, the method or use comprises administering to the subject at least three metabolic reprogramming agents that each decrease the activity of a different metabolic pathways selected from the group consisting of glutamine metabolism, glycolysis, and fatty acid synthesis in an amount effective to treat the condition, disease, or disorder.

In particular embodiments, at least one metabolic reprogramming agent decreases glutamine metabolism. In particular embodiments, at least one metabolic reprogramming agent is a glutamine antagonist. In particular embodiments, at least one metabolic reprogramming agent is a glutamine analog that interferes with a glutamine metabolic pathway. In particular embodiments, at least one metabolic reprogramming agent is selected from the group consisting of acivicin (L-(alpha S, 5S)-alpha-amino-3-chloro-4,5-dihydro-5-isoxazoleacetic acid), azaserine, and 6-diazo-5-oxo-norleucine (DON), and 5-diazo-4-oxo-L-norvaline (L-DONV). In particular embodiments, at least one metabolic reprogramming agent is a prodrug of a glutamine analog that interferes with a glutamine metabolic pathway. In particular embodiments, at least one metabolic reprogramming agent is a prodrug of acivicin, azaserine, DON, and L-DONV. In particular embodiments, at least one metabolic reprogramming agent that decreases glutamine metabolism is a compound having formula (I), formula (IIA), formula (IIB), or formula (III).

In particular embodiments, at least one metabolic reprogramming agent decreases glycolysis. In particular embodiments, at least one metabolic reprogramming agent is a glucose analog that inhibits hexokinase. In particular embodiments, at least one metabolic reprogramming agent is 2-deoxy-D-glucose (2-DG).

In particular embodiments, at least one metabolic reprogramming agent increases fatty acid oxidation. In particular embodiments, at least one metabolic reprogramming agent is an activator of 5' AMP-activated protein kinase (AMPK) activity. In particular embodiments, at least one metabolic reprogramming agent is metformin.

In particular embodiments, the condition, disease, or disorder is an immune disorder. In particular embodiments the metabolically reprogrammed cells comprise immune cells. In particular embodiments, the condition, disease, or disorder is a neurodegenerative disorder. In particular embodiments, the metabolically reprogrammed cells comprise neuronal cells. In particular embodiments, the condition, disease, or disorder is a pathology due to or associated with CNS inflammation due to an infection. In particular embodiments, the condition, disease, or disorder is cereberal malaria. In particular embodiments, the condition, disease, or disorder is a pathology due to or associated with CNS inflammation not involving an infection. In particular embodiments, the condition, disease, or disorder is amyotrophic lateral sclerosis (ALS). In particular embodiments, the condition, disease, or disorder is Alzheimer's Disease). In particular embodiments, the condition, disease, or disorder is Parkinson's Disease). In particular embodiments, the condition, disease, or disorder is neuromyelitis optica). In particular embodiments, the condition, disease, or disorder is ARDS. In particular embodiments, the condition, disease, or disorder is arthritis. In particular embodiments, the condition, disease, or disorder is asthma. In particular embodiments, the condition, disease, or disorder is allograft rejection during cell, tissue, or organ transplantation. In particular embodiments, the method for treating, preventing, or delaying a transplant rejection (e.g., allograft rejection, e.g., heart allograft rejection) further includes transplanting a cell, tissue, or organ into the subject. In particular embodiments, the cell, tissue, or organ allograft comprises a MHC mismatched allograft (e.g., complete MHC mismatch). In particular embodiments, the method further includes administering an effective amount of an immunosuppressant agent to the subject. In particular embodiments, the condition, disease, or disorder is cerebral malaria. In particular embodiments, the condition, disease, or disorder is lupus. In particular embodiments, the condition, disease, or disorder is pneumonitis. In particular embodiments, the condition, disease, or disorder is pulmonary fibrosis.

In particular embodiments, the condition, disease, or disorder is not an immune disorder comprising multiple sclerosis. In particular embodiments, the condition, disease, or disorder is not a neurodegenerative disorder selected from the group consisting of Alzheimer's disease, amyotrophic lateral sclerosis (ALS), Huntington's disease, stroke, and transient ischemic brain injury.

In an aspect, the presently disclosed subject matter provides a method for the treatment of ARDS in a subject in need thereof, the method comprising administering to the subject at least one metabolic reprogramming agent that decreases glutamine metabolism in an amount effective to treat ARDS in the subject. In an aspect, the presently disclosed subject matter involves the use of an effective amount of at least one metabolic reprogramming agent that decreases glutamine metabolism to treat ARDS in a subject in need thereof.

In an aspect, the presently disclosed subject matter provides a method for the treatment of arthritis in a subject in need thereof, the method comprising administering to the subject at least one metabolic reprogramming agent that decreases glutamine metabolism in an amount effective to treat arthritis in the subject. In an aspect, the presently disclosed subject matter involves the use of an effective amount of at least one metabolic reprogramming agent that decreases glutamine metabolism to treat arthritis in a subject in need thereof.

In an aspect, the presently disclosed subject matter provides a method for the treatment of asthma in a subject in need thereof, the method comprising administering to the subject at least one metabolic reprogramming agent that decreases glutamine metabolism in an amount effective to treat asthma in the subject. In an aspect, the presently disclosed subject matter involves the use of an effective amount of at least one metabolic reprogramming agent that decreases glutamine metabolism to treat asthma in a subject in need thereof.

In an aspect, the presently disclosed subject matter provides a method for the treatment of amyotrophic lateral sclerosis (ALS) in a subject in need thereof, the method comprising administering to the subject at least one metabolic reprogramming agent that decreases glutamine metabolism in an amount effective to treat ALS in the subject. In an aspect, the presently disclosed subject matter involves the use of an effective amount of at least one metabolic reprogramming agent that decreases glutamine metabolism to treat ALS in a subject in need thereof.

In an aspect, the presently disclosed subject matter provides a method for the treatment of Alzheimer's Disease in a subject in need thereof, the method comprising administering to the subject at least one metabolic reprogramming agent that decreases glutamine metabolism in an amount effective to treat Alzheimer's Disease in the subject. In an aspect, the presently disclosed subject matter involves the use of an effective amount of at least one metabolic reprogramming agent that decreases glutamine metabolism to treat Alzheimer's Disease in a subject in need thereof.

In an aspect, the presently disclosed subject matter provides a method for the treatment of cerebral malaria in a subject in need thereof, the method comprising administering to the subject at least one metabolic reprogramming agent that decreases glutamine metabolism in an amount effective to treat cerebral malaria in the subject. In an aspect, the presently disclosed subject matter involves the use of an effective amount of at least one metabolic reprogramming agent that decreases glutamine metabolism to treat cerebral malaria in a subject in need thereof.

In an aspect, the presently disclosed subject matter provides a method for preventing or delaying allograft rejection during cell, tissue, or organ transplantation in a subject in need thereof, the method comprising administering to a subject about to undergo, undergoing, or having undergone a cell, tissue, or organ transplantation at least one metabolic reprogramming agent that decreases glutamine metabolism in an amount effective to prevent or delay allograft rejection of the cell, tissue, or organ transplanted in the subject. In particular embodiments, the method includes comprising transplanting a cell, tissue, or organ into the subject. In particular embodiments, the method further includes administering an immunosuppressant agent to the subject. In an aspect, the presently disclosed subject matter involves the use of an effective amount of at least one metabolic reprogramming agent that decreases glutamine metabolism to treat, prevent, or delay an allograft rejection in a subject in need thereof.

In an aspect, the presently disclosed subject matter provides method for the treatment of lupus in a subject in need thereof, the method comprising administering to the subject at least one metabolic reprogramming agent that decreases glutamine metabolism in an amount effective to treat lupus in the subject. In an aspect, the presently disclosed subject matter involves the use of an effective amount of at least one metabolic reprogramming agent that decreases glutamine metabolism to treat lupus in a subject in need thereof.

In an aspect, the presently disclosed subject matter provides a method for the treatment of neuromyeletis optica in a subject in need thereof, the method comprising administering to the subject at least one metabolic reprogramming agent that decreases glutamine metabolism in an amount effective to treat neuromyeletis optica in the subject. In an aspect, the presently disclosed subject matter involves the use of an effective amount of at least one metabolic reprogramming agent that decreases glutamine metabolism to treat neuromyeletis optica in a subject in need thereof.

In an aspect, the presently disclosed subject matter provides a method for the treatment of Parkinson's Disease in a subject in need thereof, the method comprising administering to the subject at least one metabolic reprogramming agent that decreases glutamine metabolism in an amount effective to treat Parkinson's Disease in the subject. In an aspect, the presently disclosed subject matter involves the use of an effective amount of at least one metabolic reprogramming agent that decreases glutamine metabolism to treat Parkinson's Disease in a subject in need thereof.

In an aspect, the presently disclosed subject matter provides a method for the treatment of pneumonitis in a subject in need thereof, the method comprising administering to the subject at least one metabolic reprogramming agent that decreases glutamine metabolism in an amount effective to treat pneumonitis in the subject. In an aspect, the presently disclosed subject matter involves the use of an effective amount of at least one metabolic reprogramming agent that decreases glutamine metabolism to treat pneumonitis in a subject in need thereof.

In an aspect, the presently disclosed subject matter provides a method for the treatment of pulmonary fibrosis in a subject in need thereof, the method comprising administering to the subject at least one metabolic reprogramming agent that decreases glutamine metabolism in an amount effective to treat pulmonary fibrosis in the subject. In an aspect, the presently disclosed subject matter involves the use of an effective amount of at least one metabolic reprogramming agent that decreases glutamine metabolism to treat pulmonary fibrosis in a subject in need thereof.

In particular embodiments, at least one metabolic reprogramming agent that decreases glutamine metabolism comprises a glutamine antagonist. In particular embodiments, at least one metabolic reprogramming agent that decreases glutamine metabolism comprises a glutamine analog that interferes with a glutamine metabolic pathway. In particular embodiments, at least one metabolic reprogramming agent that decreases glutamine metabolism is selected from the group consisting of acivicin, azaserine, and DON, and L-DONV. In particular embodiments, at least one metabolic reprogramming agent that decreases glutamine metabolism is a prodrug of a glutamine analog that interferes with a glutamine metabolic pathway. In particular embodiments, at least one metabolic reprogramming agent that decreases glutamine metabolism is a prodrug of acivicin (L-(alpha S, 5S)-alpha-amino-3-chloro-4,5-dihydro-5-isoxazoleacetic acid), azaserine, and 6-diazo-5-oxo-norleucine (DON). In particular embodiments, at least one metabolic reprogramming agent that decreases glutamine metabolism is a compound having formula (I), formula (IIA), formula (IIB), or formula (III).

In particular embodiments, the methods of treatment (e.g., ARDS, arthritis, ALS, Alzheimer's Disease, cerebral malaria, allograft rejection, lupus, neuromyeletis optica, Parkinson's Disease, pneumonitis, pulmonary fibrosis, etc.) or uses further include or involve administering to the subject an effective amount of at least one metabolic reprogramming agent that decreases glycolysis. In particular embodiments, at least one metabolic reprogramming agent that decreases glycolysis is a glucose analog that inhibits hexokinase. In particular embodiments, at least one metabolic reprogramming agent that decreases glycolysis is 2-deoxy-D-glucose (2-DG).

In particular embodiments, the methods of treatment (e.g., ARDS, arthritis, ALS, Alzheimer's Disease, cerebral malaria, allograft rejection, lupus, neuromyeletis optica, Parkinson's Disease, pneumonitis, pulmonary fibrosis, etc.) or uses further include or involve administering to the subject an effective amount of at least one metabolic reprogramming agent that increases fatty acid oxidation. In particular embodiments, at least one metabolic reprogramming agent that increases fatty acid oxidation is an activator of 5' AMP-activated protein kinase (AMPK) activity. In particular embodiments, at least one metabolic reprogramming agent that increases fatty acid oxidation is metformin.

Applicant has found that compounds of the disclosure having formula (I), formula (IIA), formula (IIB), and formula (III) are stable in plasma, liver microsomes, liver tissue, and gastrointestinal tissue, yet these compounds are cleaved in certain tissue cells to liberate DON. The unexpected properties of compounds having formula (I), formula (IIA), formula (IIB), and formula (III) result in a surprising improvement in therapeutic index for treating a condition, disease, or disorder with DON and provide the maximum therapeutic benefit to a subject in need of such treatment.

Applicant has also found unexpectedly that compounds of the disclosure having formula (I), formula (IIA), formula (IIB), and formula (III) exhibit unexpected enhanced CSF to plasma partitioning after administration, making them uniquely useful for the treatment a condition, disease, or disorder where central nervous system (CNS) penetration is required.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Having thus described the presently disclosed subject matter in general terms, reference will now be made to the accompanying Figures, which are not necessarily drawn to scale.

Figure 1A:
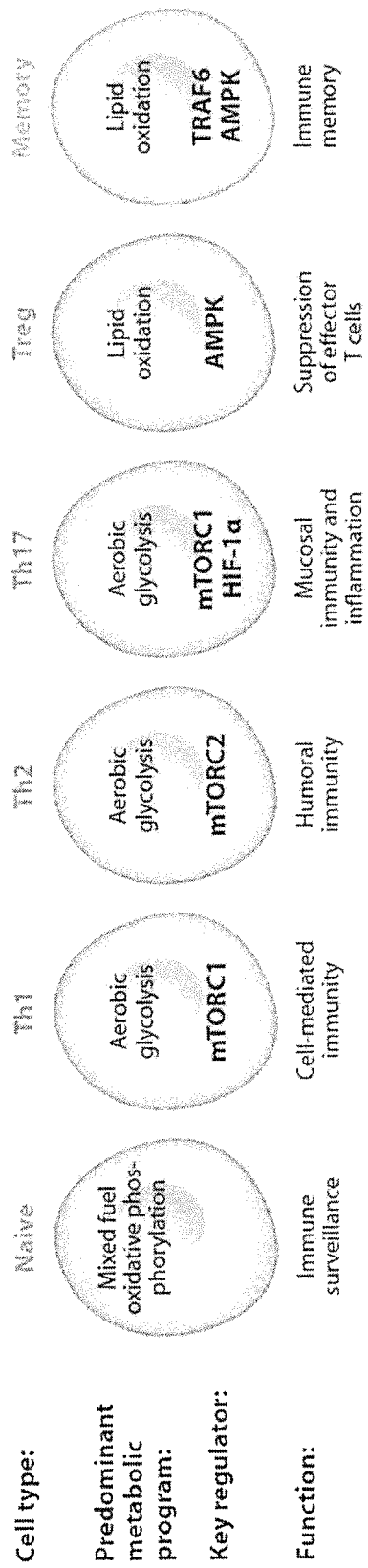

FIG. 1A is an illustration showing that metabolic reprogramming is a critical component of immune cell differentiation and function.

Figure 1B:
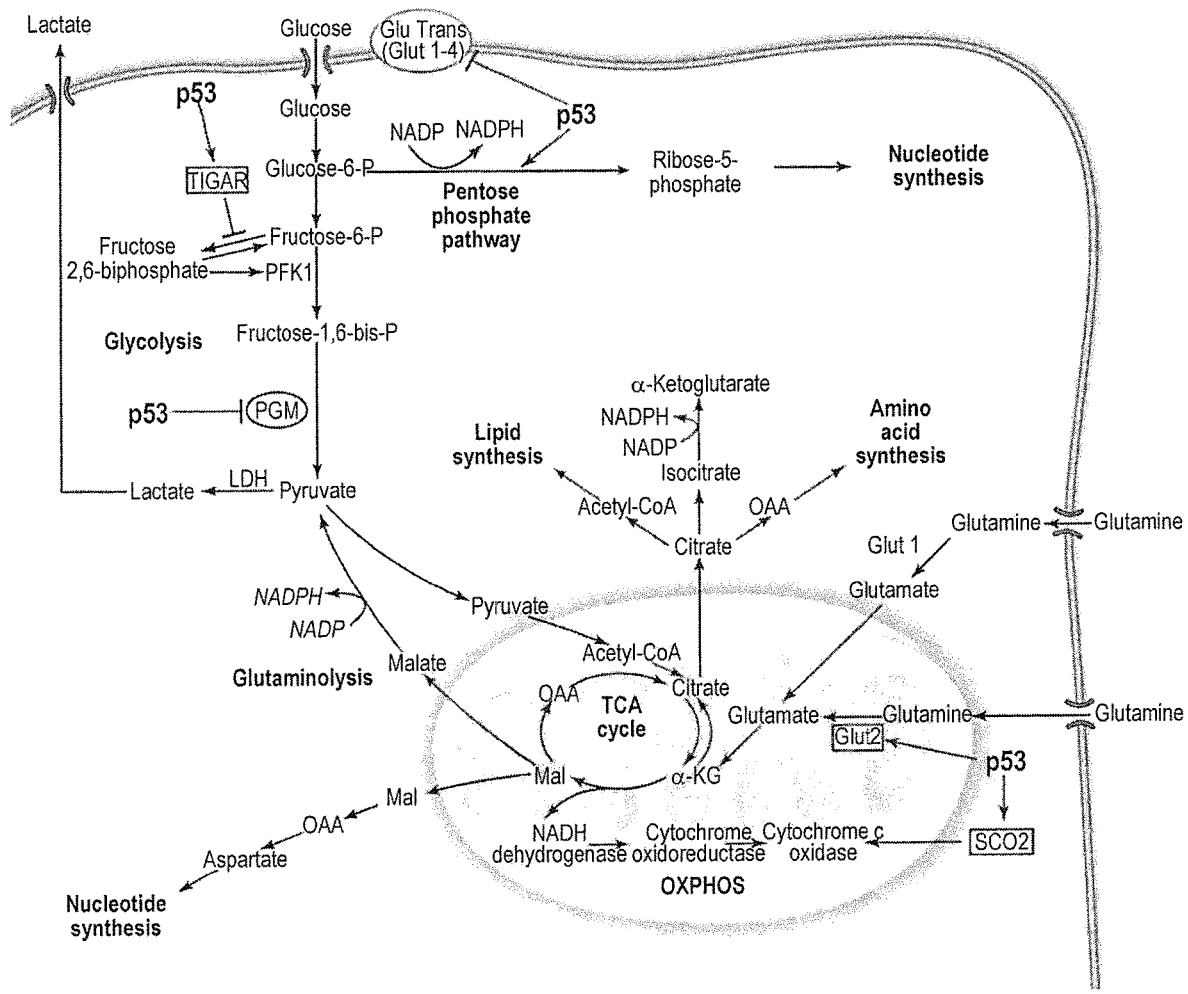

FIG. 1B is an illustration showing the targeting of glutamine metabolism to regulate immune effector function.

Figure 1D:
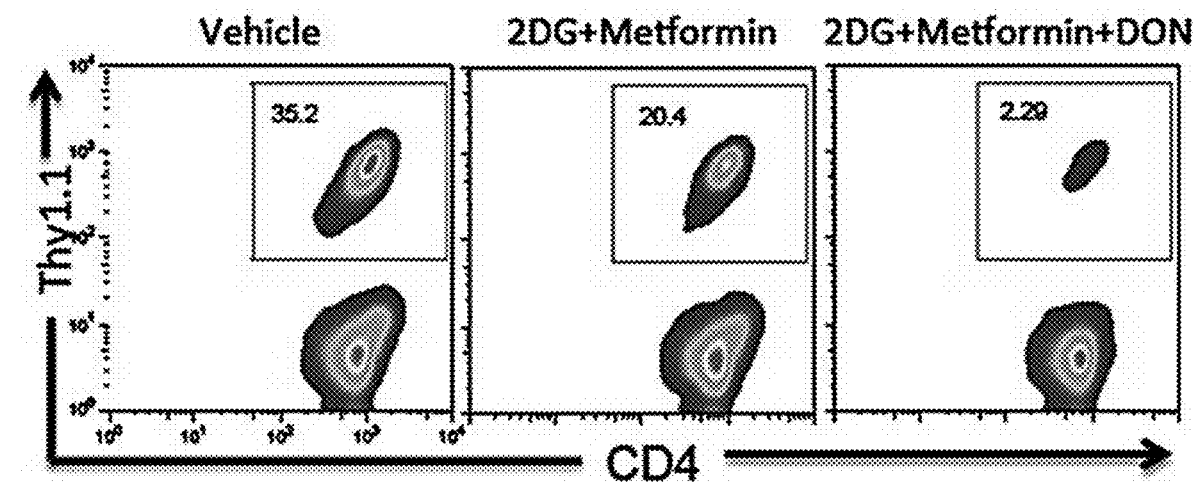
Figure 1E:
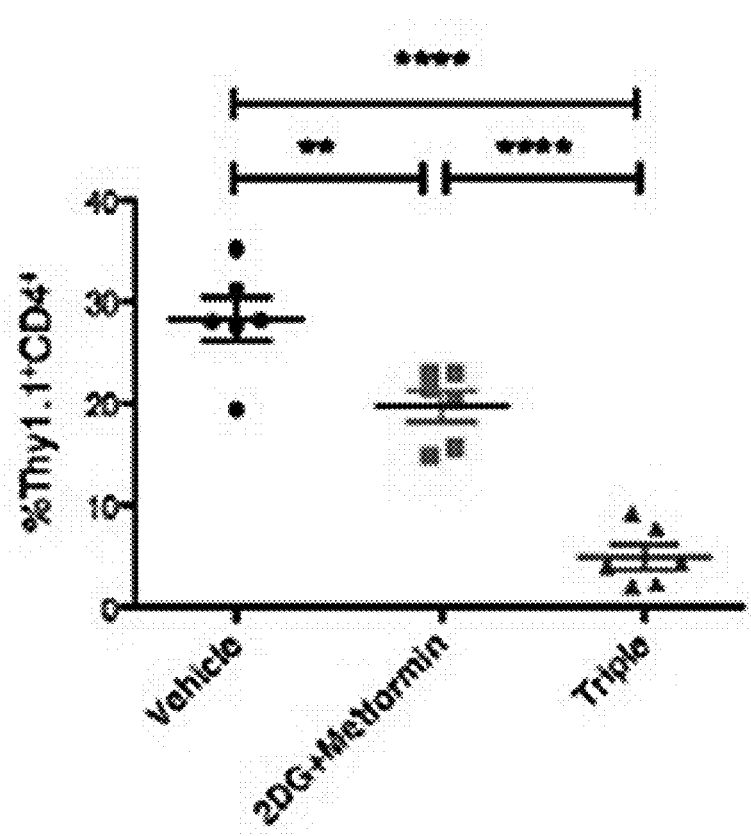
Figure 1F:
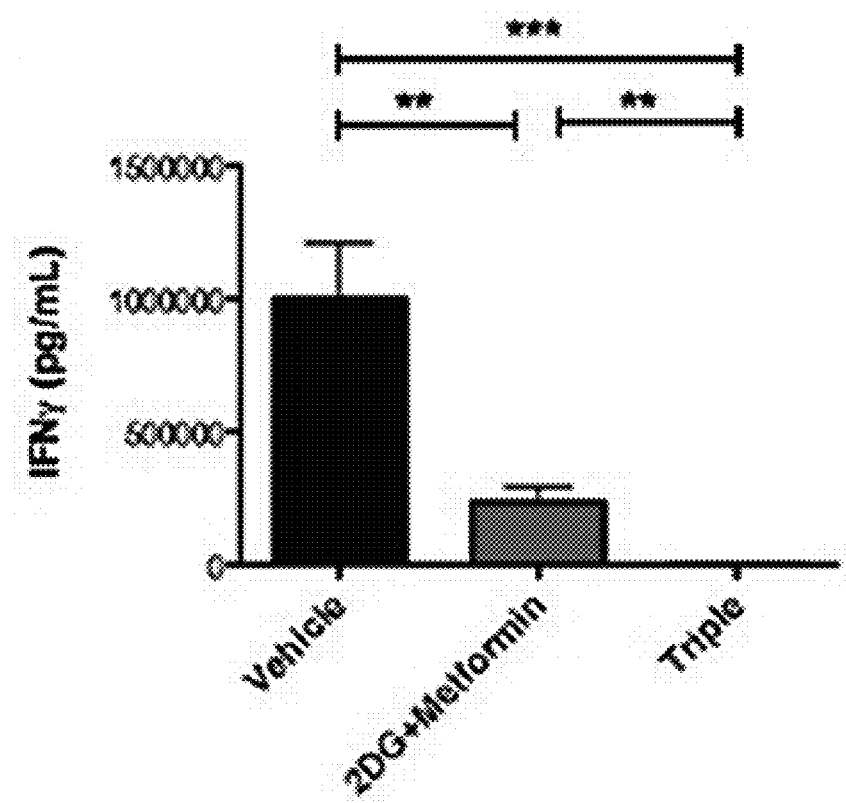

FIG. 1C, is an illustration, FIG. 1D is an illustration, FIG. 1E is a graph, and FIG. 1F is a bar graph showing that metabolic reprogramming agents suppress antigen-specific effector $CD4^+$ T cells proliferation and function. $Thy1.2^+$ WT B6 mice were treated with vehicle, metabolic reprogramming therapy with at least two metabolic reprogramming agents (e.g., 2DG+Metformin), or metabolic reprogramming therapy with at least three metabolic reprogramming agents (e.g., 2DG+Metformin+DON). DON was found to be a potent inhibitor of $CD4^+$ T cell effector function.

Figure 2A:
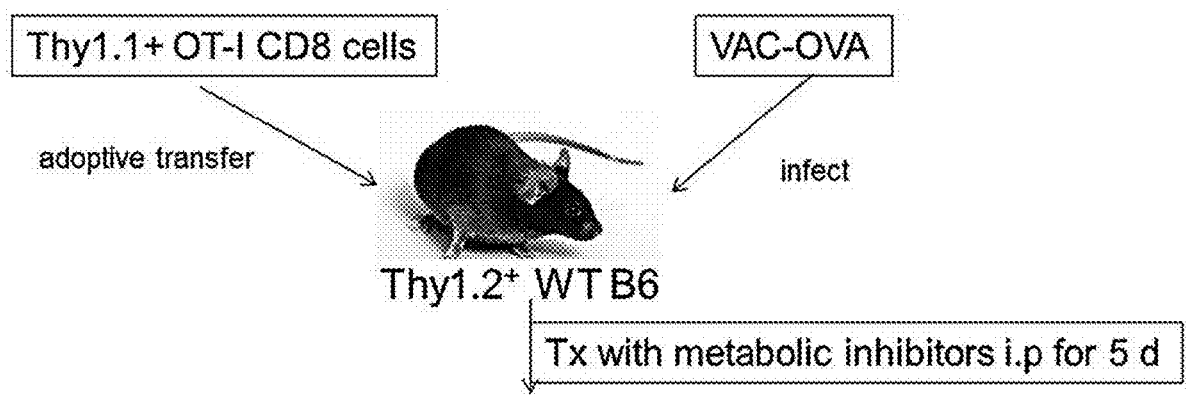
Figure 2B:
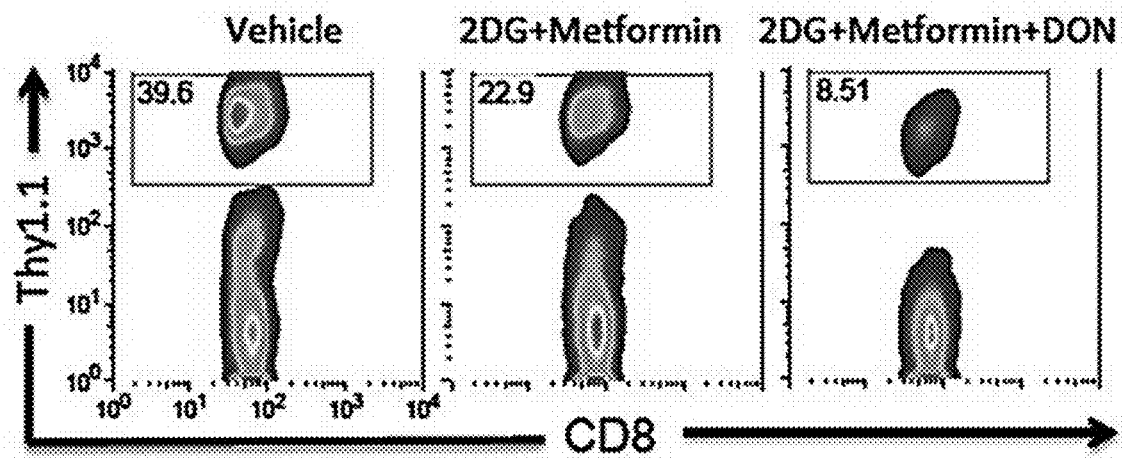
Figure 2C:
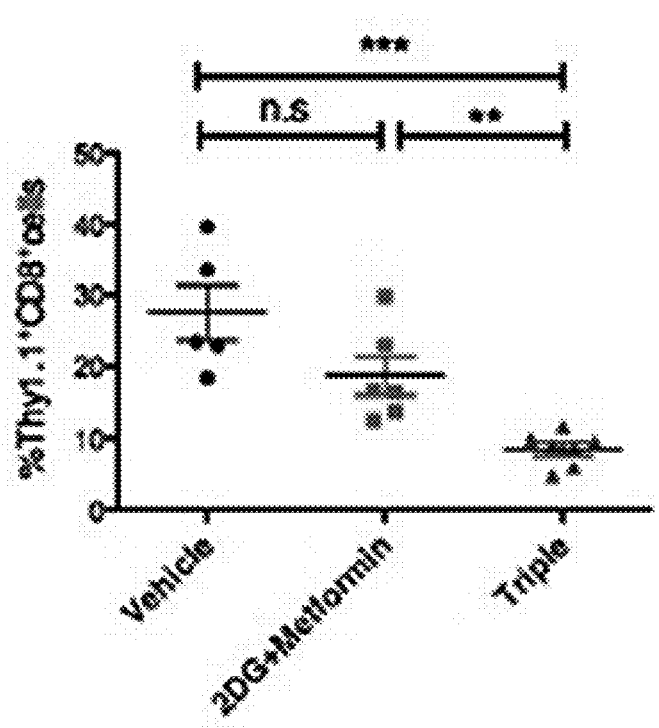
Figure 2D:
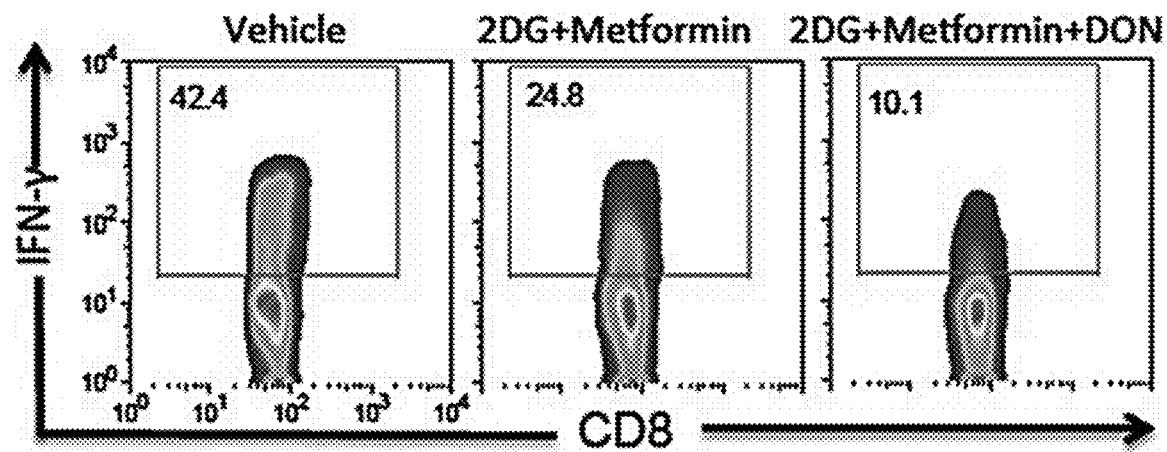
Figure 2E:
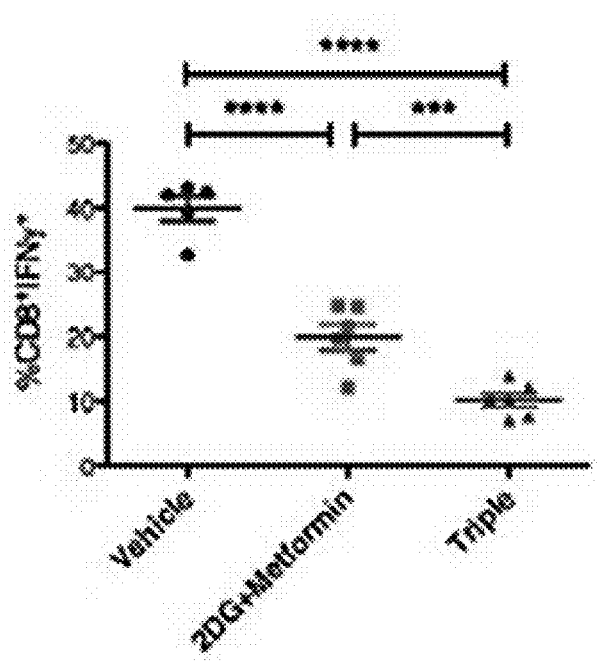

FIG. 2A is an illustration, FIG. 2B is an illustration, FIG. 2C a graph, FIG. 2D is an illustration, and FIG. 2E a graph showing that the presently disclosed metabolic reprogramming agents suppress antigen-specific $CD8^+$ T cells responses in vivo. $Thy1.2^+$ WT B6 mice were treated with vehicle, metabolic reprogramming therapy with at least two metabolic reprogramming agents (e.g., 2DG+Metformin), or metabolic reprogramming therapy with at least three metabolic reprogramming agents (e.g., 2DG+Metformin+DON). DON was found to be a very potent inhibitor of $CD8^+$ T cell effector function.

Figure 3:
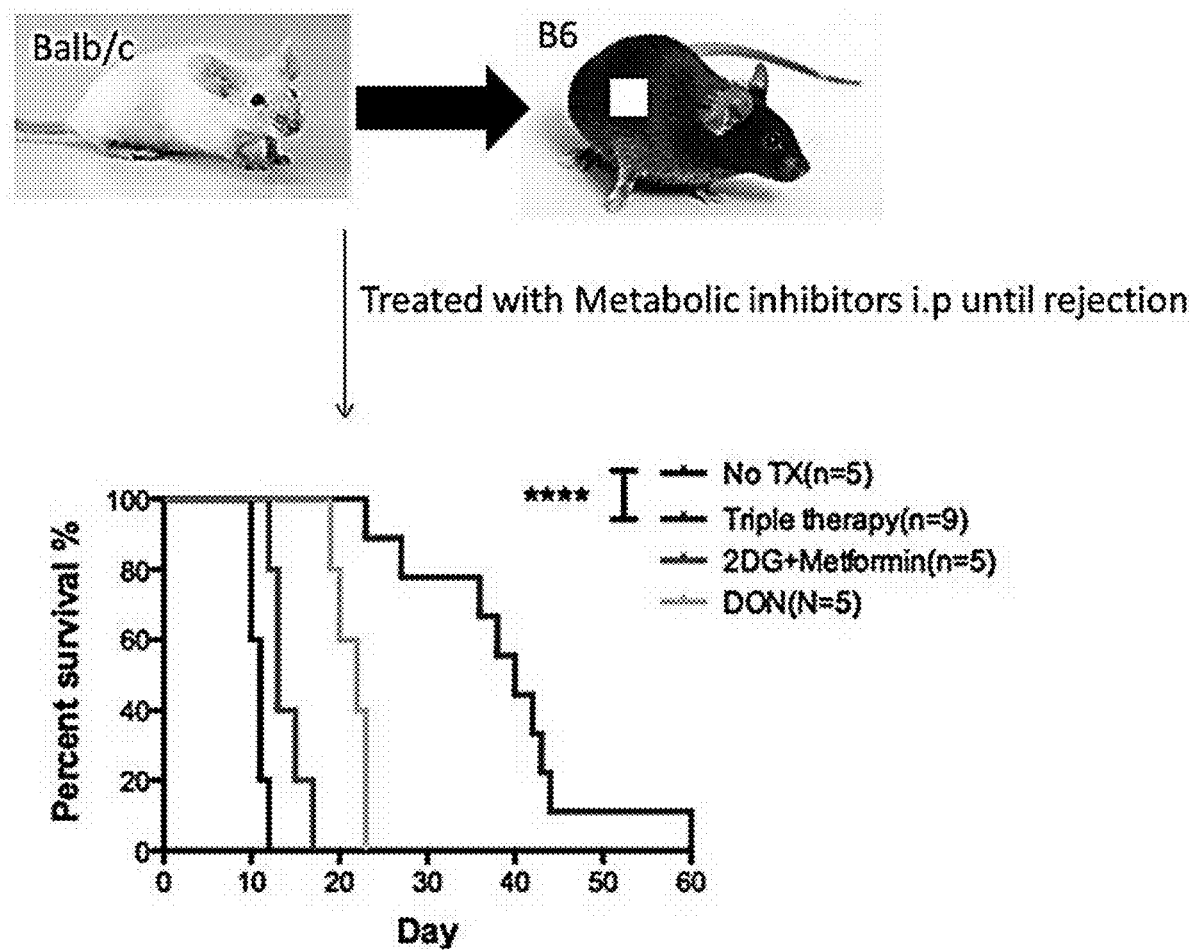

FIG. 3 is an illustration and Kaplan-Meier graph showing that DON prevents transplant rejection and prolongs skin graft survival. Mouse full thickness skin from Balb/c mice were transplanted onto B6 mice and the mice were not treated with metabolic reprogramming therapy (No TX), or treated with metabolic reprogramming therapy with at least two metabolic reprogramming agents (e.g., 2DG+Metformin), metabolic reprogramming therapy with at least three metabolic reprogramming agents (e.g., 2DG+Metformin+DON), or metabolic reprogramming therapy with at least one metabolic reprogramming agent (e.g., DON).

Figure 4:
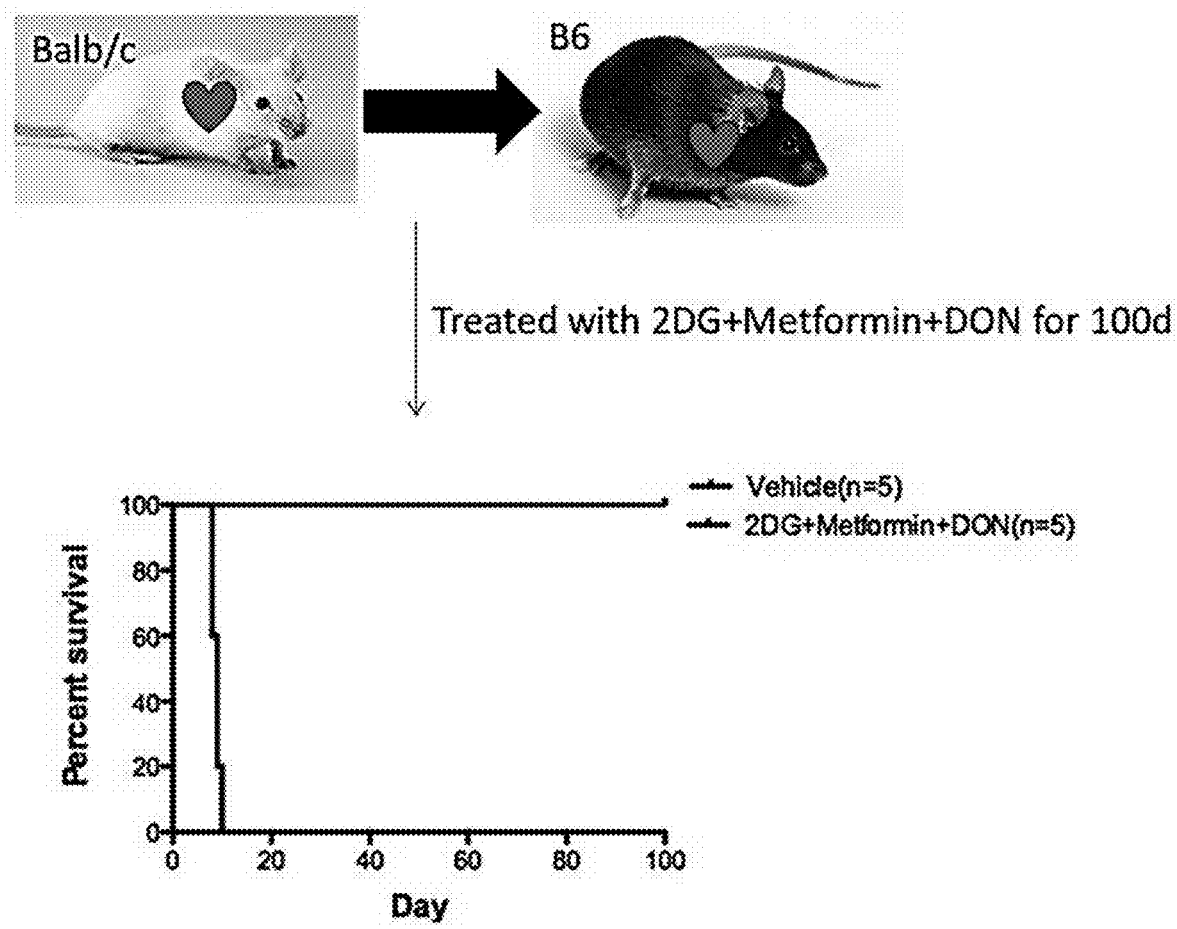

FIG. 4 is an illustration and Kaplan-Meier graph showing that DON prevents heart transplant rejection. Hearts from Balb/c mice were transplanted into B6 mice and the mice were not treated with metabolic reprogramming therapy (vehicle) or treated with metabolic reprogramming therapy with at least three metabolic reprogramming agents (e.g., 2DG+Metformin+DON) for 100 days.

Figure 5A:
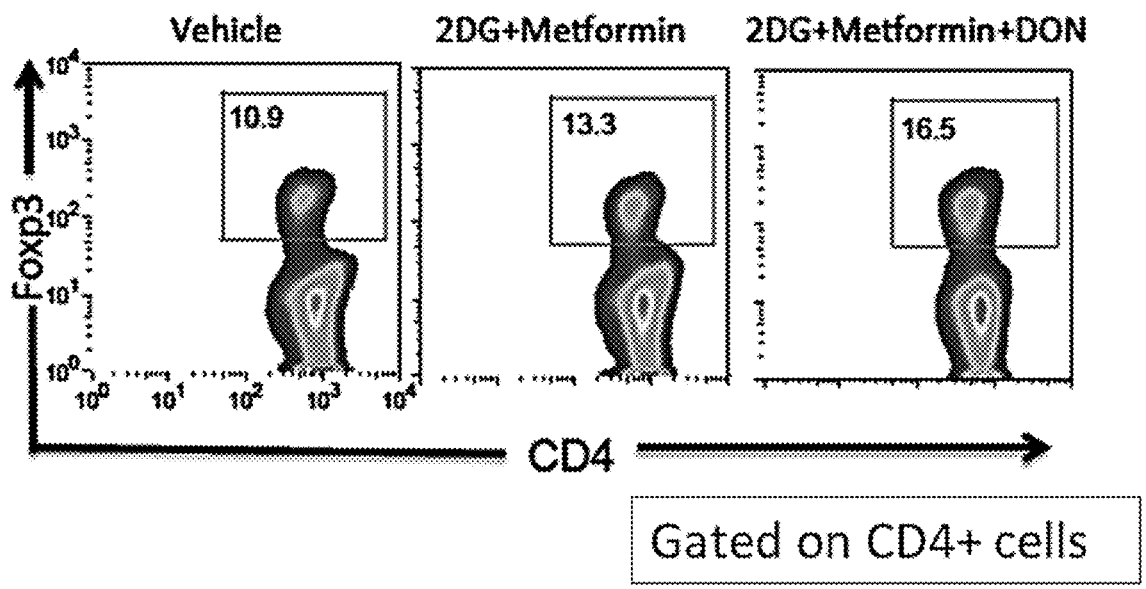
Figure 5B:
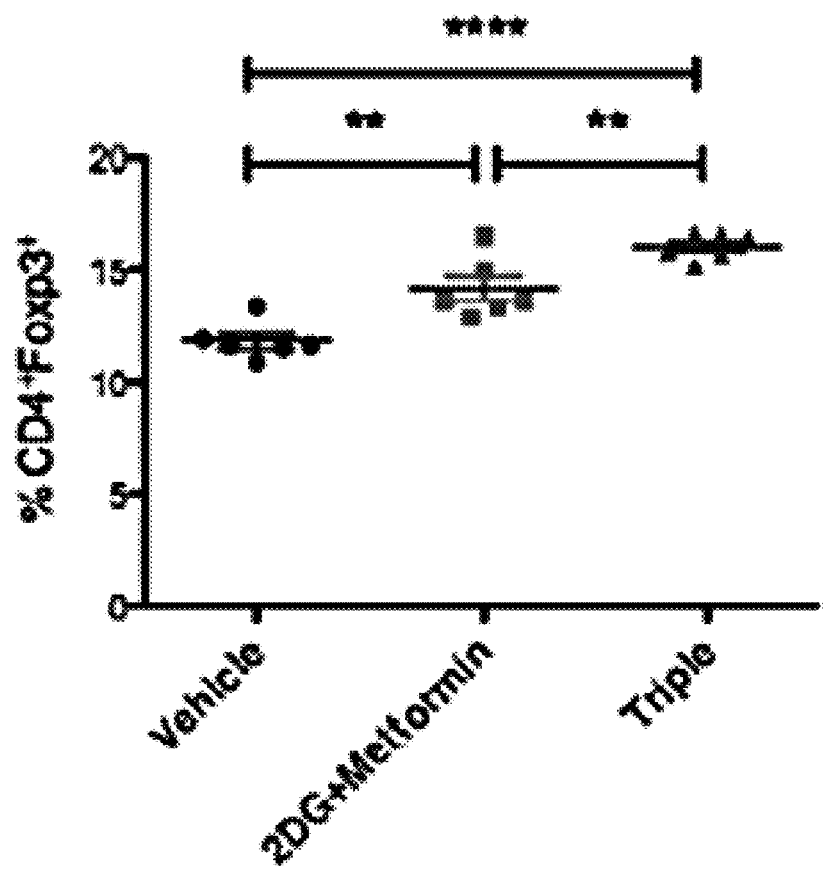
Figure 5C:
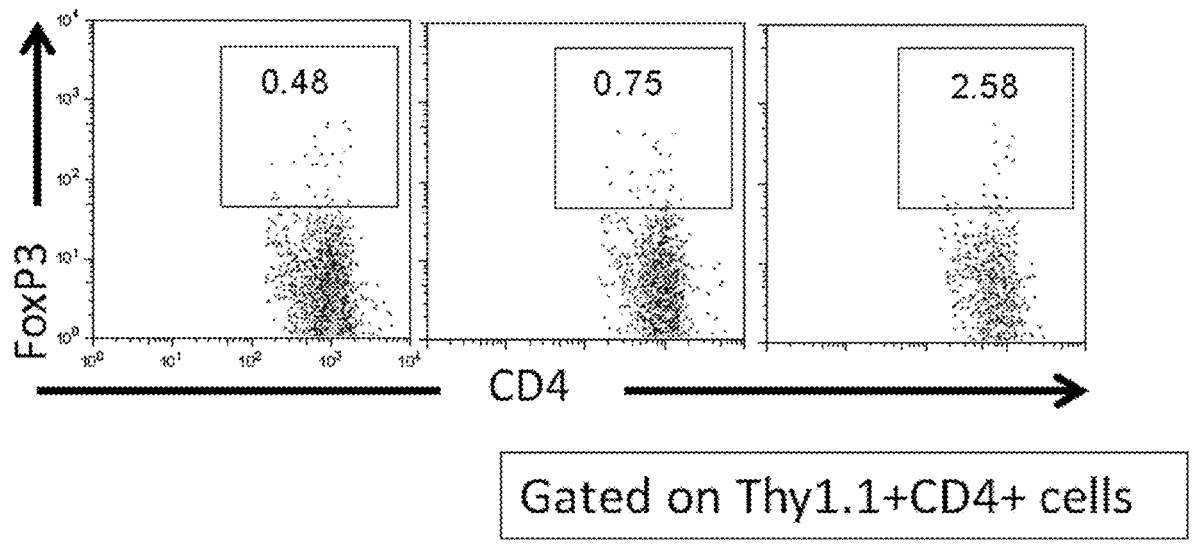
Figure 5D:
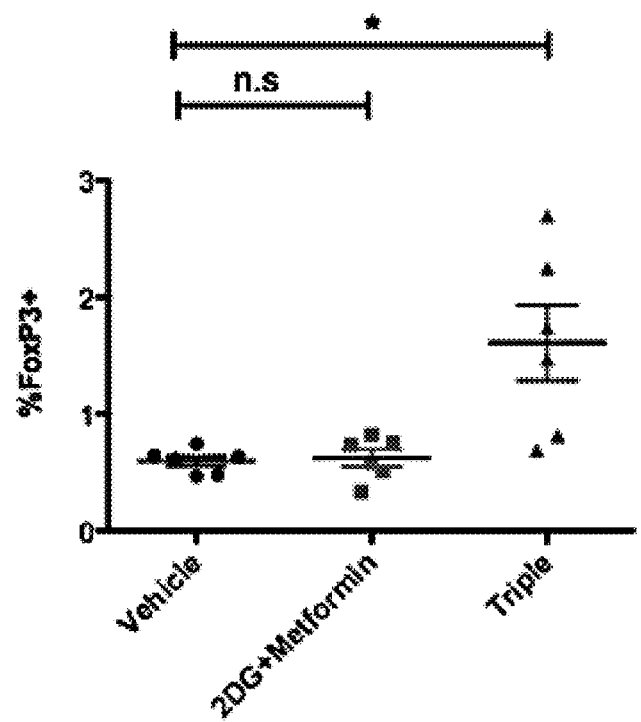

FIG. 5A is an illustration, FIG. 5B is a graph, FIG. 5C is an illustration, and FIG. 5D is a graph showing that the metabolic reprogramming agents increase the relative frequency of regulatory T cells (Tregs) in vivo. Mice were not treated with metabolic reprogramming therapy (vehicle), or treated with metabolic reprogramming therapy with at least two metabolic reprogramming agents (e.g., 2DG+Metformin), or metabolic reprogramming therapy with at least three metabolic reprogramming agents (e.g., 2DG+Metformin+DON).

Figure 6:
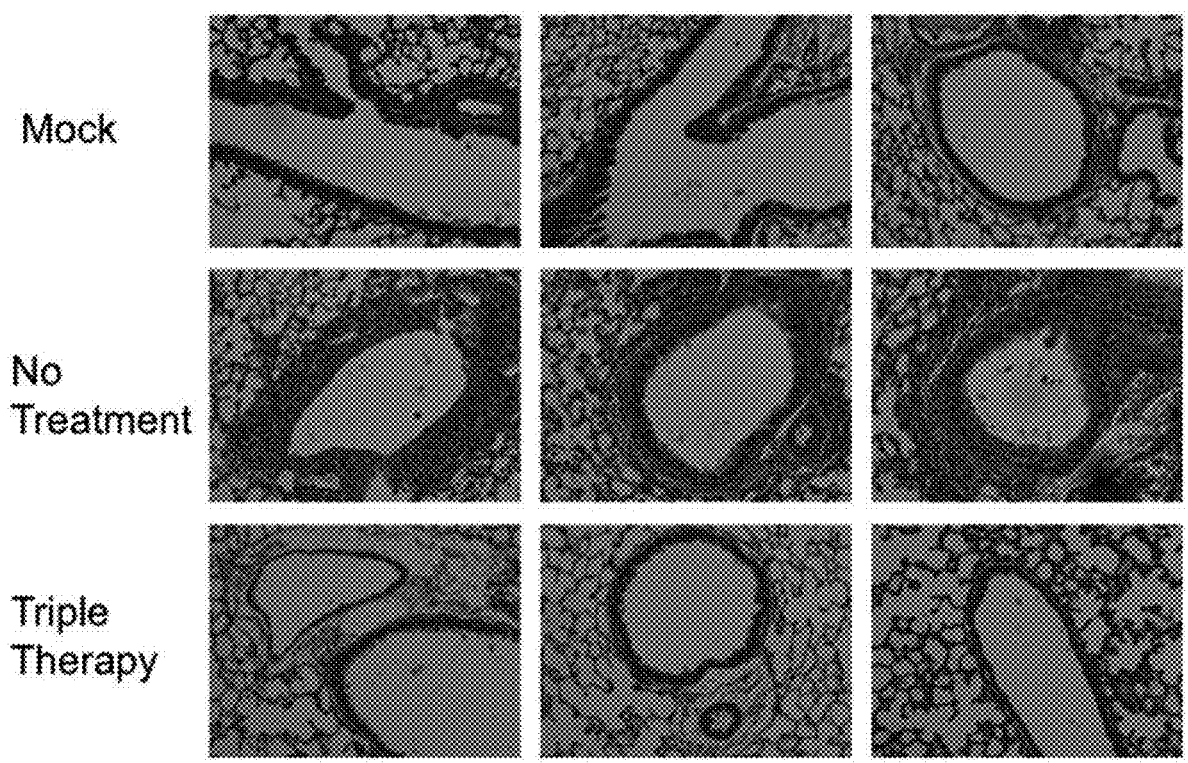

FIG. 6 is an illustration showing reprogramming metabolism in asthma with mock, no treatment, or metabolic reprogramming therapy with at least three metabolic reprogramming agents (e.g., 2DG+Metformin+DON).

Figure 7:
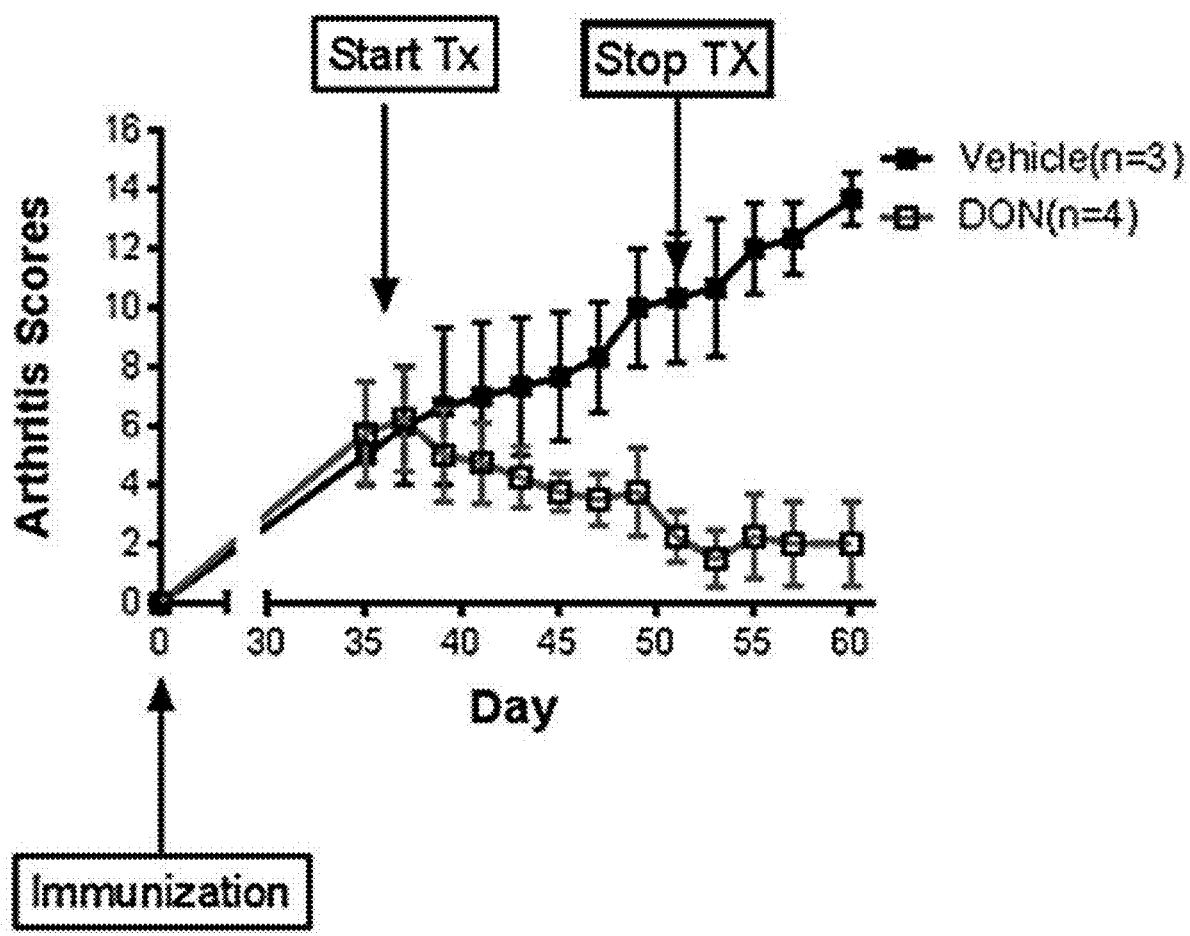

FIG. 7 is a line graph showing that metabolic reprogramming therapy with at least one metabolic reprogramming agent (e.g., DON) treats arthritis in a mouse model.

Figure 8:
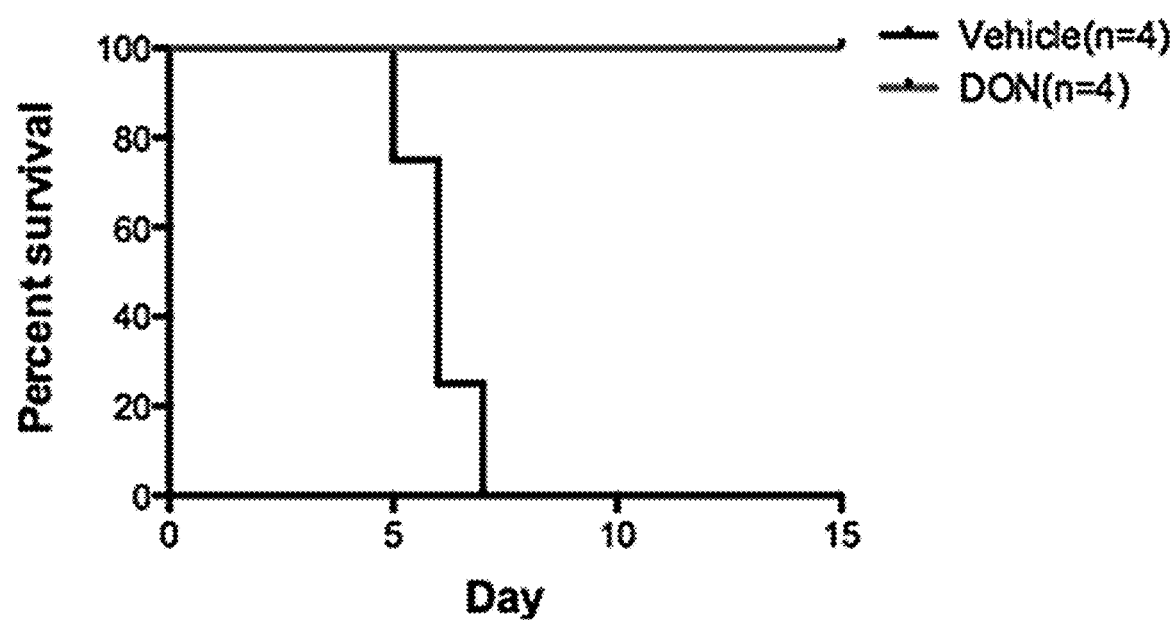

FIG. 8 is a Kaplan-Meier graph showing that metabolic reprogramming therapy with at least one metabolic reprogramming agent (e.g., DON) treats pneumonitis in a mouse model.

Figure 9A:
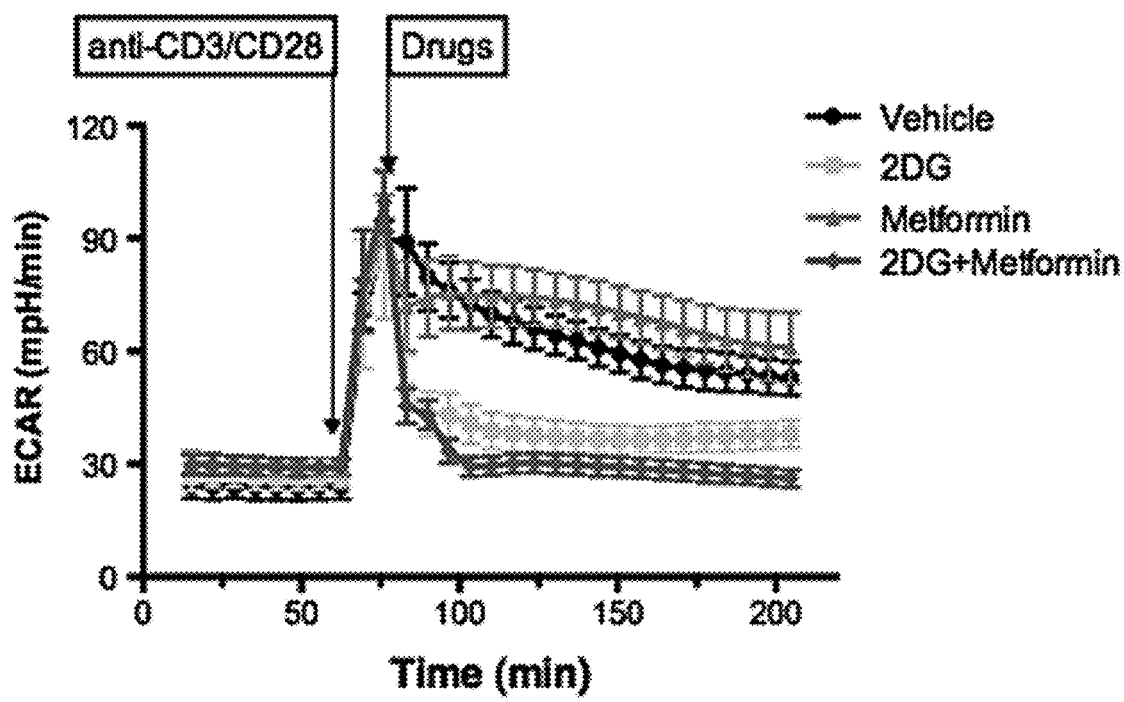
Figure 9B:
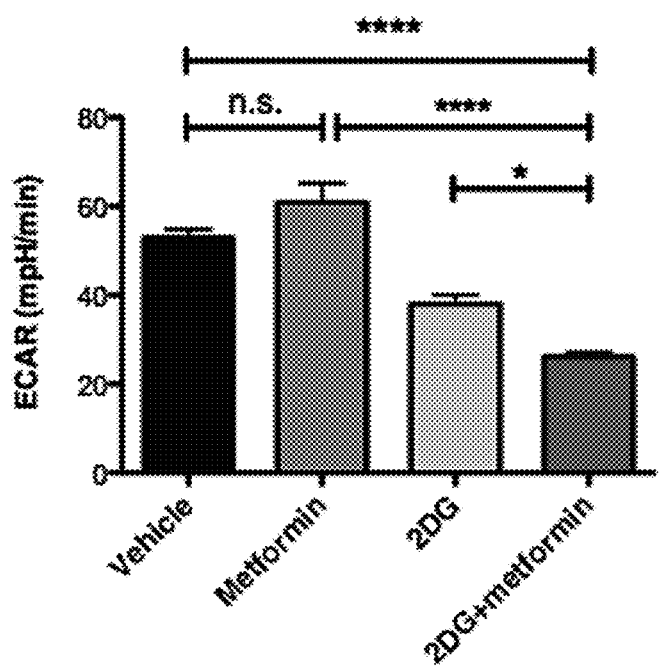
Figure 9C:
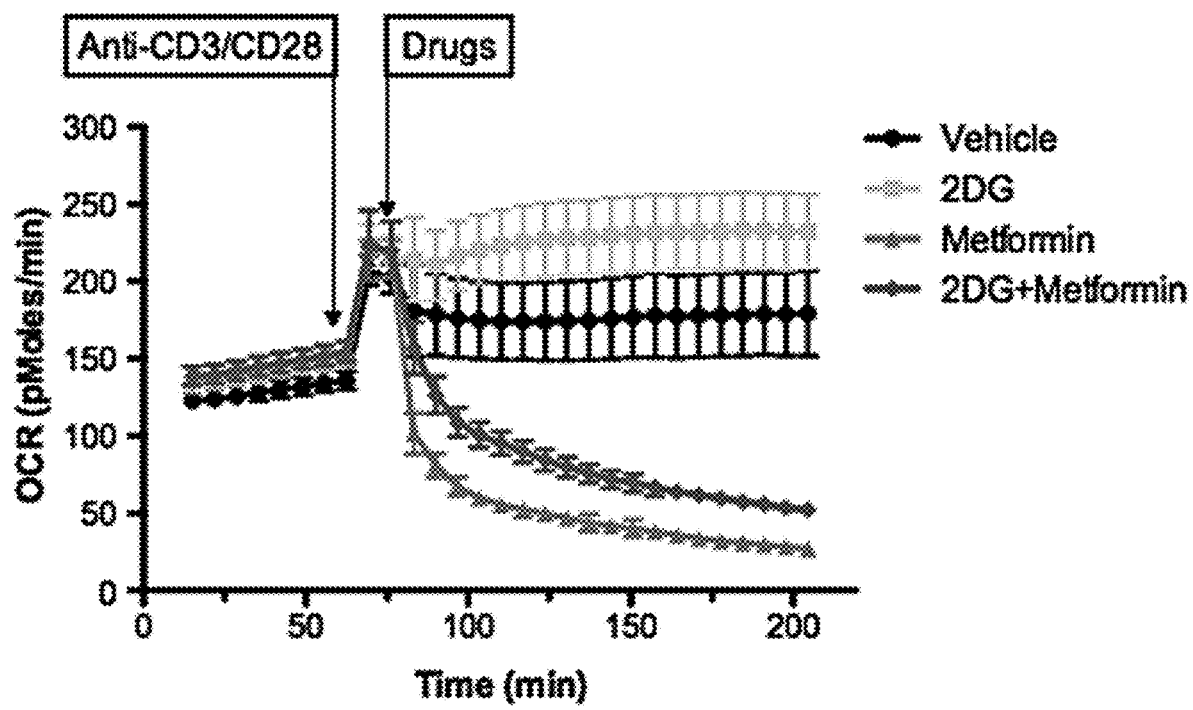
Figure 9D:
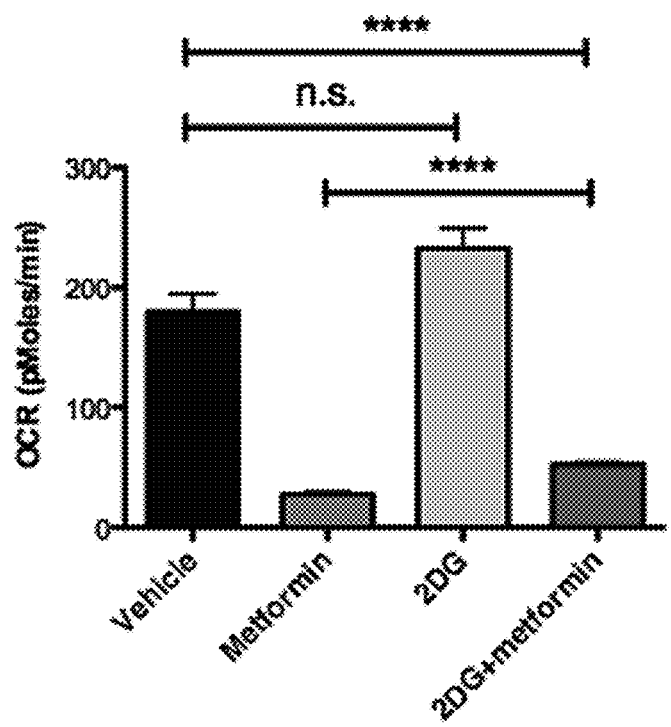
Figure 9E:
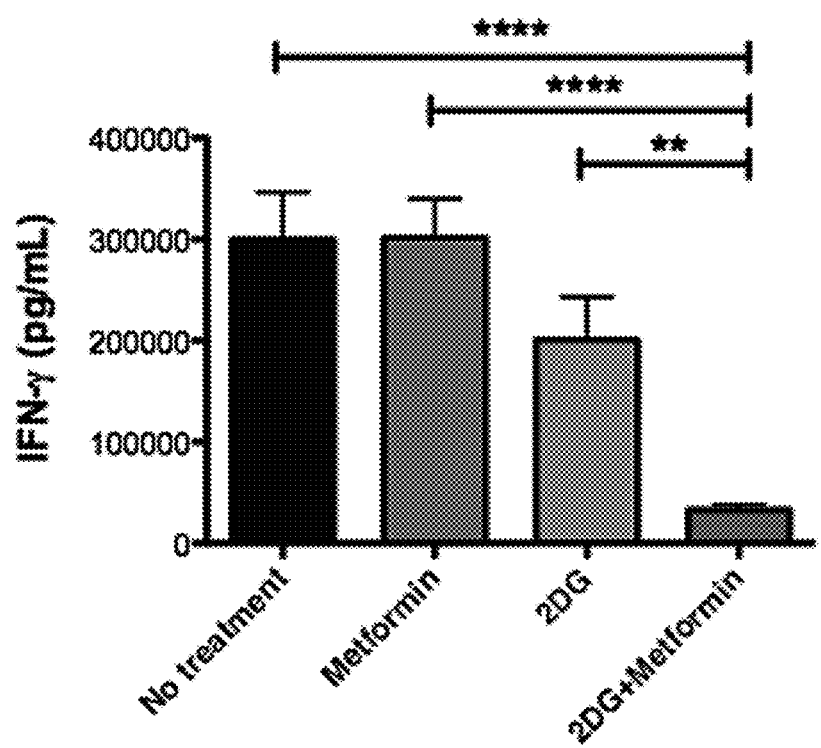
Figure 9F:
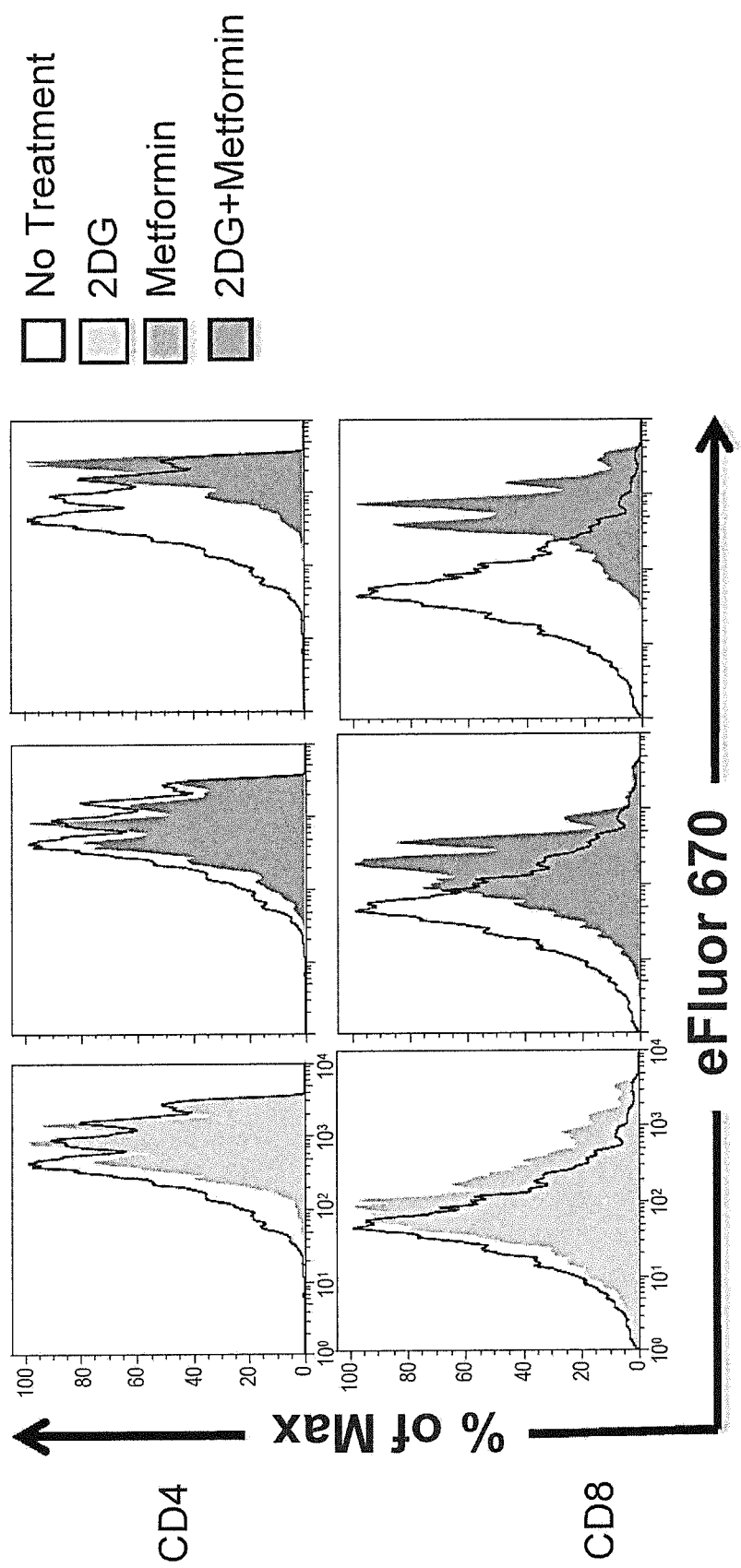

FIG. 9A is a line graph, FIG. 9B is a bar graph, FIG. 9C is a line graph, and FIG. 9D is a bar graph, FIG. 9E is a bar graph, and FIG. 9F is an illustration showing that metabolic reprogramming therapy with metabolic reprogramming agent 2-DG combined with metabolic reprogramming agent metformin inhibits T cell responses through suppression of glycolysis. FIG. 9A and FIG. 9B show ECAR and OCR of resting $CD4^+$ cells measured in real time under basal conditions and in response to anti-CD3/CD28 (anti-CD3, 2 μg/ml; anti-CD28, 2 μg/ml) with or without the presence of individual or combination of metabolic reprogramming agents (2-DG, 10 mM; Metformin, 50 mM). Bar graphs display data of ECAR and OCR measured at the endpoint of the experiment (205 min). Data are shown as mean±SEM of 5 measurements. FIG. 9C and FIG. 9D show that naïve splenocytes labeled with cell proliferation dye eFluor 670 were stimulated with anti-CD3 in the presence of media control, 2-DG alone, metformin alone or 2-DG+metformin (2-DG, 0.6 mM; Metformin, 1 mM). FIG. 9C shows that 24-hour IFN-γ secretion to supernatants was interrogated by enzyme-linked immunosorbent assay (ELISA). Data are shown as mean±SEM of three independent samples. FIG. 9D shows 72-hour eFluor dilution of $CD4^+$ and $CD8^+$ T cells. n.s., not significant, *p<0.05, p<0.01, **p<0.0001 (Student's t test). Data are representative of at least two independent experiments.

Figure 10A:
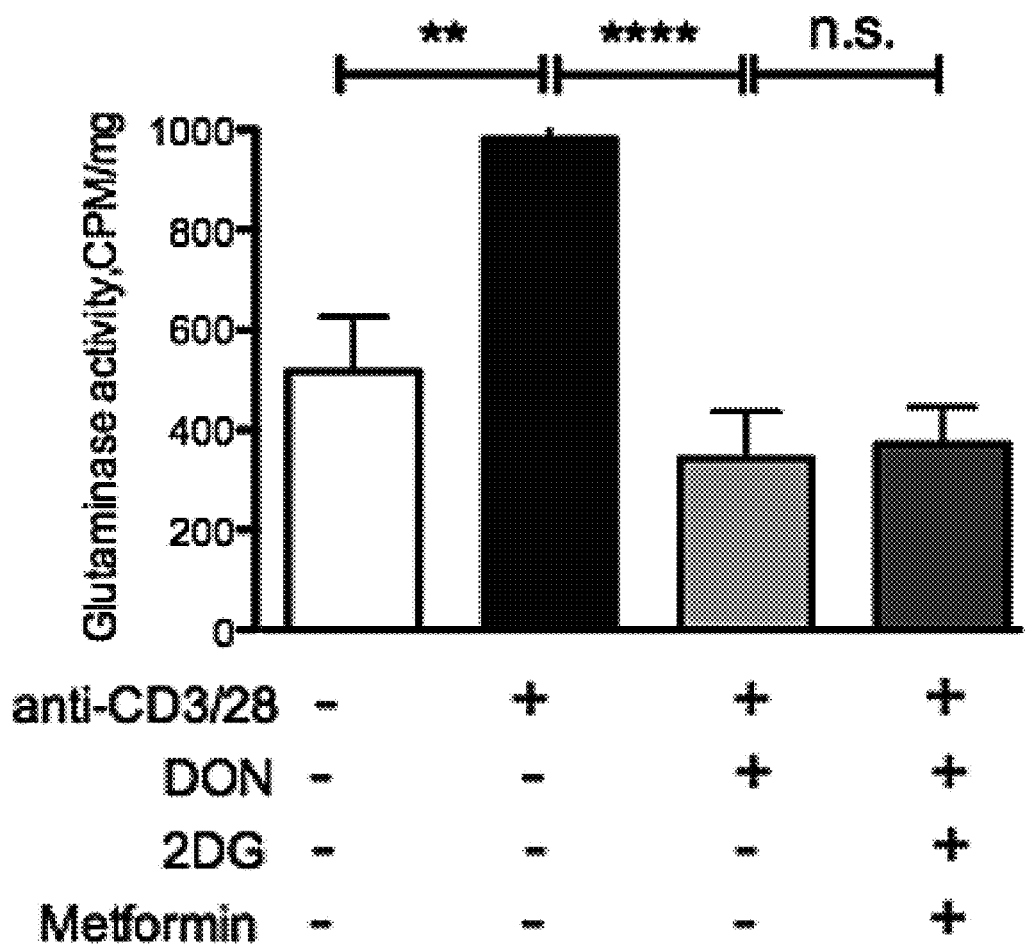
Figure 10B:
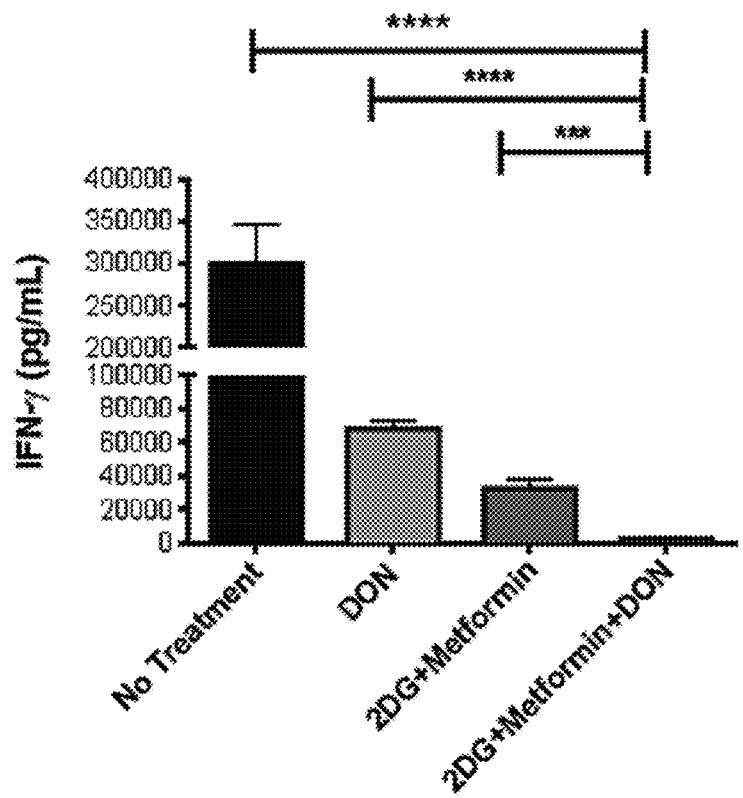
Figure 10C:
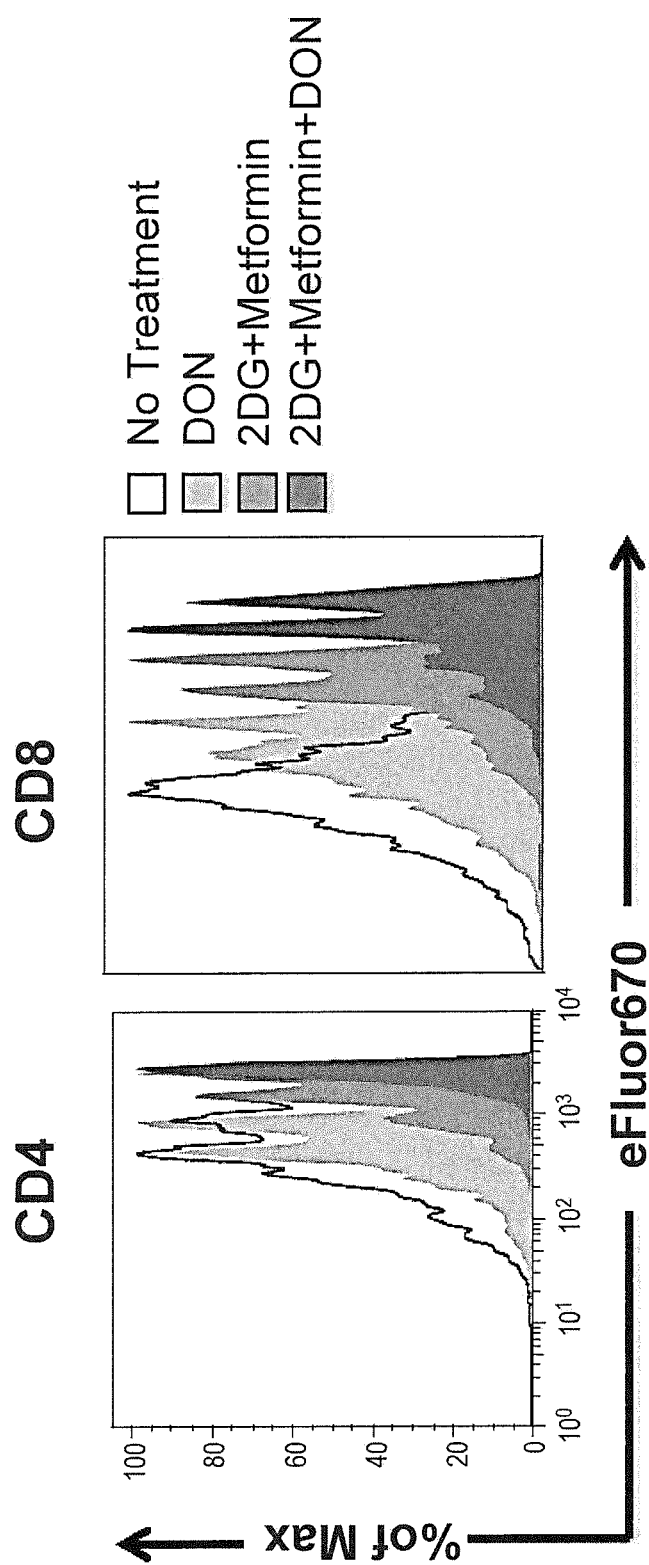

FIG. 10A and FIG. 10B are bar graphs, and FIG. 10C is an illustration showing that the combined inhibition of at least two metabolic pathways (e.g., glycolysis and glutaminolysis) profoundly suppresses T cell responses. FIG. 10A shows the glutaminase activity of $CD4^+$ T cells cultured for 24 hours in different conditions (anti-CD3, 2 μg/ml; anti-CD28, 2 μg/ml; DON, 5 μM; 2-DG, 0.6 mM; Metformin, 1 mM). Data are shown as mean±SEM of three independent experiments. FIG. 10B and FIG. 10C show naïve WT C57BL/6 splenocytes labeled with eFluor 670 and stimulated with anti-CD3 in medium containing indicated metabolic reprogramming agents (DON, 5 μM; 2-DG, 0.6 mM; Metformin, 1 mM). FIG. 10B shows 24-hour IFN-γ secretion to supernatants as interrogated by ELISA. Data are shown as mean±SEM of three independent samples. FIG. 10C shows proliferation of $CD4^+$ and $CD8^+$ T cells at 72 h measured by dilution of eFluor 670. n.s., not significant, $p<0.01$, $*p<0.001$, $****p<0.0001$ (Student's t test). Data are representative of at least two independent experiments.

Figure 11:
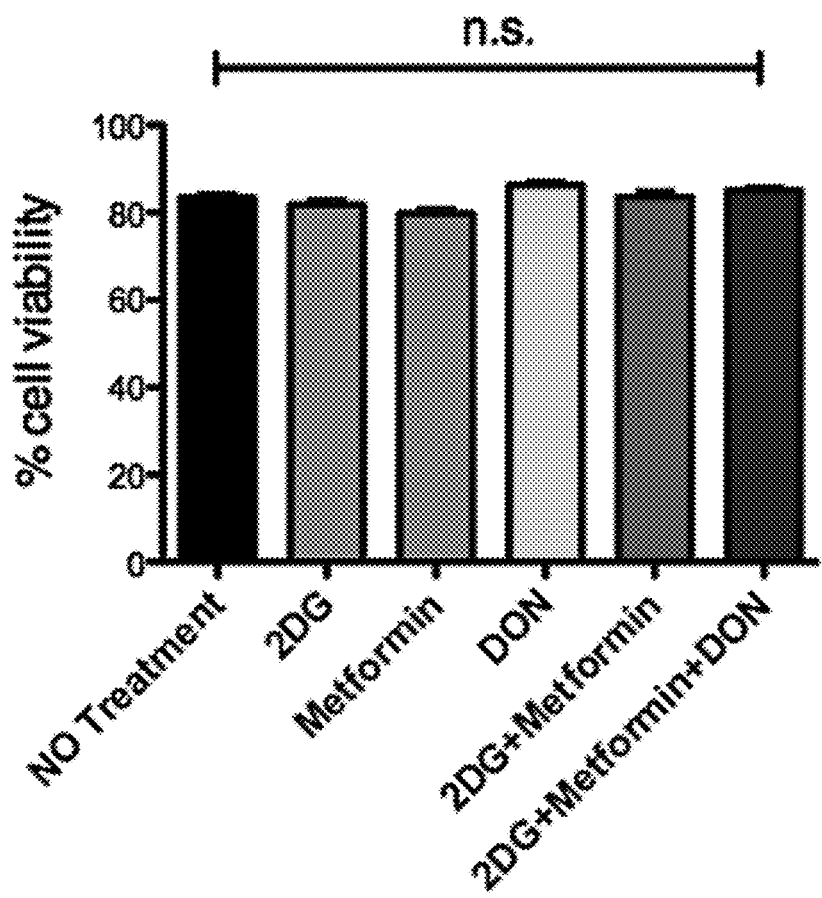

FIG. 11 is a bar graph showing the cell viability of T cells in different culture conditions. Splenocytes from C57BL/6 mice were stimulated with anti-CD3 (1 μg/ml) in medium containing indicated metabolic reprogramming agents (DON, 5 μM; 2DG, 0.6 mM; Metformin, 1 mM) or media control. Cell viability was determined by 7-aminoactinomycin D (7-AAD) exclusion at 24 h by flow cytometry. Data are merged results of $CD4^+$ and $CD8^+$ cells and are shown as mean±SEM. n.s., not significant (ANOVA). Data are representative of three independent experiments.

Figure 12A:
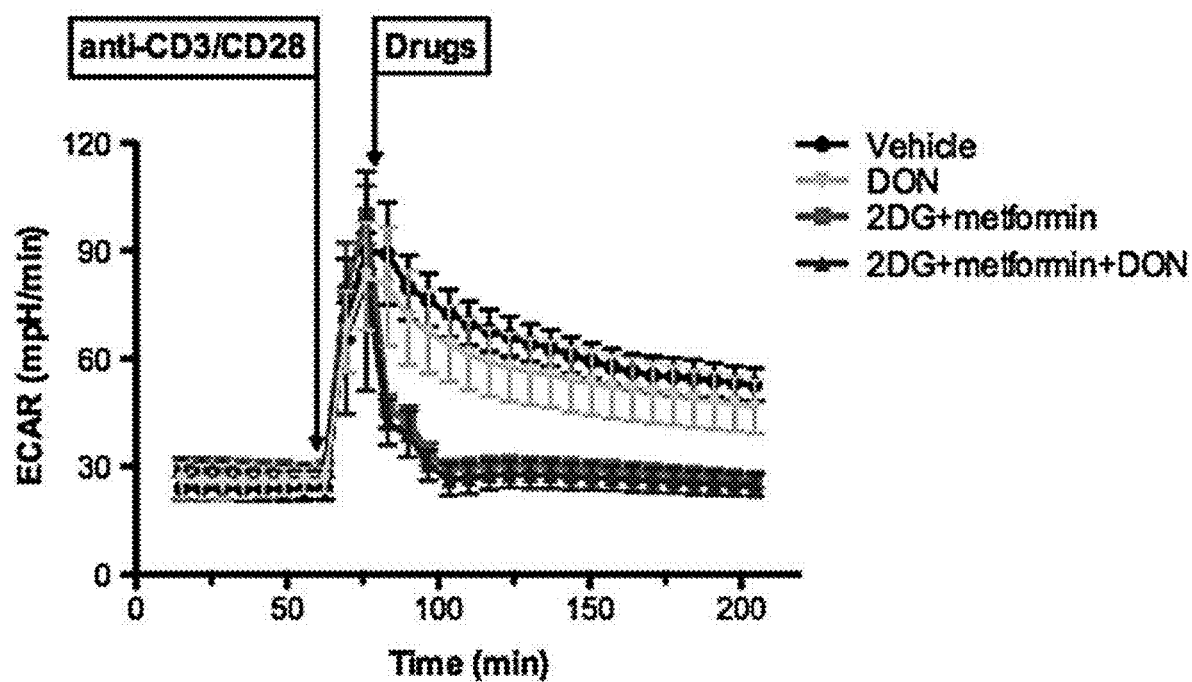
Figure 12B:
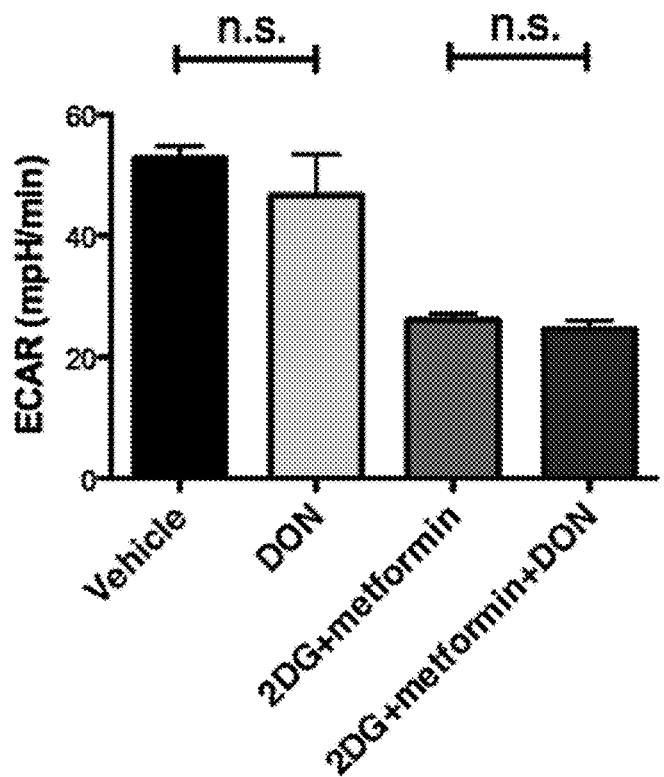
Figure 12C:
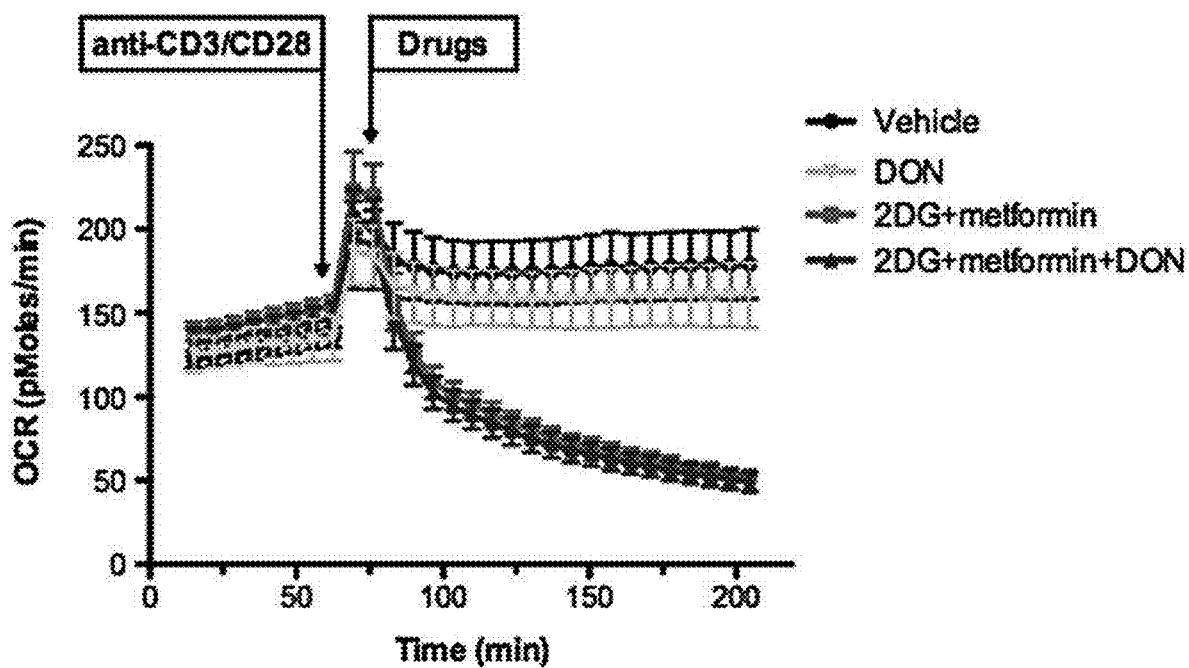
Figure 12D:
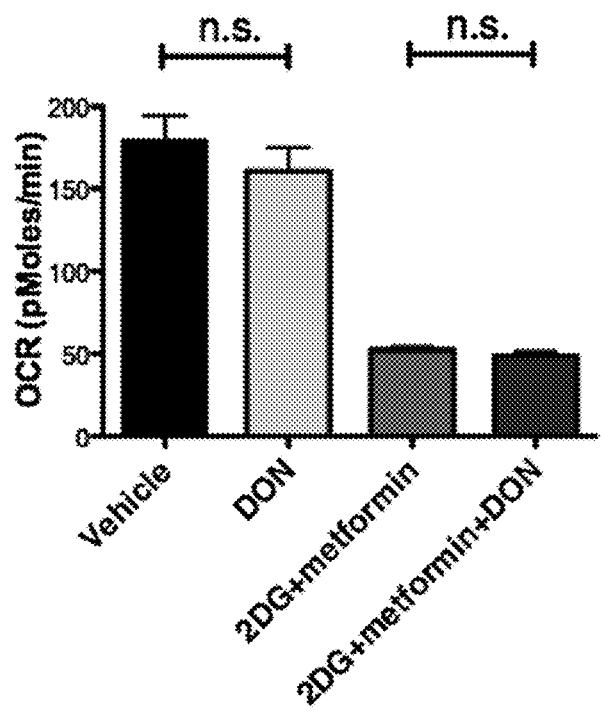

FIG. 12A is a line graph, FIG. 12B is a bar graph, FIG. 12C is a line graph, and FIG. 12D is a bar graph showing that DON does not affect ECAR and OCR of activated T cells. ECAR (FIG. 12A) and OCR (FIG. 12B) of resting $CD4^+$ cells measured in real time under basal conditions and in response to anti-CD3/CD28 (anti-CD3, 2 μg/ml; anti-CD28, 2 μg/ml) with or without the presence of individual or combined metabolic reprogramming agents (2-DG, 10 mM; Metformin, 50 mM; DON, 30 μM). Bar graphs display ECAR and OCR data measured at the endpoint of the experiment (205 min). All data are shown as mean±SEM of five measurements. n.s., not significant (Student's t test). Data are representative of two independent experiments.

Figure 13A:
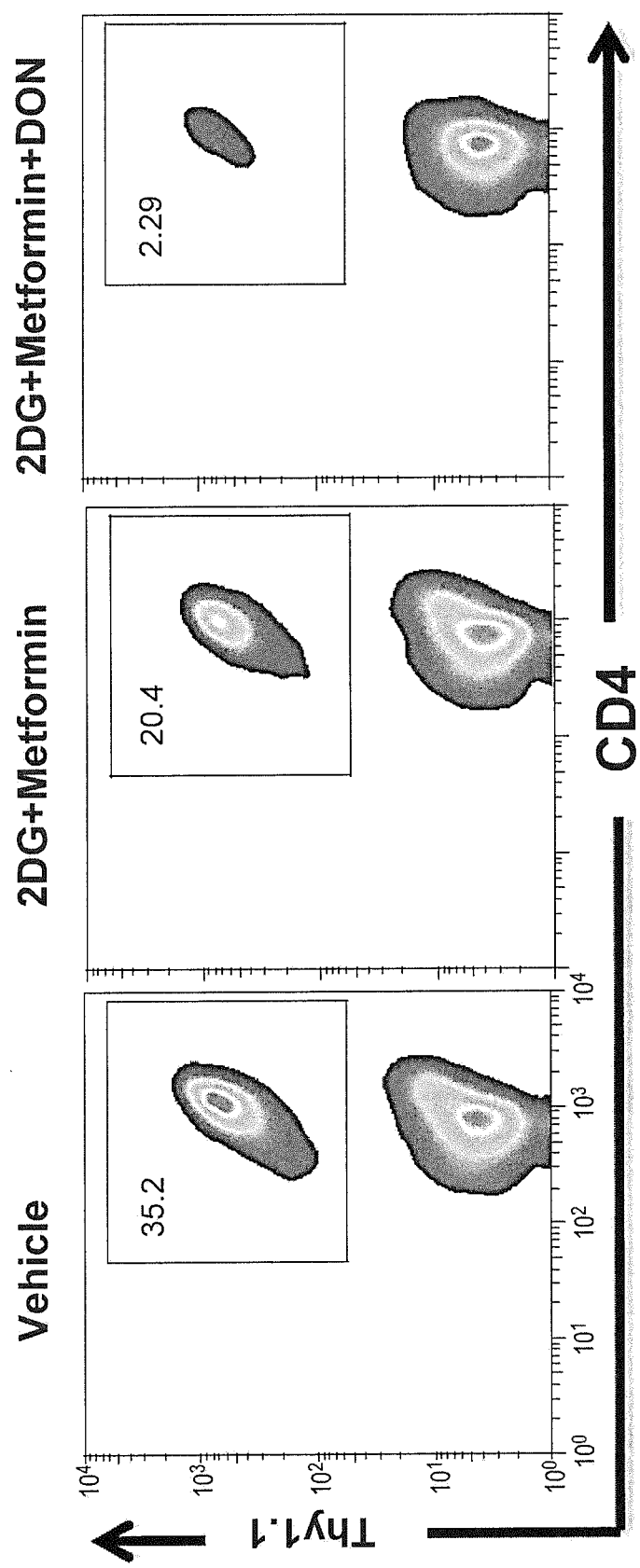
Figure 13D:
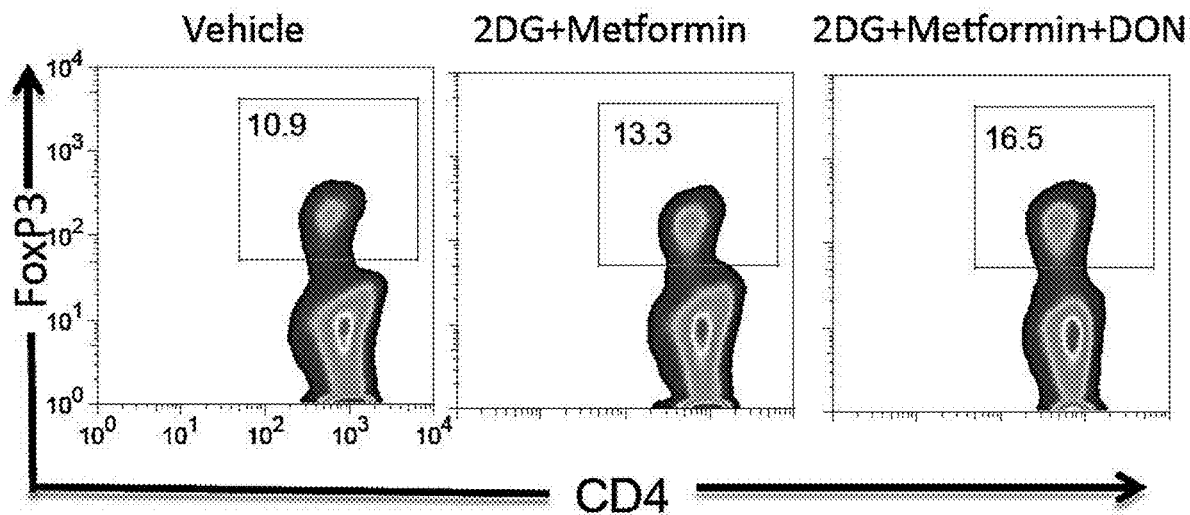
Figure 13E:
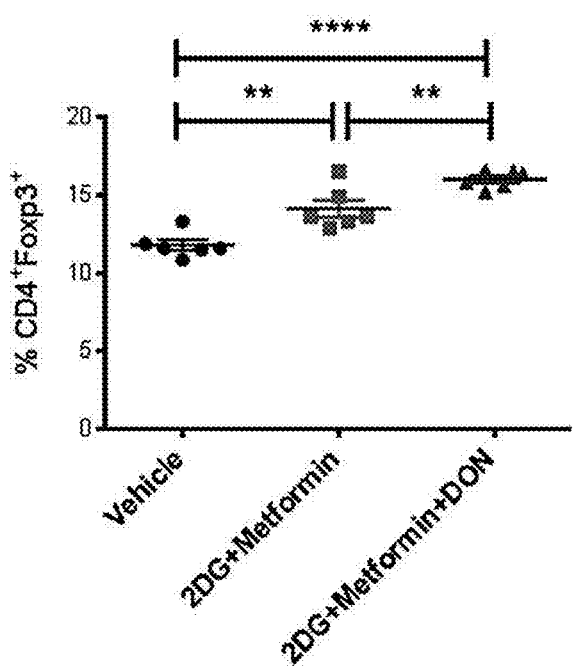
Figure 13F:
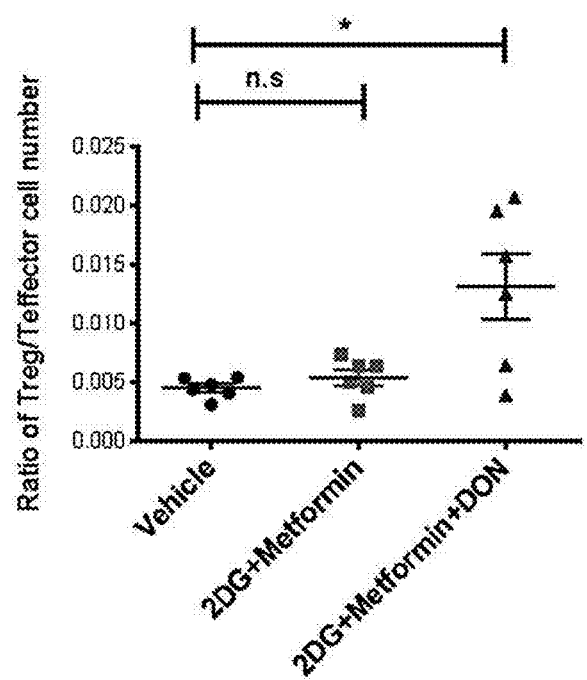

FIG. 13A is an illustration, FIG. 13B is a graph, FIG. 13C is a bar graph, FIG. 13D is an illustration, FIG. 13E is a graph, and FIG. 13F is a bar graph showing that metabolic reprogramming agents suppress the proliferation and function of antigen-specific $CD4^+$ T cells while increasing the relative frequency of Tregs in vivo. OT-II ($Thy1.1^+$) $CD4^+$ T cells were adoptively transferred into WT ($Thy1.2^+$) recipient mice. The recipients were infected with OVA-expressing vaccinia virus and treated with vehicle, 2-DG+Metformin or 2-DG+metformin+DON (2-DG, 500 mg/kg once daily; metformin, 150 mg/kg once daily; DON, 1.6 mg/kg once every other day) for 3 days. Splenocytes from the recipients were harvested at day 4 to interrogate the frequency of antigen-specific T cells and regulatory T cells. The percentage of $Thy1.1^+$ cells relative to $CD4^+$ cells were analyzed by flow cytometry (left) and plotted as cumulative data (right) (FIG. 13A). OT-II cells were re-challenged with OVA peptide class II (10 μg/ml) ex vivo for 24 hours (FIG. 13B). The supernatants were interrogated for IFN-γ production by ELISA. Data are mean±SEM (n=6). Percentage of Foxp3+ cells relative to CD4+ cells (left) and plotted as cumulative data (right) (FIG. 13C). The ratio of OVA-specific Foxp3+ T cells:Effector cells (FIG. 13D). Each symbol represents an individual mouse. Horizontal lines indicate mean±SEM. n.s., not significant, $*p<0.05$, $p<0.01$, $*p<0.001$, $****p<0.0001$ (Student's t test). Data are representative of more than three independent experiments.

Figure 14A:
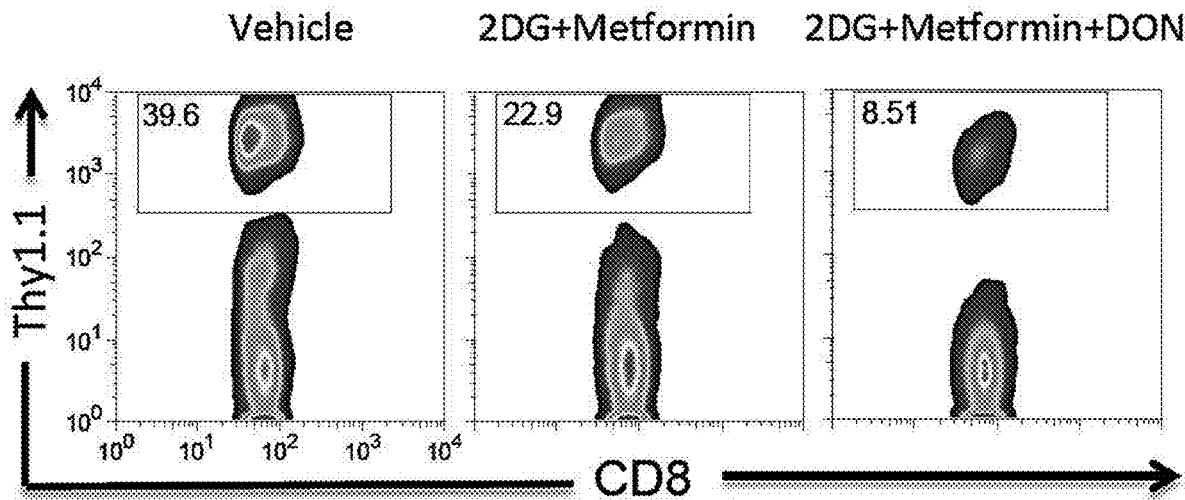
Figure 14B:
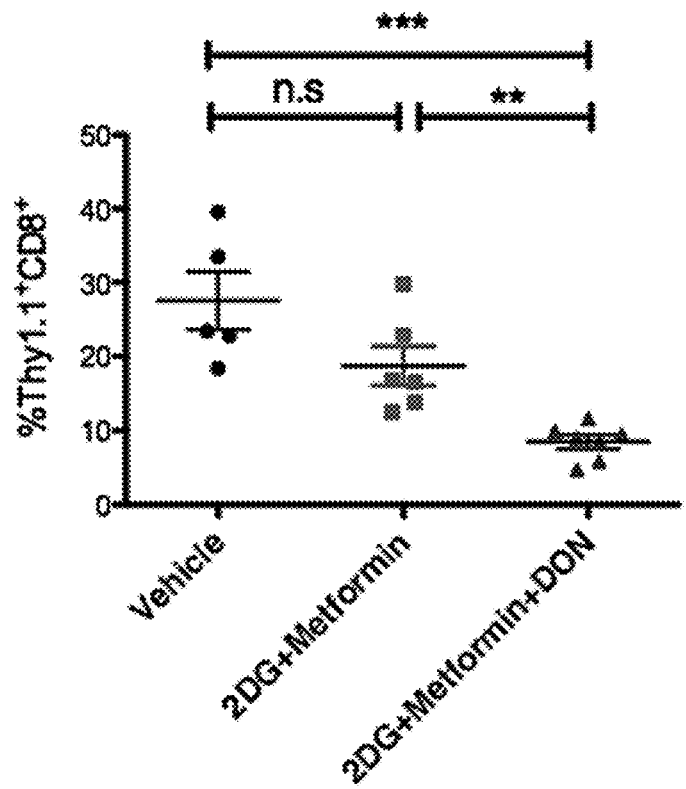
Figure 14C:
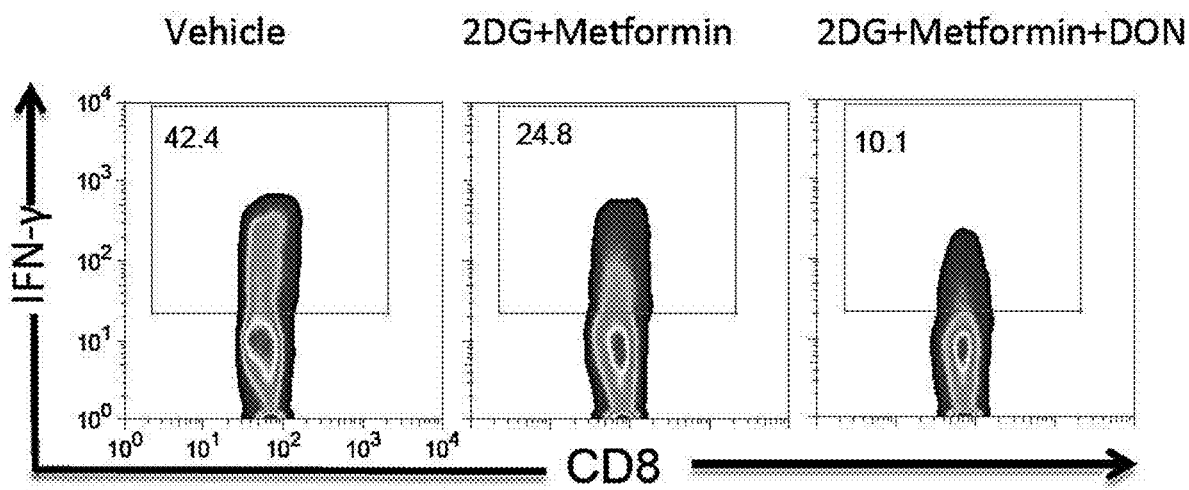
Figure 14D:
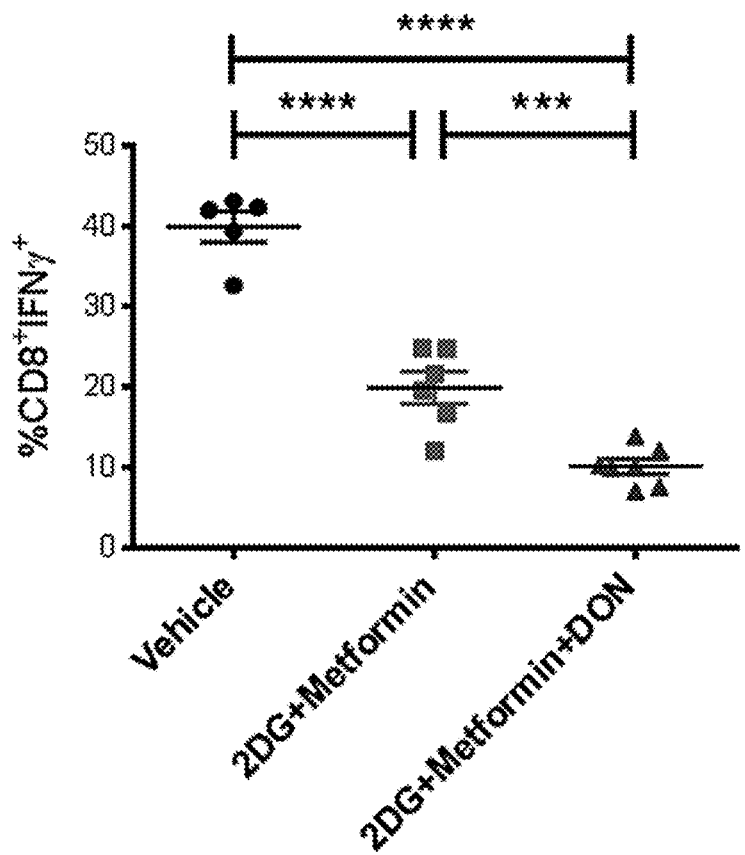
Figure 14E:
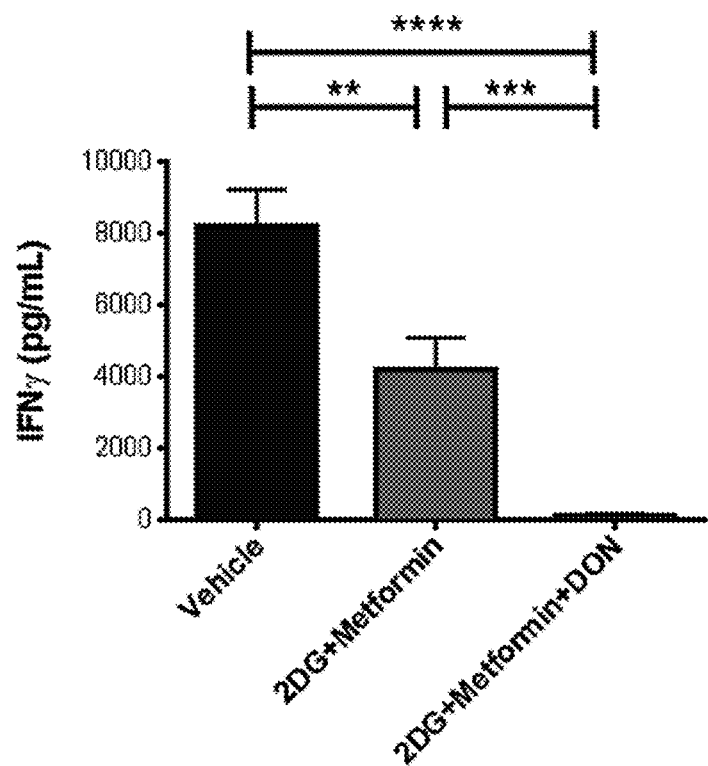
Figure 14F:
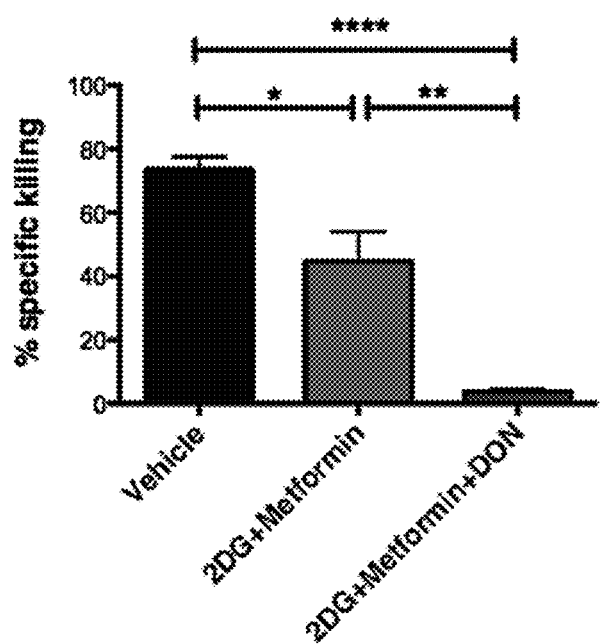

FIG. 14A is an illustration, FIG. 14B is a graph, FIG. 14C is an illustration, FIG. 14D is a graph, and FIGS. 14E and 14F are bar graphs showing that metabolic reprogramming agents suppress antigen-specific $CD8^+$ T cells responses in vivo. For FIG. 14A, FIG. 14B, and FIG. 14C, OT-I ($Thy1.1^+$) $CD8^+$ T cells were adoptively transferred into WT ($Thy1.2^+$) recipient mice. The hosts were infected with vaccinia-OVA and treated with vehicle, metabolic reprogramming therapy with at least two metabolic reprogramming agents (e.g., 2-DG+metformin) or metabolic reprogramming therapy with at least three metabolic reprogramming agents (e.g., 2-DG+metformin+DON) for 5 days. Host splenocytes were harvested at day 6 to interrogate the proliferation and function of antigen-specific $CD8^+$ T cells. Percent $Thy1.1^+$ cells relative to $CD8^+$ cells were analyzed by flow cytometry (left) and plotted as cumulative data (right) (FIG. 14A). Percent IFN-γ-producing cells relative to $CD8^+$ cells (left) and plotted as cumulative data (right) (FIG. 14B). OT-I cells were re-challenged with OVA peptide class I (10 μ/ml) ex vivo for 24 hours (FIG. 14C). The supernatants were interrogated for IFN-γ production by ELISA. Data are mean±SEM (n=5~6). The ability of metabolic reprogramming agents to suppress endogenous effector $CD8^+$ T cells development was assessed with an in vivo CTL assay (FIG. 14D). Percent of specific killing was determined at 10 h after transferring target cells. Data are mean±SEM (n=3 mice/group). Each symbol represents an individual mouse. Horizontal lines indicate mean±SEM. n.s., not significant, $*p<0.05$, $p<0.01$, $*p<0.001$, $****p<0.0001$ (Student's t test). All data are representative of more than three independent experiments.

Figure 15E:
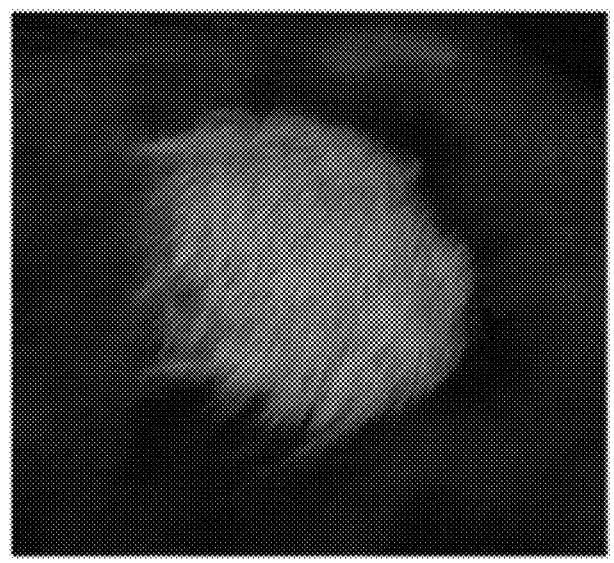
Figure 15F:
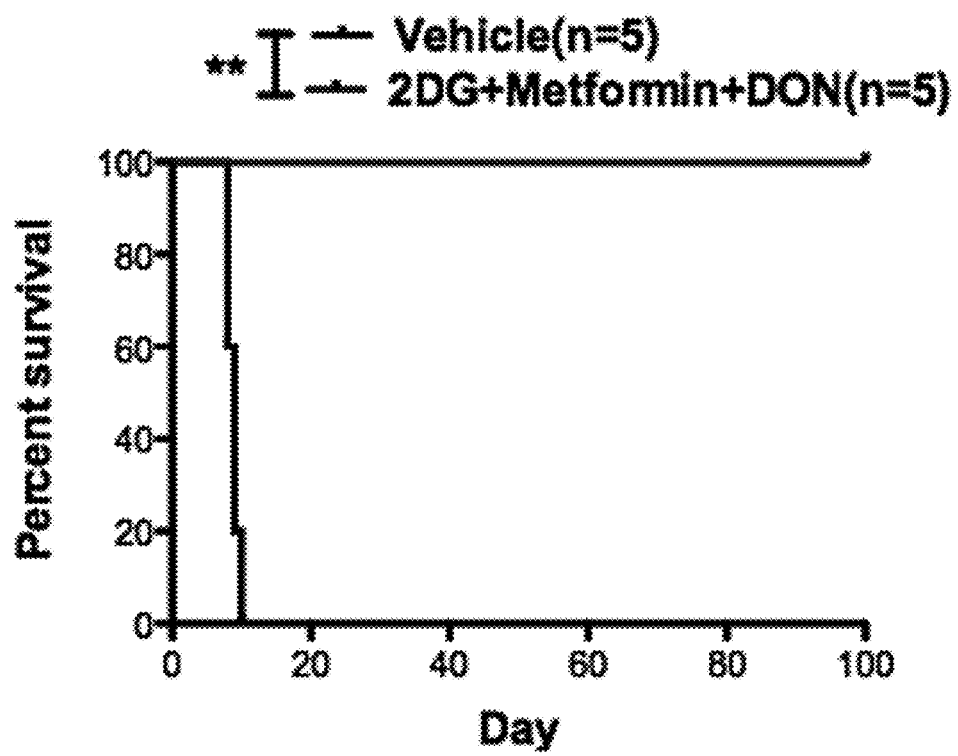
Figure 15G:
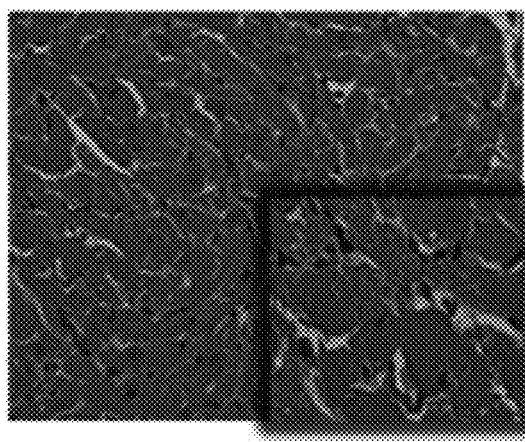
Figure 15H:
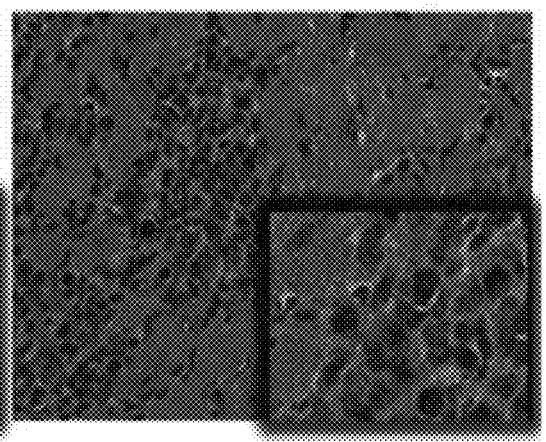
Figure 15I:
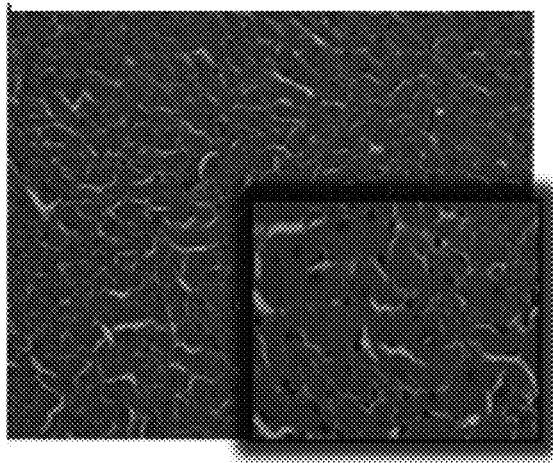
Figure 15J:
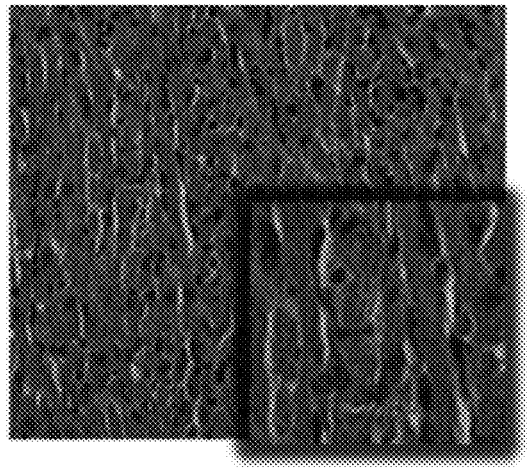

FIG. 15A is a Kaplan-Meier graph, FIG. 15B, FIG. 15C, and FIG. 15D are illustrations, FIG. 15E is an illustration, FIG. 15F is a Kaplan-Meier graph, and FIG. 15G, FIG. 15H, FIG. 15I, and FIG. 15J are illustrations showing that metabolic reprogramming agents promote allograft survival. FIG. 15A shows Balb/c to C57BL/6 skin graft survival, as monitored daily by assessment of macroscopic signs of rejection. FIG. 15B, FIG. 15C, and FIG. 15D show representative photomicrographs of skin graft histology (hematoxylin and eosin (H&E) staining) on post-transplant day 7 under an optical microscope (outlet, X100; inlet: X200). FIG. 15E shows a representative photograph of Balb/c skin graft at day 40. FIG. 15F shows Balb/c to C57BL/6 heart graft survival, as monitored daily by palpation of heart beating. FIG. 15G, FIG. 15H, FIG. 15I, and FIG. 15J show representative photomicrographs of cardiac graft histology (H&E staining) on the indicated post-transplant day under an optical microscope (outlet, X200; inlet, X400). The metabolic reprogramming treatment was started from the day of graft (day 0) until rejection in both models. The dosages of all drugs were the same as described in the FIG. 13 brief description. $p<0.01$, $**p<0.001$ (Log-rank analysis). Data are representative of two independent experiments.

Figure 16A:
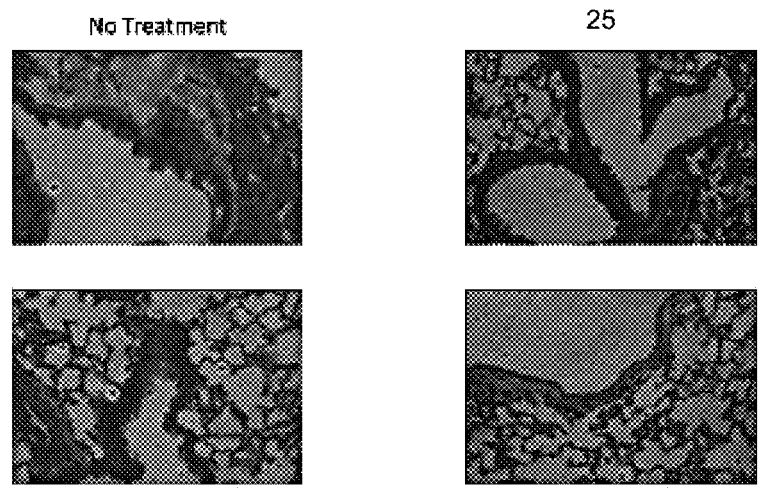
Figure 16B:
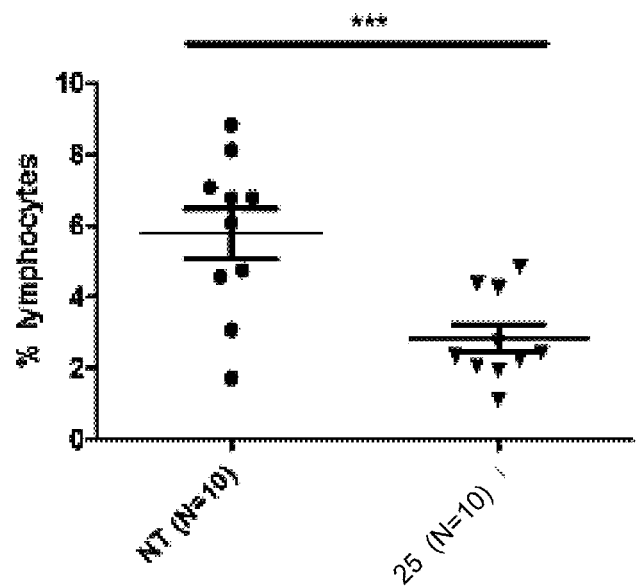
Figure 16C:
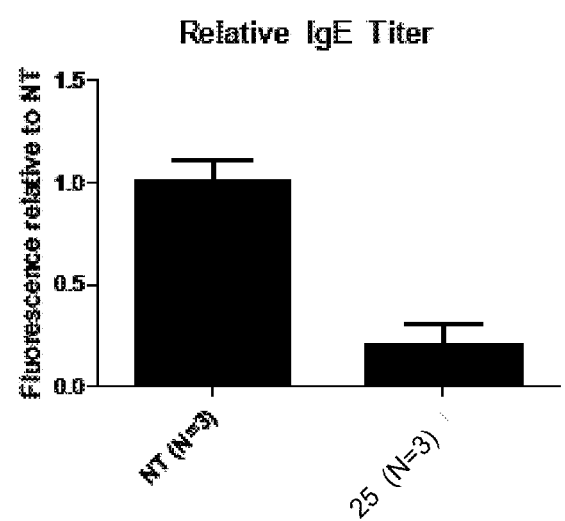

FIG. 16A is an illustration, FIG. 16B is a graph, and FIG. 16C is a bar graph showing the efficacy of the targeting of glutamine metabolism in a mouse model of asthma. Mice were sensitized to House Dust Mite antigen (HDM) in the absence of drug. Upon intratracheal rechallenge the mice were treated with vehicle or 25. In this model during the acute lung rechallenge 25 inhibited pathology, the recruitment/generation of Th2 cells and reduced the levels of HDM specific IgE.

Figure 17A:
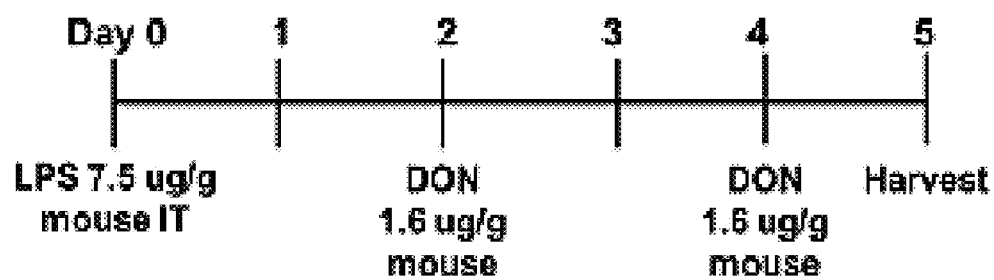
Figure 17B:
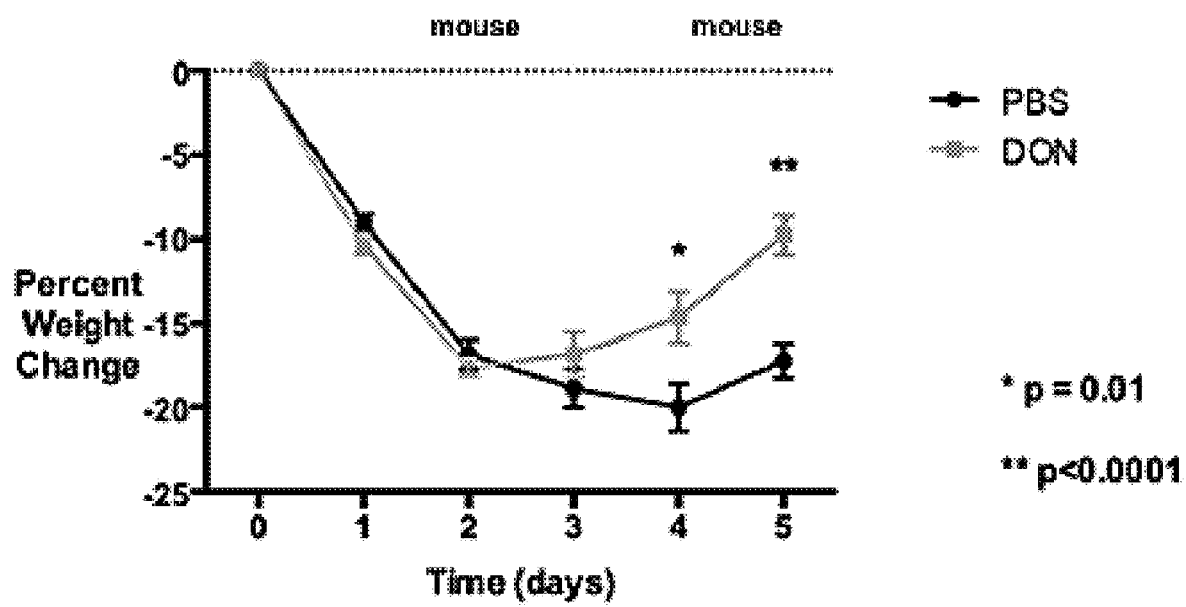
Figure 17C:
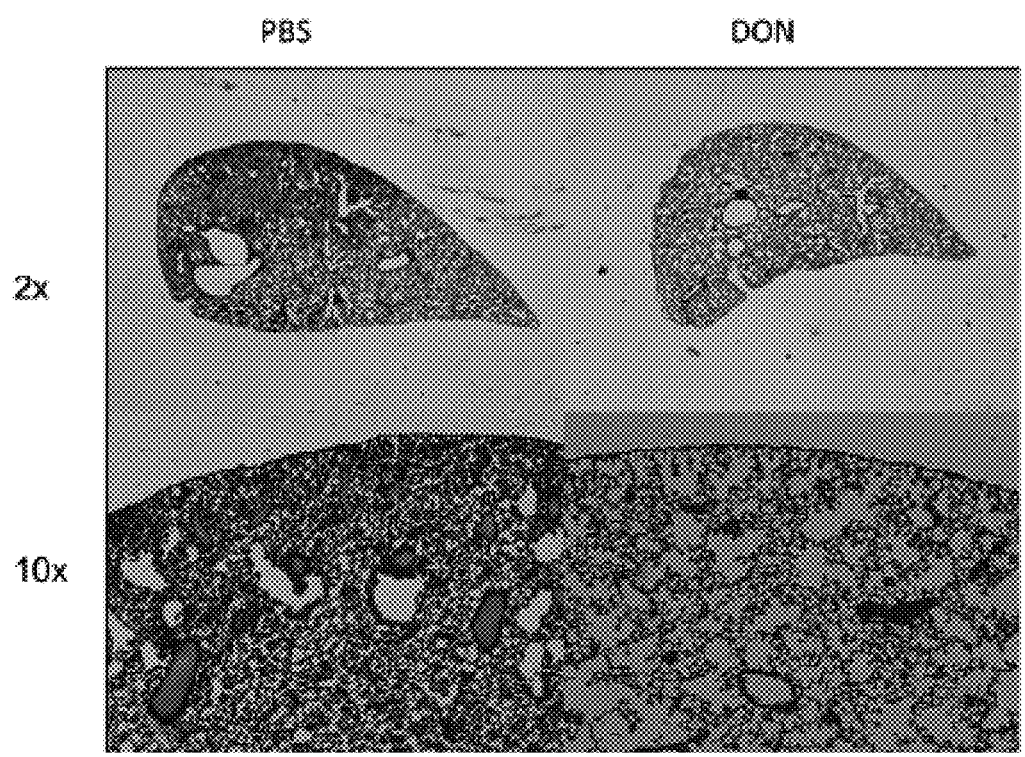

FIG. 17A is an illustration, FIG. 17B is a line graph, and FIG. 17C is an illustration showing the efficacy of the targeting glutamine metabolism in a mouse model of Acute Respiratory Distress Syndrome (ARDS). Mice were challenged with Ips (FIG. 17A) to induce (ARDS) and treated with DON on day 2 & 4. Treatment promoted a more rapid recovery (weight gain) and less lung damage.

Figure 18A:
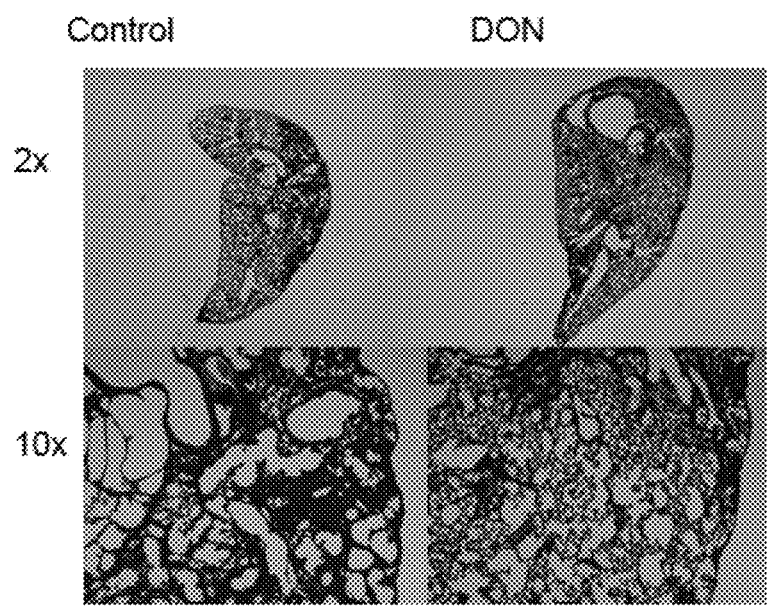
Figure 18B:
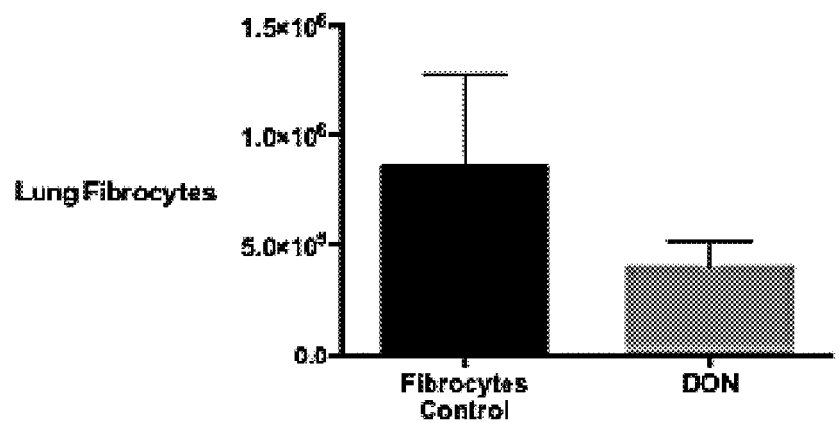

FIG. 18A is an illustration and FIG. 18B is a bar graph showing the efficacy of the targeting of glutamine metabolism in a mouse model of Pulmonary Fibrosis. Mice were treated with intratracheal bleomycin to induce fibrosis. DON treated mice demonstrated markedly decreased lung damage as well as a decrease in the recruitment/generation of lung fibrocytes.

Figure 19A:
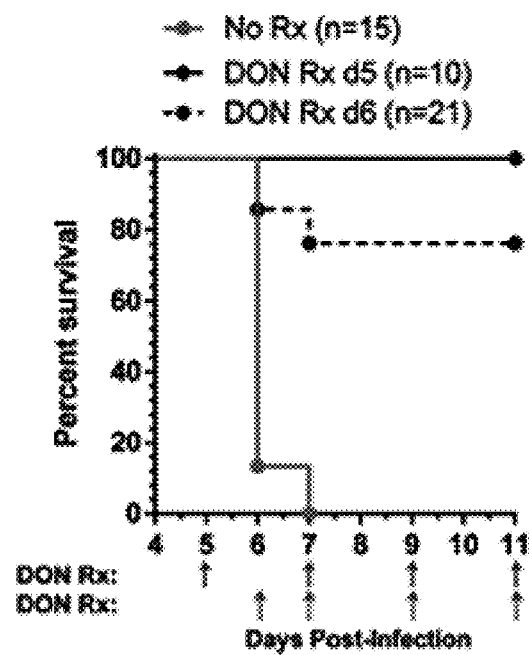
Figure 19B:
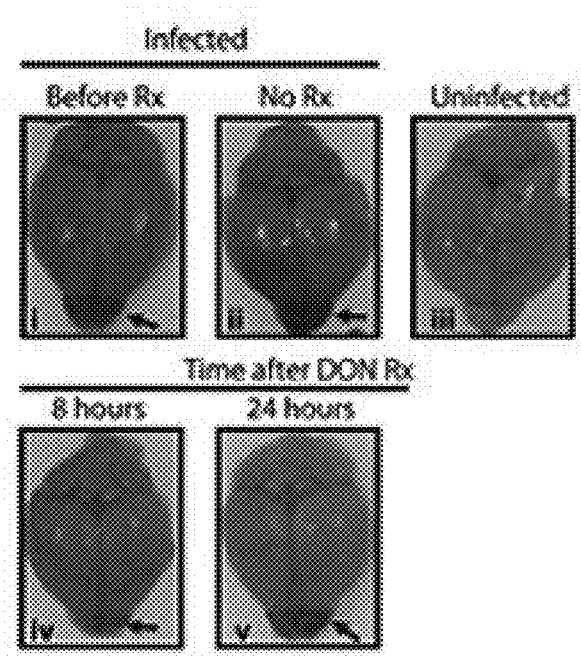

FIG. 19A is a Kaplan-Meier graph and FIG. 19B is an illustration showing the efficacy of the targeting of glutamine metabolism to cure cerebral malaria. Mice were treated on day 5 post infection and on day 6 (12 hours before subsequent death) with DON every other day. The unexpected ability of DON to prevent death at such a late stage of disease highlights the robust ability to treat CNS inflammation.

Figure 20:
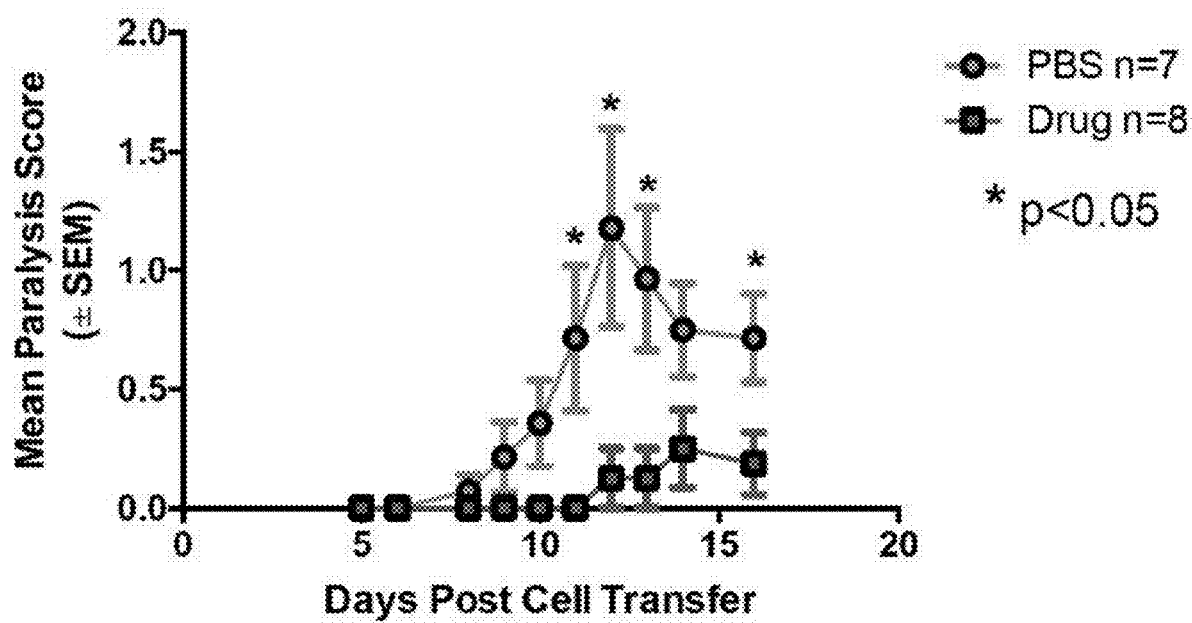

FIG. 20 is a line graph showing the efficacy of the targeting of glutamine metabolism in Neuromyelitis Optica. Auto-reactive T cells were adoptively transferred into mice treated with PBS or 25 and mean paralysis scores were measured.

Figure 21A:
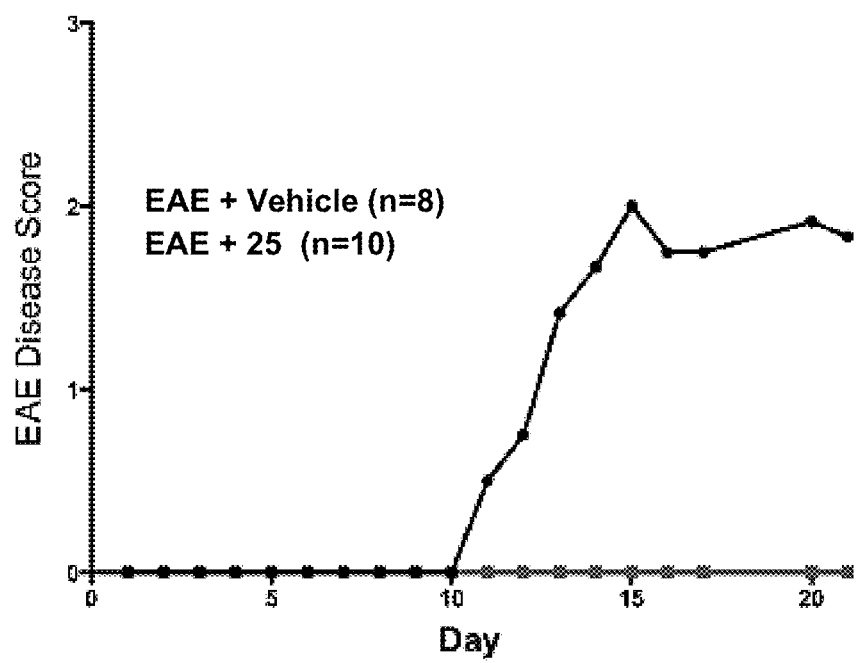
Figure 21B:
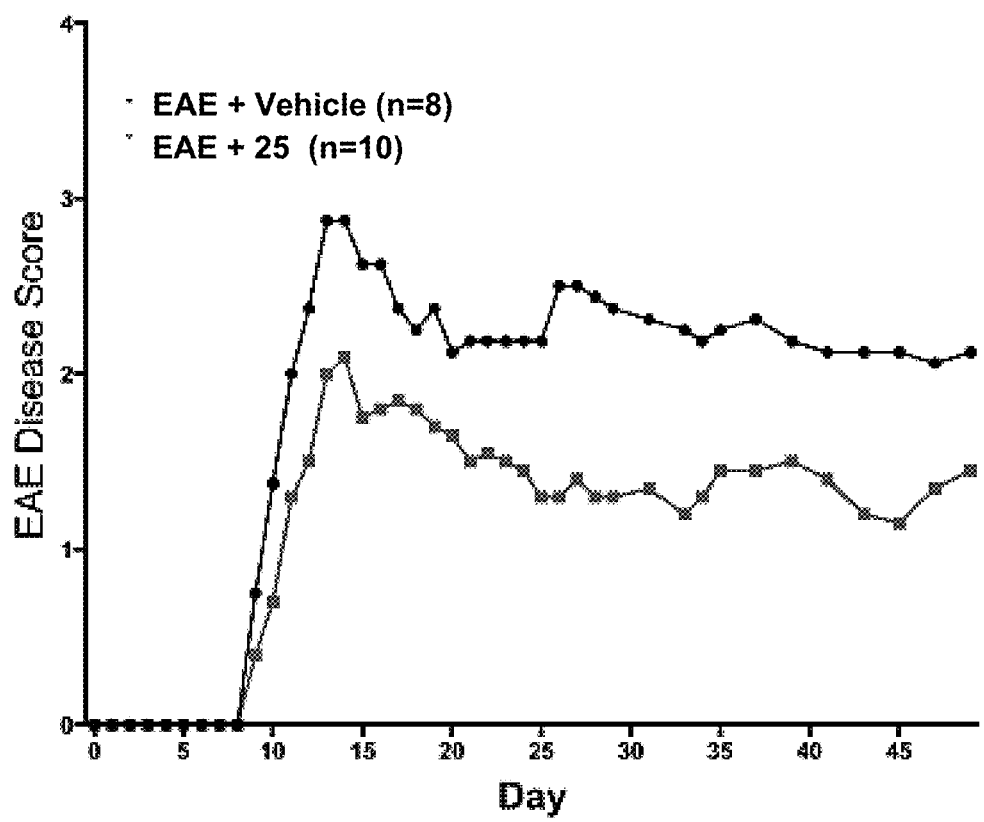

FIG. 21A and FIG. 21B are line graphs showing the efficacy of the targeting of glutamine metabolism in Multiple Sclerosis. Animals were immunized for EAE (C57BL/6+ MOG35-55). Mice were treated with Vehicle or 25 either q.d. from the day of immunization (Day 0, left), or b.d. from the time of disease onset (EAE Disease Score≥1, right).

Figure 22:
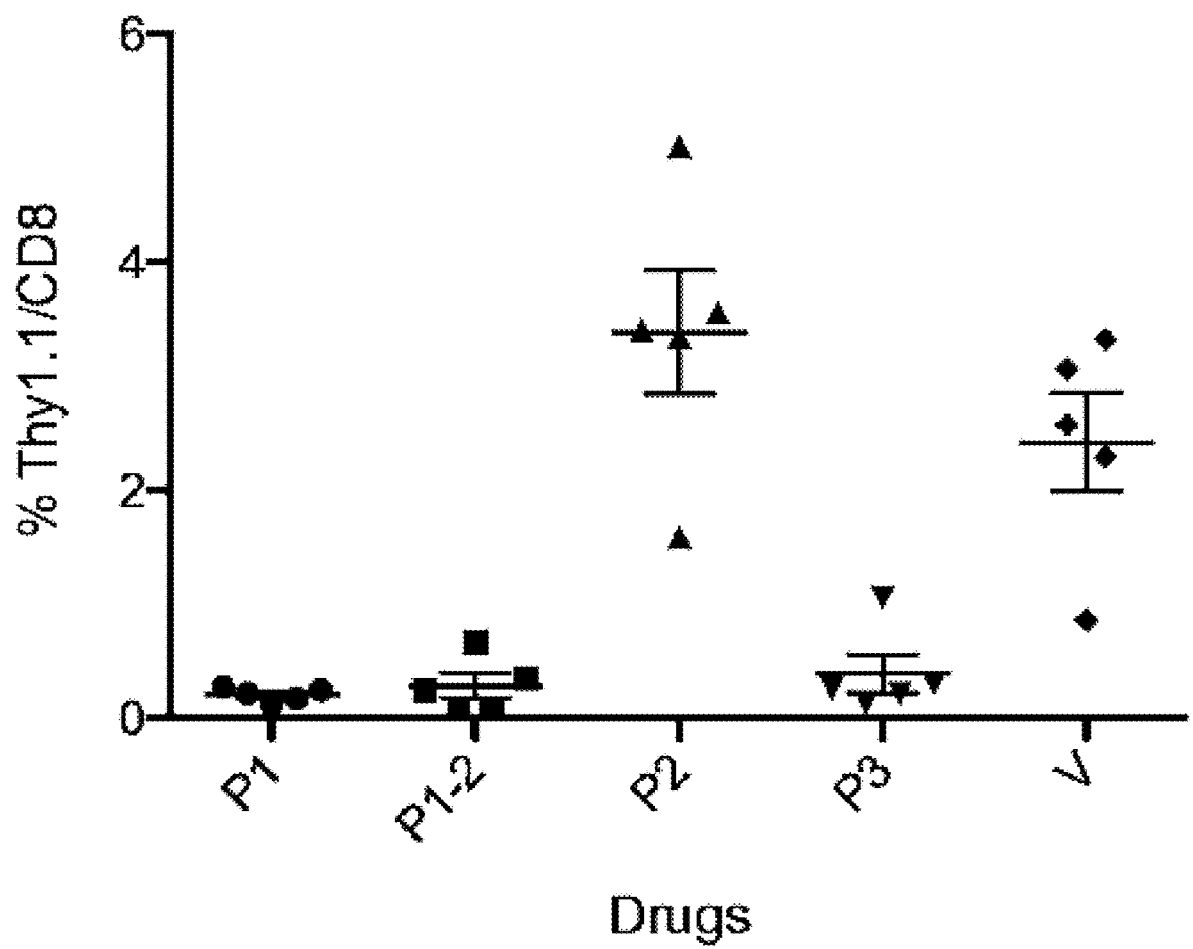

FIG. 22 is a graph showing the results of the screening of prodrugs in vivo: Thy1.1+ OT-1 cells were adoptively transferred into mice infected with vaccinia ova. The mice were treated with prodrugs or vehicle (V) and the Ova-specific response was monitored. In this case drugs P1, P1-2 and P3 effectively inhibited the T cell response.

Figure 24:
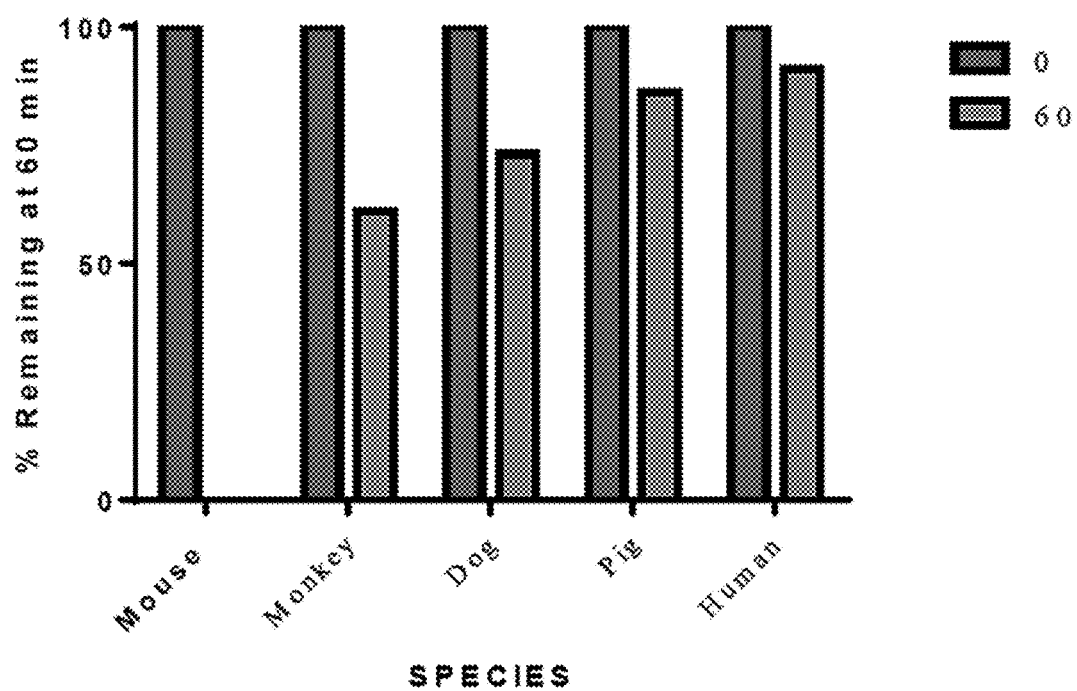

FIG. 23A is a line graph, FIG. 23B is a bar graph, and FIG. 23C is a table showing the in vivo pharmacokinetics of DON following i.v. administration of DON (1) and 14b in monkey plasma and cerebrospinal fluid (CSF). 1 and 14b were dosed in two pigtail macaques at 1.6 mg/kg equivalent of 1 via i.v. administration and plasma (0.25-6 h) and CSF (30 min) concentrations of DON were evaluated via LC/MS. Relative to 1, 14b delivered substantially lower DON plasma concentration. The reverse was observed in CSF, where 14b delivered significantly higher DON CSF concentrations, achieving a 10-fold enhanced CSF to plasma ratio at 30 minute post dose. Note the bold numbers following the terms "DON", "DON prodrugs", "DON-based prodrugs", and the like, refer to particular compounds disclosed in then international PCT application directed to "Prodrugs of Glutamine Analogs," (PCT/US2016/044767 (WO 2017/023774 A1), and herein incorporated by reference in its entirety). Specifically, other than 1, which refers to DON, the bold numbers refer to prodrugs (e.g., DON-prodrugs);

FIG. 24 is a bar graph showing species specific plasma stability of (14b); 14b is stable in plasma of human, pig, dog and monkeys, but rapidly metabolized in mice.

Figure 25:
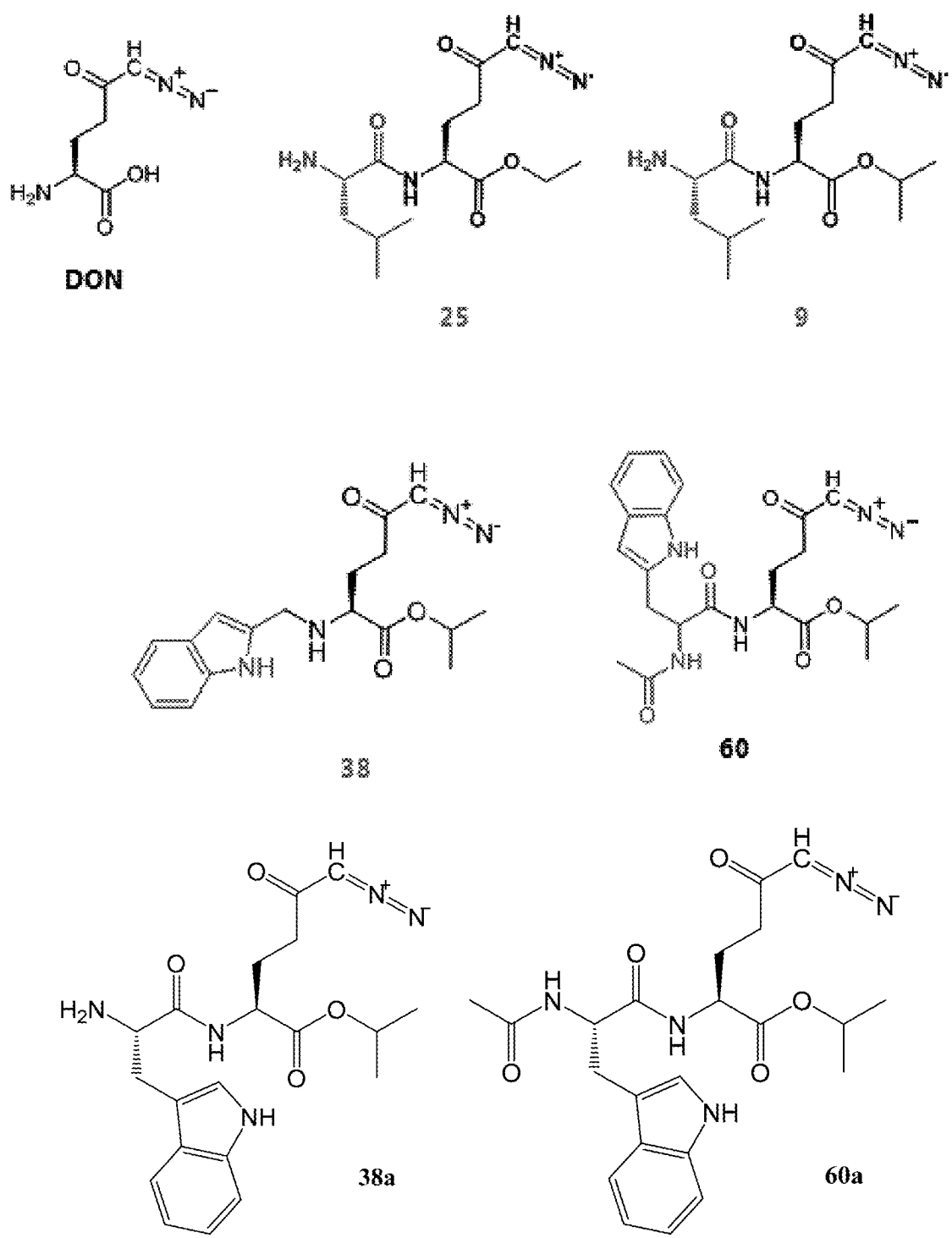
Figure 26A:
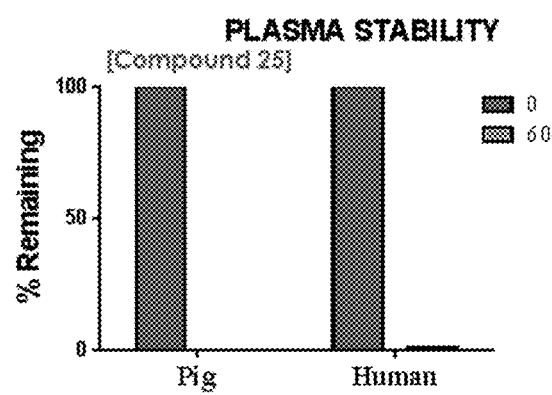
Figure 26B:
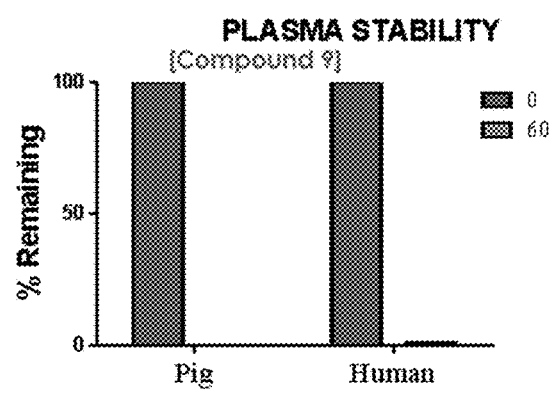
Figure 26C:
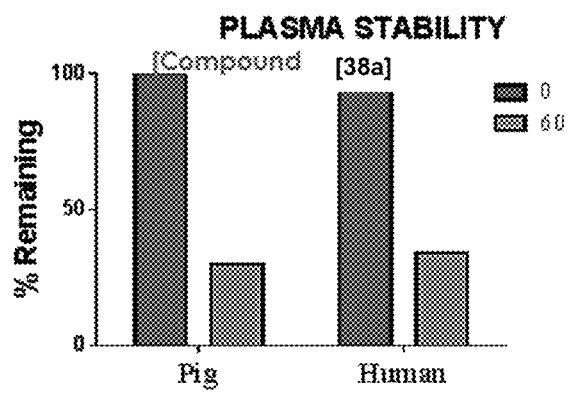
Figure 26D:
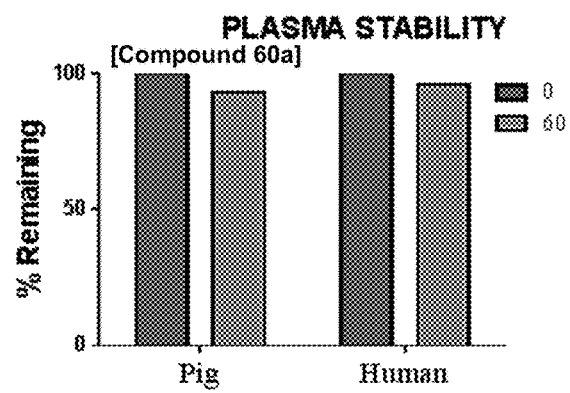
Figure 27A:
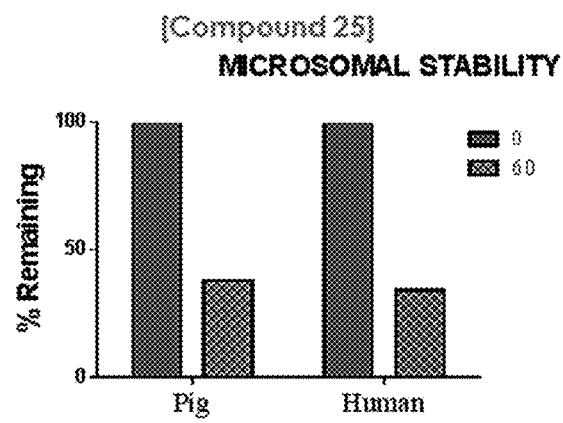
Figure 27B:
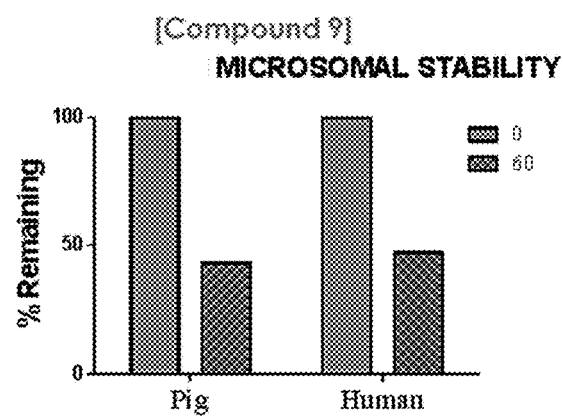
Figure 27C:
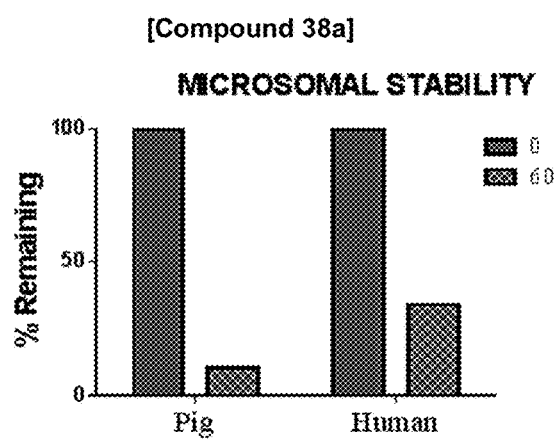
Figure 27D:
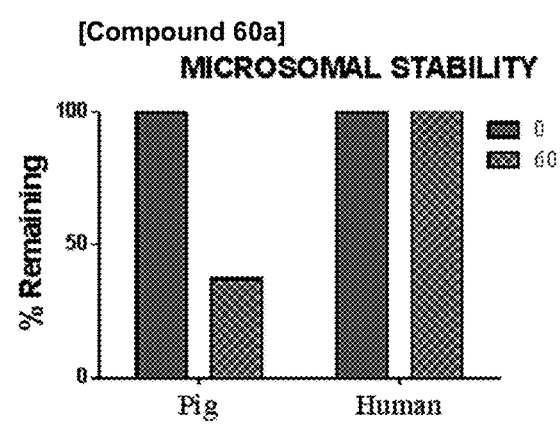
Figure 28A:
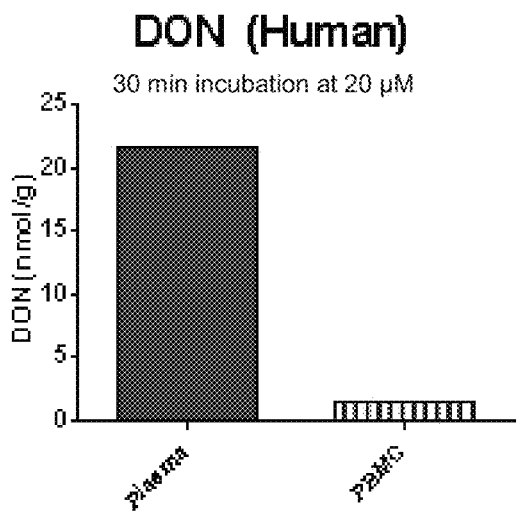
Figure 28B:
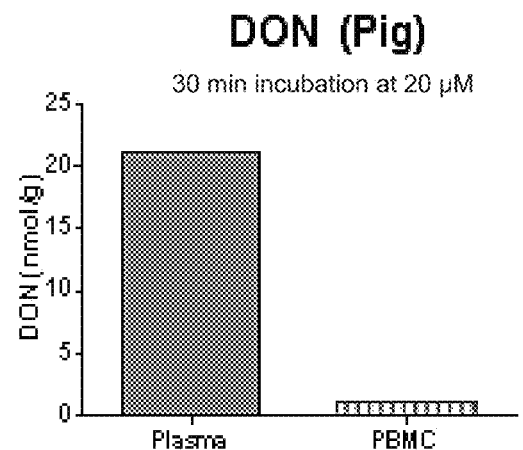
Figure 28C:
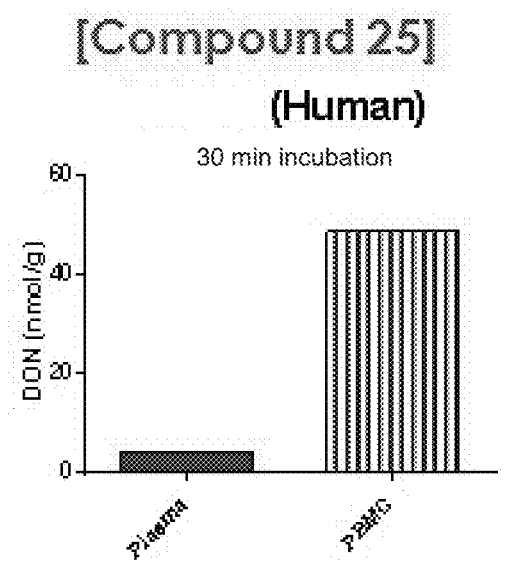
Figure 28D:
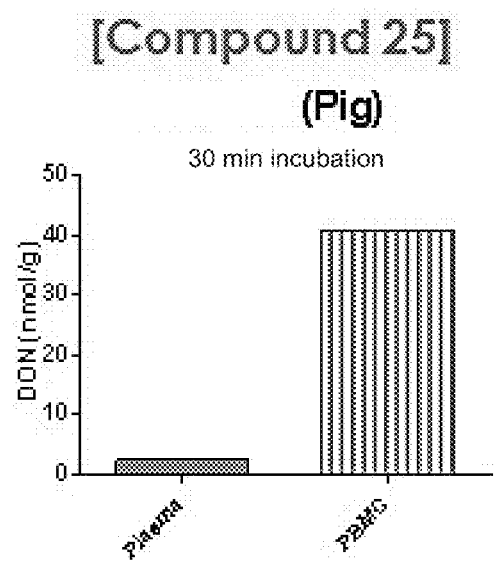
Figure 28E:
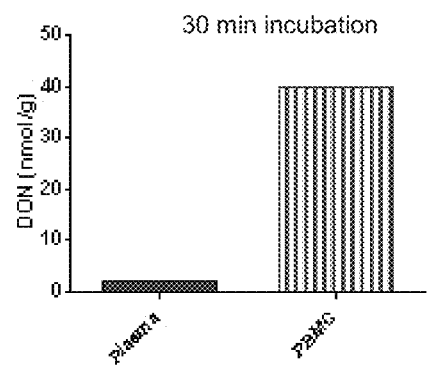
Figure 28F:
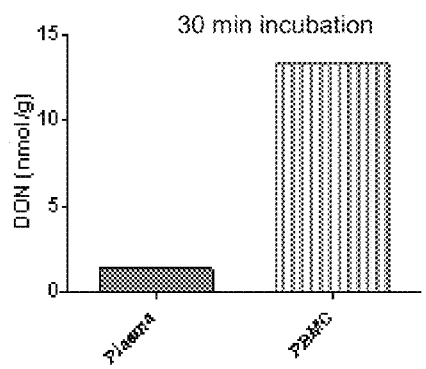
Figure 28G:
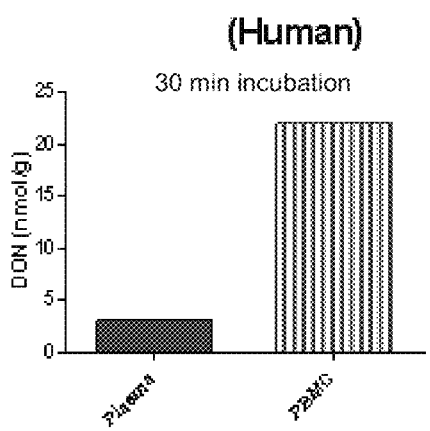
Figure 28H:
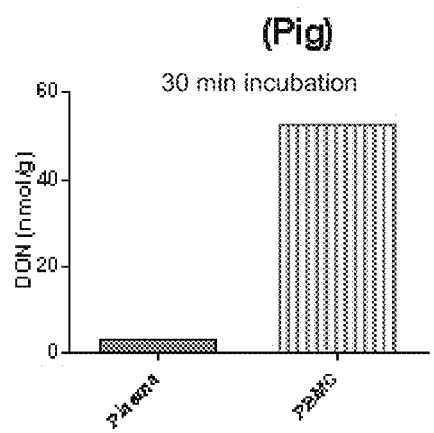
Figure 28I:
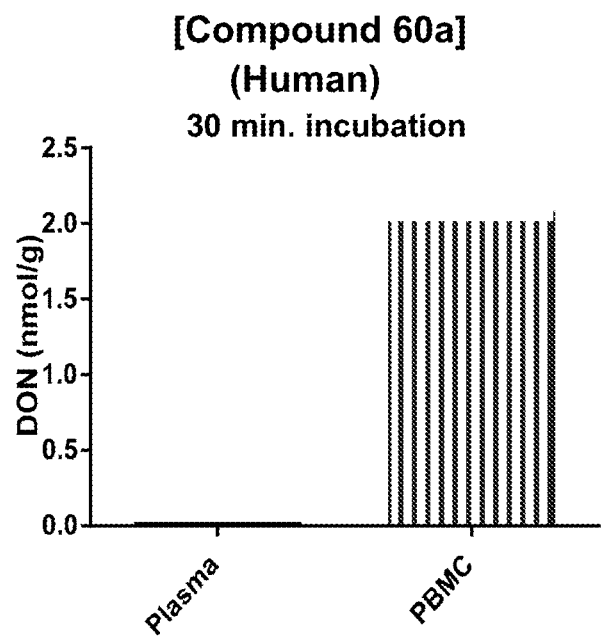
Figure 28J:
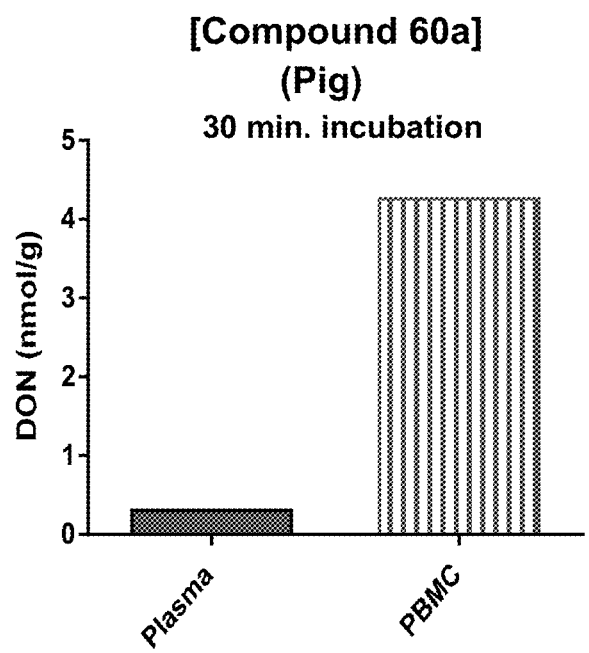
Figure 29A:
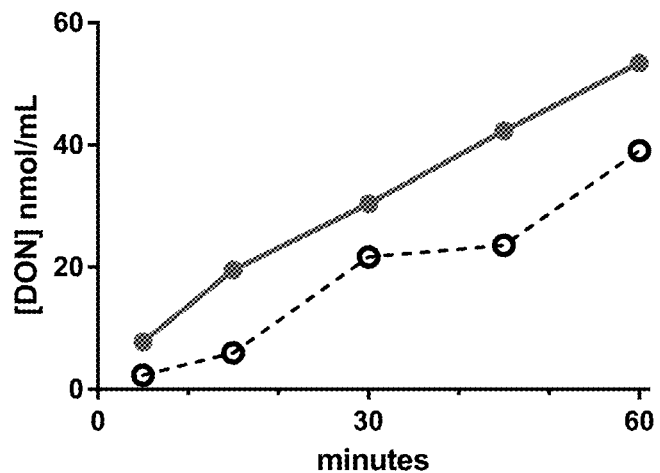
Figure 29B:
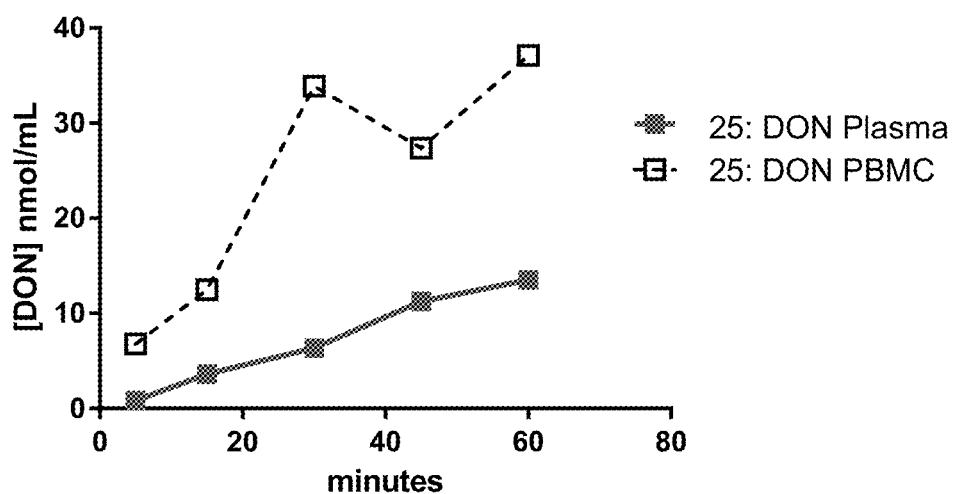
Figure 29C:
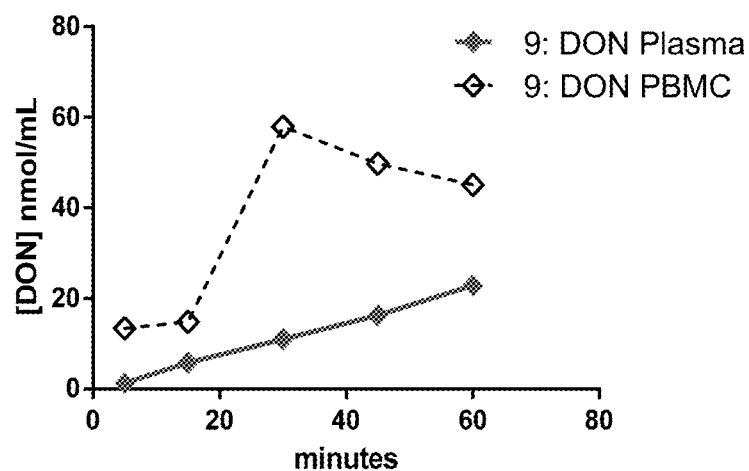
Figure 29D:
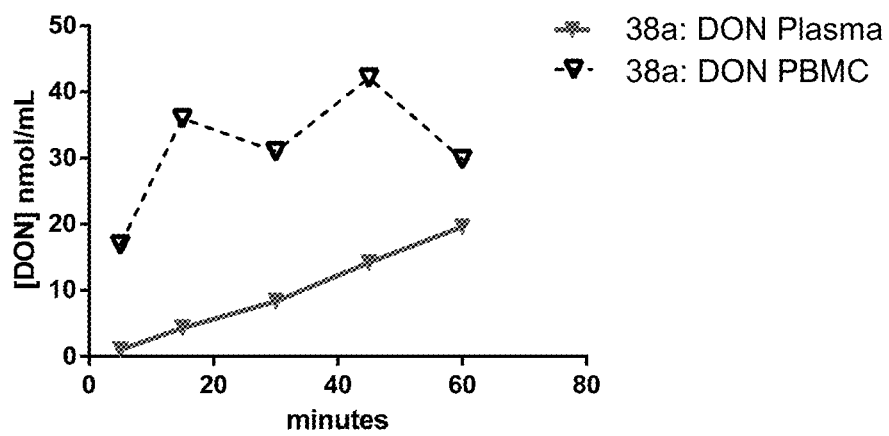
Figure 29E:
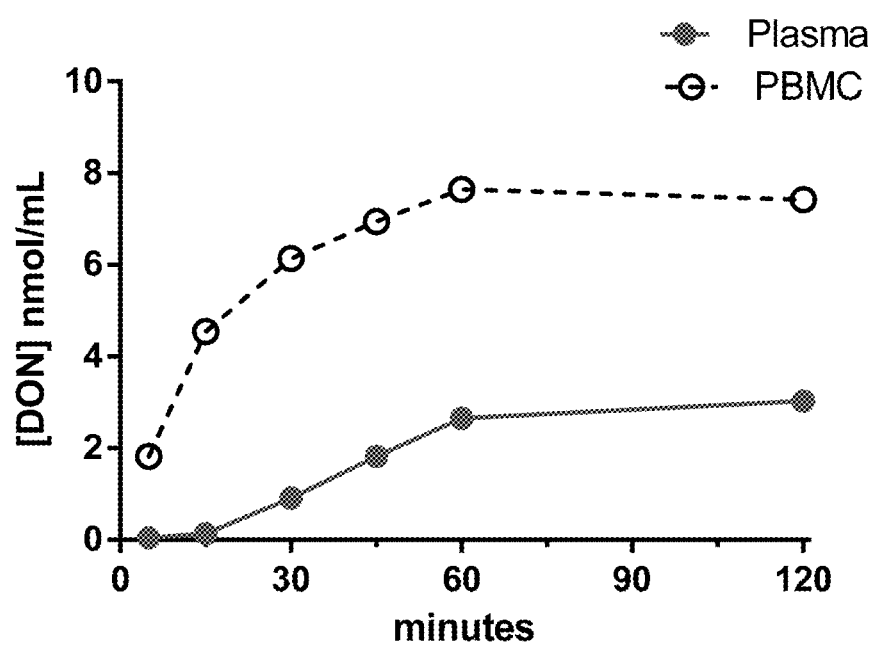

FIG. 25 is an illustration showing exemplary structures of DON and DON-based prodrugs 25, 9, 38, 60, 38a and 60a; different N-amino acid promoeities (e.g. leucine, tryptophan) provide differential plasmas and microsomal stability.

FIG. 26A, FIG. 26B, FIG. 26C, and FIG. 26D are bar graphs showing the in vitro plasma stability of DON prodrugs 9, 25, 9, 38a, and 60a. Metabolism occurs via removal of N-protecting group; both ethyl and isopropyl esters are stable in plasma of pigs and humans.

FIG. 27A, FIG. 27B, FIG. 27C, and FIG. 27D are bar graphs showing the in vitro liver microsomal stability of DON prodrugs 25, 9, 38a and 60a; all prodrugs showed moderate-high stability in human and pig microsomes.

FIG. 28A, FIG. 28B, FIG. 28C, FIG. 28D, FIG. 28E, FIG. 28F, FIG. 28G, FIG. 28H, FIG. 28I, and FIG. 28J are bar graphs showing the results of ex-vivo studies in whole human and pig blood of 9, 25, 38a and 60a; DON prodrugs selectively deliver DON to PBMCs in both humans and pigs vs plasma; compared to DON, the PBMC/plasma ratio was unexpectedly enhanced 10-100+ fold.

FIG. 29A FIG. 29B, FIG. 29C, FIG. 29D and FIG. 29E are line graphs showing the results of pig in vivo studies with DON prodrugs of 9, 25, 38a and 60a; DON prodrugs selectively deliver DON to PBMCs vs plasma; compared to DON, the PBMC/plasma ratio was enhanced 6- to 10-fold.

Figure 30A:
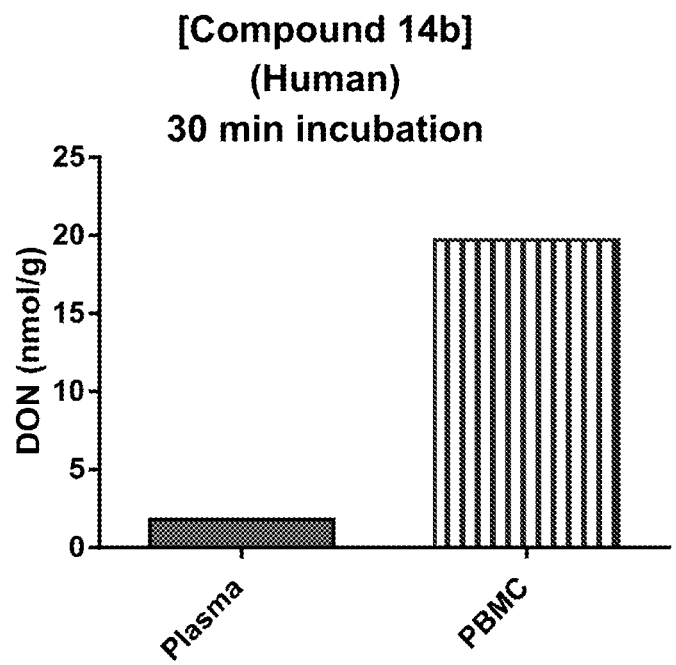
Figure 30B:
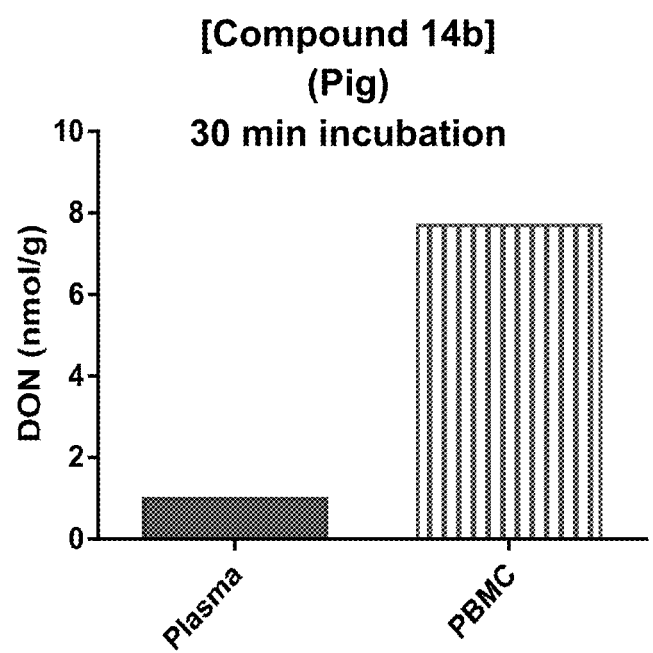
Figure 30C:
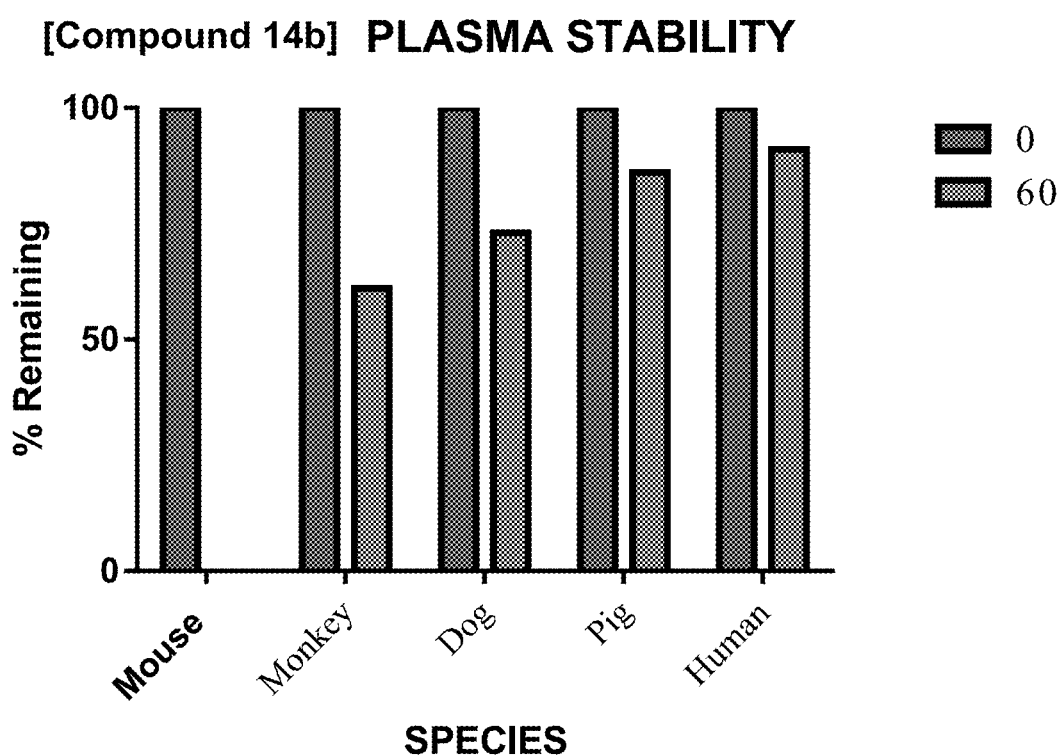

FIG. 30A, FIG. 30B, and FIG. 30C are bar graphs showing the plasma stability of compound Methyl-POM 14b and its derivatives.

Figure 31:
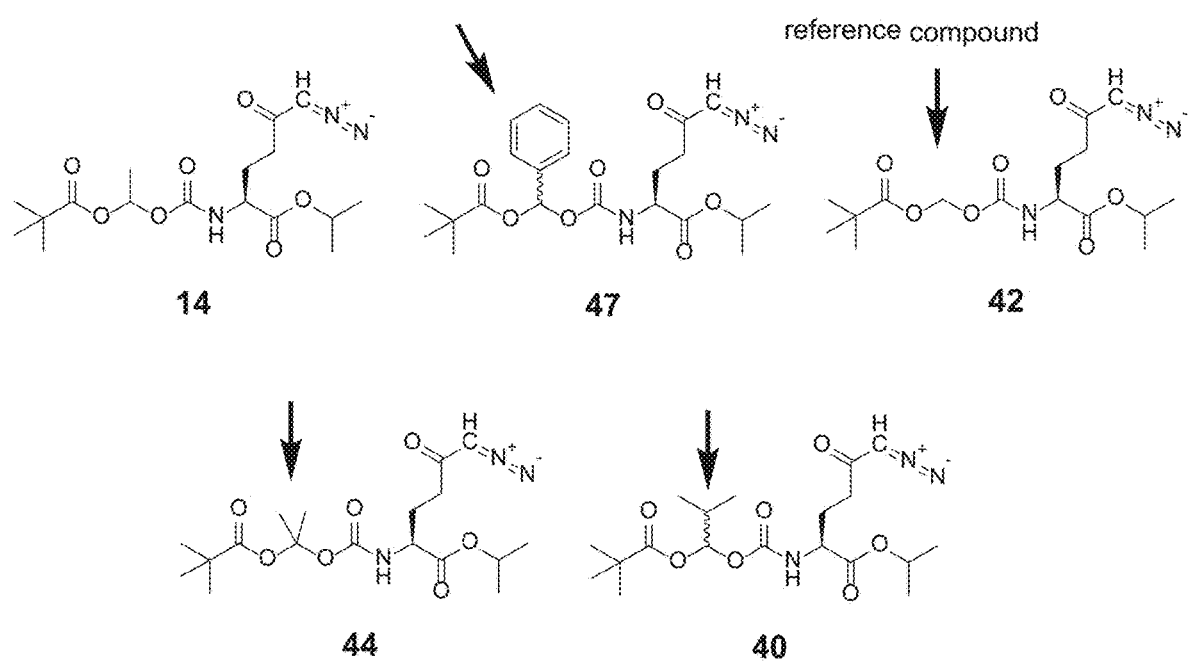

FIG. 31 is an illustration showing exemplary structures of N-acylalkyloxy DON-based prodrug analogs for intracellular targeting and brain penetration; the addition of steric bulk to the "bridge" might result in a slower hydrolysis.

Figure 32A:
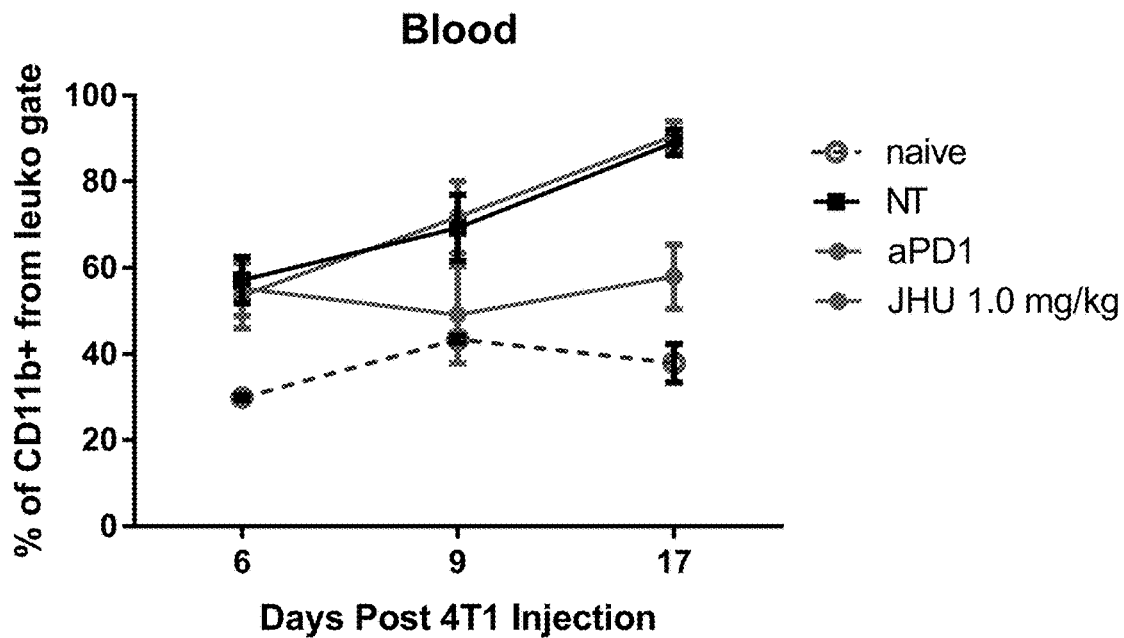
Figure 32B:
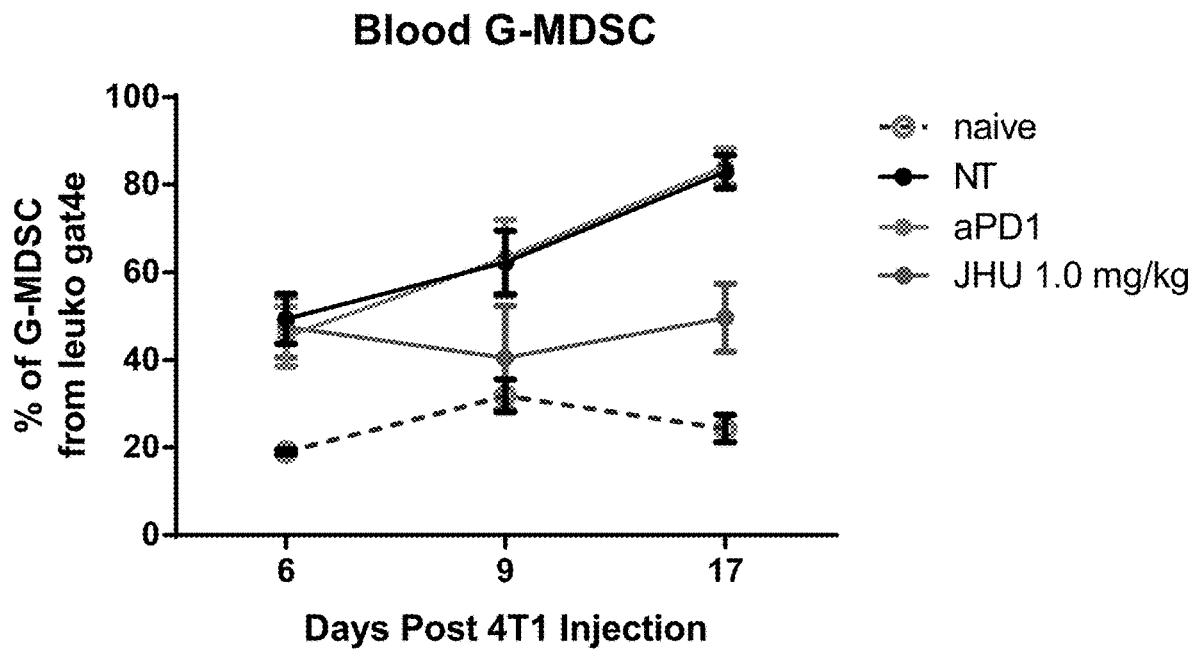
Figure 32C:
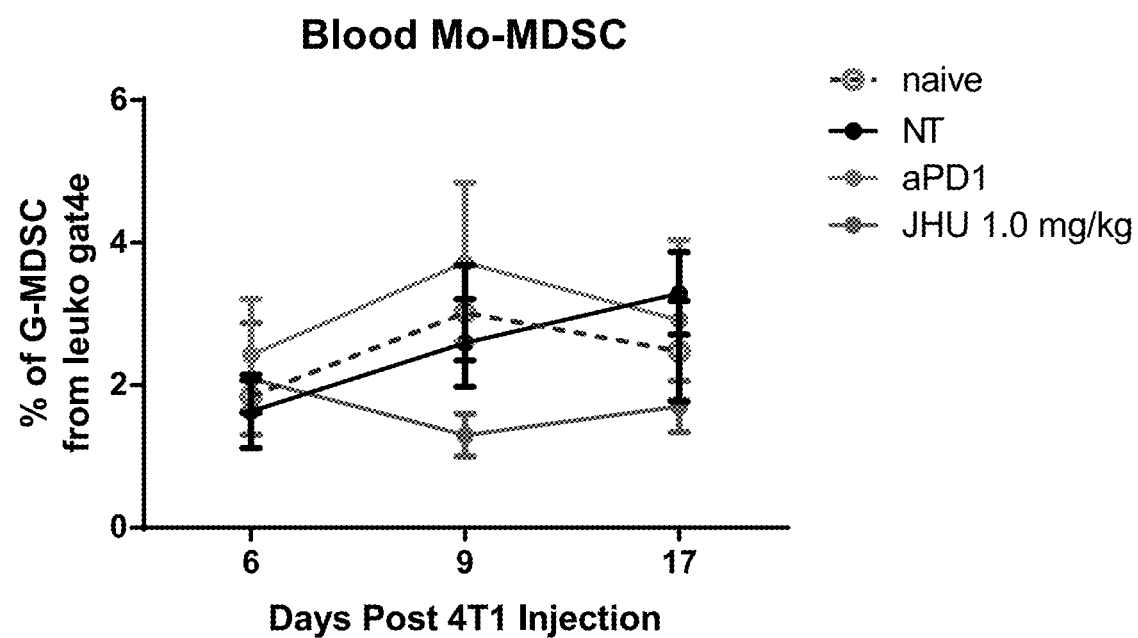

FIGS. 32A-C are line graphs illustrating reduced CD11b+ cells and G-MDSCs in compound 25 (referred to in the figures as "JHU")-treated mice, demonstrating that metabolic reprogramming agents that decrease glutamine metabolic activity inhibit myeloid derived suppressor cells. 4T1-Luc tumor cells (0.1 million) were injected into the mammary fat pads of 8-week-old female BALB/c mice. Mice received vehicle (PBS) or 1 mg/kg 25 daily from day 7 to day 17. Anti-PD1 antibody (5 mg/Kg) was administered i.p. on day 5, 8, 12 and 17. Percentages of myeloid-derived suppressor cell (MDSC) from circulating blood were monitored on day 6, 9 and 17 by flow cytometry with CD11b and Ly6C/Ly6G. Granulocytic MDSC (G-MDSC): CD11b+ Ly6g+ Ly6c low Monocytic MDSC (Mo-MDSC): CD11b+ Ly6G-Ly6c Hi.

Figure 33:
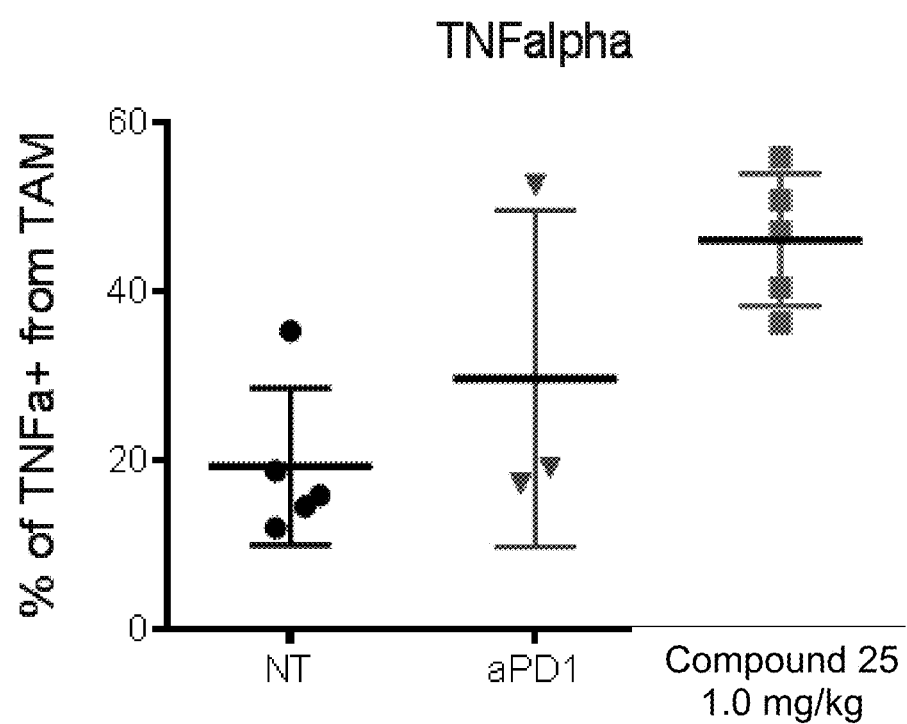

FIG. 33 is a graph illustrating increased TNF alpha in compound 25-treated mice, demonstrating that metabolic reprogramming agents that decrease glutamine metabolic activity increase inflammatory tumor associated macrophages (TAM). 4T1-Luc tumor cells (0.2 million) were injected into the mammary fat pads of 8-week-old female BALB/c mice. Mice received vehicle (PBS) or 1 mg/kg compound 25 daily from day 7 to day 17. Anti-PD1 antibody (5 mg/Kg) was administered on day 5, 8, 12 and 17. Tumors were evaluated for tumor infiltrating cells on day 21. Cells were seeded on plates and golgi plug 200 ul were added to inhibit cytokine secretion for overnight (no additional stimulation). Tumor associated macrophages markers: Live/CD45+/CD11b+/F4-80+/CD8− for flow cytometry analysis. Macrophages derived from tumor. The cells were incubated with Golgi plug o.n. w/o stim. TAM: Live/CD45+/CD11b+/F4-80+/CD8−.

Figure 34A:
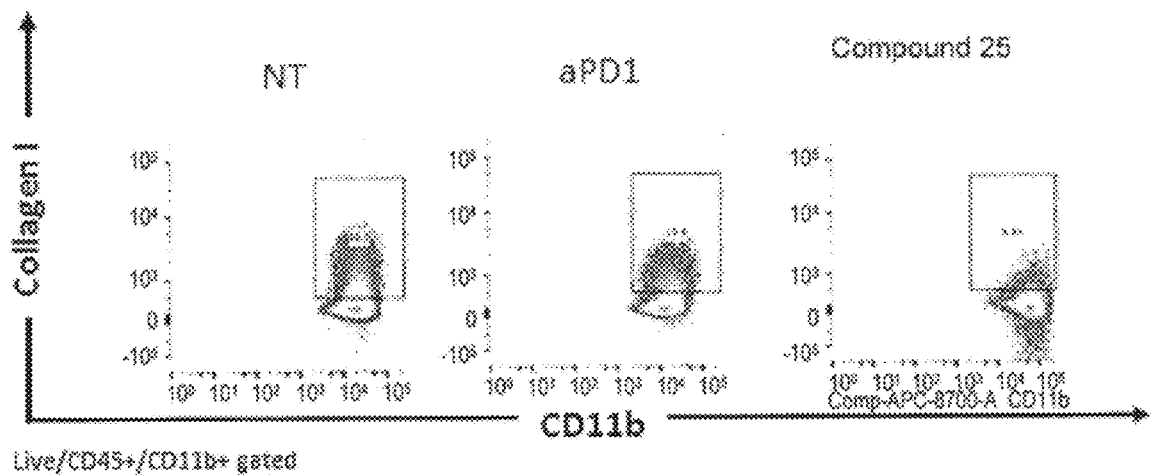
Figure 34B:
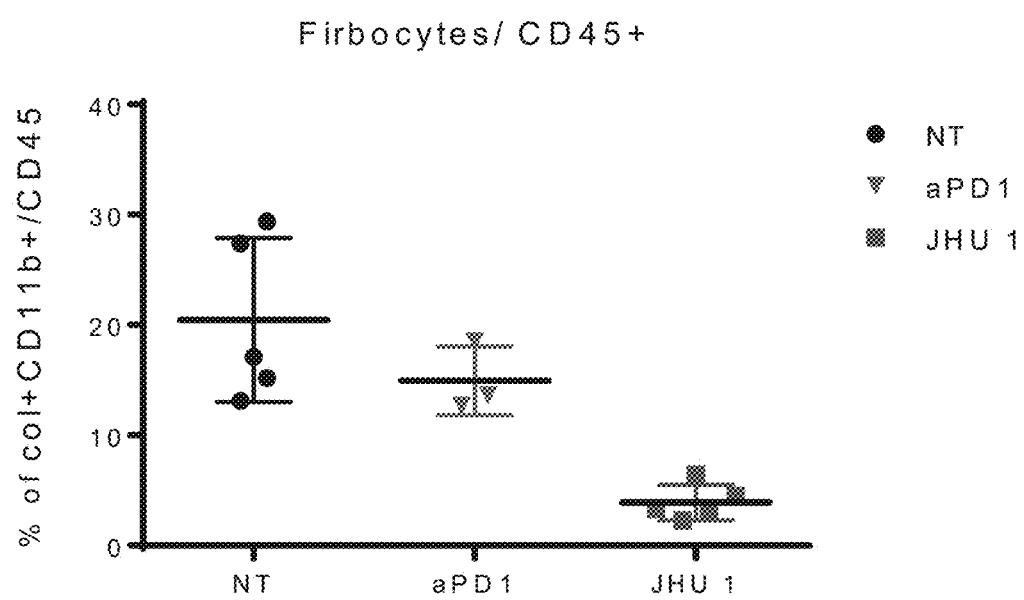

FIG. 34A an illustration and FIG. 34B is a graph showing reduced fibrocytes in compound 25 (referred to as JHU1)-treated mice, demonstrating that metabolic reprogramming agents that decrease glutamine metabolic activity inhibit bone marrow derived fibrocytes which are thought to play a role in inhibiting immunotherapy, as well as generating an extracellular matrix that surrounds tumors and inhibits chemotherapy. 4T1-Luc tumor cells (0.1 million) were injected into the mammary fat pads of 8-week-old female BALB/c mice. Mice received vehicle (PBS) or 1 mg/kg 25 daily from day 7 to day 17. Anti-PD1 antibody (5 mg/Kg) was administered on day 5, 8, 12 and 17. Tumors were evaluated for tumor infiltrating cells on day 21. Fibrocytes markers: CollagenI+CD11b+CD45+ live were used for flow cytometry analysis.

Figure 35A:
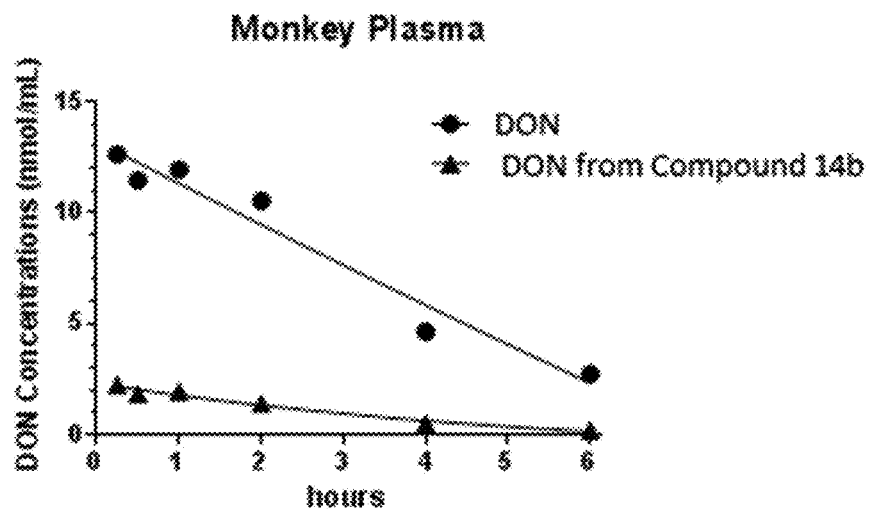

FIG. 35A is a line graph demonstrating different DON plasma profiles in Monkey for DON and compound 14b.

Figure 35B:
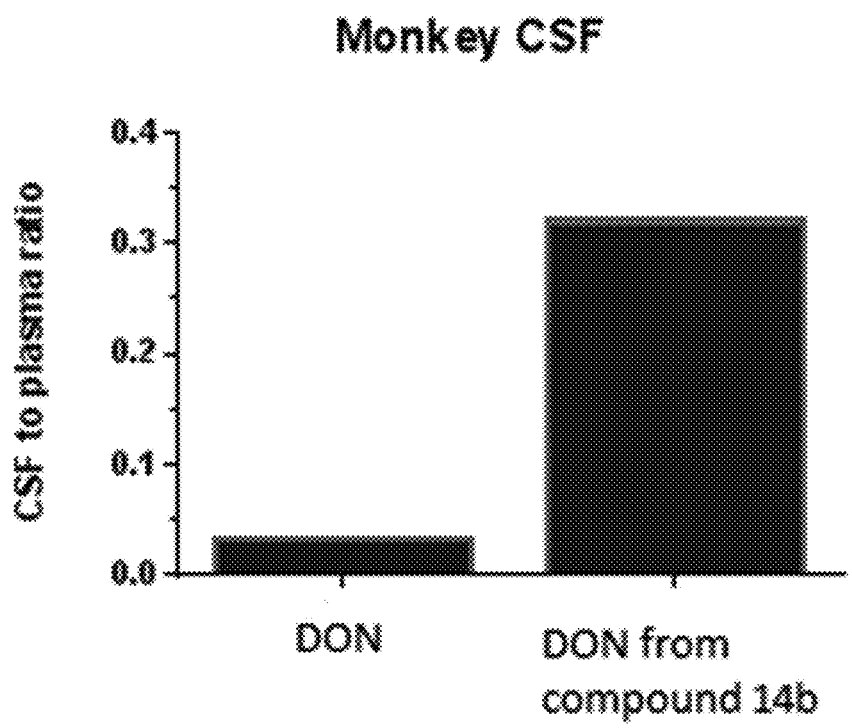

FIG. 35B is a bar graph showing that compound 14b exhibited enhanced CSF:plasma ratio of DON in Monkey.

Figure 36A:
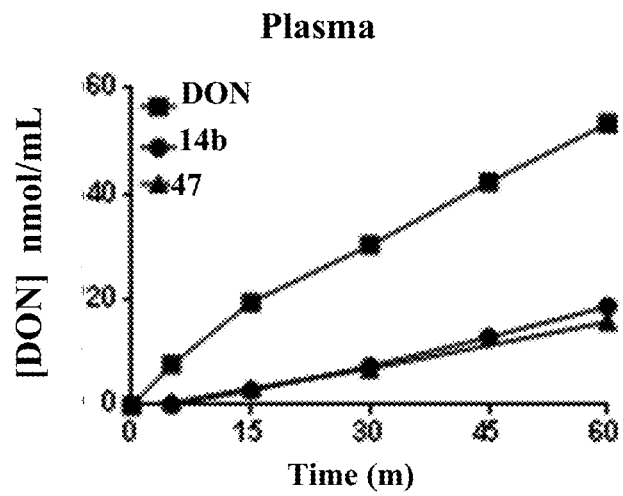

FIG. 36A is a line graph demonstrating different DON plasma profiles in swine for DON, compound 14b and compound 47.

Figure 36B:
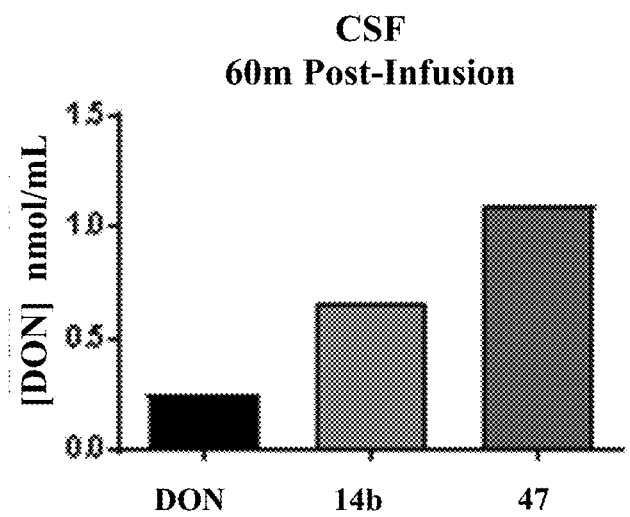
Figure 36C:
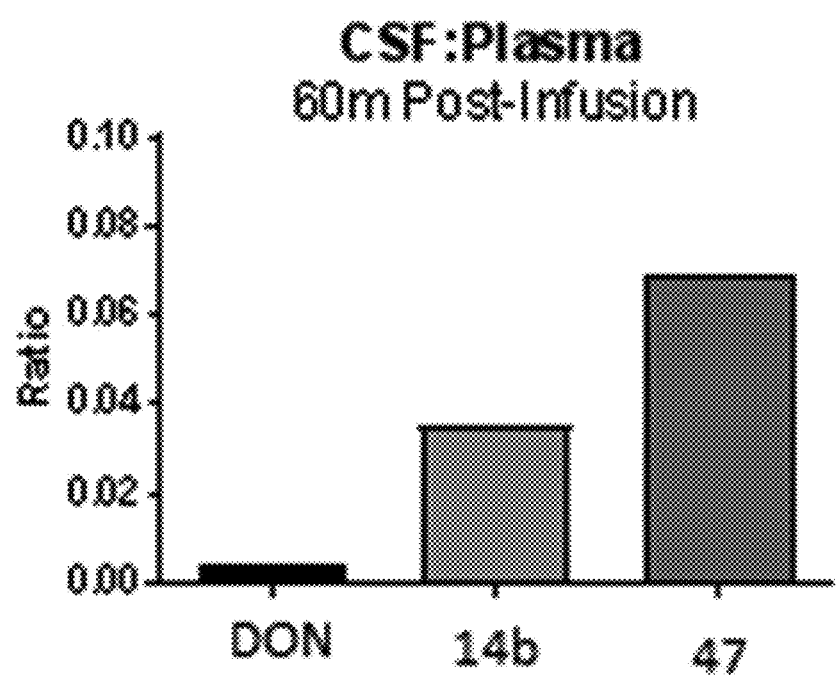

FIG. 36B is a bar graph showing that compounds 14b and 47 exhibited enhanced CSF delivery of DON at 60 min post-administration in swine FIG. 36C is a bar graph showing that compounds 14b and 47 exhibited enhanced CSF:plasma ratio of DON at 60 min post-administration in swine.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter demonstrates that certain conditions, diseases, and/or disorders involve metabolically reprogrammed cells whose activation, function, growth, proliferation, and/or survival in an abnormal, harmful, and/or unhealthy state depend on increased activity of at least one, at least two, or at least three metabolic pathways selected from the group consisting of glutamine metabolism, glycolysis, and fatty acid synthesis. It should be appreciated that the abnormal, harmful, and/or unhealthy state of the cell refers to its effect on or relative to the subject whose cells are affected by the condition, disease, or disorder rather than on or relative to the cell itself which exhibits an increased ability to thrive in the abnormal, harmful, and/or unhealthy state in a manner that is believed to be proportionate to the increase in the activity of at least one, at least two, or at least three metabolic pathways (e.g., glutamine metabolism, glycolysis, and/or fatty acid synthesis).

The presently disclosed subject matter have demonstrated that certain of such conditions, diseases, and/or disorders, referred to herein as "metabolic reprogramming disorders," are amenable to treatment using at least one, at least two, or at least three metabolic reprogramming agents that decrease activity of at least one, at least two, or at least three metabolic pathways selected from the group consisting of glutamine metabolism, glycolysis, and fatty acid synthesis. In some instances, the metabolic reprogramming disorders comprise conditions, diseases, or disorders that involve aberrant and/or excessive glutamine metabolism, aberrant and/or excessive glycolysis, or aberrant and/or excessive fatty acid synthesis.

As used herein, the term "excessive glutamine metabolism" means an increase in the amount of glutamine metabolic activity in a subject with a condition, disease, or disorder (e.g., a metabolic reprogramming disorder) as compared to the amount of glutamine metabolic activity in a subject without a similar disease or condition, such as an increase of approximately 100%, 100%, 200%, 300%, 400%, 500%, 600%, 700%, 800%, 900%, 1000%, or more. As used herein, the term "aberrant glutamine metabolism" means a change in the biological activity of glutamine in a subject with a condition, disease or disorder (e.g., a metabolic reprogramming disorder) as compared to the glutamine activity in a subject without a similar condition, disease, or disorder, such as increased utilization of glutamine in the growth and/or proliferation of malignant, neoplastic, or other pathologic cellular processes (e.g., immune disorders, neurodegenerative disorders, inflammatory disorders, etc.).

As used herein, the term "excessive glycolysis metabolism" means an increase in the amount of glycolytic metabolic activity in a subject with a condition, disease, or disorder (e.g., a metabolic reprogramming disorder) as compared to the amount of glycolytic metabolic activity in a subject without a similar disease or condition, such as an increase of approximately 100%, 100%, 200%, 300%, 400%, 500%, 600%, 700%, 800%, 900%, 1000%, or more. As used herein, the term "aberrant glycolytic metabolism" means a change in the biological activity of glycolysis in a subject with a condition, disease or disorder (e.g., a metabolic reprogramming disorder) as compared to the glycolytic activity in a subject without a similar condition, disease, or disorder, such as increased utilization of glucose in the growth and/or proliferation of malignant, neoplastic, or other pathologic cellular processes (e.g., immune disorders, neurodegenerative disorders, inflammatory disorders, etc.).

As used herein, the term "excessive fatty acid synthesis" means an increase in the amount of fatty acid synthesis in a subject with a condition, disease, or disorder (e.g., a metabolic reprogramming disorder) as compared to the amount of fatty acid synthesis in a subject without a similar condition, disease, or disorder, such as an increase of approximately 100%, 100%, 200%, 300%, 400%, 500%, 600%, 700%, 800%, 900%, 1000%, or more. As used herein, the term "aberrant fatty acid synthesis" means a change in the biological activity of fatty acid synthesis in a subject with a condition, disease or disorder (e.g., a metabolic reprogramming disorder) as compared to the fatty acid synthesis in a subject without a similar condition, disease, or disorder, such as increased utilization of fatty acids in the growth and/or proliferation of malignant, neoplastic, or other pathologic cellular processes (e.g., immune disorders, neurodegenerative disorders, inflammatory disorders, etc.).

As used herein, a "metabolically reprogrammed" cell refers to a cell in which the activity of at least one, at least two, or at least three metabolic pathways (e.g., glutamine metabolism, glycolysis, and fatty acid synthesis) has increased in response to the cells energetic and biosynthetic demands placed on the cell in order for the cell to become activated, function, grow, proliferate, and/or survive in the abnormal, harmful, and/or unhealthy state. As used herein, a "metabolic reprogramming agent" refers to an agent that is capable of reversing the metabolic reprogramming of a cell from a cell whose activation, function, growth, proliferation, and/or survival in an abnormal, harmful, and/or unhealthy state depends on increased activity of at least one, at least two, or at least three metabolic pathways (e.g., glutamine metabolism, glycolysis, and fatty acid synthesis) to a cell that has a decreased capacity or has lost its ability to thrive (e.g., activate, function, grow, proliferate, and/or survive) in the abnormal, harmful and/or unhealthy state. In some contexts, a "metabolic reprogramming agent" inhibits at least one of, at least two of, or all of aberrant and/or excessive glutamine metabolism, aberrant and/or excessive glycolysis, and aberrant and/or excessive fatty acid synthesis.

The presently compositions, methods, and agents for metabolic reprogramming may provide a number of advantages over existing therapies, including without limitation, inhibition of effector T cells while enhancing regulatory T cells, promoting immune tolerance as opposed to inhibiting it, providing a positive effect on systemic metabolism (e.g., avoids conditions such as steroid-induced metabolic syndrome/diabetes), inhibiting the replication of CMV and other viruses and other complications of immunosuppression, and providing a robust therapeutic index as demonstrated by in vivo studies (e.g., due to cellular selectivity based upon metabolic demand).

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Methods of Treatment Using Metabolic Reprogramming Agents

In one aspect, the presently disclosed subject matter provides a method for treating a subject having a condition, disease, or disorder that involves metabolically reprogrammed cells whose activation, function, growth, proliferation, and/or survival depends on increased activity of at least one metabolic pathway selected from the group consisting of glutamine metabolism, glycolysis, and fatty acid synthesis, the method comprising administering to the subject at least one metabolic reprogramming agent that decreases activity of at least one metabolic pathway selected from the group consisting of glutamine metabolism, glycolysis, and fatty acid synthesis in an amount effective to treat the condition, disease, or disorder.

In particular embodiments, the presently disclosed subject matter provides a method for treating a condition, disease, or disorder that involves metabolically reprogrammed cells whose activation, function, growth, proliferation, and/or survival depends on increased glutamine metabolic activity, the method comprising administering to the subject an effective amount of an agent that decrases glutamine metabolic activity.

In some aspects, the presently disclosed subject matter provides a method for treating a subject having a condition, disease, or disorder that involves at least one of aberrant and/or excessive glutamine metabolism, aberrant and/or excessive glycolysis, or aberrant and/or excessive fatty acid synthesis, the method comprising administering to the subject at least one metabolic reprogramming agent that decreases activity of at least one metabolic pathway selected from the group consisting of glutamine metabolism, glycolysis, and fatty acid synthesis in an amount effective to treat the condition, disease, or disorder.

In particular embodiments, the presently disclosed subject matter provides a method for treating a subject having a condition, disease, or disorder that involves aberrant and/or excessive glutamine metabolism, the method comprising administering to the subject an effective amount of an agent that decreases glutamine metabolic activity.

In general, the presently disclosed methods result in a decrease in the severity of a condition, disease, or disorder (e.g., a metabolic reprogramming disorder) in a subject. The term "decrease" is meant to inhibit, suppress, attenuate, diminish, arrest, or stabilize a symptom of the condition, disease, or disorder. As used herein, the terms "treat," "treating," "treatment," and the like refer to reducing or ameliorating a disease or condition, and/or symptoms associated therewith. It will be appreciated that, although not precluded, treating a disease or condition does not require that the disorder, condition or symptoms associated therewith be completely eliminated.

In some embodiments, the method comprises administering to the subject at least two metabolic reprogramming agents that decrease the activity of at least two metabolic pathways selected from the group consisting of glutamine metabolism, glycolysis, and fatty acid synthesis in an amount effective to treat the condition, disease, or disorder. In other embodiments, the method comprises administering to the subject at least three metabolic reprogramming agents that each decrease the activity of a different metabolic pathway selected from the group consisting of glutamine metabolism, glycolysis, and fatty acid synthesis in an amount effective to treat the condition, disease, or disorder. In still other embodiments, the method comprises administering at least four, five, six, or more metabolic reprogramming agents to the subject.

The terms "subject" and "patient" are used interchangeably herein. The subject treated by the presently disclosed methods, uses, metabolic reprogramming agents and compositions comprising those agents in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease.

A. Immune Disorders

Aspects of the disclosure involve the use of at least one, at least two, or at least three metabolic reprogramming agents, alone, or optionally together in combination with an immunosuppressant agent and/or an anti-inflammatory agent, for the treatment of an immune disorder (e.g., an autoimmune disorder). Accordingly, in some embodiments, the condition, disease, or disorder is an immune disorder. In such embodiments, the metabolically reprogrammed cells comprise immune cells. Examples of immune cells whose activation, function, growth, proliferation, and/or survival in an abnormal, harmful, or unhealthy state depends on increased metabolic activity of at least one, at least two, or at least three metabolic pathways selected from the group consisting of glutamine metabolism, glycolysis and fatty acid synthesis include, but are not limited to, antigen-specific effector CD4+ T cells, antigen-specific effector CD8+ t cells, and regulatory T cells.

As used herein, the term "immune disorders" includes diseases involving the immune system that can include but not be limited to allergies, autoimmune diseases, immune complex diseases, immunodeficiency diseases and cancers of the immune system. Autoimmunity is the failure of an organism to recognize its own constituent parts (down to the sub-molecular levels) as "self", which results in an immune response against its own cells and tissues. Any disease that results from such an aberrant immune response is termed an autoimmune disease. An unwanted immune response may be, for example, immune responses associated with an autoimmune disorder, transplants, allergies, or inflammatory disorders.

Exemplary autoimmune diseases and disorders that may be treated with the presently disclosed methods, uses, and compositions comprising one or more metabolic reprogramming agents include, for example, inflammatory responses, such as inflammatory skin diseases, including psoriasis and dermatitis (e.g. atopic dermatitis); dermatomyositis; systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions, such as eczema and asthma, and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases, Hashimoto's thyroiditis, Wegener's granulomatosis, cold agglutinin disease associated with indolent lymphoma, acquired factor VIII inhibitors disease, etc.

The term "immune disorders" are diseases involving the immune system that can include but not be limited to allergies, autoimmune diseases, immune complex diseases, immunodeficiency diseases and cancers of the immune system. The term "autoimmune diseases" may include but not be limited to Acute disseminated encephalomyelitis, Addison's disease, Ankylosing spondylitisis, Antiphospholipid antibody syndrome, Aplastic anemia, Autoimmune hepatitis, Autoimmune Oophoritis, Coeliac disease, Crohn's disease, Diabetes mellitus, Gestational pemphigoid, Goodpasture's syndrome, Grave's disease, Guillan-Barre syndrome, Hashimoto's disease, Idiopathic thrombocytopenic purpura, Lupus erythematosus, Multiple sclerosis, Myasthenia gravis, Opsoclonus myoclonus syndrome, Optic neuritis, Ord's thyroiditis, Pemphigus, Pernicious anemia, Polyarthritis, Primary biliary cirrhosis, Rheumatoid arthritis, Reiter's syndrome, Sjogren's syndrome, Takayasu's arteritis, Warm autoimmune hemolytic anemia, and Wegener's granulomatosis. The term "chronic inflammatory diseases" may include but not be limited to Tuberculosis, Chronic cholecystitis, Bronchiectasis, ulcerative colitis, silicosis and other pneumoconiosis as well as the above listed autoimmune diseases.

In some embodiments, the condition, disease, or disorder is ARDS.

Accordingly, in an aspect the presently disclosed subject matter provides a method for the treatment of ARDS in a subject in need thereof, the method comprising administering to the subject at least one metabolic reprogramming agent that decreases glutamine metabolism in an amount effective to treat ARDS in the subject.

In some embodiments, the condition, disease, or disorder is arthritis. Accordingly, in an aspect the presently disclosed subject matter provides a method for the treatment of arthritis in a subject in need thereof, the method comprising administering to the subject at least one metabolic reprogramming agent that decreases glutamine metabolism in an amount effective to treat arthritis in the subject.

In some embodiments, the condition, disease, or disorder is asthma. Accordingly, in an aspect the presently disclosed subject matter provides a method for the treatment of asthma in a subject in need thereof, the method comprising administering to the subject at least one metabolic reprogramming agent that decreases glutamine metabolism in an amount effective to treat asthma in the subject.

The presently disclosed methods, compositions, and agents can be used to treat or prevent transplant rejections.

In some embodiments, the condition, disease, or disorder is allograft rejection during cell, tissue, or organ transplantation. Accordingly, in an aspect the presently disclosed subject matter provides a method for preventing or delaying allograft rejection during cell, tissue, or organ transplantation in a subject in need thereof, the method comprising administering to a subject about to undergo, undergoing, or having undergone a cell, tissue, or organ transplantation at least one metabolic reprogramming agent that decreases glutamine metabolism in an amount effective to prevent or delay allograft rejection of the cell, tissue, or organ transplanted in the subject.

In particular embodiments, a method for preventing or delaying a heart allograft rejection comprises administering to a subject about to undergo, undergoing, or having undergone a heart allograft transplantation an effective amount of at least one metabolic reprogramming agent, at least two metabolic reprogramming agents, or at least three metabolic reprogramming agents selected from the group consisting of a metabolic reprogramming agent that decreases activity of glutamine metabolism, a metabolic reprogramming agent that decreases activity of glycolysis, and a metabolic reprogramming agent that decreases activity of fatty acid synthesis, thereby preventing or delaying rejection of the heart allograft in the subject. In some embodiments, the subject receiving the heart allograft transplantation is a full MHC mismatch relative to the donor of the heart allograft. In some embodiments, the subject is administered at least one metabolic reprogramming agent to prevent or delay the heart allograft rejection. In some embodiments, the subject is administered at least two metabolic reprogramming agents to prevent or delay the heart allograft rejection. In some embodiments, the subject is administered at least three metabolic reprogramming agent to prevent or delay the heart allograft rejection.

In some embodiments, the condition, disease, or disorder is graft versus host disease (GVHD). Accordingly, in an aspect the presently disclosed subject matter provides a method for treating or preventing GVHD in a subject in need thereof, the method comprising administering to a subject about to undergo, undergoing, or having undergone a cell, tissue, or organ transplantation at least one metabolic reprogramming agent that decreases glutamine metabolism in an amount effective to treat or prevent GVHD in the subject.

In some embodiments, the condition, disease, or disorder is lupus. Accordingly, in an aspect the presently disclosed subject matter provides a method for the treatment of lupus in a subject in need thereof, the method comprising administering to the subject at least one metabolic reprogramming agent that decreases glutamine metabolism in an amount effective to treat lupus in the subject.

In some embodiments, the condition, disease, or disorder is multiple sclerosis. Accordingly, in an aspect the presently disclosed subject matter provides a method for the treatment of multiple sclerosis in a subject in need thereof, the method comprising administering to the subject at least one metabolic reprogramming agent that decreases glutamine metabolism in an amount effective to treat multiple sclerosis in the subject. In another aspect the presently disclosed subject matter provides a method for the prevention of multiple sclerosis in a subject in need thereof, the method comprising administering to the subject at least one metabolic reprogramming agent that decreases glutamine metabolism in an amount effective to prevent multiple sclerosis in the subject. As used herein "prevention" in the context of multiple sclerosis includes preventing the onset of the disease, as well as progression and/or severity of the progression of the disease. In some embodiments, the prevention method includes selecting a subject at risk of developing multiple sclerosis. For example, it is believed that having a first-degree relative such as a parent or sibling with multiple sclerosis increases an individual's risk of developing the disease. As such, the method contemplates selecting such subject and administering at least one metabolic reprogramming agent to the subject to prevent the onset of multiple sclerosis in the subject. In some embodiments, the prevention method includes preventing the progress and/or severity of progression of multiple sclerosis. In such embodiments, a subject, for example one who has recently been diagnosed as having multiple sclerosis, can be administered the at least one metabolic reprogramming agent to prevent the disease from progressing.

In some embodiments, the condition, disease, or disorder is neuromyelitis optica. Accordingly, in an aspect the presently disclosed subject matter provides a method for the treatment of neuromyelitis optica in a subject in need thereof, the method comprising administering to the subject at least one metabolic reprogramming agent that decreases glutamine metabolism in an amount effective to treat neuromyelitis optica in the subject.

In some embodiments, the condition, disease, or disorder is pneumonitis. Accordingly, in an aspect the presently disclosed subject matter provides a method for the treatment of pneumonitis in a subject in need thereof, the method comprising administering to the subject at least one metabolic reprogramming agent that decreases glutamine metabolism in an amount effective to treat pneumonitis in the subject.

In some embodiments, the condition, disease, or disorder is pulmonary fibrosis. Accordingly, in an aspect the presently disclosed subject matter provides a method for the treatment of pulmonary fibrosis in a subject in need thereof, the method comprising administering to the subject at least one metabolic reprogramming agent that decreases glutamine metabolism in an amount effective to treat pulmonary fibrosis in the subject.

In some embodiments, the condition, disease, or disorder is not an immune disorder comprising multiple sclerosis.

B. Neurodegenerative Disorders

Aspects of the disclosure involve the use of at least one, at least two, or at least three metabolic reprogramming agents, alone, or optionally together in combination with a neuroprotective agent, a neurotrophic factor, a neuroregenerative agent, an immunosuppressant agent, and/or an anti-inflammatory agent, for the treatment of a neurodegenerative disorder. Accordingly, in some embodiments, the condition, disease, or disorder is a neurodegenerative disorder. In such embodiments, the metabolically reprogrammed cells comprise neuronal cells. Examples of neuronal cells whose activation, function, growth, proliferation, and/or survival in an abnormal, harmful, or unhealthy state depends on increased metabolic activity of at least one, at least two, or at least three metabolic pathways selected from the group consisting of glutamine metabolism, glycolysis and fatty acid synthesis include, but are not limited to, glial cells (e.g., microglial cells), and astrocytes.

A "neurodegenerative disorder" is a disease, disorder, or condition that is characterized by the progressive loss of the structure or function of neurons (e.g., degeneration or dysfunction of neurons or other neural cells). Such diseases, disorders, or conditions include, but are not limited to, glaucoma, and neurodegenerative diseases, disorders, or conditions of the nervous systems, such as or associated with amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease, Huntington's disease, Parkinson's disease, Parkinson's-plus diseases, multiple system atrophy, progressive supranuclear palsy, corticobasal degeneration, demyelinating diseases, Guillain-Barre syndrome, multiple sclerosis, Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, and epilepsy.

Other neurodegenerative diseases, disorders, or conditions of the nervous systems, such as or associated with alcoholism, Alexander's disease, Alper's disease, ataxia telangiectasia, Batten disease (also known as Spielmeyer-Vogt-Sjogren-Batten disease), Canavan disease, Cockayne syndrome, diabetic neuropathy, frontotemporal lobar degeneration, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, such as retinitis pigmentosa and associated diseases, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), Steele-Richardson-Olszewski disease, and tabes dorsalis.

Several further aspects of the presently disclosed subject matter relate to correcting defects associated with a wide range of genetic brain diseases. For example, genetic brain diseases may include but are not limited to Adrenoleukodystrophy, Agenesis of the Corpus Callosum, Aicardi Syndrome, Alpers' Disease. Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly.

In other embodiments, the neurodegenerative disease, disorder, or condition is or is associated with a disease, disorder, or condition of the nervous system selected from the group consisting of amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease, Huntington's disease, Parkinson's disease, Parkinson's-plus diseases, multiple system atrophy, progressive supranuclear palsy, corticobasal degeneration, demyelinating diseases, Guillain-Barre syndrome, multiple sclerosis, Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, epilepsy, alcoholism, Alexander's disease, Alper's disease, ataxia telangiectasia, Batten disease, Canavan disease, Cockayne syndrome, diabetic neuropathy, frontotemporal lobar degeneration, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), Steele-Richardson-Olszewski disease, and tabes dorsalis.

In yet other embodiments, the neurodegenerative disease, disorder, or condition comprises one or more conditions that are secondary to a disease, disorder, condition, or therapy having a primary effect outside of the nervous system selected from the group consisting of: peripheral neuropathy or neuralgia caused by diabetes, cancer, hepatitis, kidney dysfunction, Colorado tick fever, diphtheria, leprosy, Lyme disease, polyarteritis nodosa, rheumatoid arthritis, sarcoidosis, Sjogren syndrome, syphilis, systemic lupus erythematosus, viral encephalitis, and amyloidosis. In some embodiments, the disease, condition, or disorder is viral encephalitis.

In other embodiments, the neurodegenerative disease, disorder, or condition is associated with pain selected from the group consisting of chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neurogenic or neuropathic pain, nerve inflammation or damage, shingles, herniated disc, a torn ligament, and diabetes.

In further embodiments, the neurodegenerative disease, disorder, or condition is associated with one or more injuries to the nervous system. In particular embodiments, the one or more injuries to the nervous system is related to nerve damage caused by exposure to one or more agents selected from the group consisting of toxic compounds, heavy metals, industrial solvents, drugs, chemotherapeutic agents, dapsone, cholesterol lowering drugs, heart or blood pressure medications, and metronidazole.

In more particular embodiments, the one or more injuries to the nervous system is related to nerve damage caused by one or more conditions selected from the group consisting of burn, wound, surgery, accidents, ischemia, prolonged exposure to cold temperature, stroke, intracranial hemorrhage, and cerebral hemorrhage.

In yet other embodiments, the neurodegenerative disease, disorder, or condition comprises a psychiatric disorder. In particular embodiments, the psychiatric disorder is selected from the group consisting of schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, mood disorders, bipolar disorder, depression, stress disorder, panic disorder, agoraphobia, social phobia, post-traumatic stress disorder, anxiety disorder, and impulse control disorders.

In some embodiments, the condition, disease, or disorder is Alzheimer's Disease. Accordingly, in an aspect the presently disclosed subject matter provides a method for the treatment or prevention of Alzheimer's Disease in a subject in need thereof, the method comprising administering to the subject at least one metabolic reprogramming agent that decreases glutamine metabolism in an amount effective to treat or prevent Alzheimer's Disease in the subject.

In some embodiments, the condition, disease, or disorder is amyotrophic lateral sclerosis (ALS). Accordingly, in an aspect the presently disclosed subject matter provides a method for the treatment or prevention of amyotrophic lateral sclerosis (ALS) in a subject in need thereof, the method comprising administering to the subject at least one metabolic reprogramming agent that decreases glutamine metabolism in an amount effective to treat ALS in the subject.

In some embodiments, the condition, disease, or disorder is Parkinson's Disease. Accordingly, in an aspect the presently disclosed subject matter provides a method for the treatment or prevention of Parkinson's Disease in a subject in need thereof, the method comprising administering to the subject at least one metabolic reprogramming agent that decreases glutamine metabolism in an amount effective to treat or prevent Parkinson's Disease in the subject.

It is believed that certain of the presently disclosed metabolic reprogramming agents and compositions are particularly useful in the treatment of CNS inflammatory diseases. In particular, the data described in FIG. 23A, FIG. 23B, FIG. 23C, FIG. 30A, FIG. 30B, FIG. 30C and FIG. 31 demonstrate that certain metabolic reprogramming agents (e.g., prodrugs of glutamine analogs, e.g., DON prodrugs) effectively target and deliver DON to the brain, for example, achieving as much as a 10-fold enhanced CSF to plasma ratio at 30 minute post dosing. Accordingly, certain of the presently disclosed metabolic reprogramming agents are contemplated for use in the treatment of CNS inflammatory diseases, for example, due to their ability to selectively deliver metabolic reprogramming agents that decrease glutamine metabolism to the CNS.

In some embodiments, the condition, disease, or disorder is a pathology due to or associate with CNS inflammation due to an infection. Accordingly, in an aspect the presently disclosed subject matter provides a method for the treatment or prevention of a pathology due to CNS inflammation due to an infection in a subject in need thereof, the method comprising administering to the subject at least one metabolic reprogramming agent that decreases glutamine metabolism in an amount effective to treat or prevent the CNS inflammation due to the infection.

In some embodiments, the presently disclosed subject matter provides a method for the treatment or prevention of cerebral malaria, the method comprising administering to the subject an effective amount of at least one metabolic reprogramming agent that decreases glutamine metabolism in an amount effective to treat or prevent cerebral malaria. In some embodiments, at least one metabolic reprogramming agent treats or prevents the CNS inflammation and/or a symptom of the pathology. In some embodiments, the method includes selecting a subject with an infection (e.g., cerebral malaria, e.g., a subject who tests positive for a causative agent, e.g., infection with *Plasmodium falciparum*) for treatment with at least one metabolic reprogramming agent.

In other embodiments, the condition, disease, or disorder is a pathology due to or associated with CNS inflammation not involving an infection. Accordingly, in an aspect the presently disclosed subject matter provides a method for the treatment or prevention of a pathology due to CNS inflammation non involving an infection in a subject in need thereof, the method comprising administering to the subject at least one metabolic reprogramming agent that decreases glutamine metabolism in an amount effective to treat or prevent the CNS inflammation in the subject, thereby treating or preventing the pathology due to or associated with CNS inflammation in the subject. In some embodiments, the method includes selecting a subject having a pathology due to or associated with CNS inflammation not involving an infection. For example, a subject suffering from a pathology can be blood tested for one or more inflammatory markers (e.g., erythrocyte sedimention rate (ESR), C-reactive protein (CRP) and/or plasma viscosity (PV), and upon testing positive for one or more inflammatory markers, the subject can be tested for an infection. Subjects suffering from the pathology who test positive for inflammation and negative for an infection can be selected for treatment with at least one metabolic reprogramming agent to treat the pathology due to or associated with CNS inflammation not involving an infection. Examples of such pathologies include, but are not limited to amyotrophic lateral sclerosis, Alzheimer's Disease, and Parkinson's Disease.

In some embodiments, the condition, disease, or disorder is not a neurodegenerative disorder selected from the group consisting of Alzheimer's disease, amyotrophic lateral sclerosis (ALS), Huntington's disease, stroke, and transient ischemic brain injury.

II. Metabolic Reprogramming Agents

The presently disclosed subject matter contemplates the use of various agents in connection with the methods, uses, and compositions described herein. Certain of the methods and compositions described herein relate to the metabolic reprogramming of cells using at least one metabolic reprogramming agent described herein to treat conditions, diseases, or disorders that involve metabolically reprogrammed cells whose activation, function, growth, proliferation, and/or survival depends on increased activity of at least one, at least two, or at least three metabolic pathways selected from the group consisting of glutamine metabolism, glycolysis, and fatty acid synthesis. Aspects of the methods and compositions described herein relate to the use of at least one metabolic reprogramming agent described herein to treat conditions, diseases, or disorders that involve aberrant and/or excessive amounts of at least one, at least two, or at least three metabolic pathways selected from the group consisting of aberrant and/or excessive glutamine metabolism, aberrant and/or excessive glycolysis, or aberrant and/or excessive fatty acid synthesis.

As used herein, "metabolic reprogramming agent" generally refers to an agent that modulates the metabolic activity of at least one metabolic pathway in a cell, for example, to alter activation, function, growth, proliferation, and/or survival of the cell. As used herein, "modulate" broadly means to cause or facilitate a qualitative or quantitative change, alteration, or modification in a molecule, a process, pathway, or phenomenon of interest. Without limitation, such change may be an increase, decrease, a change in binding characteristics, or change in relative strength or activity of different components or branches of the process, pathway, or phenomenon. The term "modulator" broadly refers to any molecule or agent that causes or facilitates a qualitative or quantitative change, alteration, or modification in a process, pathway, or phenomenon of interest. As used herein, the term "modulator" comprises both inhibitors and activators of a metabolic pathway or target. For example, "modulator" comprises both inhibitors and activators of expression and/or activity of a component involved glutamine metabolism, a component involved in glycolysis, and/or a component involved in fatty acid metabolism (e.g., fatty acid synthesis or fatty acid oxidation).

As used herein, the phrase "modulation of a metabolic pathway" refers to modulation of activity of at least one component of the metabolic pathway. It is contemplated herein that modulator of the metabolic pathway can be, for example, a receptor ligand (e.g., a small molecule, an antibody, a siRNA), a ligand sequestrant (e.g., an antibody, a binding protein), a modulator of phosphorylation of a pathway component or a combination of such modulators. One of skill in the art can easily test an agent to determine if it modulates a metabolic pathway by assessing, for example, phosphorylation status of a receptor or expression or synthesis of downstream proteins or enzymes controlled by the pathway in cultured cells and comparing the results to cells not treated with a modulator. A modulator is determined to be a metabolic pathway modulator if the level of phosphorylation of the receptor or expression of or synthesis of downstream proteins or enzymes in a culture of cells is reduced by at least 20% compared to the level of phosphorylation of the receptor or expression or synthesis of downstream proteins or enzymes in cells that are cultured in the absence of the modulator; preferably the level of phosphorylation or expression or synthesis of downstream proteins or enzymes is altered by at least 30%, at least 40%, at least 50%, at least 60%, at least 70%, at least 80%, at least 90%, at least 95%, or at least 99% in the presence of a metabolic pathway modulator.

The terms "decrease", "reduced", "reduction", "decrease" or "inhibit" are all used herein generally to mean a decrease by a statistically significant amount. However, for avoidance of doubt, "reduced", "reduction", "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%, where the decrease is less than 100%. In one embodiment, the decrease includes a 100% decrease (e.g. absent level as compared to a reference sample), or any decrease between 10-100% as compared to a reference level.

The terms "increased", "increase", "enhance" or "activate" are all used herein to generally mean an increase by a statically significant amount; for the avoidance of any doubt, the terms "increased", "increase", "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

Certain methods, compositions, and agents contemplated herein modulate an immune response and/or an inflammatory response. In the contexts of decreasing an immune response or inflammation, the methods, compositions, and agents contemplated herein can decrease the immune response or inflammation by at least about 10%, 20%, 30%, 40%, 50%, 60%, 70%, 80, 90%, or as much as 100% as compared to a reference level (e.g., an objective measure of the immune response or inflammation before employing the method, composition, and/or agent). In the contexts of increasing an immune response or inflammation, the methods, compositions, and agents contemplated herein can increase the immune response or inflammation by at least about 10%, 20%, 30%, 40%, 50%, 60%, 70%, 80, 90%, or as much as 100%, at least about a 2-fold, or at least about a 3-fold, or at least about a 4-fold, or at least about a 5-fold or at least about a 10-fold increase, or any increase between 2-fold and 10-fold or greater as compared to a reference level (e.g., an objective measure of the immune response or inflammation before employing the method, composition, and/or agent).

Certain methods, compositions, and agents contemplated herein modulate neurodegeneration, dysfunction, and/or survival of neuronal cells. In the context of decreasing neurodegeneration and/or dysfunction of neuronal cells, the methods, compositions, and agents contemplated herein can decrease the neurodegeneration and/or dysfunction of neuronal cells by at least about 10%, 20%, 30%, 40%, 50%, 60%, 70%, 80, 90%, or as much as 100% as compared to a reference level (e.g., an objective measure of the neurodegeneration and/or dysfunction of neuronal cells before employing the method, composition, and/or agent). In the context of increasing or promoting survival of neuronal cells, the methods, compositions, and agents contemplated herein can increase or promote survival of neuronal cells by at least about 10%, 20%, 30%, 40%, 50%, 60%, 70%, 80, 90%, or as much as 100%, at least about a 2-fold, or at least about a 3-fold, or at least about a 4-fold, or at least about a 5-fold or at least about a 10-fold increase, or any increase between 2-fold and 10-fold or greater as compared to a reference level (e.g., an objective measure of the survival of neuronal cells before employing the method, composition, and/or agent).

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used more particularly herein in some contexts, "modulates", "modulating", and "modulation" are used interchangeably and refer to any one or a combination of a decrease in glutamine metabolism, a decrease in glycolysis, and a decrease in fatty acid synthesis. In other contexts, "modulates", "modulating", and "modulation" are used interchangeably and refer to any one or a combination of an increase in glutamine metabolism, an increase in glycolysis, and an increase in fatty acid synthesis. In certain contexts, "modulates", "modulating", and "modulation" are used interchangeably and refer to any one or a combination of an increase in oxidative phosphorylation.

Glutamine (2-amino-4-carbamoylbutanoic acid), is used by the cell for both bioenergetic and biosynthetic needs. Glutamine can be used as an amino acid for protein synthesis, as a carbon source, or as the primary nitrogen donor for multiple essential biosynthetic reactions in the cell. Once taken up by the cell, much of the glutamine is converted to glutamate by mitochondrial glutaminase. Both glutamine and glutamate contribute to anabolic metabolism; glutamine supplies nitrogen for nucleotide and hexosamine synthesis while glutamate is the nitrogen donor for the synthesis of many nonessential amino acids. Glutamate can be used to support the production of NADPH or converted to the metabolic intermediates pyruvate and α-ketoglutarate. As used herein, the term "glutamine metabolism" or "glutamine metabolic activity" refers to the chemical reactions, enzymes, and pathways involving glutamine. As used herein, the term "glutamine metabolic pathway" is a biochemical pathway that involves glutamine.

As can be envisioned by a person with skill in the art, a metabolic reprogramming agent can modulate any of the chemical reactions, enzymes and/or pathways involving glutamine. In some embodiments, at least one metabolic reprogramming agent can modulate chemical reactions, enzymes and/or pathways that do not directly involve glutamine, such as the conversion of pyruvate to acetyl CoA or the citric acid cycle, but indirectly affect any of the chemical reactions, enzymes and/or pathways involving glutamine. Certain methods, compositions, and metabolic reprogramming agents contemplated herein decrease glutamine metabolism in cells. In the context of decreasing glutamine metabolism in cells, the methods, compositions, and agents contemplated herein can decrease glutamine metabolism in cells by at least about 10%, 20%, 30%, 40%, 50%, 60%, 70%, 80, 90%, or as much as 100% as compared to a reference level (e.g., an objective measure of the glutamine metabolic activity before employing the method, composition, and/or agent).

In some embodiments, at least one metabolic reprogramming agent is a glutamine antagonist. As used herein, the term "glutamine antagonist" refers to an agent that blocks or interferes with the synthesis or use of glutamine in a cell, and preferably in a cell that is part of a living organism. When it is said that the glutamine antagonist interferes with the synthesis of glutamine, it is meant that the antagonist acts to reduce the amount or rate of glutamine synthesis to less than the amount or rate that would be experienced in the absence of the glutamine antagonist. When it is said that the glutamine antagonist interferes with the use of glutamine, it is meant that the antagonist acts to inhibit or block a metabolic pathway downstream of glutamine, that is, a pathway in which glutamine acts as a precursor of one or more non-glutamine compounds, or that the antagonist acts to deplete glutamine in a cell or an organism by reacting the glutamine to form a non-glutamine product, or by reversibly or irreversibly binding with glutamine to reduce its availability.

In some embodiments, at least one metabolic reprogramming agent of the presently disclosed subject matter can be a glutamine analog that interferes with a glutamine metabolic pathway, an antagonist that inhibits the synthesis of glutamine, a glutamine depleting enzyme, a compound that reacts with glutamine under intracellular conditions to form a non-glutamine product, an antagonist that inhibits glutamine uptake by cells, an agent that inhibits glutamine oxidation, an agent that inhibits a glutamine transporter, an agent that inhibits glutaminolysis (a series of biochemical reactions by which glutamine is lysed to glutamate, aspartate, carbon dioxide, pyruvate, lactate, alanine and/or citrate), or a glutamine binding compound that reduces the biological availability of glutamine. It should be recognized that a compound that is a useful metabolic reprogramming agent may have two or more of these characteristics. For example, a compound that is a glutamine analog that interferes with a glutamine metabolic pathway might also act as an antagonist that inhibits the synthesis of glutamine.

In some embodiments, at least one metabolic reprogramming agent can be an antagonist that inhibits the synthesis of glutamine. Examples of compounds having this activity include inhibitors of glutamine synthase (EC 6.3.1.2), such as L-methionine-DL-sulfoximine, and phosphinothricin; inhibitors of glutamate synthase (EC 1.4.1.13); inhibitors of amidophosphoribosyltransferase (EC 2.4.2.14); and inhibitors of glutamate dehydrogenase; and mixtures of any two or more of these.

In some embodiments, at least one metabolic reprogramming agent can be a glutamine depleting enzyme. Examples of such enzymes include carbamoyl-phosphate synthase (EC 6.3.5.5), glutamine-pyruvate transaminase (EC 2.6.1.15), glutamine-tRNA ligase (EC 6.1.1.18), glutaminase (EC 3.5.1.2), D-glutaminase (EC 3.5.1.35), glutamine N-acyltransferase (EC2.3.1.68), glutaminase-asparaginase (in particular glutaminase-asparaginase of *Pseudomonas* 7a and *Acinatobacter* sp.), and mixtures of any two or more of these.

In some embodiments, at least one metabolic reprogramming agent can be a compound that reacts with glutamine under intracellular conditions to form a non-glutamine product. An example of a compound having this property is phenylbutyrate (See Darmaun et al., Phenylbutyrate-induce glutamine depletion in humans: effect on leucine metabolism, pp. E801-E807, in Glutamine Depletion and Protein Catabolism, Am. Physiol. Soc. (1998)). Another example of a glutamine antagonist having this characteristic is phenylacetate (See, U.S. Pat. No. 6,362,226).

In some embodiments, at least one metabolic reprogramming agent can be an antagonist that inhibits glutamine uptake by cells. Examples of compounds having this property include alpha-methylaminoisobutyric acid (inhibits GynT plasma membrane glutamine transporter; See, Varoqui et al., *J. Biol. Chem.*, 275(6):4049-4054 (2000), wortmannin, and LY-294002 (inhibits hepatic glutamine transporter; See, Pawlik et al., *Am. J. Physiol. Gastrointest. Liver Physiol.*, 278:G532-G541 (2000)).

In some embodiments, at least one metabolic reprogramming agent can be a glutamine binding compound that reduces the biological availability of glutamine.

In some embodiments, at least one metabolic reprogramming agent can be a glutamine analog that interferes with a glutamine metabolic pathway. Examples of compounds that can act in this manner include acivicin (L-(alpha S,5S)-alpha-amino-3-chloro-4,5-dihydro-5-isoxazoleacetic acid), DON (6-diazo-5-oxo-L-norleucine), azaserine, azotomycin, chloroketone (L-2-amino-4-oxo-5-chloropentanoic acid), $N^3$-(4-methoxyfumaroyl)-L-2,3-diaminopropanoic acid (FMDP) (inactivates glucosamine-6-phosphate synthase (EC 2.6.1.16), See, Zgòdka et al., *Microbiology*, 147:1955-1959 (2001)), (3S,4R)-3,4-dimethyl-L-glutamine, (3S,4R)-3,4-dimethyl-L-pyroglutamic acid (See, Acevedo et al., *Tetrahedron.*, 57:6353-6359 (2001)), 1,5-N,N'-disubstituted-2-(substituted benzenesulphonyl) glutamamides (See, Srikanth et al., *Bioorganic and Medicinal Chemistry*, (2002)), or a mixture of any two or more of these. In some embodiments, at least one metabolic reprogramming agent is selected from the group consisting of acivicin (L-(alpha S, 5S)-alpha-amino-3-chloro-4,5-dihydro-5-isoxazoleacetic acid), azaserine, 6-diazo-5-oxo-norleucine (DON), and 5-diazo-4-oxo-L-norvaline (L-DONV).

In some embodiments, at least one metabolic reprogramming agent is a prodrug of a glutamine analog that interferes with a glutamine metabolic pathway. In some embodiments, at least one metabolic reprogramming agent is a prodrug of acivicin (L-(alpha S, 5S)-alpha-amino-3-chloro-4,5-dihydro-5-isoxazoleacetic acid), azaserine, 6-diazo-5-oxo-norleucine (DON), and 5-diazo-4-oxo-L-norvaline (L-DONV). Suitable exemplary prodrugs of acivicin, azaserine, DON, and L-DONV can be found in "Prodrugs of Glutamine Analogs" (U.S. application Ser. No. 62/199,566, filed Jul. 31, 2015, and herein incorporated by reference in its entirety).

In some aspects, a prodrug of a glutamine antagonist, or a pharmaceutically acceptable salt or ester thereof has a structure of formula (I):

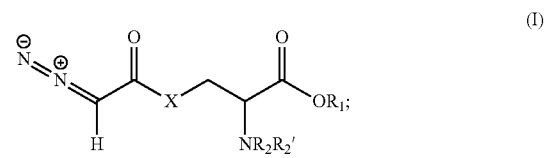

wherein: X is selected from the group consisting of a bond, —O—, and —$(CH_2)_n$—, wherein n is an integer selected from the group consisting of 1, 2, 3, 4, 5, 6, 7, and 8; $R_1$ is selected from the group consisting of H and a first prodrug-forming moiety capable of forming a salt or an ester; and $R_2$ is H or a second prodrug-forming moiety capable of forming an amide linkage, a carbamate linkage, a phosphoramidate linkage or a phosphorodiamidate linkage with the nitrogen adjacent to $R_2$; $R_2'$ is selected from the group consisting of H, $C_1$-$C_6$ alkyl, substituted $C_1$-$C_6$ alkyl, or $R_2$ and $R_2'$ together form a ring structure comprising —C(=O)-G-C(=O)—, wherein G is selected from the group consisting of $C_1$-$C_8$ alkylene, $C_1$-$C_8$ heteroalkylene, $C_5$-$C_8$ cycloalkylene, $C_6$-$C_{12}$ arylene, $C_5$-$C_{14}$ heteroarylene, bivalent $C_4$-$C_{10}$ heterocycle, each of which can be optionally substituted; or $R_1$ and $R_2'$ together form a 4- to 6-membered heterocylic ring comprising the oxygen atom adjacent to $R_1$ and the nitrogen atom adjacent to $R_2'$; provided that the compound has at least one prodrug-forming moiety selected from the group consisting of the first and the second prodrug-forming moieties.

As used herein, the term "amide linkage" comprises a structure represented by the formula:

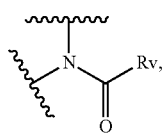

wherein $R_v$ is selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "carbamate linkage" comprises a structure represented by the formula:

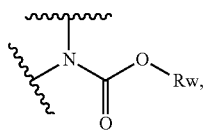

wherein $R_w$ is selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "phosphoramidate linkage" comprises a structure represented by the formula:

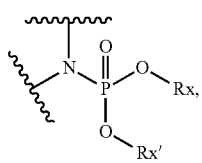

wherein $R_x$ and $R_x'$ are each independently selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "phosphorodiamidate linkage" comprises a structure represented by the formula:

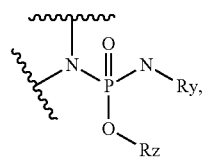

wherein $R_y$ and $R_z$ are each independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —(CR_3R_4)$_m$—Z, —(CR_3R_4)$_m$-Q-Z, aryl, substituted aryl, alkylamine, substituted alkylamine, heteroaryl, substituted heteroaryl, and

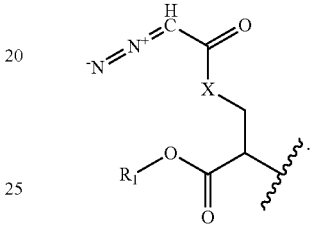

In some embodiments, X is —CH$_2$—, and n is 1.

In other embodiments, X is –0-. In some embodiments, the prodrug compound has both the first prodrug-forming moiety and the second prodrug-forming moiety. In some embodiments, the glutamine analog is a glutamine antagonist, i.e., the prodrug is a prodrug of a glutamine analog that antagonizes a glutamine pathway. Exemplary glutamine antagonists include, without limitation, 6-diazo-5-oxo-norleucine (DON), and aza-serine, and 5-diazo-4-oxo-L-norvaline (L-DONV).

In some embodiments, the presently disclosed subject matter provides a prodrug of DON. In some embodiments, the prodrug of DON has a structure of formula (I). In some embodiments, the presently disclosed subject matter provides a prodrug of L-DONV. In some embodiments, the prodrug of L-DONV has a structure of formula (I). In some embodiments, the presently disclosed subject matter provides a prodrug of azaserine. In some embodiments, the prodrug of azaserine has a structure of formula (I).

In some embodiments, $R_1$ of formula (I) comprises a residue PRO$_1$ of the prodrug-forming moiety, which, together with a basic moiety and the terminal hydroxyl group forms a salt.

In some embodiments, $R_1$ of formula (I) comprises a residue PRO$_1$ of the prodrug-forming moiety, which, together with an alkyl group and the oxygen of an adjoining hydroxyl group forms an ester.

In some embodiments, $R_1$ of formula (I) comprises a residue PRO$_1$ of the prodrug-forming moiety, which, together with an alkyl group and the nitrogen adjoining the $R_2'$ group, forms an azlactone or an oxazolidone.

In some embodiments, $R_1$ of formula (I) is selected from the group consisting of H, alkyl, substituted alkyl, cycloalkyl, substituted cycloalkyl, alkenyl, substituted alkenyl, alkynyl, substituted alkynyl, cycloalkenyl, substituted cycloalkenyl, tri(hydrocarbyl)ammonium, and tetra(hydrocarbyl)ammonium. Preferred alkyl group, cycloalkyl group, alkenyl group, alkynyl group, and cycloalkenyl group substituents include alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl.

In some embodiments, $R_1$ of formula (I) is not H. In some embodiments, $R_1$ of formula (I) is not H when $R_2$ and $R_2'$ are H. In some embodiments, $R_2$ and $R_2'$ of formula (I) are each H when and $R_1$ is not H.

In some embodiments, $R_1$ of formula (I) is selected from the group consisting of a $C_{1-6}$ straight-chain alkyl, a substituted $C_{1-6}$ straight-chain alkyl, a $C_{1-6}$ branched alkyl, a substituted $C_{1-6}$ branched alkyl, tri($C_1$-$C_8$-alkyl)ammonium, tetra($C_1$-$C_8$-alkyl)ammonium, triphenylammonium, tri(hydroxy-$C_1$-$C_8$-alkyl)ammonium, and tetra(hydroxy-$C_1$-$C_8$-alkyl)ammonium.

In some embodiments, $R_1$ of formula (I) is selected from the group consisting of methyl, ethyl, isopropyl, cyclopentyl, cyclohexyl, trimethylammonium, triethylammonium, tri(hydroxyethyl)ammonium, tripropylammonium, and tri(hydroxypropyl)ammonium. In some embodiments, $R_1$ of formula (I) is methyl. In some embodiments, $R_1$ of formula (I) is ethyl. In some embodiments, $R_1$ of formula (I) is isopropyl.

In some embodiments, $R_2$ of formula (I) comprises a residue $PRO_2$ of the second prodrug-forming moiety, which, together with a carbonyl, oxy carbonyl, or phosphonyl group and the nitrogen of the adjoining NH, forms an amide, a carbamate, phosphoramidate, or phosphorodiamidate linkage.

In some embodiments, $R_2$ of formula (I) comprises a moiety selected from the group consisting of an amino acid, an N-substituted amino acid, a peptide, a substituted peptide, a monocyclic ring, a substituted monocyclic ring, a bicyclic ring, a substituted bicyclic ring, a purine nucleoside, a substituted purine nucleoside, a pyrimidine nucleoside, and a substituted pyrimidine nucleoside.

In some embodiments, $R_2$ of formula (I) is selected from the group consisting of H, alkyl, —C(=O)—Ar, —C(=O)—Y—(CR$_3$R$_4$)$_m$—Ar, —C(=O)—Y—(CR$_3$R$_4$)$_m$—NR$_5$R$_6$, —P(=O)(OR$_7$)$_n$(NHR$_9$)$_o$, —C(=O)—Y—(CR$_3$R$_4$)$_m$—Ar—O—C(=O)—R$_8$, —C(=O)—Y—(CR$_3$R$_4$)$_m$—Ar—O—R$_8$, —C(=O)—O—(CR$_3$R$_4$)$_m$—O—C(=O)—R$_{10}$, —C(=O)—O—R$_9$, —C(=O)—Y—(CR$_3$R$_4$)$_m$—Ar—O—C(=O)—Ar, and —C(=O)—Y—(CR$_3$R$_4$)$_m$—Ar—NR$_5$R$_6$; wherein: Y is —O— or a bond; m is an integer selected from the group consisting of 0, 1, 2, 3, 4, 5, 6, 7, and 8; each n and o is an integer from 0 to 2 provided that the sum of n and o is 2; $R_3$ and $R_4$ is independently H, $C_1$-$C_6$ alkyl or substituted $C_1$-$C_6$ alkyl, aryl or substituted aryl, —(CR$_3$R$_4$)$_m$—NR$_5$R$_6$, or

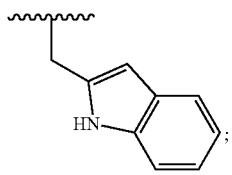 [SMILES: *Cc1cc2ccccc2[nH]1]

each $R_5$ and $R_6$ is independently H, alkyl, —C(=O)—(CR$_3$R$_4$)$_m$H, —C(=O)—(NR$_5$R$_6$), or —C(=O)—(CR$_3$R$_4$)$_m$—NR$_5$R$_6$; each $R_7$ is independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —(CR$_3$R$_4$)$_m$—Z, —(CR$_3$R$_4$)$_m$-Q-Z, wherein Q is a monosaccharide, aryl, substituted aryl, heteroaryl, substituted heteroaryl, and wherein Z is

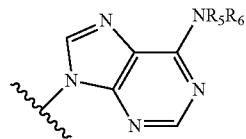

or wherein $R_7$ together with the oxygen atom to which it is attached forms a purine or pyrimidine nucleoside; each $R_9$ is independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —(CR$_3$R$_4$)$_m$—Z, aryl, substituted aryl, heteroaryl, substituted heteroaryl, and

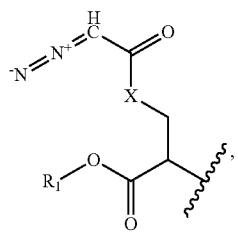

wherein $R_1$ and X are as defined above, provided that $R_1$ is not H; each $R_8$ is independently alkyl, substituted alkyl, cycloalkyl, substituted cycloalkyl, monosaccharide, acylated monosaccharide, aryl, substituted aryl, heteroaryl, substituted heteroaryl; each $R_{10}$ is independently alkyl, substituted alkyl, cycloalkyl, substituted cycloalkyl, monosaccharide, acylated monosaccharide, aryl, substituted aryl, heteroaryl, substituted heteroaryl; and Ar is aryl, substituted aryl, heteroaryl, or substituted heteroaryl. It should be appreciated that in addition to substitutions on the amino group of Z, one or more substitutions $R_3$, $R_4$, $R_5$, and/or $R_6$ can be made to the 5 or 6 membered rings of Z.

The disclosure also provides the following particular embodiments numbered Embodiments I-XLVII.

Embodiment I. A method for treating a condition, disease, or disorder in a subject that involves;

(i) metabolically reprogrammed cells whose activation, function, growth, proliferation, or survival depends on increased activity of at least one metabolic pathway selected from the group consisting of glutamine metabolism, glycolysis, and fatty acid synthesis; and (ii) at least one of:
(a) aberrant glutamine metabolism;
(b) aberrant glycolysis; or
(c) aberrant fatty acid synthesis, the method comprising administering to the subject in need thereof a compound, or a pharmaceutically acceptable salt thereof, having formula (I):

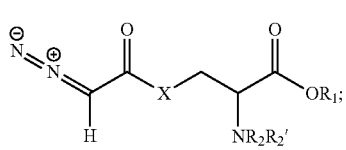

(I)

wherein:

X is selected from the group consisting of a bond, —O—, and —(CH$_2$)$_n$—, wherein n is an integer selected from the group consisting of 1, 2, 3, 4, 5, 6, 7, and 8;

R$_1$ is selected from the group consisting of C$_{1-6}$ alkyl and substituted C$_{1-6}$ alkyl; R$_2$ is an amino acid, an N-substituted amino acid, or —C(=O)—O—(CR$_3$R$_4$)$_m$—O—C(=O)—R$_{10}$;

R$_2$' is selected from the group consisting of H, C$_1$-C$_6$ alkyl, and substituted C$_1$-C$_6$ alkyl;

each R$_3$ and R$_4$ are independently H, C$_1$-C$_6$ alkyl, substituted C$_1$-C$_6$ alkyl, aryl, substituted aryl, —(CR$_3$R$_4$)$_m$—NR$_5$R$_6$, or

[structure: indolylmethyl group]

m is an integer selected from the group consisting of 1, 2, 3, 4, 5, 6, 7, and 8;

R$_5$ and R$_6$ are independently H or alkyl; and

R$_{10}$ is selected from the group consisting of alkyl, substituted alkyl, cycloalkyl, substituted cycloalkyl, monosaccharide, acylated monosaccharide, aryl, substituted aryl, heteroaryl, and substituted heteroaryl.

Embodiment II. The method of Embodiment I, wherein X is —CH$_2$—.

Embodiment III. The method of Embodiment I, wherein X is —O—.

Embodiment IV. The method of Embodiment I, wherein R$_1$ is selected from the group consisting of methyl, ethyl, isopropyl, cyclopentyl, cyclohexyl, trimethylammonium, triethylammonium, tri(hydroxyethyl)ammonium, tripropylammonium, and tri(hydroxypropyl)ammonium.

Embodiment V. The method of Embodiment I, wherein R$_2$ is selected from the group consisting of —C(=O)—Y—(CR$_3$R$_4$)$_m$—NR$_5$R$_6$, and —C(=O)—O—(CR$_3$R$_4$)$_m$—O—C(=O)—R$_{10}$; wherein:

Y is —O— or a bond;

m is an integer selected from the group consisting of 1, 2, 3, 4, 5, 6, 7, and 8; and each R$_3$ and R$_4$ is independently H, C$_1$-C$_6$ alkyl or substituted C$_1$-C$_6$ alkyl, aryl or substituted aryl;

R$_{10}$ is selected from the group consisting of alkyl, substituted alkyl, cycloalkyl, substituted cycloalkyl, aryl, substituted aryl, heteroaryl, and substituted heteroaryl.

Embodiment VI. The method of Embodiment V, wherein:

Y is a bond;

m is 1;

R$_5$ and R$_6$ are each H.

Embodiment VII. The method of Embodiment I, wherein R$_2$ is an amino acid.

Embodiment VIII. The method of Embodiment VII, wherein the amino acid is tryptophan.

Embodiment IX. The method of Embodiment I, wherein R$_2$ is a N-acyl amino acid.

Embodiment X. The method of Embodiment IX, wherein the amino acid is tryptophan.

Embodiment XI. The method of Embodiment I, wherein the compound having formula (I) is a compound having formula (IIA):

[structure (IIA)]

wherein:

R$_1$ is selected from the group consisting of H and C$_{1-6}$ alkyl;

R$_{11}$ is selected from the group consisting of H, methyl, isopropyl, sec-butyl, CH$_2$CH(CH$_3$)$_2$, benzyl, p-hydroxybenzyl CH$_2$OH, CH(OH)CH$_3$, CH$_2$-3-indoyl, CH$_2$COOH, CH$_2$CH$_2$COOH, —CH$_2$C(O)NH$_2$, CH$_2$CH$_2$C(O)NH$_2$, CH$_2$SH, CH$_2$CH$_2$SCH$_3$, (CH$_2$)$_4$NH$_2$, (CH$_2$)$_3$NHC(=NH)NH$_2$, and CH$_2$-3-imidazoyl;

R$_{12}$ is selected from the group consisting of H, C$_{1-4}$ alkyl, and —C(=O)R$_{13}$; and R$_{13}$ is C$_{1-4}$ alkyl.

Embodiment XII. The method of Embodiment I, wherein the compound having formula (I) is a compound having formula (IIB):

[structure (IIB)]

wherein:

R$_1$ is selected from the group consisting of H and C$_{1-6}$ alkyl;

R$_{11}$ is selected from the group consisting of H, methyl, isopropyl, sec-butyl, CH$_2$CH(CH$_3$)$_2$, benzyl, p-hydroxybenzyl CH$_2$OH, CH(OH)CH$_3$, CH$_2$-3-indoyl, CH$_2$COOH, CH$_2$CH$_2$COOH, —CH$_2$C(O)NH$_2$, CH$_2$CH$_2$C(O)NH$_2$, CH$_2$SH, CH$_2$CH$_2$SCH$_3$, (CH$_2$)$_4$NH$_2$, (CH$_2$)$_3$NHC(=NH)NH$_2$, and CH$_2$-3-imidazoyl;

R$_{12}$ is selected from the group consisting of H, C$_{1-4}$ alkyl, and —C(=O)R$_{13}$; and R$_{13}$ is C$_{1-4}$ alkyl.

Embodiment XIII. The method of Embodiments XI or XII, wherein:

R$_1$ is C$_{1-4}$ alkyl;

R$_{11}$ is selected from the group consisting of isopropyl, sec-butyl, CH$_2$CH(CH$_3$)$_2$, and CH$_2$-3-indoyl;

R$_{12}$ is selected from the group consisting of H and —C(=O)R$_{13}$; and

R$_{13}$ is C$_{1-4}$ alkyl.

Embodiment XIV. The method of Embodiment I, wherein the compound of formula (I) is selected from the group consisting of:

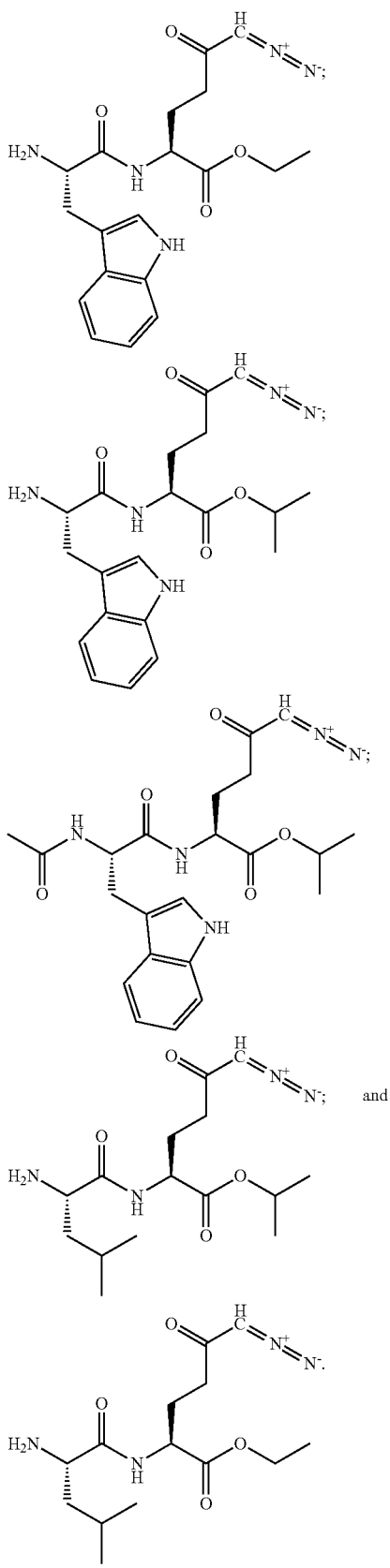

Embodiment XV. The method of Embodiment XIV, wherein the compound is:

Embodiment XVI. The method of Embodiment I, wherein the compound having formula (I) is a compound having formula (III):

(III)

wherein:

$R_1$ is selected from the group consisting of H and $C_{1-6}$ alkyl;

$R_3$ and $R_4$ are independently selected from the group consisting of H, $C_1$-$C_6$ alkyl, substituted $C_1$-$C_6$ alkyl, aryl, and substituted aryl; and $R_{10}$ is $C_{1-6}$ alkyl.

Embodiment XVII. The method of Embodiment XVII, wherein:

$R_3$ is selected from the group consisting of $C_1$-$C_6$ alkyl, substituted $C_1$-$C_6$ alkyl, aryl, and substituted aryl; and $R_4$ is H.

Embodiment XVIII. The method of Embodiment XVII, wherein:

$R_3$ is H; and $R_4$ is selected from the group consisting of $C_1$-$C_6$ alkyl, substituted $C_1$-$C_6$ alkyl, aryl, and substituted aryl.

Embodiment XIX. The method of Embodiment I, wherein the compound of formula (I) is selected from the group consisting of:

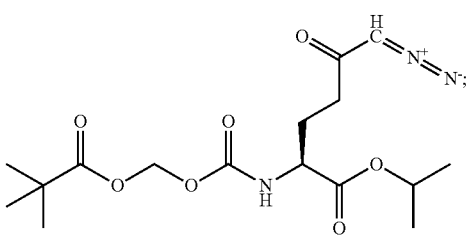

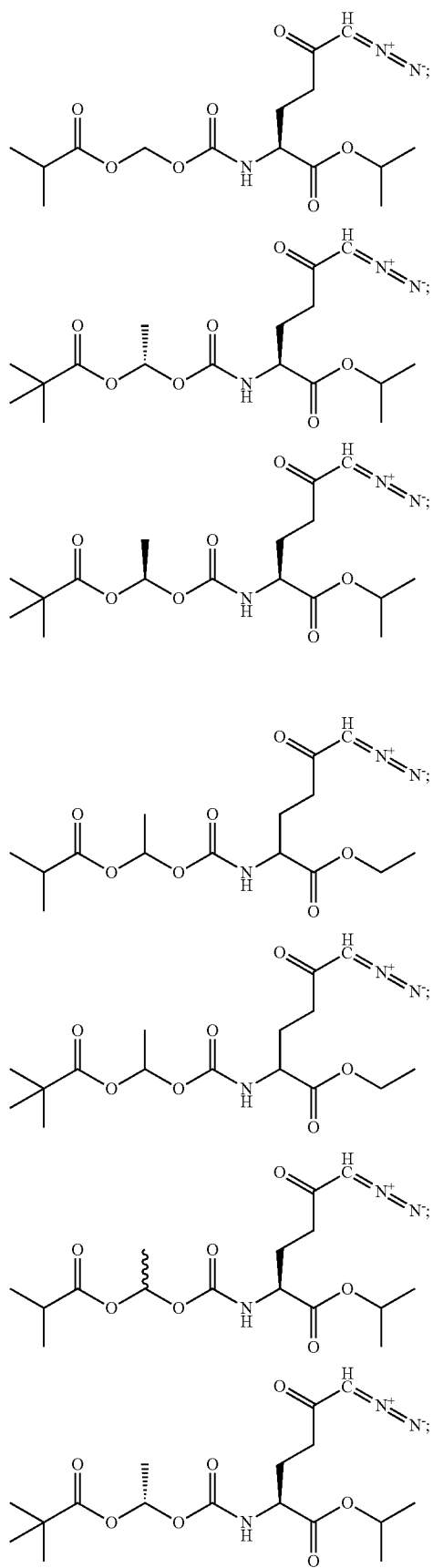
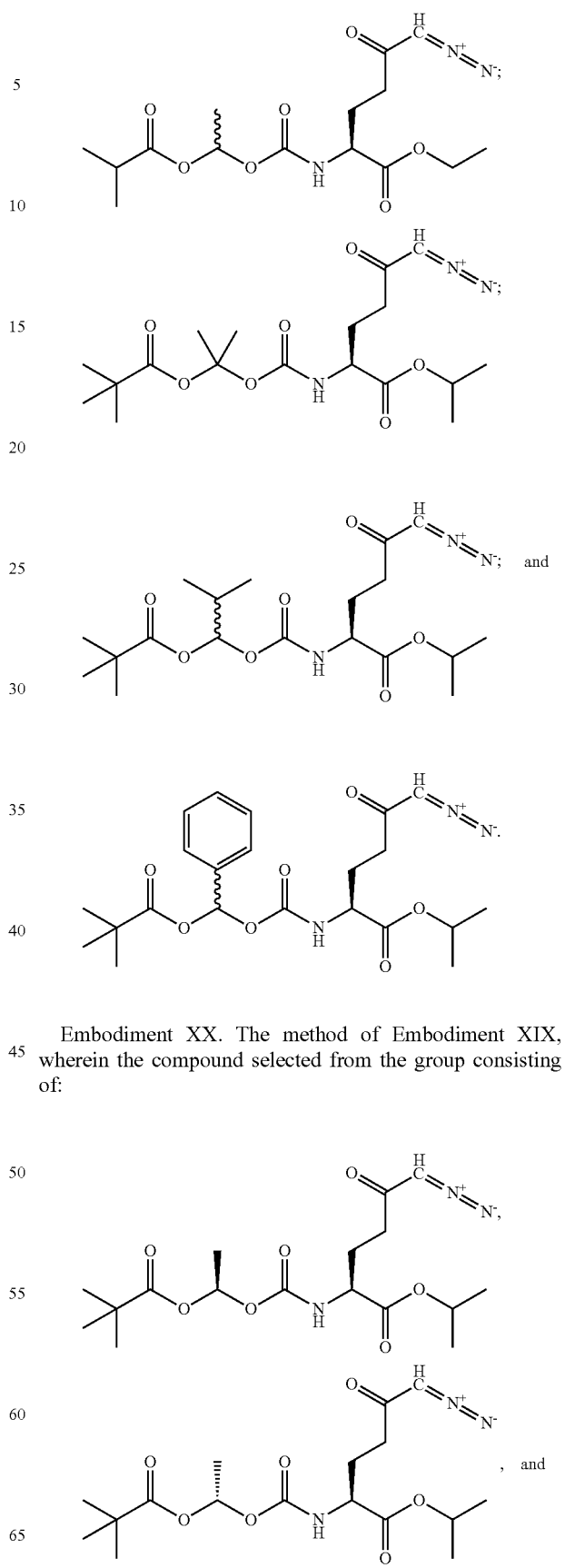
Embodiment XX. The method of Embodiment XIX, wherein the compound selected from the group consisting of:

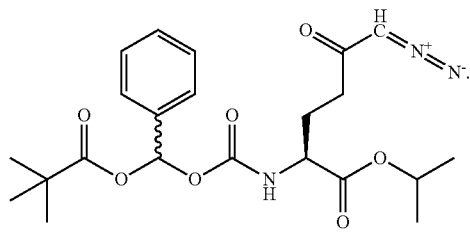

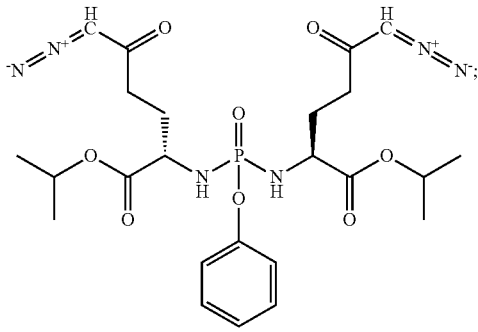

Embodiment XXI. A method for treating a condition, disease, or disorder in a subject that involves;

(i) metabolically reprogrammed cells whose activation, function, growth, proliferation, and/or survival depends on increased activity of at least one metabolic pathway selected from the group consisting of glutamine metabolism, glycolysis, and fatty acid synthesis; or (ii) at least one of:

(a) aberrant glutamine metabolism;

(b) aberrant glycolysis; or (c) aberrant fatty acid synthesis, the method comprising administering to the subject in need thereof a compound, or a pharmaceutically acceptable salt thereof, selected from the group consisting of:

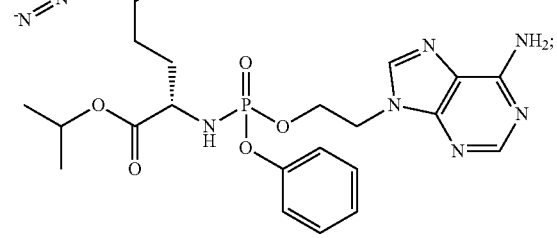

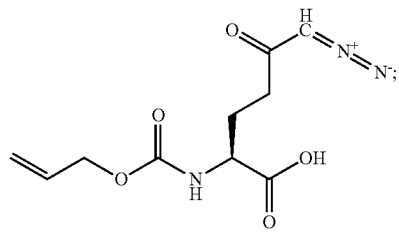

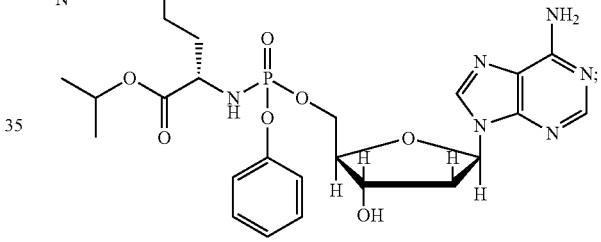

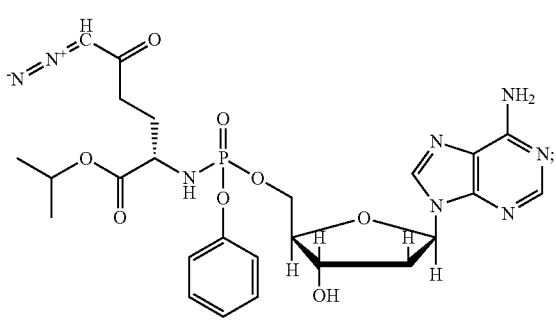

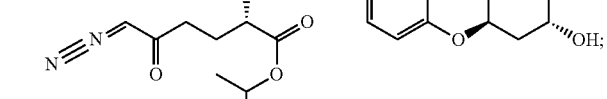

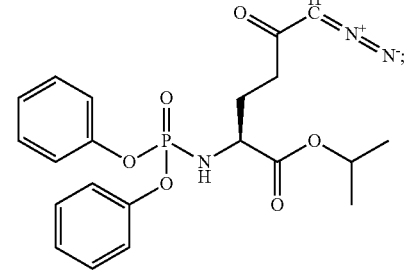

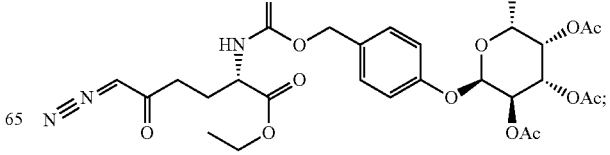

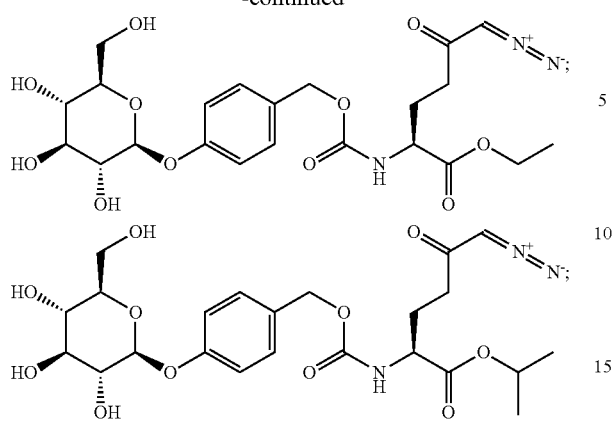
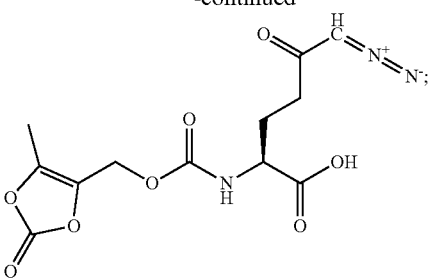

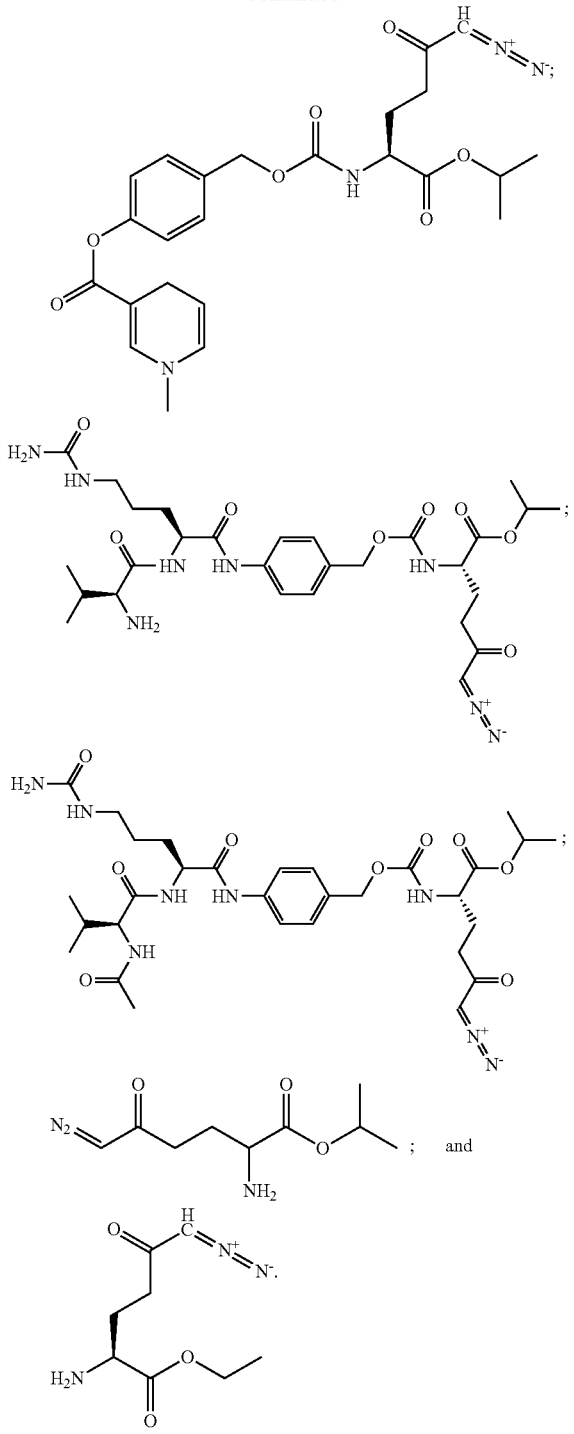

Embodiment XXII. The method of any one of Embodiments I-XXI further comprising simultaneously or sequentially administering a therapeutically effective amount of:

(ii) at least one metabolic reprogramming agent decreases glycolysis; or (ii) at least one metabolic reprogramming agent increases fatty acid oxidation; or (iii) least one metabolic reprogramming agent decreases glycolysis and at least one metabolic reprogramming agent increases fatty acid oxidation.

Embodiment XXIII. The method of Embodiment XXII, wherein the at least one metabolic reprogramming agent that decreases glycolysis is:

(i) a glucose analog that inhibits hexokinase; or (ii) 2-deoxy-D-glucose (2-DG); and combinations thereof Embodiment XXIV. The method of Embodiments XXII or XXIII, wherein the at least one metabolic reprogramming agent that increases fatty acid oxidation is:

(i) an activator of 5' AMP-activated protein kinase (AMPK) activity; or (ii) metformin; and combinations thereof.

Embodiment XXV. The method of any one of Embodiments I-XXIV, wherein the condition, disease, or disorder is selected from the group consisting of an immune disorder, transplant rejection, graft versus host disease, inflammation, CNS or brain inflammation, a pathology due to or associated with CNS inflammation due to an infection, a pathology due to or associated with CNS inflammation not involving an infection, and a neurodegenerative disorder.

Embodiment XXVI. The method of any one of Embodiments I-XXIV, wherein the condition, disease, or disorder is selected from the group consisting of acute respiratory distress syndrome (ARDS), allograft rejection during cell, tissue, or organ transplantation, Alzheimer's Disease, amyotrophic lateral sclerotis (ALS), arthritis, asthma, cerebral malaria, lupus, neuromyelitis optica, Parkinson's Disease, pneumonitis, and pulmonary fibrosis.

Embodiment XXVII. The method of any one of Embodiments I-XXVI, wherein the metabolically reprogrammed cells are selected from the group consisting of immune cells and neuronal cells.

Embodiment XXVIII. A method for treating an immune disorder, transplant rejection, graft versus host disease, inflammation, CNS or brain inflammation, a pathology due to or associated with CNS inflammation due to an infection, a pathology due to or associated with CNS inflammation not involving an infection, a neurodegenerative disorder, acute respiratory distress syndrome (ARDS), allograft rejection during cell, tissue, or organ transplantation, Alzheimer's Disease, amyotrophic lateral sclerotis (ALS), arthritis, asthma, cerebral malaria, lupus, neuromyelitis optica, Parkinson's Disease, pneumonitis, or pulmonary fibrosis in a subject, the method comprising administering to the subject in need thereof a compound, or a pharmaceutically acceptable salt thereof, having formula (I):

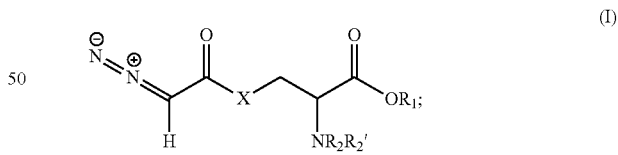

wherein:

X is selected from the group consisting of a bond, —O—, and —$(CH_2)_n$—, wherein n is an integer selected from the group consisting of 1, 2, 3, 4, 5, 6, 7, and 8;

$R_1$ is selected from the group consisting of $C_{1-6}$ alkyl and substituted $C_{1-6}$ alkyl;

$R_2$ is an amino acid, an N-substituted amino acid, or —C(=O)—O—$(CR_3R_4)_m$—O—C(=O)—$R_{10}$;

$R_2'$ is selected from the group consisting of H, $C_1$-$C_6$ alkyl, and substituted $C_1$-$C_6$ alkyl;

each $R_3$ and $R_4$ are independently H, $C_1$-$C_6$ alkyl, substituted $C_1$-$C_6$ alkyl, aryl, substituted aryl, —$(CR_3R_4)_m$—$NR_5R_6$, or

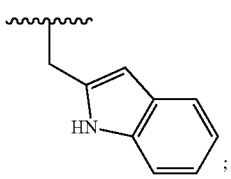 [SMILES: *Cc1cc2ccccc2[nH]1]

m is an integer selected from the group consisting of 1, 2, 3, 4, 5, 6, 7, and 8;

$R_5$ and $R_6$ are independently H or alkyl; and $R_{10}$ is selected from the group consisting of alkyl, substituted alkyl, cycloalkyl, substituted cycloalkyl, monosaccharide, acylated monosaccharide, aryl, substituted aryl, heteroaryl, and substituted heteroaryl.

Embodiment XXIX. The method of Embodiment XXVIII, wherein X is —CH$_2$—.

Embodiment XXX. The method of Embodiment XXVIII, wherein X is —O—.

Embodiment XXXI. The method of Embodiment I, wherein $R_1$ is selected from the group consisting of methyl, ethyl, isopropyl, cyclopentyl, cyclohexyl, trimethylammonium, triethylammonium, tri(hydroxyethyl)ammonium, tripropylammonium, and tri(hydroxypropyl)ammonium.

Embodiment XXXII. The method of Embodiment XXVIII, wherein $R_2$ is selected from the group consisting of —C(=O)—Y—(CR$_3$R$_4$)$_m$—NR$_5$R$_6$, and —C(=O)—O—(CR$_3$R$_4$)$_m$—O—C(=O)—R$_{10}$;

wherein:

Y is —O— or a bond;

m is an integer selected from the group consisting of 1, 2, 3, 4, 5, 6, 7, and 8; and each $R_3$ and $R_4$ is independently H, $C_1$-$C_6$ alkyl or substituted $C_1$-$C_6$ alkyl, aryl or substituted aryl;

$R_{10}$ is selected from the group consisting of alkyl, substituted alkyl, cycloalkyl, substituted cycloalkyl, aryl, substituted aryl, heteroaryl, and substituted heteroaryl.

Embodiment XXXIII. The method of Embodiment XXXII, wherein:

Y is a bond;

m is 1;

$R_5$ and $R_6$ are each H.

Embodiment XXXIV. The method of Embodiment XXVIII, wherein $R_2$ is an amino acid.

Embodiment XXXV. The method of Embodiment XXXIV, wherein the amino acid is tryptophan.

Embodiment XXXVI. The method of Embodiment XXVIII, wherein $R_2$ is a N-acyl amino acid.

Embodiment XXXVII. The method of Embodiment XXXVI, wherein the amino acid is tryptophan.

Embodiment XXXVIII. The method of Embodiment XXVIII, wherein the compound having formula (I) is a compound having formula (IIA):

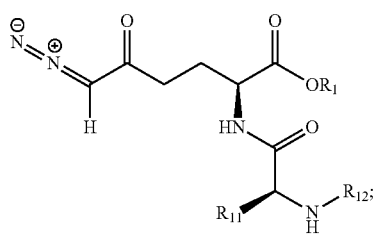

(IIA)

wherein:

$R_1$ is selected from the group consisting of H and $C_{1-6}$ alkyl;

$R_{11}$ is selected from the group consisting of H, methyl, isopropyl, sec-butyl, CH$_2$CH(CH$_3$)$_2$, benzyl, p-hydroxybenzyl, CH$_2$OH, CH(OH)CH$_3$, CH$_2$-3-indoyl, CH$_2$COOH, CH$_2$CH$_2$COOH, —CH$_2$C(O)NH$_2$, CH$_2$CH$_2$C(O)NH$_2$, CH$_2$SH, CH$_2$CH$_2$SCH$_3$, (CH$_2$)$_4$NH$_2$, (CH$_2$)$_3$NHC(=NH)NH$_2$, and CH$_2$-3-imidazoyl;

$R_{12}$ is selected from the group consisting of H, $C_{1-4}$ alkyl, and —C(=O)R$_{13}$; and $R_{13}$ is $C_{1-4}$ alkyl.

Embodiment XXXIX. The method of Embodiment XXVIII, wherein the compound having formula (I) is a compound having formula (IIB):

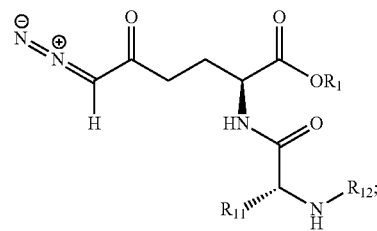

(IIB)

wherein:

$R_1$ is selected from the group consisting of H and $C_{1-6}$ alkyl;

$R_{11}$ is selected from the group consisting of H, methyl, isopropyl, sec-butyl, CH$_2$CH(CH$_3$)$_2$, benzyl, p-hydroxybenzyl, CH$_2$OH, CH(OH)CH$_3$, CH$_2$-3-indoyl, CH$_2$COOH, CH$_2$CH$_2$COOH, —CH$_2$C(O)NH$_2$, CH$_2$CH$_2$C(O)NH$_2$, CH$_2$SH, CH$_2$CH$_2$SCH$_3$, (CH$_2$)$_4$NH$_2$, (CH$_2$)$_3$NHC(=NH)NH$_2$, and CH$_2$-3-imidazoyl;

$R_{12}$ is selected from the group consisting of H, $C_{1-4}$ alkyl, and —C(=O)R$_{13}$; and $R_{13}$ is $C_{1-4}$ alkyl.

Embodiment XIII. The method of Embodiments XI or XII, wherein:

$R_1$ is $C_{1-4}$ alkyl;

$R_{11}$ is selected from the group consisting of isopropyl, sec-butyl, CH$_2$CH(CH$_3$)$_2$, and CH$_2$-3-indoyl;

$R_{12}$ is selected from the group consisting of H and —C(=O)R$_{13}$; and $R_{13}$ is $C_{1-4}$ alkyl.

Embodiment XL. The method of Embodiment XXVIII, wherein the compound of formula (I) is selected from the group consisting of:

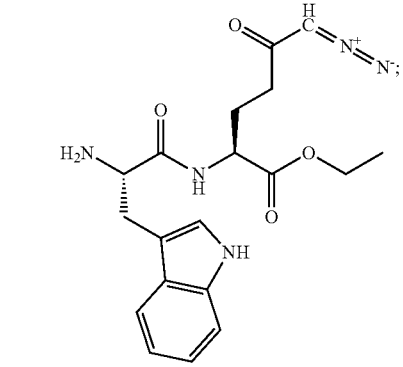

-continued

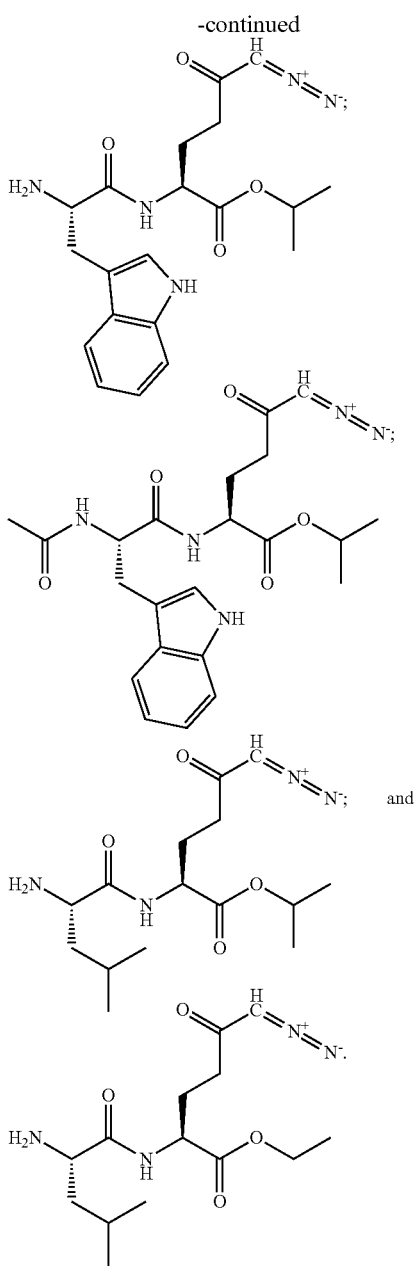

Embodiment XLI. The method of Embodiment XL, wherein the compound is:

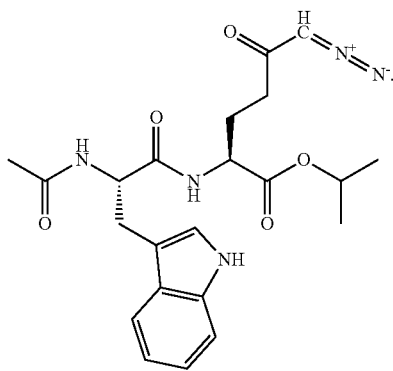

Embodiment XLII. The method of Embodiment XXVIII, wherein the compound having formula (I) is a compound having formula

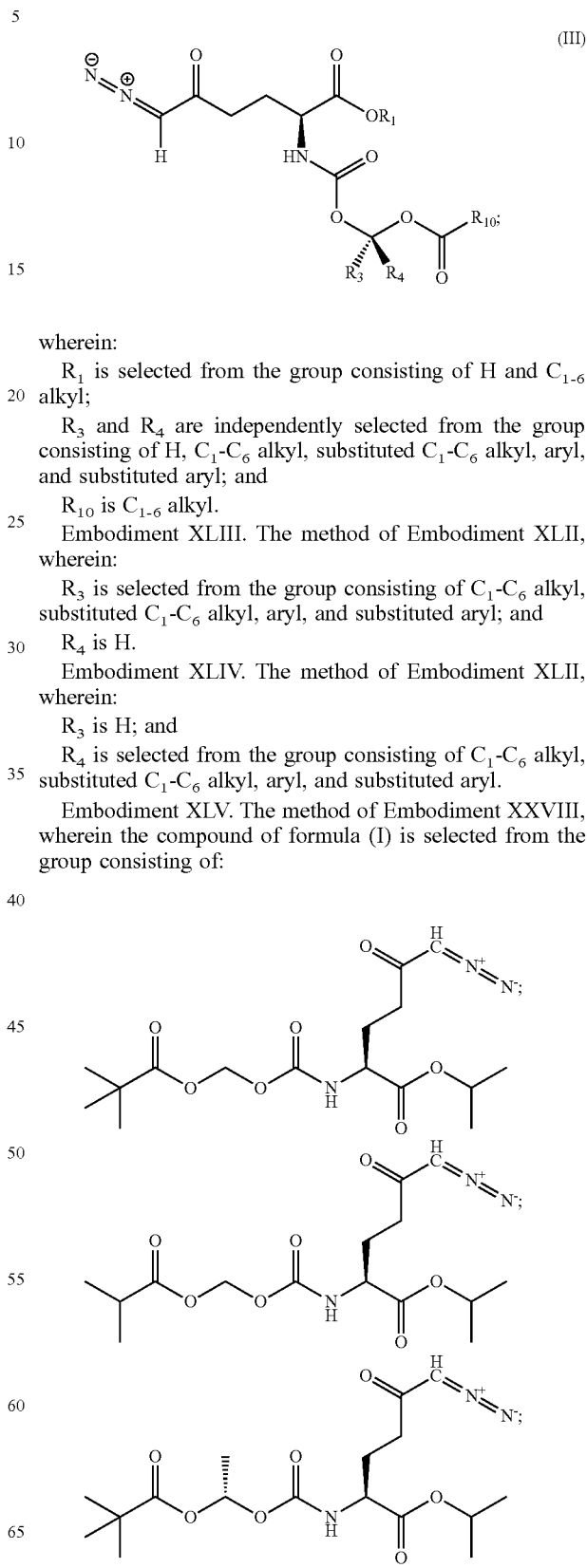

wherein:

$R_1$ is selected from the group consisting of H and $C_{1-6}$ alkyl;

$R_3$ and $R_4$ are independently selected from the group consisting of H, $C_1$-$C_6$ alkyl, substituted $C_1$-$C_6$ alkyl, aryl, and substituted aryl; and $R_{10}$ is $C_{1-6}$ alkyl.

Embodiment XLIII. The method of Embodiment XLII, wherein:

$R_3$ is selected from the group consisting of $C_1$-$C_6$ alkyl, substituted $C_1$-$C_6$ alkyl, aryl, and substituted aryl; and $R_4$ is H.

Embodiment XLIV. The method of Embodiment XLII, wherein:

$R_3$ is H; and $R_4$ is selected from the group consisting of $C_1$-$C_6$ alkyl, substituted $C_1$-$C_6$ alkyl, aryl, and substituted aryl.

Embodiment XLV. The method of Embodiment XXVIII, wherein the compound of formula (I) is selected from the group consisting of:

-continued

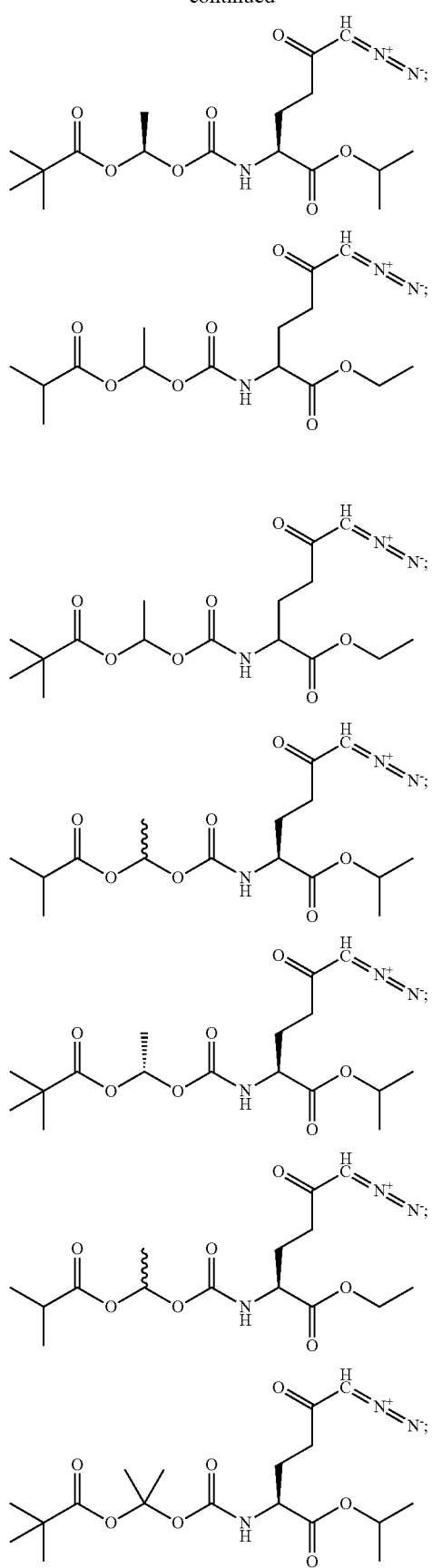

-continued

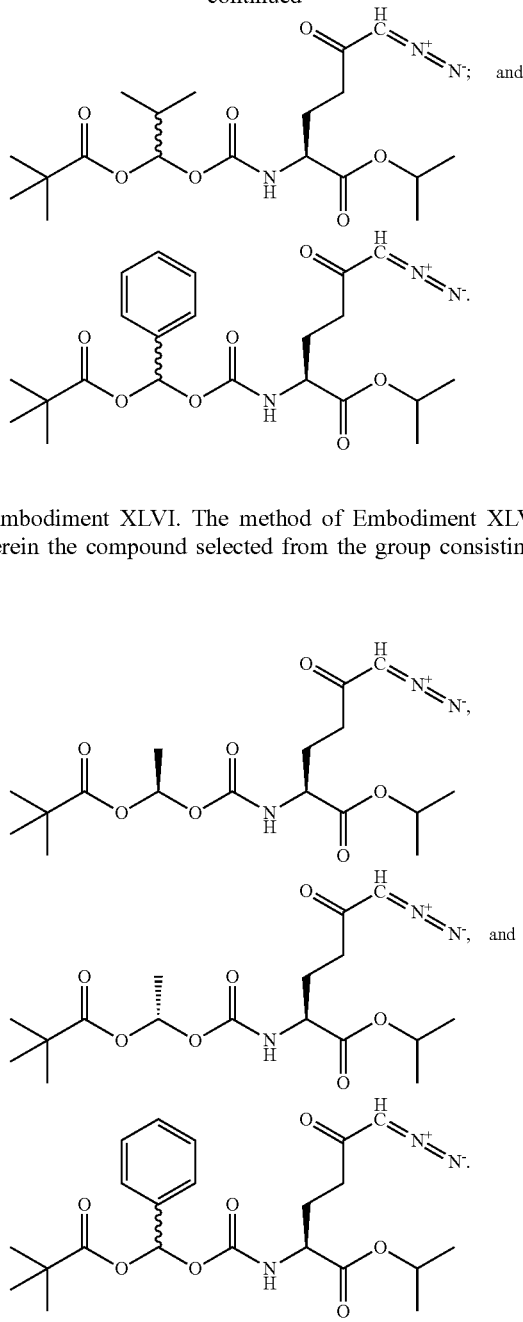

Embodiment XLVI. The method of Embodiment XLV, wherein the compound selected from the group consisting of:

Embodiment XLVII. A method for treating an immune disorder, transplant rejection, graft versus host disease, inflammation, CNS or brain inflammation, a pathology due to or associated with CNS inflammation due to an infection, a pathology due to or associated with CNS inflammation not involving an infection, a neurodegenerative disorder, acute respiratory distress syndrome (ARDS), allograft rejection during cell, tissue, or organ transplantation, Alzheimer's Disease, amyotrophic lateral sclerotis (ALS), arthritis, asthma, cerebral malaria, lupus, neuromyelitis optica, Parkinson's Disease, pneumonitis, or pulmonary fibrosis in a subject, the method comprising administering to the subject in need thereof a compound, or a pharmaceutically acceptable salt thereof, selected from the group consisting of:

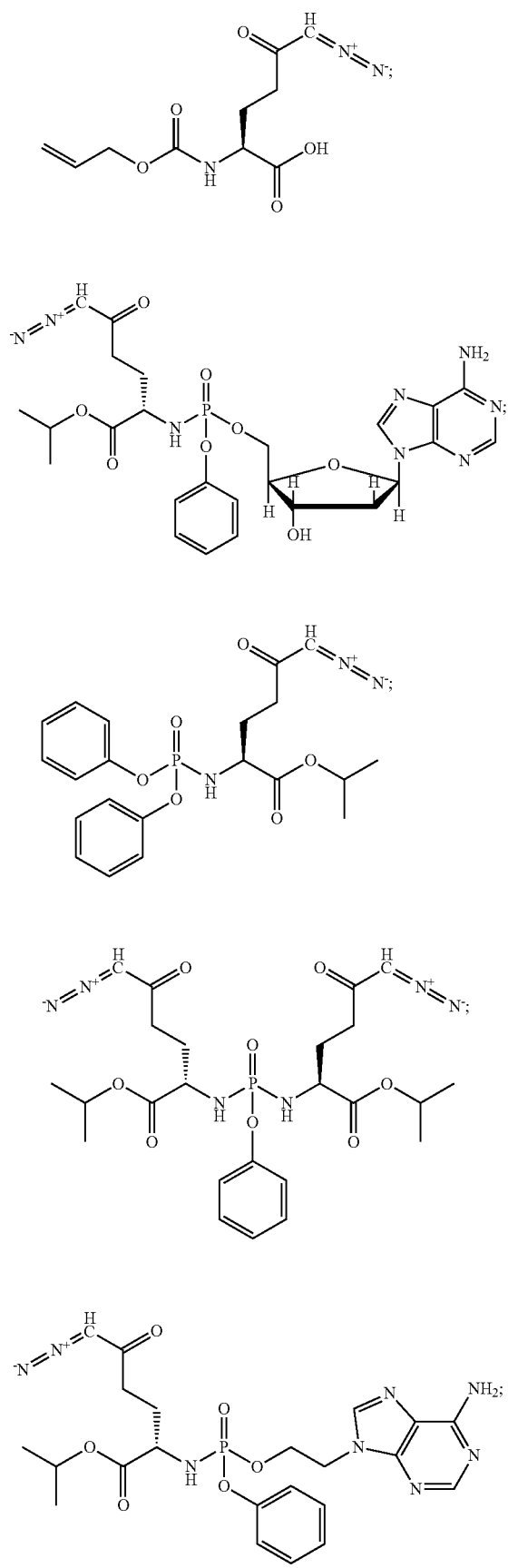
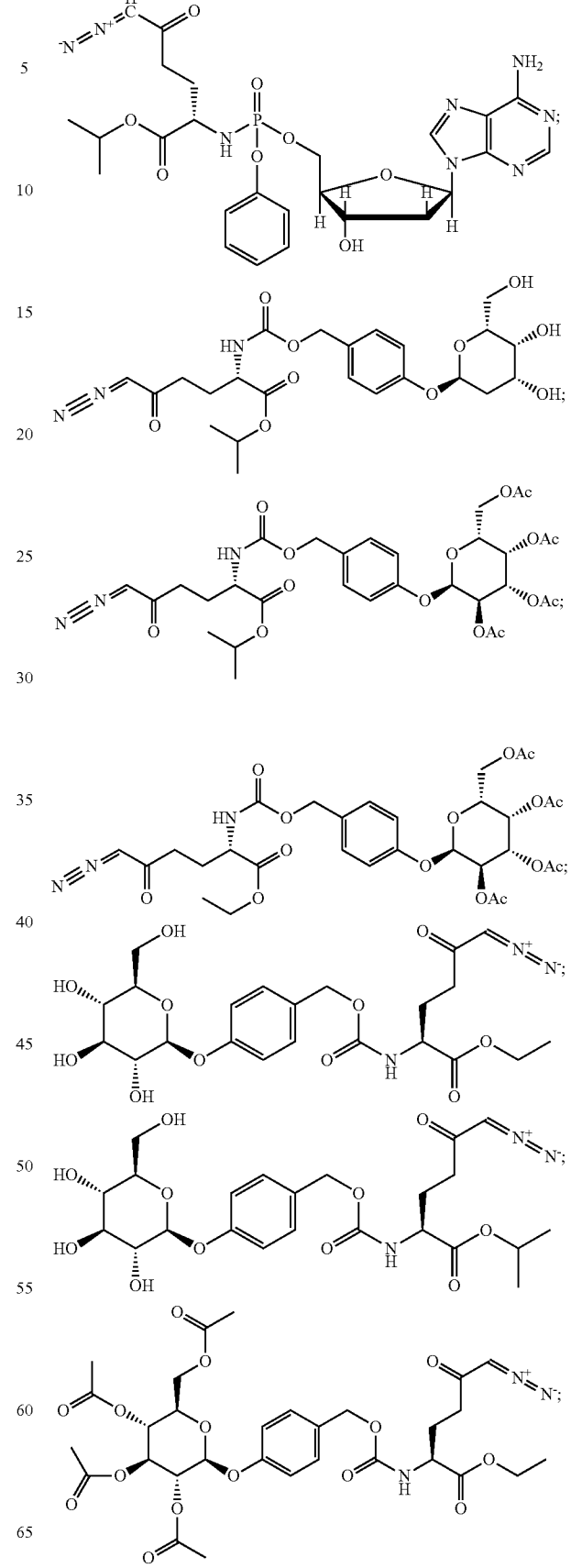

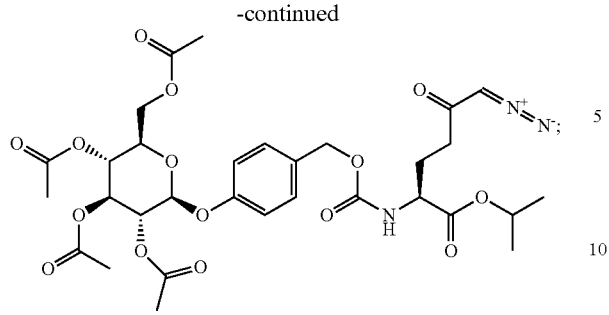
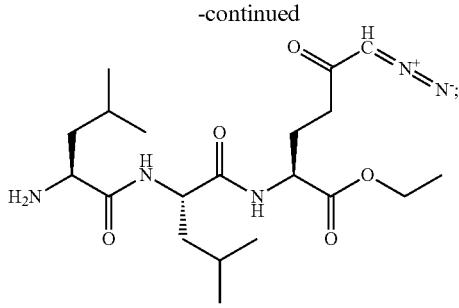
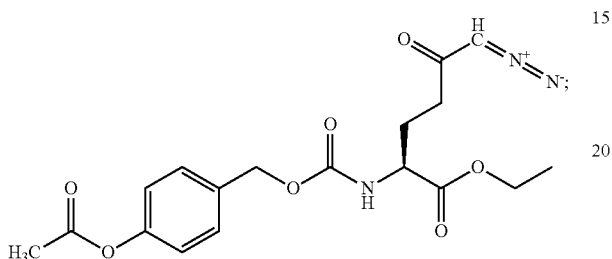
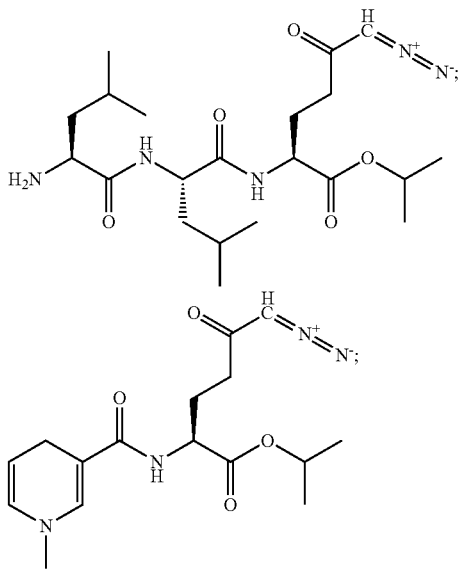
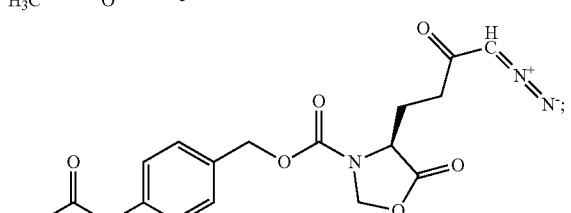
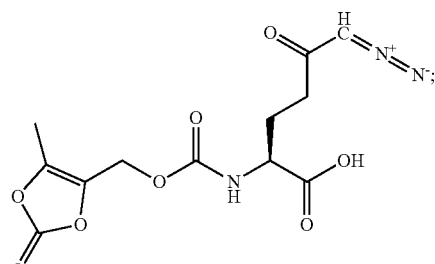
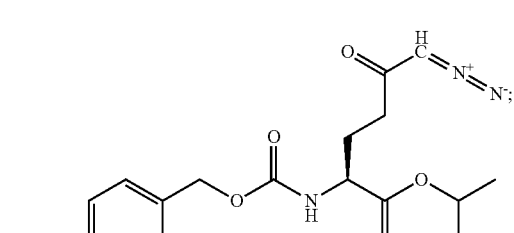
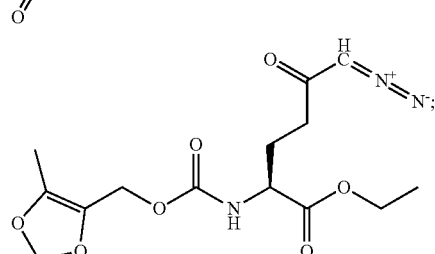
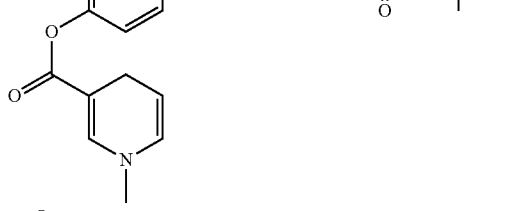
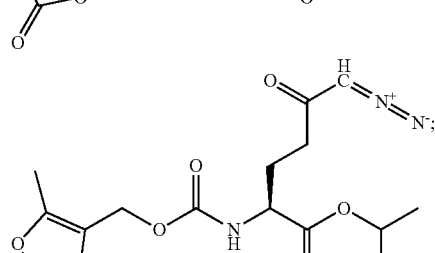
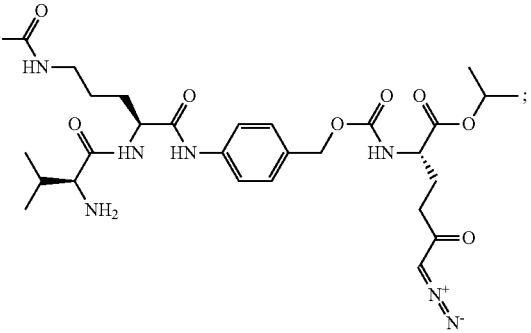

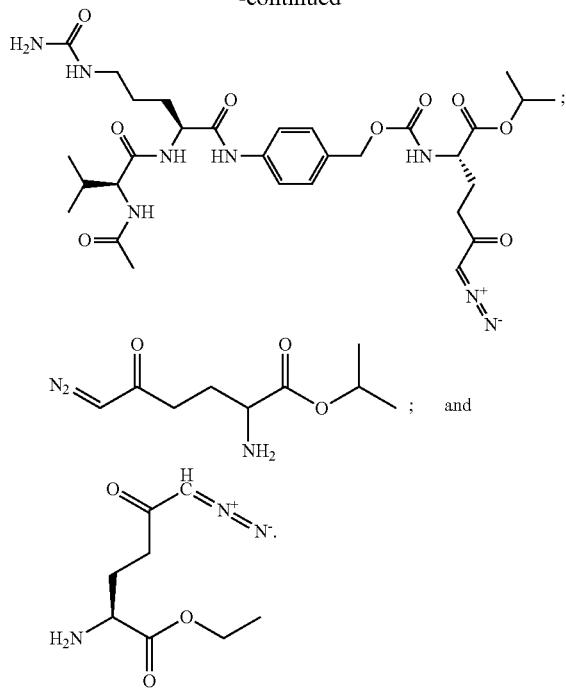

The disclosure also provides the following particular embodiments numbered Embodiments 1-20.

Embodiment 1. A method for treating a subject having a condition, disease, or disorder that involves (i) metabolically reprogrammed cells whose activation, function, growth, proliferation, and/or survival depends on increased activity of at least one metabolic pathway selected from the group consisting of glutamine metabolism, glycolysis, and fatty acid synthesis, and/or (ii) at least one of aberrant and/or excessive glutamine metabolism, aberrant and/or excessive glycolysis, or aberrant and/or excessive fatty acid synthesis, the method comprising administering to the subject at least one, at least two, or at least three metabolic reprogramming agents that decrease activity of at least one, at least two, or at least three metabolic pathways selected from the group consisting of glutamine metabolism, glycolysis, and fatty acid synthesis in an amount effective to treat the condition, disease, or disorder.

Embodiment 2. The method of Embodiment 1, wherein:
(i) at least one metabolic reprogramming agent decreases glutamine metabolism;
(ii) at least one metabolic reprogramming agent decreases glycolysis; and/or
(ii) at least one metabolic reprogramming agent increases fatty acid oxidation.

Embodiment 3. The method of Embodiment 2, wherein the at least one metabolic reprogramming agent that decreases glutamine metabolism is:
(i) a glutamine antagonist;
(ii) a glutamine analog that interferes with a glutamine metabolic pathway;
(iii) at least one metabolic reprogramming agent is selected from the group consisting of acivicin (L-(alpha S, 5S)-alpha-amino-3-chloro-4,5-dihydro-5-isoxazoleacetic acid), azaserine, and 6-diazo-5-oxo-norleucine (DON), and 5-diazo-4-oxo-L-norvaline (L-DONV);
(iv) a prodrug of a glutamine analog that interferes with a glutamine metabolic pathway; or
(v) a prodrug of acivicin, azaserine, DON, and L-DONV; and combinations thereof.

Embodiment 4. The method of Embodiment 2, wherein the at least one metabolic reprogramming agent that decreases glycolysis is:
(i) a glucose analog that inhibits hexokinase; or
(ii) 2-deoxy-D-glucose (2-DG); and combinations thereof Embodiment 5. The method of Embodiment 2, wherein the at least one metabolic reprogramming agent that increases fatty acid oxidation is:
(i) an activator of 5' AMP-activated protein kinase (AMPK) activity; or
(ii) metformin; and combinations thereof.

Embodiment 6. The method of Embodiment 1, wherein the condition, disease, or disorder is selected from the group consisting of an immune disorder, transplant rejection, graft versus host disease, inflammation, CNS or brain inflammation, a pathology due to or associated with CNS inflammation due to an infection, a pathology due to or associated with CNS inflammation not involving an infection, and a neurodegenerative disorder.

Embodiment 7. The method of Embodiment 1, wherein the condition, disease, or disorder is selected from the group consisting of acute respiratory distress syndrome (ARDS), allograft rejection during cell, tissue, or organ transplantation, Alzheimer's Disease, amyotrophic lateral sclerotis (ALS), arthritis, asthma, cerebral malaria, lupus, neuromyelitis optica, Parkinson's Disease, pneumonitis, and pulmonary fibrosis.

Embodiment 8. The method of Embodiment 1, wherein the metabolically reprogrammed cells are selected from the group consisting of immune cells and neuronal cells.

Embodiment 9. A pharmaceutical composition comprising an effective amount of at least one, at least two, or at least three metabolic reprogramming agents that decrease the activity of at least one, at least two, or at least three metabolic pathways selected from the group consisting of glutamine metabolism, glycolysis, and fatty acid synthesis, and a pharmaceutically acceptable carrier, diluent, or excipient.

Embodiment 10. The composition of Embodiment 9, wherein:
(i) at least one metabolic reprogramming agent decreases glutamine metabolism;
(ii) at least one metabolic reprogramming agent decreases glycolysis; and/or
(ii) at least one metabolic reprogramming agent increases fatty acid oxidation.

Embodiment 11. The method of Embodiment 10, wherein the at least one metabolic reprogramming agent that decreases glutamine metabolism is:
(i) a glutamine antagonist;
(ii) a glutamine analog that interferes with a glutamine metabolic pathway;
(iii) at least one metabolic reprogramming agent is selected from the group consisting of acivicin (L-(alpha S, 5S)-alpha-amino-3-chloro-4,5-dihydro-5-isoxazoleacetic acid), azaserine, and 6-diazo-5-oxo-norleucine (DON), and 5-diazo-4-oxo-L-norvaline (L-DONV);
(iv) a prodrug of a glutamine analog that interferes with a glutamine metabolic pathway; or
(v) a prodrug of acivicin, azaserine, DON, and L-DONV; and combinations thereof.

Embodiment 12. The method of Embodiment 10, wherein the at least one metabolic reprogramming agent that decreases glycolysis is:

(i) a glucose analog that inhibits hexokinase; or
(ii) 2-deoxy-D-glucose (2-DG); and combinations thereof Embodiment 13. The method of Embodiment 10, wherein the at least one metabolic reprogramming agent that increases fatty acid oxidation is:
(i) an activator of 5' AMP-activated protein kinase (AMPK) activity; or
(ii) metformin; and combinations thereof.

Embodiment 14. The composition of Embodiment 9 further comprising an additional therapeutic agent selected from the group consisting of an immunotherapeutic agent, an immunosuppressant agent, a radiotherapeutic agent, an anti-inflammatory agent, and a neuroprotective agent Structures of representative DON prodrugs are provided in Table 1.

TABLE 1

Structures of Representative DON Prodrugs

| IOCB No./ Compound No. | Structure | MW |
|---|---|---|
| Compound 1 (DON) | 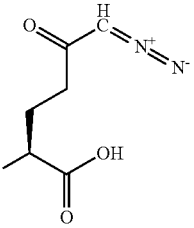 | 171.15 |
| Compound 3 | 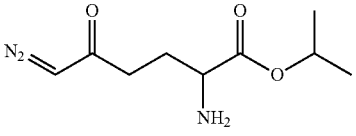 | 213.24 |
| Compound 4 | 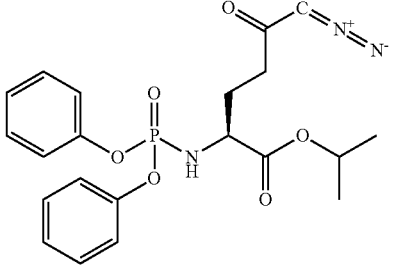 | 445.41 |
| Compound 6 | 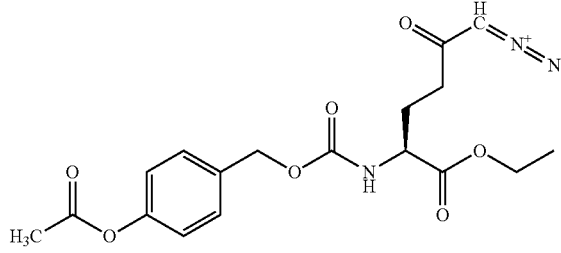 | 391.38 |
| Compound 7 | 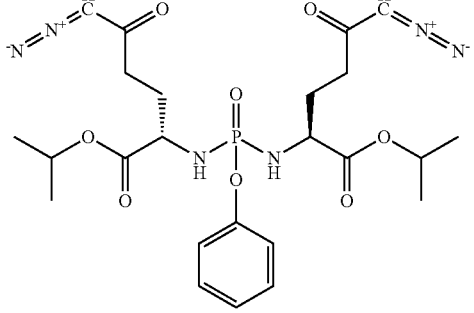 | 564.53 |

TABLE 1-continued

Structures of Representative DON Prodrugs

| IOCB No./Compound No. | Structure | MW |
|---|---|---|
| Compound 9 | 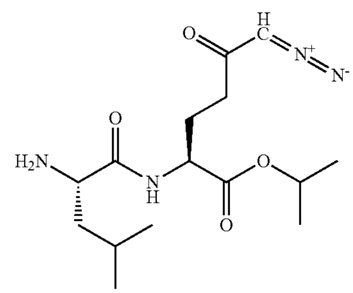 [SMILES: CC(C)C[C@H](N)C(=O)N[C@@H](CCC(=O)C=[N+]=[N-])C(=O)OC(C)C] | 326.39 |
| Compound 11 | 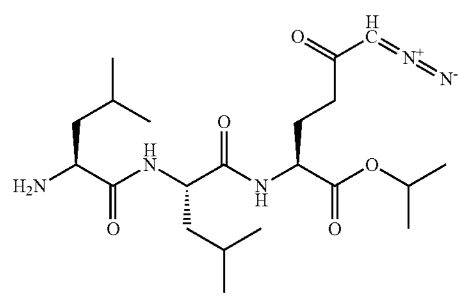 [SMILES: CC(C)C[C@H](NC(=O)[C@@H](N)CC(C)C)C(=O)N[C@@H](CCC(=O)C=[N+]=[N-])C(=O)OC(C)C] | 439.55 |
| Compound 13 | 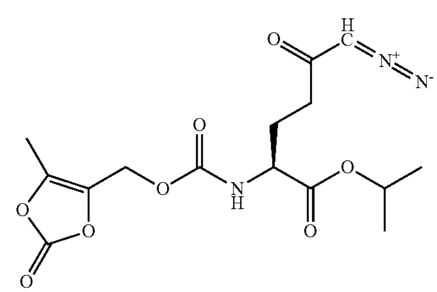 [SMILES: Cc1oc(=O)oc1COC(=O)N[C@@H](CCC(=O)C=[N+]=[N-])C(=O)OC(C)C] | 369.18 |
| Compound 14a # | 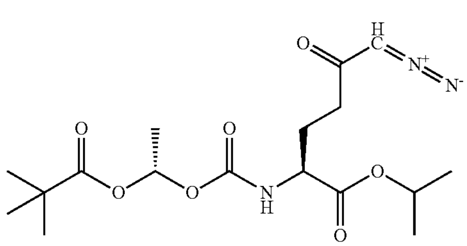 [SMILES: CC(C)OC(=O)[C@H](CCC(=O)C=[N+]=[N-])NC(=O)O[C@@H](C)OC(=O)C(C)(C)C] | 385.41 |
| Compound 14b # | 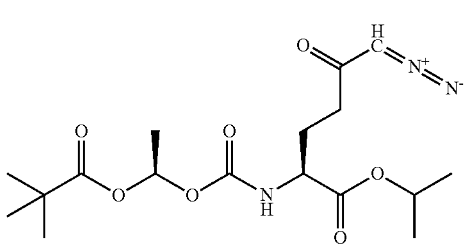 [SMILES: CC(C)OC(=O)[C@H](CCC(=O)C=[N+]=[N-])NC(=O)O[C@H](C)OC(=O)C(C)(C)C] | |

TABLE 1-continued

Structures of Representative DON Prodrugs

| IOCB No./<br>Compound No. | Structure | MW |
|---|---|---|
| Compound 15 | 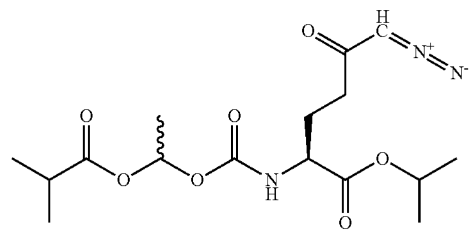 [SMILES: CC(C)OC(=O)[C@H](CCC(=O)C=[N+]=[N-])NC(=O)OC(C)OC(=O)C(C)C] | 371.39 |
| Compound 17 | 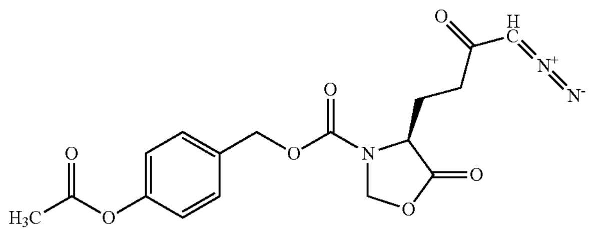 [SMILES: CC(=O)Oc1ccc(COC(=O)N2COC(=O)[C@@H]2CCC(=O)C=[N+]=[N-])cc1] | 375.33 |
| Compound 20 | 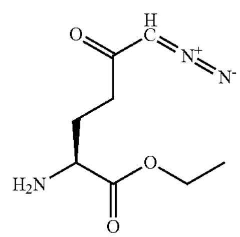 | 199.21 |
| Compound 22 | 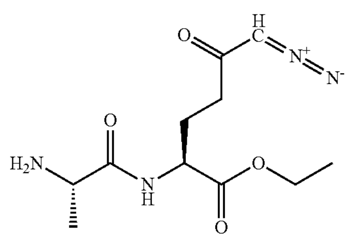 [SMILES: CCOC(=O)[C@H](CCC(=O)C=[N+]=[N-])NC(=O)[C@H](C)N] | 270.28 |
| Compound 23 | · Et₃N | 343.42 |
| Compound 25 | 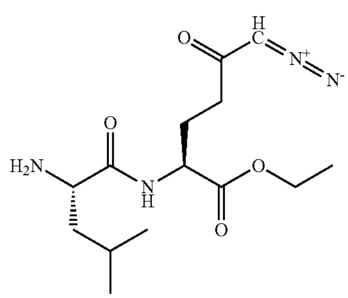 [SMILES: CCOC(=O)[C@H](CCC(=O)C=[N+]=[N-])NC(=O)[C@@H](N)CC(C)C] | 312.36 |

TABLE 1-continued
Structures of Representative DON Prodrugs
| IOCB No./ Compound No. | Structure | MW |
|---|---|---|
| Compound 26 | 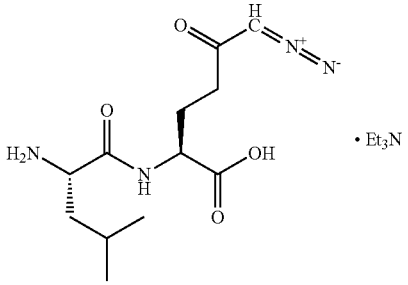 [SMILES: "· Et3N" ; CC(C)C[C@H](N)C(=O)N[C@@H](CCC(=O)C=[N+]=[N-])C(=O)O] | 385.50 |
| Compound 28 | 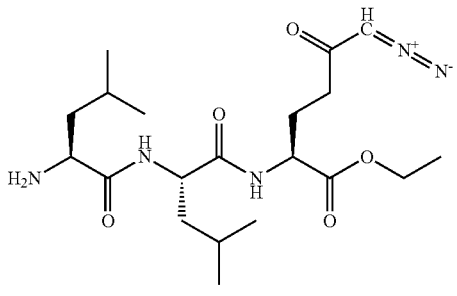 | 425.52 |
| Compound 29 | 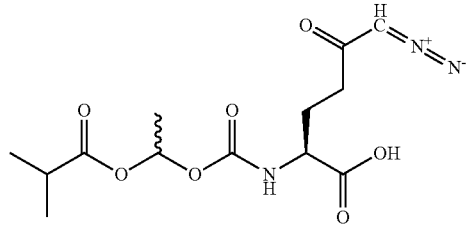 [SMILES: CC(OC(=O)N[C@@H](CCC(=O)C=[N+]=[N-])C(=O)O)OC(=O)C(C)C] | 329.31 |
| Compound 30 | 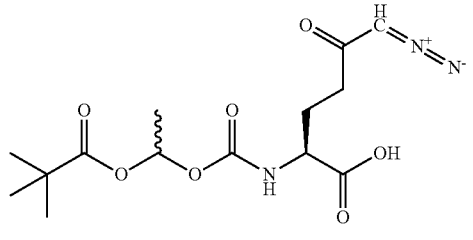 [SMILES: CC(OC(=O)N[C@@H](CCC(=O)C=[N+]=[N-])C(=O)O)OC(=O)C(C)(C)C] | 343.33 |
| Compound 31 | 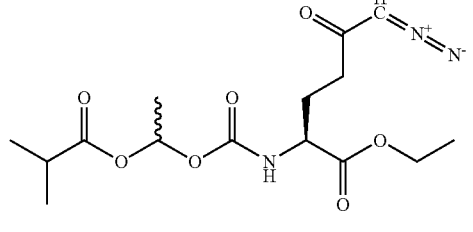 | 357.37 |
| Compound 32 | 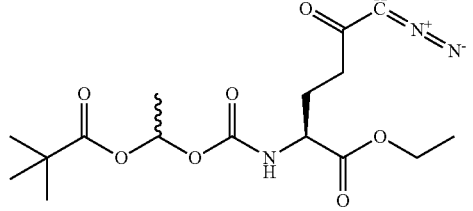 | 371.39 |

TABLE 1-continued

Structures of Representative DON Prodrugs

| IOCB No./Compound No. | Structure | MW |
|---|---|---|
| Compound 34 | 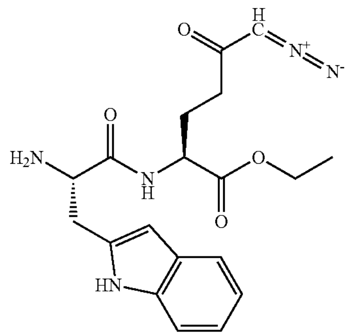 [SMILES: CCOC(=O)[C@H](CCC(=O)C=[N+]=[N-])NC(=O)[C@@H](N)Cc1cc2ccccc2[nH]1] | 385.42 |
| Compound 35 | 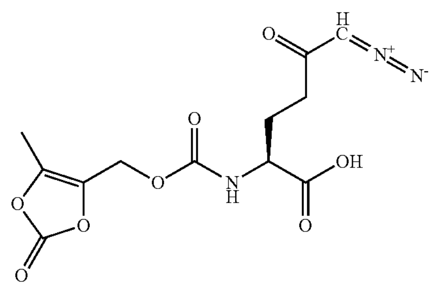 [SMILES: Cc1oc(=O)oc1COC(=O)N[C@@H](CCC(=O)C=[N+]=[N-])C(=O)O] | 327.25 |
| Compound 36 | 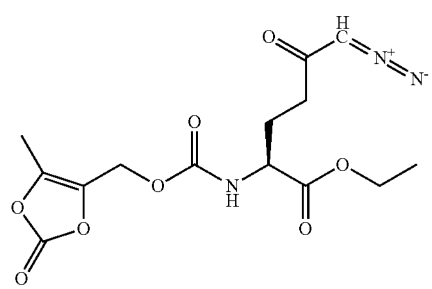 [SMILES: CCOC(=O)[C@H](CCC(=O)C=[N+]=[N-])NC(=O)OCc1oc(=O)oc1C] | 355.30 |
| Compound 38 | 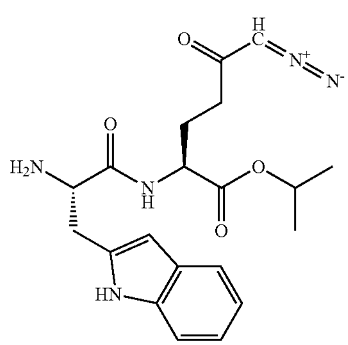 [SMILES: CC(C)OC(=O)[C@H](CCC(=O)C=[N+]=[N-])NC(=O)[C@@H](N)Cc1cc2ccccc2[nH]1] | 399.45 |

TABLE 1-continued
Structures of Representative DON Prodrugs
| IOCB No./ Compound No. | Structure | MW |
|---|---|---|
| Compound 38a | 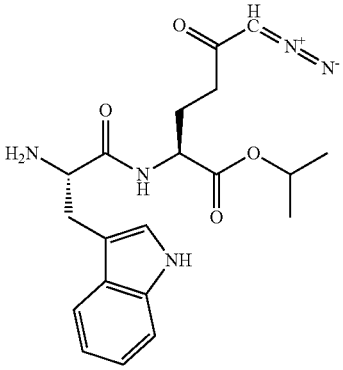 [SMILES: CC(C)OC(=O)[C@H](CCC(=O)C=[N+]=[N-])NC(=O)[C@@H](N)Cc1c[nH]c2ccccc12] | |
| Compound 40 | 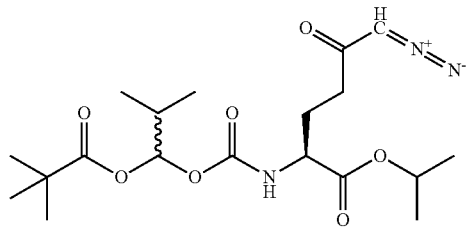 [SMILES: CC(C)OC(=O)[C@H](CCC(=O)C=[N+]=[N-])NC(=O)OC(OC(=O)C(C)(C)C)C(C)C] | 413.47 |
| Compound 42 | 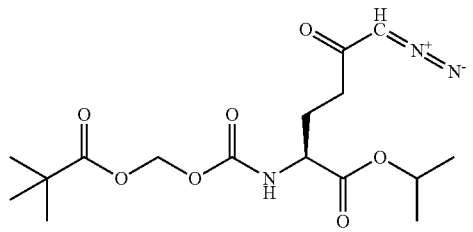 [SMILES: CC(C)OC(=O)[C@H](CCC(=O)C=[N+]=[N-])NC(=O)OCOC(=O)C(C)(C)C] | 371.39 |
| Compound 44 | 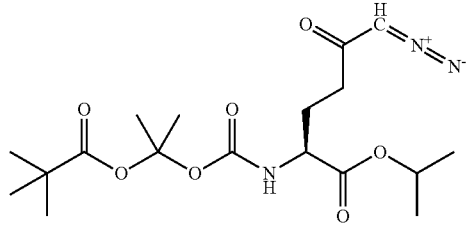 [SMILES: CC(C)OC(=O)[C@H](CCC(=O)C=[N+]=[N-])NC(=O)OC(C)(C)OC(=O)C(C)(C)C] | 2.44 |
| Compound 47 | 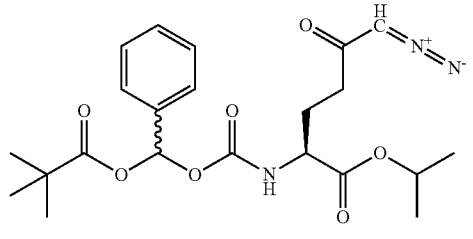 [SMILES: CC(C)OC(=O)[C@H](CCC(=O)C=[N+]=[N-])NC(=O)OC(OC(=O)C(C)(C)C)c1ccccc1] | 447.49 |

TABLE 1-continued

Structures of Representative DON Prodrugs

| IOCB No./ Compound No. | Structure | MW |
|---|---|---|
| Compound 49 | 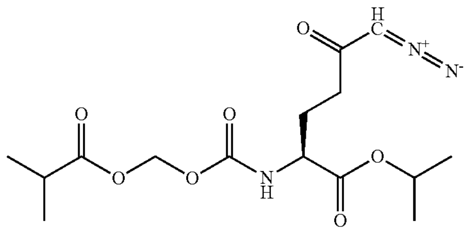 [SMILES: CC(C)OC(=O)[C@H](CCC(=O)C=[N+]=[N-])NC(=O)OCOC(=O)C(C)C] | 357.36 |
| Compound 51 | 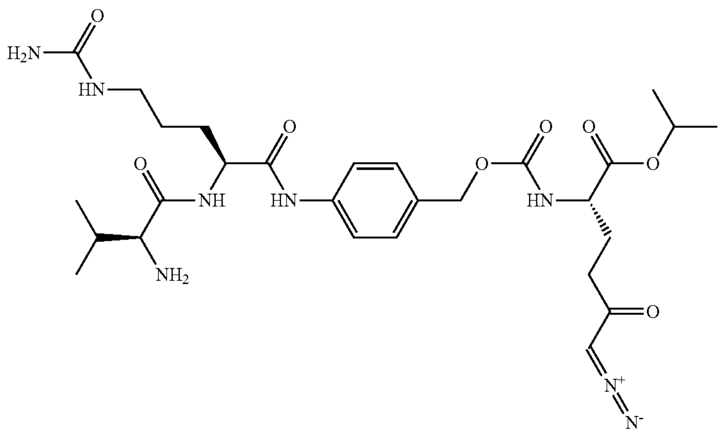 [SMILES: CC(C)OC(=O)[C@H](CCC(=O)C=[N+]=[N-])NC(=O)OCc1ccc(NC(=O)[C@H](CCCNC(N)=O)NC(=O)[C@@H](N)C(C)C)cc1] | 618.69 |
| Compound 52 | 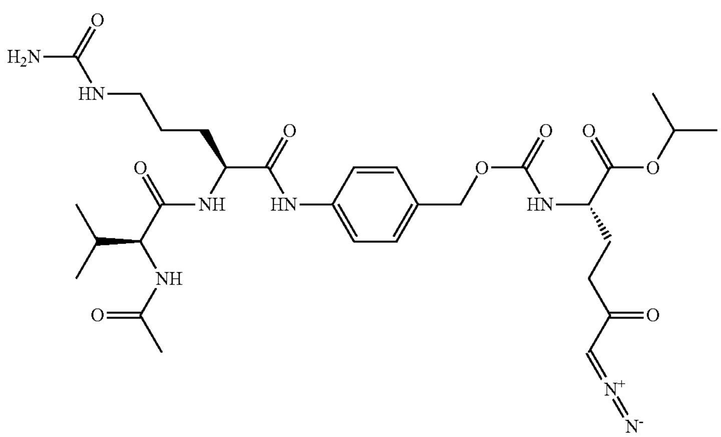 [SMILES: CC(=O)N[C@H](C(=O)N[C@@H](CCCNC(N)=O)C(=O)Nc1ccc(COC(=O)N[C@@H](CCC(=O)C=[N+]=[N-])C(=O)OC(C)C)cc1)C(C)C] | 660.73 |
| Compound 56 | 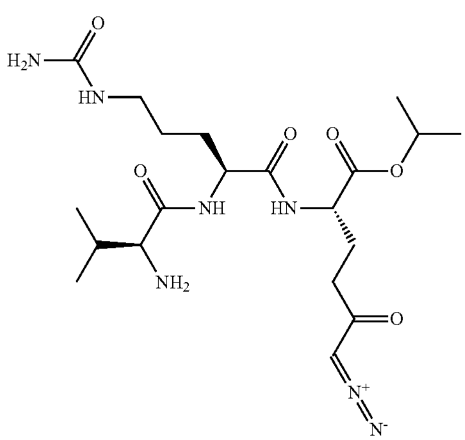 [SMILES: CC(C)OC(=O)[C@H](CCC(=O)C=[N+]=[N-])NC(=O)[C@H](CCCNC(N)=O)NC(=O)[C@@H](N)C(C)C] | 469.54 |

TABLE 1-continued

Structures of Representative DON Prodrugs

| IOCB No./ Compound No. | Structure | MW |
|---|---|---|
| Compound 57 | 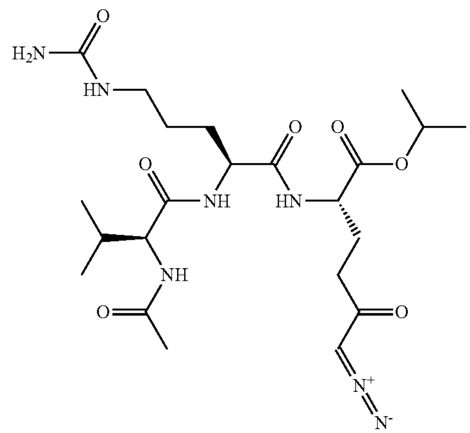 [SMILES: CC(=O)N[C@H](C(=O)N[C@@H](CCCNC(N)=O)C(=O)N[C@@H](CCC(=O)C=[N+]=[N-])C(=O)OC(C)C)C(C)C] | 511.58 |
| Compound 59 | 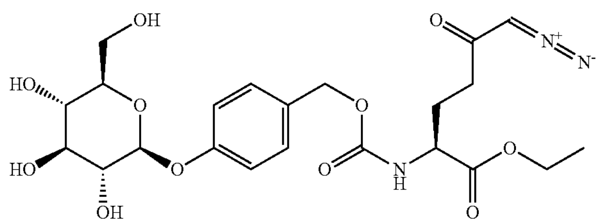 | 511.48 |
| Compound 60 | 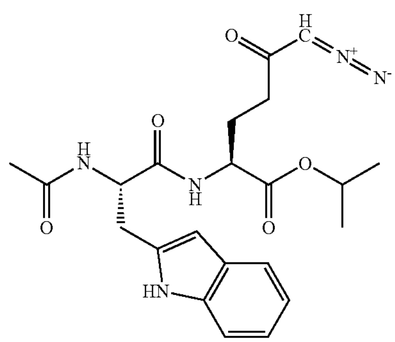 [SMILES: CC(=O)N[C@@H](Cc1cc2ccccc2[nH]1)C(=O)N[C@@H](CCC(=O)C=[N+]=[N-])C(=O)OC(C)C] | 464.19 |
| Compound 60a | 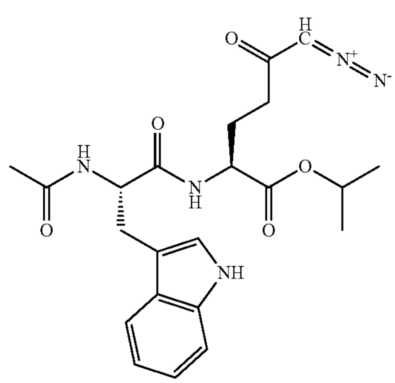 [SMILES: CC(=O)N[C@@H](Cc1c[nH]c2ccccc12)C(=O)N[C@@H](CCC(=O)C=[N+]=[N-])C(=O)OC(C)C] | |

TABLE 1-continued
Structures of Representative DON Prodrugs
| IOCB No./ Compound No. | Structure | MW |
|---|---|---|
| A | 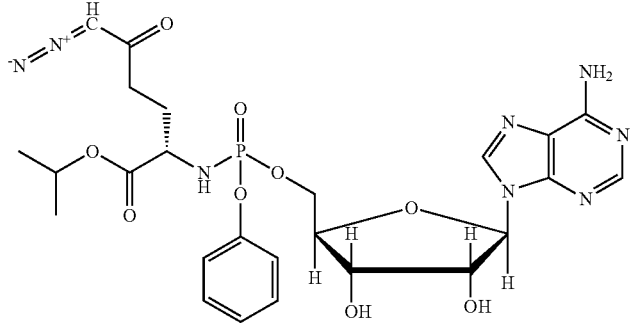 | 618.54 |
| B | 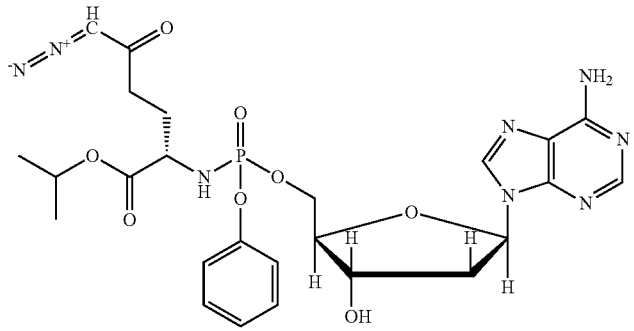 | 602.54 |
| C | 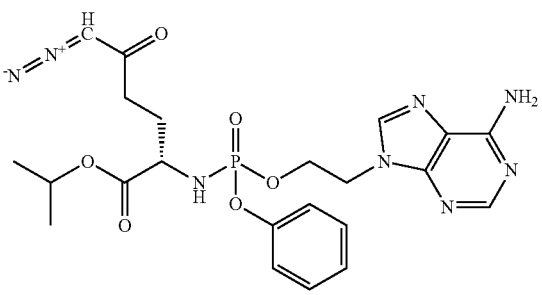 | 530.47 |
| D | 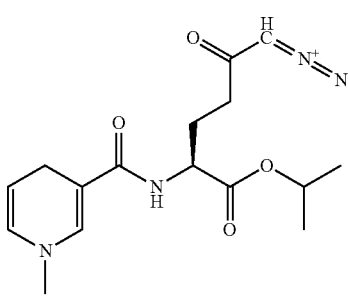 | 334.38 |

TABLE 1-continued

Structures of Representative DON Prodrugs

| IOCB No./ Compound No. | Structure | MW |
| --- | --- | --- |
| E | 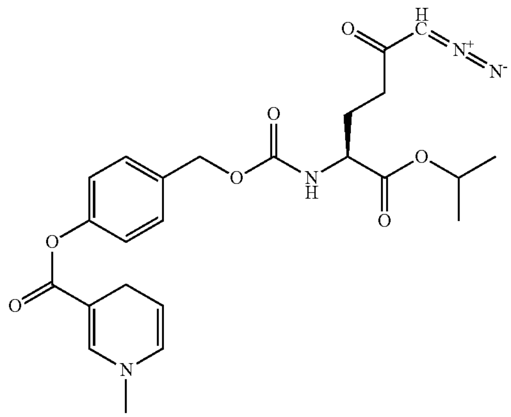 [SMILES: CC(C)OC(=O)[C@H](CCC(=O)C=[N+]=[N-])NC(=O)OCc1ccc(OC(=O)C2=CN(C)C=CC2)cc1] | 484.51 |
| F | 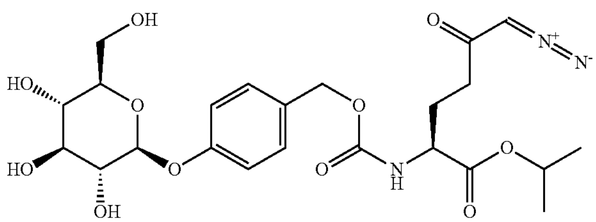 [SMILES: CC(C)OC(=O)[C@H](CCC(=O)C=[N+]=[N-])NC(=O)OCc1ccc(O[C@@H]2O[C@H](CO)[C@@H](O)[C@H](O)[C@H]2O)cc1] | 525.51 |
| G | 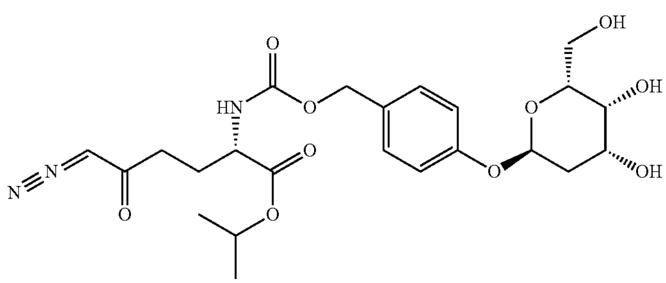 [SMILES: CC(C)OC(=O)[C@H](CCC(=O)C=[N+]=[N-])NC(=O)OCc1ccc(O[C@@H]2C[C@@H](O)[C@@H](O)[C@@H](CO)O2)cc1] | 509.51 |
| LTP 073 | 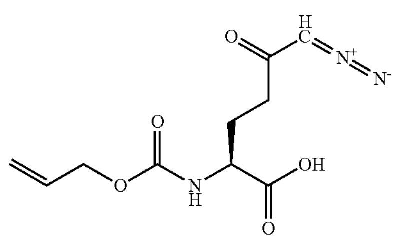 [SMILES: C=CCOC(=O)N[C@@H](CCC(=O)C=[N+]=[N-])C(=O)O] | 255.23 |
| JAM0351 | 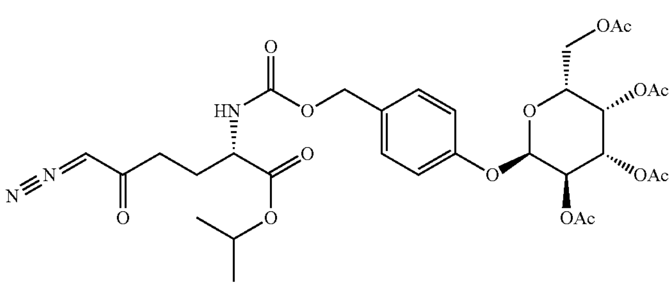 [SMILES: CC(=O)OC[C@H]1O[C@H](Oc2ccc(COC(=O)N[C@@H](CCC(=O)C=[N+]=[N-])C(=O)OC(C)C)cc2)[C@H](OC(C)=O)[C@@H](OC(C)=O)[C@H]1OC(C)=O] | 693.66 |

TABLE 1-continued

Structures of Representative DON Prodrugs

| IOCB No./Compound No. | Structure | MW |
|---|---|---|
| JAM0359 | (structure shown) | 679.63 |

A diastereomeric mixture of isopropyl (2S)-6-diazo-5-oxo-2-(((1 (pivaloyloxy)ethoxy)carbonyl)amino)hexanoate was prepared and separated by column chromatography to give isopropyl (S)-6-diazo-5-oxo-2-((((S)-1-(pivaloyloxy)ethoxy)carbonyl)amino)hexanoate and isopropyl (S)-6-diazo-5-oxo-2- ((((R)-1-(pivaloyloxy)ethoxy)carbonyl) amino)hexanoate. The S,S-isomer was arbitrarily designated compound 14a, and the S,R-isomer was arbitrarily designated compound 14b. The actual stereochemistry of the acetal methyl group was not determined. The diastereoisomer that was arbitrarily designated compound 14b was used in the biological studies described herein. See PCT/US2016/044767 (WO 2017/023774 A1), which is fully incorporated by reference herein.

Glycolysis is the metabolic pathway that converts glucose into pyruvate with the concurrent production of ATP. Pyruvate is a metabolic intermediate that can then enter the tricarboxylic acid (TCA) cycle within mitochondria to produce NADH and $FADH_2$. The first step in glycolysis is the phosphorylation of glucose by hexokinase to form glucose 6-phosphate.

In some embodiments, at least one metabolic reprogramming agent can modulate any of the chemical reactions and/or enzymes involved in glycolysis. In some embodiments, at least one metabolic reprogramming agent can modulate chemical reactions, enzymes and/or pathways that do not directly involve glycolysis, but indirectly affect any of the chemical reactions, enzymes and/or pathways involving glycolysis. Certain methods, compositions, and metabolic reprogramming agents contemplated herein decrease glycolysis in cells. In the context of decreasing glycolysis in cells, the methods, compositions, and agents contemplated herein can decrease glycolysis in cells by at least about 10%, 20%, 30%, 40%, 50%, 60%, 70%, 80, 90%, or as much as 100% as compared to a reference level (e.g., an objective measure of the glycolytic metabolic activity before employing the method, composition, and/or agent). As used herein, the term "glycolytic metabolic activity" refers to the chemical reactions and enzymes involving the glycolysis pathway.

In some embodiments, at least one metabolic reprogramming agent of the presently disclosed subject matter can be an agent that interferes with glycolysis or a related pathway that affects glycolysis; an agent that inhibits the synthesis of pyruvate and/or one of the intermediate products of glycolysis; an agent that inhibits one or more of the enzymes involved in glycolysis, such as hexokinase, phosphoglucose isomerase, phosphofructokinase, fructose-bisphosphate aldolase, triophosphate isomerase, glyceraldehyde phosphate dehydrogenase, phosphoglycerate kinase, phosphoglycerate mutase, enolase, and/or pyruvate kinase; an agent that depletes glucose-6-phosphate, one of the rate-limiting products in glycolysis; an agent that inhibits glucose uptake and/or transport across the plasma membrane by cells; or a glucose binding compound that reduces the biological availability of glucose. It should be recognized that a compound that is a useful metabolic reprogramming agent may have two or more of these characteristics.

In some embodiments, at least one metabolic reprogramming agent interferes or inhibits the expression and/or activity of hexokinase. Examples of inhibitors of hexokinase include, but are not limited to, 2-deoxyglucose (2-DG), 3-bromopyruvate (3-BrPA), lonidamine (LND), sodium fluoride, and potassium fluoride. In some embodiments, at least one metabolic reprogramming agent is 2-deoxy-D-glucose (2-DG).

Fatty acid synthesis is the process in the cell that creates fatty acids from acetyl-CoA and malonyl-CoA precursors. Fatty acid oxidation is the process by which fatty acid molecules are broken down in the mitochondria to generate acetyl-CoA, which enters the citric acid cycle, and NADH and $FADH_2$, which are used in the electron transport chain. The enzyme AMP-activated protein kinase (AMPK) plays a role in cellular energy homeostasis and is a stimulator of fatty acid oxidation.

In some embodiments, at least one metabolic reprogramming agent can modulate any of the chemical reactions and/or enzymes involved in fatty acid synthesis and/or fatty acid oxidation. In some embodiments, at least one metabolic reprogramming agent can modulate chemical reactions, enzymes and/or pathways that do not directly involve fatty acid synthesis and/or fatty acid oxidation, but indirectly affect any of the chemical reactions, enzymes and/or pathways involving fatty acid synthesis and/or fatty acid oxidation.

Certain methods, compositions, and metabolic reprogramming agents contemplated herein decrease fatty acid synthesis and/or increase fatty acid oxidation in cells. In the context of decreasing fatty acid synthesis and/or increasing fatty acid oxidation in cells, the methods, compositions, and agents contemplated herein can decrease fatty acid synthesis and/or increase fatty acid oxidation in cells by at least about 10%, 20%, 30%, 40%, 50%, 60%, 70%, 80, 90%, or as much as 100% as compared to a reference level (e.g., an objective measure of the synthesis of fatty before employing the method, composition, and/or agent).

In some embodiments, at least one metabolic reprogramming agent of the presently disclosed subject matter can be an agent that interferes with fatty acid synthesis and/or fatty acid oxidation or a related pathway that affects fatty acid synthesis and/or fatty acid oxidation; an agent that increases fatty acid oxidation; an agent that increases one or more of the products of fatty acid oxidation; an agent that increases the expression and/or activity of one or more of the enzymes involved in fatty acid oxidation, such as acyl CoA dehydrogenase, enoyl CoA hydratase, 3-hydroxyacyl-CoA dehydrogenase, and β-ketothiolase; an agent that increases expression and/or activity of AMP-activated protein kinase (AMPK); an agent that increases uptake and/or transfer of activated fatty acids across the mitochondrial membrane; and an agent that increases the expression and/or activity of enzymes involved in the uptake and/or transfer of activated fatty acids across the mitochondrial membrane. It should be recognized that a compound that is a useful metabolic reprogramming agent may have two or more of these characteristics. In some embodiments, at least one metabolic reprogramming agent is an activator of 5' AMP-activated protein kinase (AMPK) activity.

At least one metabolic reprogramming agent that is an activator of AMPK activity can be an agent that increases concentrations of AMP in the cell; an AMP analogue, such as 5-amino-4-imidazolecarboxamide ribotide (ZMP); an agent that increases phosphorylation of AMPK, such as an agent that increases the expression and/or activity of a kinase that can phosphorylate AMPK; and an agent that is an allosteric modulator of AMPK, such as one that can modify AMPK to make it a better substrate for a kinase that can phosphorylate AMPK.

In some embodiments, at least one metabolic reprogramming agent is metformin.

It should be appreciated that modulation of glutamine metabolism, glycolysis, and fatty acid metabolism may result in modulation of one or more genes or expression products of genes or biosynthesis or degradation of one or more enzymes.

The term "expression" means the process by which information from a gene or nucleic acid (e.g., DNA) is used in the synthesis of gene products (e.g., mRNA, RNA and/or proteins) and includes, but is not limited to, one or more of the steps of replication, transcription and translation. The steps of expression which may be modulated by the agents contemplated herein may include, for example, transcription, splicing, translation and post-translational modification of a protein. Those skilled in the art will appreciate that the method of modulating any particular protein may depend on the type of protein (e.g., protein kinase, transcriptional regulator, enzyme, etc.), its function (e.g., transcriptional regulation, catalysis, phosphorylation, signal transduction, etc.), and its subcellular localization (e.g., extracellular space, cytoplasm, nucleus, membrane, etc.). Those skilled in the art will readily appreciate appropriate agents to be used for modulation depending on the particular context (e.g., type of protein, biological function, subcellular localization, composition, method of use, mode of inhibition, etc.). For example, an agent can be used to inhibit enzymatic activity of an enzyme (e.g., at least one metabolic reprogramming agent that inhibits glutaminolysis catalyzed by glutaminase (e.g., a glutamine antagonist), at least one metabolic reprogramming agent that inhibits glycolysis catalyzed in part by hexokinase (e.g., 2-DG), etc.), inhibits the level or activity of phosphorylation of a protein kinase, inhibit activation of transcription or a signaling pathway.

The metabolic reprogramming agents, cytotoxic agents, immunotherapeutic agents, immunosuppressant agents, radiotherapeutic agents, anti-inflammatory agents, and neuroprotective agents described herein can be any type of agent. Exemplary types of agents that can be used as such agents in the methods, compositions, and uses described herein include small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; microcarrier or nanocarrier consisting of one or more polymers, proteins, nucleic acids, lips, or metals; and any combination thereof.

As used herein, the term "small molecule" can refer to agents that are "natural product-like," however, the term "small molecule" is not limited to "natural product-like" agents. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule have a molecular weight equal to or less than 700 Daltons.

As used herein, an "RNA interference molecule" refers to an agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), microRNA (miRNA) and small molecules which interfere with or inhibit expression of a target gene by RNA interference (RNAi).

The term "polynucleotide" is used herein interchangeably with "nucleic acid" to indicate a polymer of nucleosides. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. Polynucleotide sequence" as used herein can refer to the polynucleotide material itself and/or to the sequence information (e.g. the succession of letters used as abbreviations for bases) that biochemically characterizes a specific nucleic acid. A polynucleotide sequence presented herein is presented in a 5' to 3' direction unless otherwise indicated.

The nucleic acid molecules that modulate the metabolic pathways or targets described herein can, in some embodiments, be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. Proc. Natl. Acad. Sci. USA 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids, such as the 20 L-amino acids that are most commonly found in proteins. However, other amino acids and/or amino acid analogs known in the art can be used. One or more of the amino acids in a polypeptide may be modified, for example, by the addition of a chemical entity, such as a carbohydrate group, a phosphate group, a fatty acid group, a linker for conjugation, functionalization, etc. A polypeptide that has a non-polypeptide moiety covalently or non-covalently associated therewith is still considered a "polypeptide". Exemplary modifications include glycosylation and palmitoylation. Polypeptides may be purified from natural sources, produced using recombinant DNA technology, synthesized through chemical means, such as conventional solid phase peptide synthesis, etc. The term "polypeptide sequence" or "amino acid sequence" as used herein can refer to the polypeptide material itself and/or to the sequence information (e.g., the succession of letters or three letter codes used as abbreviations for amino acid names) that biochemically characterizes a polypeptide. A polypeptide sequence presented herein is presented in an N-terminal to C-terminal direction unless otherwise indicated.

The term "identity" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs known in the art. For example, computer programs, such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. Sci. USA 87:22264-2268, 1990) modified as in Karlin and Altschul, Proc. Natl. Acad. Sci. USA 90:5873-5877, 1993 is incorporated into the NBLAST and XBLAST programs of Altschul et al. (Altschul, et al., J. MoT Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL www.ncbi.nlm.nih.gov for these programs. In a specific embodiment, percent identity is calculated using BLAST2 with default parameters as provided by the NCBI.

Generally, at least one metabolic reprogramming agent described herein can be used in combination with an additional therapeutic agent (e.g., a pharmaceutically active agent, e.g., a drug approved by a regulatory agency). The therapeutic agent may act synergistically with the agent described herein, or they may independently exert their intended effects. The disclosure contemplates any therapeutic agent which a skilled artisan would use in connection with a method, use, or composition described herein. Examples of therapeutic agents contemplated for use in the presently disclosed methods, uses and compositions in combination with the metabolic reprogramming agents include, but are not limited to, chemotherapeutic agents, immunotherapeutic agents, immunosuppressant agents, anti-inflammatory agents, neuroprotective agents, neuroregenerative agents, neurotrophic factors, radiotherapeutic agents, and stem and progenitor cells used to replace and/or repair endogenous populations of abnormal, harmful, or unhealthy cells.

As used herein, the term "immunotherapeutic agent" refers to a molecule that can aid in the treatment of a disease by inducing, enhancing, or suppressing an immune response in a cell, tissue, organ or subject. Examples of immunotherapeutic agents contemplated for use in combination with at least one metabolic reprogramming agent, at least two metabolic reprogramming agents, or at least three metabolic reprogramming agents described herein include, but are not limited to, immune checkpoint molecules (e.g., antibodies to immune checkpoint proteins), interleukins (e.g., IL-2, IL-7, IL-12, IL-15), cytokines (e.g., interferons, G-CSF, imiquimod), chemokines (e.g., CCL3, CCL26, CXCL7), vaccines (e.g., peptide vaccines, dendritic cell (DC) vaccines, EGFRvIII vaccines, mesothilin vaccine, G-VAX, listeria vaccines), and adoptive T cell therapy including chimeric antigen receptor T cells (CAR T cells).

As used herein, "immunosuppressant agent" means an agent which may be used in immunotherapy to reduce or prevent an immune response in a cell, organ, tissue, or subject. Examples of immunosuppressant agents contemplated for use in combination with at least one metabolic reprogramming agent, at least two metabolic reprogramming agents, or at least three metabolic reprogramming agents include, without limitation, corticosteroids, calcineurin inhibitors, antiproliferative agents, SIP receptor agonists, kinase inhibitors, monoclonal antilymphocyte antibodies and polyclonal antilymphocyte antibodies. Non-limiting examples of corticosteroids include Prednisone (Deltasone® and Orasone®) and Methylprednisolone (SoluMedrol®). Non-limiting examples of calcineurin inhibitors include Cyclosporine (Cyclosporin A, SangCya, Sandimmune®, Neoral®, Gengraf®), ISA, Tx247, ABT-281, ASM 981 and Tacrolimus (Prograf®, FK506). Non-limiting examples of antiproliferative agents include Mycophenolate Mofetil (CellCept®), Azathioprene (Imuran®), and Sirolimus (Rapamune®). Non-limiting examples of SIP receptor agonists include FTY 720 or analogues thereof. Non-limiting examples of kinase inhibitors include mTOR kinase inhibitors, which are compounds, proteins or antibodies that target, decrease or inhibit the activity and/or function of members of the serine/threonine mTOR family. These include, without limitation, CCI-779, ABT578, SAR543, rapamycin and derivatives or analogs thereof, including 40-O-(2-hydroxyethyl)-rapamycin, rapalogs, including AP23573, AP23464, AP23675 and AP23841 from Ariad, Everolimus (CERTICAN, RAD001), biolimus 7, biolimus 9 and sirolimus (RAPAMUNE). Kinase inhibitors also include protein kinase C inhibitors, which include the compounds described the PCT publications WO 2005/097108 and WO 2005/068455, which are herein incorporated by reference in their entireties. Non-limiting examples of monoclonal antilymphocyte antibodies include Muromonab-CD3 (Orthoclone OKT3®), Interleukin-2 Receptor Antagonist (Basiliximab, Simulect®), and Daclizumab (Zenapax®). Non-limiting examples of polyclonal antilymphocyte antibodies include Antithymocyte globulin-equine (Atgam®) and Antithymocyte globulin-rabbit (RATG, Thymoglobulin®). Other immunosuppressants include, without limitation, SERP-1, a serine protease inhibitor produced by malignant rabbit fibroma virus (MRV) and myxoma virus (MYX), described in US Patent Publication No. 2004/0029801, which is incorporated herein by reference.

Immunosuppressant agents can be classified according to their specific molecular mode of action. The four main categories of immunosuppressant drugs currently used in treating patients with transplanted organs are the following. Calcineurin inhibitors inhibit T-cell activation, thus preventing T-cells from attacking the transplanted organ. Azathioprines disrupt the synthesis of DNA and RNA as well as the process of cell division. Monoclonal antibodies inhibit the binding of interleukin-2, which in turn slows down the production of T-cells in the patient's immune system. Corticosteroids suppress inflammation associated with transplant rejection.

Immunosuppressants can also be classified according to the specific organ that is transplanted. Basiliximab (Simulect) is also used in combination with such other drugs as cyclosporine and corticosteroids in kidney transplants. IL-2 blockers, including Simulect from Novartis, FK506 or CyA, MMF, prednisone or Rapamycin are also used in kidney transplants. Daclizumab (Zenapax) is also used in combination with such other drugs as cyclosporin and corticosteroids in kidney transplants. Similar drugs are used in heart transplants, but anti-lymphocyte globulin (ALG) is often used instead of Simulect. Muromonab CD3 (Orthoclone OKT3) is used along with cyclosporine in kidney, liver and heart transplants. Tacrolimus (Prograf) is used in liver and kidney transplants. It is under study for bone marrow, heart, pancreas, pancreatic island cell and small bowel transplantation.

As used herein, "anti-inflammatory agent" refers to an agent that may be used to prevent or reduce an inflammatory response or inflammation in a cell, tissue, organ, or subject. Exemplary anti-inflammatory agents contemplated for use in combination with at least one metabolic reprogramming agent, at least two metabolic reprogramming agents, or at least three metabolic reprogramming agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Exemplary neuroprotective agents include, without limitation, L-dopa, dopamine agonists (e.g., apomorphine, bromocriptine, pergolide, ropinirole, pramipexole, or cabergoline), adenosine A2a antagonists (Shah et al., Curr. Opin. Drug Discov. Devel. 13:466-80 (2010)); serotonin receptor agonists; continuous-release levodopa (Sinemet CR®, MSD, Israel); continuous duodenal levodopa administration (Duodopa®, Abbott, UK); catechol-O-methyltransferase (COMT) inhibitors (e.g., Stalevo®, Novartis Pharma, USA; entacapone (Comtan®, Novartis Pharma, USA)); tolcapone; coenzyme Q10, and/or MAO-B inhibitors (e.g., Selegiline or Rasagiline). Additional neuroprotective agents are described in, e.g., Hart et al., Mov. Disord. 24: 647-54 (2009).

As used herein, a "radiotherapeutic agent" refers to those agents conventionally adopted in the therapeutic field of cancer treatment and includes photons having enough energy for chemical bond ionization, such as, for instance, alpha ($\alpha$), beta ($\beta$), and gamma ($\gamma$) rays from radioactive nuclei as well as x-rays. The radiation may be high-LET (linear energy transfer) or low-LET. LET is the energy transferred per unit length of the distance. High LET is said to be densely ionizing radiation and Low LET is said to be sparsely ionizing radiation. Representative examples of high-LET are neutrons and alpha particles. Representative examples of low-LET are x-ray and gamma rays. Low LET radiation including both x-rays and γrays is most commonly used for radiotherapy of cancer patients. The radiation may be used for external radiation therapy that is usually given on an outpatient basis or for internal radiation therapy that uses radiation that is placed very close to or inside the tumor. In case of internal radiation therapy, the radiation source is usually sealed in a small holder called an implant. Implants may be in the form of thin wires, plastic tubes called catheters, ribbons, capsules, or seeds. The implant is put directly into the body. Internal radiation therapy may require a hospital stay. The ionizing radiation source is provided as a unit dose of radiation and is preferably an x-ray tube since it provides many advantages, such as convenient adjustable dosing where the source may be easily turned on and off, minimal disposal problems, and the like. A unit dose of radiation is generally measured in gray (Gy). The ionizing radiation source may also comprise a radioisotope, such as a solid radioisotopic source (e.g., wire, strip, pellet, seed, bead, or the like), or a liquid radioisotopic filled balloon. In the latter case, the balloon has been specially configured to prevent leakage of the radioisotopic material from the balloon into the body lumen or blood stream. Still further, the ionizing radiation source may comprise a receptacle in the catheter body for receiving radioisotopic materials like pellets or liquids. The radioisotopic material may be selected to emit α, β and γ. Usually, α and β radiations are preferred since they may be quickly absorbed by the surrounding tissue and will not penetrate substantially beyond the wall of the body lumen being treated. Accordingly, incidental irradiation of the heart and other organs adjacent to the treatment region can be substantially eliminated. The total number of units provided will be an amount determined to be therapeutically effective by one skilled in treatment using ionizing radiation. This amount will vary with the subject and the type of malignancy or neoplasm being treated. The amount may vary but a patient may receive a dosage of about 30-75 Gy over several weeks.

Exemplary radiotherapeutic agents contemplated for use in combination with at least one metabolic reprogramming agent, at least two metabolic reprogramming agents, or at least three metabolic reprogramming agents include, factors that cause DNA damage, such as γ-rays, X-rays, and/or the directed delivery of radioisotopes to tumor cells. Other forms of DNA damaging factors are also contemplated, such as microwaves and UV-irradiation. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the target cell. In some embodiments, the radiotherapeutic agent is selected from the group consisting of $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193}$MPt, $^{197}$H, $^{43}$K, $^{43}$K, $^{52}$Fe, $^{57}$Co, $^{67}$Cu, $^{67}$Ga, $^{68}$Ga, $^{77}$Br, $^{81}$Rb/$^{81}$MKr, $^{87}$MSr, $^{99}$MTc, $^{111}$In, $^{113}$MIn, $^{127}$Cs, $^{129}$Cs, $^{132}$I, $^{197}$Hg, $^{203}$Pb and $^{206}$Bi, as described in U.S. Pat. No. 8,946,168, the entirety of which is incorporated herein by reference.

In some contexts, an agent described herein can be administered with an antigen (e.g., to induce an immune response). In some embodiments, an adjuvant can be used in combination with the antigen.

An agent described herein can also be used in combination with an imaging agent. An agent (e.g., a metabolic reprogramming agent) can be attached to imaging agents for imaging and diagnosis of various diseased organs, tissues or cell types. The agent can be labeled or conjugated a fluorophore or radiotracer for use as an imaging agent. Many appropriate imaging agents are known in the art, as are methods for their attachment to agents (e.g., attaching an imaging agent to a proteins or peptides using metal chelate complexes, radioisotopes, fluorescent markers, or enzymes whose presence can be detected using a colorimetric markers (such as, but not limited to, urease, alkaline phosphatase, (horseradish) hydrogen peroxidase and glucose oxidase)). An agent may also be dual labeled with a radioisotope in order to combine imaging through nuclear approaches and be made into a unique cyclic structure and optimized for binding affinity and pharmacokinetics. Such agents can be administered by any number of methods known to those of ordinary skill in the art including, but not limited to, oral administration, inhalation, subcutaneous (sub-q), intravenous (I.V.), intraperitoneal (I.P.), intramuscular (I.M.), intratracheal, or intrathecal injection. The methods, compositions, and uses described herein can be used alone or in combination with other techniques, to diagnose access and monitor and direct therapy of metabolic reprogramming disorders. In some contexts, the imaging agent can be used for detecting and/or monitoring tumors or sites of metastasis in a subject. For example, an agent (e.g., a metabolic reprogramming agent) can be administered in vivo and monitored using an appropriate label. Exemplary methods for detecting and/or monitoring an agent labeled with an imaging agent in vivo include Gamma Scintigraphy, Positron Emission Tomography (PET), Single Photon Emission Computer Tomography (SPECT), Magnetic Resonance Imaging (MRI), X-ray, Computer Assisted X-ray Tomography (CT), Near Infrared Spectroscopy, and Ultrasound. These techniques provide information regarding detection of neoplastic involvement, particularly of inaccessible nodes in subjects with malignant diseases. Knowledge on the size of the node and the filling of nodes can also be instructive. For example, agents or compositions targeted to the lymph nodes in detection applications will contain suitable contrast or imaging agents, such as ferromagnetic materials like iron oxide, perfluorochemicals such as perfluorooctylbromide, or gamma emitting radiolabels such as Technetium-99m, Indium-111, Gallium-67, Thallium-201, Iodine-131, 125, or 123, positron emitting radiolabels, such as Fluorine-18, or those produced by neutron activation, such as Samarium-153.

Imaging agents of use in the present disclosure include radioisotopes and dyes. Any conventional method according to radiolabeling which is suitable for labeling isotopes for in vivo use will be generally suitable for labeling detection agents according to the disclosure. Internal detection procedures include intraoperative, intravascular or endoscopic, including laparoscopic, techniques, both surgically invasive and noninvasive. For example, when detecting a lymph node, a high signal-to-background ratio should to be achieved. Therapy also requires a high absolute accretion of the therapeutic agent in the lymph node, as well as a reasonably long duration of uptake and binding.

Suitable radioisotopes for the methods of the disclosure include: Actinium-225, Astatine-211, Iodine-123, Iodine-125, Iodine-126, Iodine-131, Iodine-133, Bismuth-212, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-186, Rhenium-188, Tellurium-121m, Tellurium-122m, Tellurium-125m, Thulium-165, Thulium-167, Thulium-168, Technetium-99m, Fluorine-18, Silver-111, Platinum-197, Palladium-109, Copper-67, Phosphorus-32, Phosphorus-33, Yttrium-90, Scandium-47, Samarium-153, Lutetium-177, Rhodium-105, Praseodymium-142, Praseodymium-143, Terbium-161, Holmium-166, Gold-199, Cobalt-57, Cobalt-58, Chromium-51, Iron-59, Selenium-75, Thallium-201, and Ytterbium-169. The most preferred radioisotope for use in the current disclosure is Technetium-99m. Preferably the radioisotope will emit a particle or ray in the 10-7,000 keV range, more preferably in the 50-1,500 keV range, and most preferably in the 80-250 keV range.

Isotopes preferred for external imaging include: Iodine-123, Iodine-131, Indium-111, Gallium-67, Ruthenium-97, Technetium-99m, Cobalt-57, Cobalt-58, Chromium-51, Iron-59, Selenium-75, Thallium-201, and Ytterbium-169. Technetium-99m is the most preferred radioisotope for external imaging in the disclosure.

Isotopes most preferred for internal detection include: Iodine-125, Iodine-123, Iodine-131, Indium-111, Technetium-99m and Gallium-67. Technetium-99m is the most preferred isotope for internal detection.

III. Uses of Metabolic Reprogramming Agents

The presently disclosed subject matter contemplates the use of at least one, at least two, or at least three metabolic reprogramming agents that decrease activity of at least one metabolic pathway selected from the group consisting of glutamine metabolism, glycolysis, and fatty acid synthesis, alone, or optionally together with one or more additional therapeutic agents described herein. Accordingly, in an aspect the presently disclosed subject matter involves the use of at least one metabolic reprogramming agent that decreases activity of at least one metabolic pathway selected from the group consisting of glutamine metabolism, glycolysis, and fatty acid synthesis for treating a condition, disease, or disorder that involves (i) metabolically reprogrammed cells whose activation, function, growth, proliferation, and/or survival depends on increased activity of at least one metabolic pathway selected from the group consisting of glutamine metabolism, glycolysis, and fatty acid synthesis or (ii) at least one of aberrant and/or excessive glutamine metabolism, aberrant and/or excessive glycolysis, or aberrant and/or excessive fatty acid synthesis.

In some embodiments, the presently disclosed subject matter involves the use of at least two metabolic reprogramming agents. In some embodiments, the presently disclosed subject matter involves the use of at least three metabolic reprogramming agents.

In an aspect, the presently disclosed subject matter involves the use of an effective amount of at least one metabolic reprogramming agent that decreases glutamine metabolism to treat arthritis in a subject in need thereof.

In an aspect, the presently disclosed subject matter involves the use of an effective amount of at least one metabolic reprogramming agent that decreases glutamine metabolism to treat lupus in a subject in need thereof.

In an aspect, the presently disclosed subject matter involves the use of an effective amount of at least one metabolic reprogramming agent that decreases glutamine metabolism to treat asthma in a subject in need thereof.

In an aspect, the presently disclosed subject matter involves the use of an effective amount of at least one metabolic reprogramming agent that decreases glutamine metabolism to treat acute respiratory distress syndrome (ARDS) in a subject in need thereof.

In an aspect, the presently disclosed subject matter involves the use of an effective amount of at least one metabolic reprogramming agent that decreases glutamine metabolism to treat pulmonary fibrosis in a subject in need thereof.

In an aspect, the presently disclosed subject matter involves the use of an effective amount of at least one metabolic reprogramming agent that decreases glutamine metabolism to prevent or delay allograft rejection during cell, tissue, or organ transplantation in a subject in need thereof.

In an aspect, the presently disclosed subject matter involves the use of an effective amount of at least one metabolic reprogramming agent that decreases glutamine metabolism to treat or prevent graft versus host disease in a subject in need thereof.

In an aspect, the presently disclosed subject matter involves the use of an effective amount of at least one metabolic reprogramming agent that decreases glutamine metabolism to treat multiple sclerosis in a subject in need thereof.

In an aspect, the presently disclosed subject matter involves the use of an effective amount of at least one metabolic reprogramming agent that decreases glutamine metabolism to treat neuromyolitis optica in a subject in need thereof.

In an aspect, the presently disclosed subject matter involves the use of an effective amount of at least one metabolic reprogramming agent that decreases glutamine metabolism to treat cerebral malaria in a subject in need thereof.

In an aspect, the presently disclosed subject matter involves the use of an effective amount of at least one metabolic reprogramming agent that decreases glutamine metabolism to treat a pathology due to CNS inflammation involving an infection in a subject in need thereof.

In an aspect, the presently disclosed subject matter involves the use of an effective amount of at least one metabolic reprogramming agent that decreases glutamine metabolism to treat a pathology due to CNS inflammation not involving an infection in a subject in need thereof.

In an aspect, the presently disclosed subject matter involves the use of an effective amount of at least one metabolic reprogramming agent that decreases glutamine metabolism to treat a Alzheimer's disease in a subject in need thereof.

In an aspect, the presently disclosed subject matter involves the use of an effective amount of at least one metabolic reprogramming agent that decreases glutamine metabolism to treat a Parkinson's disease in a subject in need thereof.

In an aspect, the presently disclosed subject matter involves the use of an effective amount of at least one metabolic reprogramming agent that decreases glutamine metabolism to treat amyotrophic lateral sclerosis (ALS) in a subject in need thereof.

In an aspect, the presently disclosed subject matter involves the use of an effective amount of at least one metabolic reprogramming agent that decreases glutamine metabolism to treat pneumonitis in a subject in need thereof.

In some embodiments, a use described herein further comprises using an effective amount of at least one metabolic reprogramming agent that decreases glycolysis.

In some embodiments, a use described herein further comprises uses an effective amount of at least one metabolic reprogramming agent that increases fatty acid oxidation.

IV. Pharmaceutical Compositions Comprising Metabolic Reprogramming Agents

The presently disclosed subject matter also contemplates pharmaceutical compositions comprising one or more metabolic reprogramming agents for the treatment of certain conditions, diseases, and/or disorders involving metabolically reprogrammed cells. In some embodiments, the presently disclosed methods comprise the use of the presently disclosed metabolic reprogramming agents for the manufacture of a medicament for the treatment of certain conditions, diseases, and/or disorders involve metabolically reprogrammed cells. The disclosure contemplates various pharmaceutical compositions comprising at least one, at least two, and or at least three metabolic reprogramming agents.

Accordingly, in an aspect the presently disclosed subject matter provides a pharmaceutical composition comprising an effective amount of at least one, at least two, or at least three metabolic reprogramming agents that decrease the activity of at least one metabolic pathway selected from the group consisting of glutamine metabolism, glycolysis, and fatty acid synthesis, and a pharmaceutically acceptable carrier, diluent, or excipient.

In some embodiments, the metabolic reprogramming composition comprises one or more additional therapeutic agents described herein. Generally, the presently disclosed compositions (e.g., comprising at least one metabolic reprogramming agent) can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The phrases "systemic administration", "administered systemically", "peripheral administration" and "administered peripherally" as used herein mean the administration of compositions comprising at least one metabolic reprogramming agent, such that it enters the patient's system and, thus, are subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al. (1981) *J. Biomed. Mater. Res.* 15:167; Langer (1982), *Chem. Tech.* 12:98), ethylene vinyl acetate (Langer et al. (1981) *J. Biomed. Mater. Res.* 15:167), or poly-D-(−)-3-hydroxybutyric acid (EP 133,988A). Sustained release compositions also include liposomally entrapped compositions comprising at least one metabolic reprogramming agent which can be prepared by methods known in the art (Epstein et al. (1985) *Proc. Natl. Acad. Sci. U.S.A.* 82:3688; Hwang et al. (1980) *Proc. Natl. Acad. Sci. U.S.A.* 77:4030; U.S. Pat. Nos. 4,485,045 and 4,544,545; and EP 102,324A). Ordinarily, the liposomes are of the small (about 200-800 angstroms) unilamelar type in which the lipid content is greater than about 30 mol % cholesterol, the selected proportion being adjusted for the optimal therapy. Such materials can comprise an implant, for example, for sustained release of the presently disclosed compositions, which, in some embodiments, can be implanted at a particular, pre-determined target site.

In another embodiment, the presently disclosed pharmaceutical compositions may comprise PEGylated therapeutics (e.g., PEGylated antibodies). PEGylation is a well established and validated approach for the modification of a range of antibodies, proteins, and peptides and involves the attachment of polyethylene glycol (PEG) at specific sites of the antibodies, proteins, and peptides (Chapman (2002) *Adv. Drug Deliv. Rev.* 54:531-545). Some effects of PEGylation include: (a) markedly improved circulating half-lives in vivo due to either evasion of renal clearance as a result of the polymer increasing the apparent size of the molecule to above the glomerular filtration limit, and/or through evasion of cellular clearance mechanisms; (b) improved pharmacokinetics; (c) improved solubility—PEG has been found to be soluble in many different solvents, ranging from water to many organic solvents, such as toluene, methylene chloride, ethanol and acetone; (d) PEGylated antibody fragments can be concentrated to 200 mg/ml, and the ability to do so opens up formulation and dosing options, such as subcutaneous administration of a high protein dose; this is in contrast to many other therapeutic antibodies which are typically administered intravenously; (e) enhanced proteolytic resistance of the conjugated protein (Cunningham-Rundles et. al. (1992) *J. Immunol. Meth.* 152:177-190); (f) improved bioavailability via reduced losses at subcutaneous injection sites; (g) reduced toxicity has been observed; for agents where toxicity is related to peak plasma level, a flatter pharmacokinetic profile achieved by sub-cutaneous administration of PEGylated protein is advantageous; proteins that elicit an immune response which has toxicity consequences may also benefit as a result of PEGylation; and (h) improved thermal and mechanical stability of the PEGylated molecule.

Pharmaceutical compositions for parenteral administration include aqueous solutions of compositions comprising at least one metabolic reprogramming agent. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of compositions include fatty oils, such as sesame oil, or synthetic fatty acid esters, such as ethyl oleate or triglycerides, or liposomes. Optionally, the suspension also can contain suitable stabilizers or agents that increase the solubility of the compositions comprising at least one metabolic reprogramming agent to allow for the preparation of highly concentrated solutions.

For nasal or transmucosal administration generally, penetrants appropriate to the particular barrier to be permeated are used in the formulation. Such penetrants are generally known in the art.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

Regardless of the route of administration selected, the presently disclosed compositions are formulated into pharmaceutically acceptable dosage forms, such as described herein or by other conventional methods known to those of skill in the art.

In general, the "effective amount" or "therapeutically effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

The term "combination" is used in its broadest sense and means that a subject is administered at least two agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the presently disclosed compositions can be administered alone or in combination with adjuvants that enhance stability of the agents, facilitate administration of pharmaceutical compositions containing them in certain embodiments, provide increased dissolution or dispersion, increase activity, provide adjuvant therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of at least one metabolic reprogramming agent can be varied so long as the beneficial effects of the combination of these agents are achieved. Accordingly, the phrase "in combination with" refers to the administration of at least one metabolic reprogramming agent, at least two metabolic reprogramming agents, or at least three metabolic reprogramming agents, and optionally additional agents either simultaneously, sequentially, or a combination thereof. Therefore, a subject administered a combination of at least one, at least two, or at least three metabolic reprogramming agents, and optionally additional agents can receive at least one metabolic reprogramming agent, at least two metabolic reprogramming agents, and at least three metabolic reprogramming agents, and optionally additional agents at the same time (i.e., simultaneously) or at different times (i.e., sequentially, in either order, on the same day or on different days), so long as the effect of the combination of all agents is achieved in the subject.

When administered sequentially, the agents can be administered within 1, 5, 10, 30, 60, 120, 180, 240 minutes or longer of one another. In other embodiments, agents administered sequentially, can be administered within 1, 2, 3, 4, 5, 10, 15, 20 or more days of one another. Where the agents are administered simultaneously, they can be administered to the subject as separate pharmaceutical compositions, each comprising either at least one metabolic reprogramming agent, at least two metabolic reprogramming agents, or at least three metabolic reprogramming agents, and optionally additional agents, or they can be administered to a subject as a single pharmaceutical composition comprising all agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_a Q_A + Q_b Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

In another aspect, the presently disclosed subject matter provides a pharmaceutical composition including at least one metabolic reprogramming agent, at least two metabolic reprogramming agents, at least three metabolic reprogramming agents, and optionally additional agents, alone or in combination with one or more additional therapeutic agents in admixture with a pharmaceutically acceptable excipient.

More particularly, the presently disclosed subject matter provides a pharmaceutical composition comprising at least one metabolic reprogramming agent, at least two metabolic reprogramming agents, at least three metabolic reprogramming agents, and optionally additional agents, and a pharmaceutically acceptable carrier.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams and Wilkins (2000).

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The term "instructing" a patient as used herein means providing directions for applicable therapy, medication, treatment, treatment regimens, and the like, by any means, but preferably in writing. Instructing can be in the form of prescribing a course of treatment, or can be in the form of package inserts or other written promotional material. Accordingly, aspects of the presently disclosed subject matter include instructing a patient to receive a method of treatment or use an agent to treat a metabolic reprogramming disorder described herein.

The term "promoting" as used herein means offering, advertising, selling, or describing a particular drug, combination of drugs, or treatment modality, by any means, including writing, such as in the form of package inserts. Promoting herein refers to promotion of a metabolic reprogramming agent for an indication, where such promoting is authorized by the Food and Drug Administration (FDA) as having been demonstrated to be associated with statistically significant therapeutic efficacy and acceptable safety in a population of subjects. In some embodiments, promoting is not authorized by the Food and Drug Administration (FDA) (or other health regulatory agency, such as the European Medicines Agency (EMA), and promoting is for an off-label use. Accordingly, aspects of the presently disclosed subject matter include promoting a method of treatment or use described herein.

V. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{2S}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)— $CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S($O_2$)R. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$CH_2CH_2CH_2CH_2$—, —$CH_2$CH=CH$CH_2$—, —$CH_2$CsCC$H_2$—, —$CH_2CH_2$CH($CH_2CH_2CH_3$)$CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

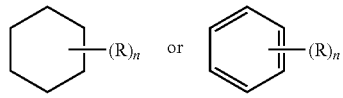

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

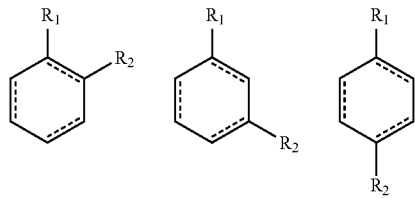

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R',—S(O)$_2$R', —S(O)$_2$NR'R", —NRSO$_2$R', —CN and —NO$_2$ in a number ranging from zero to (2 m'+1), where m' is the total number of carbon atoms in such groups. R', R", R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR'''—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'— (C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxy carbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms, such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —$S(O_2)R$.

The term "sulfoxide" refers to a compound having a sulfinyl group —S(O)R

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L-for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids, such as glutamic acid. These salts may be prepared by methods known to those skilled in art. Also included are base addition salts, such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids, such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Treatment of Immune Disorders

The presently disclosed glutamine analogues were found to suppress antigen-specific effector $CD4^+$ T cells proliferation and function (FIG. 1C, FIG. 1D, and FIG. 1E) and antigen-specific $CD8^+$ T cells responses in vivo (FIG. 2A, FIG. 2B, and FIG. 2C). The addition of DON to the metabolic reprogramming therapy resulted in very potent inhibition of both $CD4^+$ T cell effector function and $CD8^+$ T cell effector function.

To determine if this suppression of T cells by the glutamine analogues could be used to reduce transplant rejections, skin from Balb/c mice was transplanted onto B6 mice and the mice were treated with the metabolic reprogramming therapy with at least three metabolic reprogramming agents (e.g., 2DG+Metformin+DON) or DON alone (FIG. 3). The results showed that DON prevents transplant rejection and prolongs skin graft survival. Further, when hearts from Balb/c mice were transplanted into B6 mice, it was found that DON is able to prevent heart transplant rejection (FIG. 4). DON also increased the relative frequency of regulatory T cells (Tregs) in vivo (FIG. 5).

To further identify the effect of DON on the immune system, different mouse models showed that the metabolic reprogramming therapy with at least three metabolic reprogramming agents targeted asthmatic cells (FIG. 6), and that DON alone treated arthritis (FIG. 7), and treated pneumonitis (FIG. 8).

Example 2

Regulation of Immune Metabolism as the Sole Means of Preventing Allograft Rejection Summary Upon antigen recognition and co-stimulation, T lymphocytes up-regulate the metabolic machinery necessary to proliferate and sustain effector function. Hallmarks of this response include a switch to aerobic glycolysis and an increased demand for glutamine. This metabolic reprogramming in T cells is a critical regulator of T cell activation and differentiation, not just a consequence of antigen recognition. Furthermore, it is clear that while such metabolic reprogramming is important for the differentiation and function of T effector cells, the differentiation of regulatory T cells employs different metabolic reprogramming. Based on these observations, it was hypothesized that inhibition of glycolysis and glutamine metabolism might represent a novel means of preventing graft rejection by inhibiting effector generation and function while promoting regulatory T cell generation. Along these lines, an anti-rejection regimen was devised employing a glycolytic inhibitor, 2-Deoxyglucose (2-DG), an anti-Type II diabetes drug (metformin) and an inhibitor of glutamine metabolism, 6-Diazo-5-oxo-L-norleucine (DON). Using this metabolic reprogramming therapy with at least three metabolic reprogramming agents, graft rejection was prevented or delayed in fully mismatched skin and heart allograft transplantation models. The data suggest that metabolic reprogramming metabolic reprogramming therapy represents a novel and selective means of inhibiting T cell effector function while preserving mechanisms of immune regulation.

Significance

Transplantation remains the treatment of choice for patients with end-stage organ disease. However, since current mainstream anti-rejection regimens result in multiple adverse effects, new strategies to promote graft survival are of great clinical interest. Metabolic signaling pathways have emerged as playing critical roles in dictating the outcome of T cell responses. Quiescent T cells primarily use oxidative phosphorylation, whereas activated T cells must undergo metabolic reprogramming, which promotes glycolysis and glutamine oxidation to meet the biosynthetic and energy demands. It is demonstrated herein that selective targeting of T cell proliferation and function by blocking glycolysis and glutamine metabolic pathways can inhibit effector T cells response while preserving the mechanisms of immune regulation. Such a regimen can inhibit acute rejection and promote graft survival.

Materials and Methods

Mice: Mice were kept in accordance with guidelines of the Johns Hopkins University Institutional Animal Care and Use Committee. 5C.C7 mice ($RAG2^{-/-}$ $CD4^+$ TCR-transgenic mice which recognize Pigeon cytochrome c (PCC)) were from Taconic Farms. OVA-specific OT-I and OT-II TCR transgenic mice from The Jackson Laboratory were bred to $Thy1.1^+$ backgrounds. C57BL/6 ($Thy1.2^+$, $H-2^b$) and Balb/c ($H-2^d$) mice were obtained from The Jackson Laboratory.

Antibodies and reagents: The following antibodies for flow cytometry were from BD Biosciences: anti-CD4 (RM4-5), anti-CD8 (Ly-3), anti-IFN-γ (XMG1.2), and anti-Thy1.1 (OX-7). Anti-Foxp3 (FJK-16s) was from eBioscience. Class I OVA peptide and class II OVA peptide were obtained from AnaSpec. PCC peptide 81-104 was synthesized at Johns Hopkins University. 2-DG was purchased from Carbosynth. Metformin and DON were purchased from Sigma-Aldrich. For all in vivo experiments, individual metabolic reprogramming agents were dissolved in PBS and administered intraperitoneally.

Cell culture: Splenocytes or T cells were cultured in 45% RPMI 1640 and 45% EHAA media supplemented with 10% FBS, penicillin/streptomycin, glutamine and BME. For proliferation studies, T cells were labeled with 5 μM eFluor 670 cell proliferation dye (eBioscience) and were stimulated with anti-CD3 (1 μg/ml). For non-antigen specific stimulations, flat-bottomed plates were coated with anti-CD3 (5 μg/ml) diluted in PBS, and soluble anti-CD28 (2 μg/ml) was added to the cultures. For preparation of pre-activated $CD4^+$ T cells, splenocytes from 5C.C7 mice were stimulated with 5 μM PCC peptide in complete medium for 48 hrs. Mouse recombinant IL-2 (1 ng/ml; Peprotech) was then added to the culture. After 5-7 days, live cells were isolated by a Ficoll gradient (GE healthcare). Cell viability was determined by 7-aminoactinomycin D (7-AAD; BD Biosciences) exclusion.

Extracellular flux analysis: Cells were initially plated to XF assay medium, modified DMEM (Seahorse Bioscience) containing 25 mM glucose, 2 mM L-glutamine, and 1 mM sodium pyruvate, and incubated in a non-$CO_2$ incubator at 37° C. for 30 minutes. OCR and ECAR were measured at 37° C. in a XF96 Extracellular Flux Analyzer (Seahorse Bioscience) using manufacturer recommended protocols. After baseline measurements, OCR and ECAR were measured after sequentially adding anti-CD3/CD28 and metabolic reprogramming agents into each well to the indicated final concentrations using the included ports on the XF96 cartridges. All data were collected using the XF Reader software from Seahorse Bioscience.

Adoptive transfers: $CD8^+$ (or $CD4^+$) T cells were harvested from OT-I (or OT-II) mice and purified by negative selection with $CD8^+$ (or $CD4^+$) MACS cell isolation protocol (Miltenyi Biotec). $1\times10^6$ purified $CD8^+$ (or $CD4^+$) T cells were then injected intravenously into $Thy1.2^+$ C57BL/6 recipients. Vaccinia-OVA ($1\times10^6$ plaque-forming units) was simultaneously administered by injection into the retro-orbital cavernous.

Glutaminase activity analysis: Glutaminase activity measurement was adapted from previously described protocols (Thomas et al. (2013) *Biochemical and Biophysical Research Communications* 438(2):243-248). Briefly, T cells were lysed in ice-cold potassium phosphate buffer (45 mM, pH 8.2) containing protease inhibitors (Roche, Complete Protease Inhibitor Cocktail, 1 tablet in 50 ml) and incubated with 3H-glutamine (0.03 μM, 0.91 μCi) for 90 min at room temperature. The reactions were carried out in 50 μl reaction volumes in a 96-well microplate. At the end of the reaction period, the assay was terminated upon the addition of imidazole buffer (20 mM, pH 7). 96-well spin columns packed with strong anion ion-exchange resin (Bio-Rad, AG® 1-X2 Resin, 200-400 mesh, chloride form) were used to separate the substrate and the reaction product. Unreacted $^3$H-glutamine was removed by washing with imidazole buffer. $^3$H-glutamate, the reaction product, was then eluted with 0.1 N HCl and analyzed for radioactivity using Perkin Elmer's TopCount instrument in conjunction with their 96-well LumaPlates.

Flow cytometry, intracellular cytokine staining, and ELISA: Flow cytometry data were acquired with a FACS Calibur (BD Biosciences) and were analyzed with FlowJo7.6 software (TreeStar). For intracellular staining, cells were stimulated at 37° C. for 4 hrs in the presence of Monensin (GolgiStop; BD Biosciences), phorbol 12-myristate 13-acetate (PMA; Sigma), and ionomycin (Sigma). Cells were surface stained and underwent fixation/permeabilization with either a Cytofix/Cytoperm kit (BD Biosciences) or a Fixation/Permeabilization kit (eBioscience), followed by staining for intracellular cytokines. Gates were determined appropriately through the use of unstimulated control cells. Voltages were determined from unstained controls. IFN-γ concentration in the supernatant of cell cultures was analyzed by ELISA as recommended by the manufacturer (eBioscience).

In Vivo cytotoxicity assay: Splenocytes from WT mice were labeled with either 20 μM or 2 μM of carboxyfluorescein diacetate succinimidyl (CFSE, Invitrogen). The $CSFE^{high}$ cells were pulsed with class I OVA peptide (10 μM). Equal numbers ($5\times10^6$ cells) of peptide-pulsed $CFSE^{high}$ cells and unpulsed $CFSE^{low}$ cells were co-administered i.v. into syngeneic host mice that had been previously (day 7) immunized with vaccinia-OVA ($1\times10^6$ plaque-forming units). After 10 hrs, splenocytes were isolated from host spleens. The two target populations were distinguished based on the differences in their CFSE intensity by flow cytometry. The loss of peptide-pulsed target cells was indicative of cytotoxicity. The ratio of pulsed to unpulsed target cells in the indicated groups of mice was calculated and the percent killing was determined by using the formula: [1−(ratio in experimental mouse/ratio in naïve mouse)]×100%.

Murine skin transplantation: BALB/c mice served as skin donors and C57BL/6 mice served as allograft recipients. Full-thickness skin grafts were harvested from the back and then fixed on the thoracic flank of recipient mice with simple separate stitches. The size of transplanted grafts was 1×1 $cm^2$. Grafts were observed every day after the removal of the bandage at day 7 and considered rejected when ≥90% of the graft tissue became necrotic. The MST of skin grafts was observed. Seven days after surgery, skin tissue from the transplantation site was collected for optical microscopy after hematoxylin and eosin staining.

Murine heterotopic heart transplantation: BALB/c mice served as heart donors and C57BL/6 mice serve as allograft recipients. Either abdominal or cervical heterotopic heart transplantation was performed according to previously published methods (Corry et al. (1973) *Transplantation* 16(4): 343-350; Oberhube et al. (2014) *J Vis Exp* 92:e50753). Functionality of the transplanted heart was monitored daily by palpation. Clinical rejection was defined by cessation of palpable heartbeats and confirmed by autopsy. Loss of graft function within 48 hrs of transplantation was considered as a technical failure, and animals in which this occurred were omitted from the analysis.

Statistical analysis: Prism software version 5.0 (GraphPad Software) was used for statistical analyses, including unpaired Student's t-test, two-way analysis of variance (ANOVA) and log-rank analysis. A P value less than 0.05 was considered statistically significant.

Introduction

Advances in immunosuppressive regimens have played an essential role in driving forward the field of organ transplantation (Sayegh & Carpenter (2004) *The New England Journal of Medicine* 351 (26): 2761-2766). However, long-term use of immunosuppressants not only leads to susceptibility to infection, but also results in a broad range of co-morbidity. For example, calcineurin inhibitors are associated with hyperlipidemia, hyperglycemia, neuro- and nephro-toxicity, as well as an increased risk of malignancy (Crutchlow & Bloom (2007) *Clinical Journal of the American Society of Nephrology: CJASN* 2(2):343-355; Hoorn et al. (2012) *Journal of Nephrology* 25(3):269-275; Arnold et al. (2013) *Am J Transplant* 13(9):2426-2432; Guba et al. (2004) *Transplantation* 77(12):1777-1782; Roodnat et al. (2014) *Transplantation* 98(1):47-53.2-6). In addition, such agents inhibit negative regulatory and tolerance-inducing responses (Wu et al. (2012) *Transpl Immunol* 27(1):30-38). That is, the calcineurin inhibitors are truly immunosuppressive in that they inhibit both activating and inhibitory signaling pathways (Powell & Zheng (2006) *Curr Opin Investig Drugs* 7(11):1002-1007). As such, whereas the ultimate goal of anti-rejection strategies is to induce immune tolerance in the absence of long-term immunosuppression, current treatment regimens thwart this goal by inhibiting the induction of tolerance. Therefore new approaches to preventing graft rejection are required.

Recently, metabolic signaling pathways have been shown to play critical roles in dictating the outcomes of T cell responses (Yang & Chi (2012) *Seminars in Immunology* 24(6):421-428; Waickman & Powell (2012) *Immunological Reviews* 249(1):43-58; Pollizzi & Powell (2014) *Nature Reviews. Immunology* 14(7):435-446). The coordination of metabolism reprogramming and T cell function reflects the ability of how low-frequency antigen-specific naïve T cells rapidly expand in response to a pathogen (Powell et al. (2013) *Cold Spring Harbor Symposia on Quantitative Biology* 78:125-130). In the presence of oxygen, naïve or resting T cells rely on mitochondrial oxidative phosphorylation (OXPHOS) to generate energy necessary for immune surveillance (Pearce et al. (2013) *Science* 342(6155):1242454).

In contrast, both $CD4^+$ and $CD8^+$ effector T cells employ aerobic glycolysis to meet their biosynthetic demands (Pearce et al. (2013) *Science* 342(6155):1242454; Jones & Thompson (2007) *Immunity* 27(2):173-178). This use of glycolysis in the presence of oxygen was first described by Otto Warburg in cancer cells (Warburg (1956) *Science* 124 (3215):269-270) and was subsequently found to be important in activated T cells (Warburg et al. (1958) [Metabolism of leukocytes]. *Zeitschrift fur Naturforschung. Teil B: Chemie, Biochemie, Biophysik, Biologie* 13B (8):515-516). While glycolysis provides less adenosine triphosphate (ATP) than oxidative phosphorylation, it has been proposed that aerobic glycolysis permits the generation of the substrates necessary for the generation of amino acids, nucleic acids and lipids, all of which are crucial for proliferation (Vander Heiden et al. (2009) *Science* 324(5930):1029-1033). Essential for this activation-induced glycolytic response is glucose uptake (Cham et al. (2008) *European Journal of Immunology* 38(9):2438-2450; Cham & Gajewski (2005) *Journal of Immunology* 174(8):4670-4677). Indeed, the increased expression of the glucose transporter GLUT1 on the cell surface is a critical aspect of TCR-induced activation (Jacobs et al. (2008) *Journal of Immunology* 180(7):4476-4486). Similarly, the uptake and metabolism of amino acids, especially glutamine, is essential for T cell activation (Carr et al. (2010) *Journal of Immunology* 185(2):1037-1044). Glutamine deprivation blocks T cell proliferation and cytokine production (Carr et al. (2010) *Journal of Immunology* 185(2):1037-1044). While the considerations depicted above reflect the metabolic needs of T cells during activation and explosive proliferation, what has also become apparent is that different T cell subsets require different metabolic programs. For example, Th1, Th2, and Th17 effector T cells have been found to depend on glucose uptake and glycolysis. Alternatively, regulatory T cells (Tregs) are dependent upon lipid oxidation to generate energy (Michalek et al. (2011) *Journal of Immunology* 186(6):3299-3303). Blocking glycolysis inhibits effector development but promotes Treg formation (Shi et al. (2011) *The Journal of Experimental Medicine* 208(7):1367-1376). Furthermore, $CD4^+$ effector T cells with GLUT1 deficiency are impaired in proliferation and function in vivo, whereas Tregs are enriched and functionally unaffected (Macintyre et al. (2014) *Cell Metab* 20(1):61-72). Likewise, glutamine is critically required by naïve $CD4^+$ T cell to differentiate to Th1 and Th17 effector T cells but not to Tregs (Nakaya et al. (2014) *Immunity* 40(5):692-705). Thus, strategies designed to inhibit metabolic reprogramming to prevent naïve T cells from activating and differentiating into effector T cells, might provide a novel means to inhibit transplant rejection. In this study, it is demonstrated that combined inhibition of glycolysis and glutamine metabolism leads to a profound suppression in $CD4^+$ and $CD8^+$ effector T cell responses while preserving mechanisms of immune regulation. It is proposed that this antimetabolic regimen represents a novel and promising strategy to promote allograft survival.

Results

Blocking glycolysis inhibits activation-induced T cell proliferation and cytokine production: To assess the effect of metabolic reprogramming agents on the metabolic changes of resting T cells in response to stimulation, the two intrinsic cellular bioenergetic parameters, oxygen consumption rate (OCR) and extracellular acidification rate (ECAR) with XF96 extracellular flux analyzer (Seahorse Bioscience), were measured. OCR is an indicator of mitochondrial OXPHOS, and ECAR is predominantly a measure of lactic acid formed during glycolytic energy metabolism, and thus reflects overall glycolytic flux. Primary, naïve 5C.C7 $CD4^+$ T cells were incubated with pigeon cytochrome c (PCC) peptide for 48 hrs and then expanded and rested in IL-2 for an additional 5 days to generate previously activated $CD4^+$ cells. After measuring the baseline bioenergetics of these resting $CD4^+$ cells, cells were re-stimulated with anti-CD3/CD28 (FIG. 9A and FIG. 9B). Upon activation, the T cells exhibited a marked increase in ECAR and a modest increase in OCR in response to anti-CD3/CD28 (FIG. 9A and FIG. 9B). Upon reaching the peak of glycolytic flux, metabolic reprogramming agents were administered to the cells. 2-DG is a glucose analog that inhibits hexokinase, the first enzyme in the glycolytic pathway (Rowe et al. (2013) *Nature Medicine* 19(4):488-493). Adding 2-DG led to a sharp decrease of ECAR levels and an insignificant increase in OCR (FIG. 9A and FIG. 9B), reflecting that 2-DG inhibited glycolysis but minimally affected OXPHOS (Cheng et al. (2012) *Cancer Research* 72(10):2634-2644; Yamasaki et al. (2011) *Nature Reviews. Urology* 8(3):165-171). Metformin is a commonly used oral hypoglycemic that activates AMPK, inhibits mitochondrial respiratory complex I and promotes fatty acid oxidation (Buzzai et al. (2007) *Cancer Research* 67(14): 6745-6752; El-Mir et al. (2000) *The Journal of Biological Chemistry* 275(1):223-228). Consistent with its ability to inhibit Complex I (El-Mir et al. (2000) *The Journal of Biological Chemistry* 275(1):223-228), the addition of metformin led to a marked suppression of OCR and an increase in ECAR (FIG. 9A and FIG. 9B). However, concomitant use of 2-DG and metformin together has been shown to potentiate the inhibition of glycolysis in tumor cells (Cheong et al. (2011) *Molecular Cancer Therapeutics* 10(12):2350-2362; Cheng et al. (2014) *British Journal of Cancer* 111(1):85-93.31). Indeed, when combined with metformin, 2-DG inhibits ECAR in T cells more effectively than when employed alone (FIG. 9A). In addition, the combination of 2-DG and metformin led to a lower OCR compared to that of the no treatment group but higher than that of metformin alone (FIG. 9B). Thus, similar to observations in tumor cells, combining 2-DG and metformin leads to a profound decrease in glycolysis in activated T cells.

Given the critical role of glycolysis in promoting T cell effector function, the effect of 2-DG and metformin on T cell proliferation and cytokine production was determined next. To this end, splenocytes from wild-type (WT) C57BL/6 mice were stimulated with anti-CD3 in the presence of media control, 2-DG alone, metformin alone or 2-DG+metformin for 72 hrs. Initial titration studies demonstrated that 2-DG metabolic reprogramming therapy or metformin metabolic reprogramming therapy inhibited T cell proliferation and cytokine production in a dose-dependent manner (data not shown). Importantly, consistent with their combined metabolic effects, the combination of 2-DG and metformin showed a more significant inhibition of cell proliferation and IFN-γ production of activated CD4$^+$ and CD8$^+$ T cells than either compound alone (FIG. 9C and FIG. 9D). Together, these data suggest that 2-DG in combination with metformin potently inhibit both metabolic reprogramming and proliferation/cytokine production in activated T cells.

Combined inhibition of glycolysis and glutaminolysis profoundly abrogates activation-induced T cell proliferation and cytokine production: Upon activation, glutamine oxidation increases as well as glycolysis to meet biosynthetic demand and allowing for continued tricarboxylic acid (TCA) flux (MacIver et al. (2013) *Annual Review of Immunology* 31:259-283). Consequently, T cell activation, differentiation and function are critically dependent upon adequate glutamine availability (Carr et al. (2010) *Journal of Immunology* 185(2):1037-1044; Nakaya et al. (2014) *Immunity* 40(5):692-705). To this end, upon activation, T cells coordinately increase the expression of glutamine transporters and glutaminase activity required for glutamine oxidation (Carr et al. (2010) *Journal of Immunology* 185(2):1037-1044). 6-Diazo-5-oxo-L-norleucine (DON) is a glutamine analog that inhibits multiple targets in the glutamine metabolic pathway, including glutaminase and glutamine transporters (Thomas et al. (2014) *Biochemical and Biophysical Research Communications* 443(1):32-36; Thomas et al. (2013) *Biochemical and Biophysical Research Communications* 438(2):243-248). To explore the role of glutaminase activity in T cell activation, naïve CD4$^+$ T cells were stimulated with anti-CD3/CD28 in medium with or without metabolic reprogramming agents for 24 hrs. The glutaminase activity of these CD4$^+$ T cells was determined using a radiolabeled assay as described (Thomas et al. (2013) *Biochemical and Biophysical Research Communications* 438(2):243-248). It was observed that activated T cells exhibited increased glutaminase activity compared to naïve T cells (FIG. 10A), indicating metabolic reprogramming toward glutaminolysis. Notably, glutaminase activity of activated T cells was significantly abrogated in the presence of DON (FIG. 10A), and this inhibition was not affected by the presence of the glycolytic inhibitors (FIG. 10A).

Furthermore, when cultured with DON, activated CD4$^+$ and CD8$^+$ T cells had decreased proliferation and IFN-γ production (FIG. 10B and FIG. 10C). Having confirmed previous studies showing that blocking the glutamine metabolic pathway was also capable of suppressing T cell responses (Carr et al. (2010) *Journal of Immunology* 185(2):1037-1044), it was next investigated whether dual inhibition of glycolysis and glutaminolysis had an additional effect on inhibiting T cell proliferation and function. To this end, metabolic reprogramming agents 2-DG, metformin and DON were combined as a metabolic reprogramming therapy. Indeed, metabolic reprogramming therapy with at least three metabolic reprogramming agents had a more profound effect on suppressing T cell proliferation and IFN-γ production than only metabolic reprogramming therapy with at least two metabolic reprogramming agents (e.g., 2-DG and metformin) or at least one metabolic reprogramming agent (e.g., DON)(FIG. 10B and FIG. 10C). Of note, the decrease in function was not because of a decrease of cell viability (FIG. 11). In addition, although glutamate can be further catabolized to fuel TCA cycle and ATP production (Pearce et al. (2013) *Science* 342(6155): 1242454), in extracellular flux analysis, adding DON (individually or combined with 2-DG and metformin) did not have an obvious impact on either OXPHOS or glycolytic flux of activated cells (FIG. 12A and FIG. 12B). Therefore, it was concluded that the inhibition of activation-induced T cell proliferation and function was most effective by simultaneously blocking glycolysis (with 2-DG and metformin) and glutaminolysis (with DON).

Inhibition of glycolysis and glutaminolysis suppresses the proliferation and function of antigen-specific CD4$^+$ effector T cells but not Tregs in vivo: Given the observation that inhibition of glycolysis and glutaminolysis suppresses the activation of T cells in vitro, this paradigm was examined in an antigen-specific manner in vivo. To test the ability of metabolic reprogramming agents to mitigate CD4+ effector T cell responses, Thy1.1$^+$ CD4$^+$ OVA-specific (OT-II) TCR transgenic T cells were adoptively transferred into Thy1.2$^+$ WT mice that were concomitantly infected with vaccinia-OVA, a recombinant vaccinia virus carrying chicken ovalbumin (OVA) on day 0. The mice were then treated with PBS (vehicle control), 2-DG+metformin (metabolic reprogramming therapy with at least two metabolic reprogramming agents) or 2-DG+metformin+DON (metabolic reprogramming therapy with at least three metabolic reprogramming agents) for 3 days and the expansion of the OVA-specific Thy1.1$^+$ CD4$^+$ T cells was interrogated on day 4. Mice treated with 2-DG+metformin demonstrated a marked decrease in the expansion of the antigen-specific Thy1.1+ CD4+ T cells, which was even further reduced with the metabolic reprogramming therapy with at least three metabolic reprogramming agents (FIG. 13A). In addition, the metabolic reprogramming therapy with at least three metabolic reprogramming agents in vivo strongly inhibited antigen-specific IFN-γ production of splenocytes upon re-challenge with peptide ex vivo (FIG. 13B). Metabolic reprogramming therapy with at least three metabolic reprogramming agents also led to a significantly higher frequency of Foxp3+ CD4+ T cells (FIG. 13C), indicating a preservation of this mechanism of immune regulation. Of note, the expansion and absolute number of Thy1.1+ Foxp3+ T cells was decreased in the mice treated with metabolic reprogramming therapy with at least three metabolic reprogramming agents when compared to the untreated mice. This indicates that, as is the case for effector cells, the expansion of Foxp3+ T cells in response to antigen requires glycolysis and glutamine. However, the ratio of OVA-specific Thy1.1+ regulatory T cells: Effector cells was increased in the treated mice (FIG. 13D). Together, these results showed that metabolic reprogramming therapy with at least three metabolic reprogramming agents had the most robust effect on inhibiting CD4+ T cell proliferation and cytokine production upon antigen recognition, while the differentiation into antigen-specific regulatory T cells was relatively preserved.

Inhibition of glycolysis and glutaminolysis suppresses the proliferation and Function of antigen-specific CD8+ T cell: Next, the ability of the metabolic reprogramming agents to block antigen-specific CD8+ T cell responses was examined. To this end, Thy1.1+ CD8+ OVA-specific (OT-I) TCR transgenic T cells were adoptively transferred into Thy1.2+ WT mice and the mice were infected with vaccinia-OVA and treated with metabolic reprogramming agents (the same regimen used in OT-II experiments). As was the case for CD4+ T cells, treatment of the mice with metabolic reprogramming therapy with at least three metabolic reprogramming agents led to a more profound inhibition of the expansion of the antigen-specific Thy1.1+ CD8+ T cells than 2DG+metformin (FIG. 14A) or any compound alone (data not shown). Additionally, this combination of anti-metabolic metabolic reprogramming therapy strongly inhibited the generation of IFN-γ-secreting CD8+ T cells (FIG. 14B). The decreased frequency and function of Thy1.1+ CD8+ T cells was also reflected by the amount of IFN-γ secreted by splenocytes re-stimulated ex vivo with class I OVA peptide (FIG. 14C). Having demonstrated the ability of inhibitors of glycolysis and glutaminolysis to mitigate the expansion and function of exogenous effector T cells, the effect of the anti-metabolic regimen on endogenous effector CD8+ T cells was next examined with an in vivo cytotoxicity (CTL) assay. Mice were immunized with vaccinia-OVA and treated with PBS (vehicle control), metabolic reprogramming therapy with at least two metabolic reprogramming agents (e.g., 2DG metformin) or metabolic reprogramming therapy with at least three metabolic reprogramming agents (e.g., 2DG+ metforming+DON) for 7 days, then CFSE-labeled target cells were injected on day 8 and percent of specific killing was evaluated 10 hrs later. It was observed that most (96%±2%) of the OVA peptide-pulsed target cells were preserved in the mice receiving metabolic reprogramming therapy with at least three metabolic reprogramming agents, whereas 78±5% and 45±10% of the target cells were eliminated in mice receiving PBS and 2-DG+metformin treatment, respectively (FIG. 14D). These data suggest that the development of effective cytotoxic T lymphocytes is suppressed by the inhibition of glycolysis and glutamine metabolism.

Metabolic reprogramming agents promote allograft acceptance in mouse models of skin and heart transplantation: Having demonstrated the ability of combined anti-metabolic metabolic reprogramming therapy to inhibit antiviral responses in vivo, it was next investigated whether anti-metabolic metabolic reprogramming therapy could prolong allograft survival using a skin transplantation model involving C57BL/6 mice receiving allogenic skin grafts from Balb/c mice. A significantly prolonged graft median survival time (MST) was found for mice that received 2-DG+metformin or DON alone, compared to those that received no treatment (13 vs. 11 days, P=0.0048 and 22 vs. 11 days, P=0.0019, respectively) (FIG. 15A). However, blocking at least the metabolic pathways of glycolysis and glutamine metabolism with metabolic reprogramming therapy with at least three metabolic reprogramming agents resulted in a marked increase of skin graft survival compared to no treatment (MST 40 vs. 11 days, P<0.0001) (FIG. 15A). In addition, the appearance and histology of skin grafts from the group treated with metabolic reprogramming therapy with at least three metabolic reprogramming agents exhibited no evidence of tissue destruction, more intact tissue alignment, and less infiltration of inflammatory cells (FIG. 15B, FIG. 15C, FIG. 15D, and FIG. 15E). For comparison, the MST of this fully allogeneic skin allograft under the treatment of FK506 or cyclosporine has previously been reported to be less than 20 days (Gorski & Wasik (1990) *Immunology* 71(1): 148-150).

Finally, this metabolic reprogramming therapy with at least three metabolic reprogramming agents was employed in a Balb/c to C57BL/6 heart transplantation, which is a vascularized solid organ transplantation model. Strikingly, when recipient mice were treated with metabolic reprogramming therapy with at least three metabolic reprogramming agents, the grafted hearts continued beating for more than 100 days post-transplantation without rejection (FIG. 15F). Likewise, the cardiac grafts from the treatment group exhibited much healthier microscopic morphology with no evidence of necrosis, fibrosis, or lymphocyte infiltration (FIG. 15G, FIG. 15H, FIG. 15I and FIG. 15J). Together, these data support the notion that the inhibition of glycolysis and glutamine metabolic pathways represents a potent means to prevent acute rejection and promote long-term graft acceptance.

Discussion

In this study a novel approach was defined to prevent transplantation graft rejection by inhibiting metabolic pathways necessary for effector T cell function. This approach is based upon the emerging understanding that metabolic reprogramming in T cells is not simply the result of T cell activation, but rather plays a critical role in regulating T cell differentiation and function (Jones & Thompson (2007) *Immunity* 27(2):173-178; MacIver et al. (2013) *Annual Review of Immunology* 31:259-283). The therapeutic index of this approach relies on the extraordinary metabolic requirements of effector T cell response that is distinct from the more flexible and adaptive ordinary metabolic network. As such, even though the inhibitors employed are relatively non-specific, relative cellular selectivity is achieved based upon the extraordinary metabolic demands of the effector T cells. Indeed, while effector T cells employ aerobic glycolysis for energy, regulatory T cells are programmed such that they rely upon oxidative phosphorylation and fatty acid oxidation (Michalek et al. (2011) *Journal of Immunology*

186(6):3299-330322). Nonetheless, in this study, inhibiting glycolysis by the combination of 2-DG and metformin was not sufficient to prevent acute rejection or induce long-term tolerance in a fully MHC-mismatched transplantation model. Inhibition of glutamine metabolism also blocks effector T cell differentiation, proliferation and function while leaving Treg differentiation relatively intact (Carr et al. (2010) *Journal of Immunology* 185(2):1037-1044; Nakaya et al. (2014) *Immunity* 40(5):692-705). Thus, DON, a glutaminolytic inhibitor, was integrated into this protocol. As such, inhibiting both glycolysis and glutaminolysis, (a regimen that can simultaneously suppress effector T cell function while preserving Treg differentiation) proved to be the most effective in promoting graft survival (Shi et al. (2011) *The Journal of Experimental Medicine* 208(7): 1367-1376; Michalek et al. (2011) *Journal of Immunology* 186(6):3299-3303).

The cellular selectivity based on demand was not only observed for cells of the immune system but also contributed to the relative lack of side effects observed. Indeed, by tracking body weight and fur ruffling as markers of overall health of transplant recipient mice, in some cases for more than 100 days, any systemic sickness or morbidity was not observed associated with the treatment regimen. Further, the compounds employed in the study have all been employed in patients with tolerable adverse effects (Franciosi et al. (2013) *PloS one* 8(8):e71583; Sullivan et al. (1988) *Cancer Chemometabolic reprogramming therapy and Pharmacology* 21(1):78-84; Raez et al. (2013) *Cancer Chemometabolic reprogramming therapy and Pharmacology* 71(2):523-530). Thus, it is believed that the combination treatment strategy is readily translated into the clinic. Notably, in previous trials using these 2-DG or DON or metformin for the treatment of cancer, the efficacy was not as striking as what has been observed in using these agents for transplant rejection (Sullivan et al. (1988) *Cancer Chemometabolic reprogramming therapy and Pharmacology* 21(1):78-84; Raez et al. (2013) *Cancer Chemometabolic reprogramming therapy and Pharmacology* 71(2):523-530; Tsilidis et al. (2014) *Diabetes Care* 37(9):2522-2532). It is believed that this is because while T effector cells and cancer cells both demonstrate Warburg metabolism, mutations in tumors enable them to more effectively become resistant to these agents. Indeed, it is believed that the enhanced sensitivity of T cells to the combination regimen contributes to the ability to devise a regimen with doses that have relatively minor side effects.

Steroids and calcineurin inhibitors remain the backbone of most current post-transplantation regimens. Steroids have multiple adverse effects, such as increased risk of infection, hyperglycemia, accelerated atherosclerosis, and gastrointestinal bleeding, while calcineurin inhibitors are associated with neurotoxicity and nephrotoxicity, as well as risk of infection and an increased risk of cancer (Crutchlow & Bloom (2007) *Clinical Journal of the American Society of Nephrology: CJASN* 2(2):343-355; Hoorn et al. (2012) *Journal of Nephrology* 25(3):269-275; Arnold et al. (2013) *Am J Transplant* 13(9):2426-2432; Guba et al. (2004) *Transplantation* 77(12):1777-1782; Roodnat et al. (2014) *Transplantation* 98(1):47-53.2-6). The use of the presently disclosed agents is devoid of the side effects associated with current immunosuppressive regimens. At least one advantage of metabolic reprogramming therapy is that it will promote a favorable systemic metabolic profile. Indeed, the metabolic reprogramming agents employed counteract some of the metabolic abnormalities associated with current immunosuppression, such as increased blood glucose and triglycerides. Of note however, one of the major obstacles of current transplantation immunosuppression is the reactivation of cytomegalovirus. Interestingly, the agents employed in the anti-metabolic approach have been shown to inhibit viral replication (Chambers et al. (2010) *J Virol* 84(4):1867-1873). In addition, while calcineurin inhibitors are associated with an increased risk of developing neoplasm (Guba et al. (2004) *Transplantation* 77(12):1777-1782, targeting both glycolysis and glutamine pathway inhibits the growth of tumor cells (Cheong et al. (2011) *Molecular Cancer Therapeutics* 10(12):2350-2362; Cheng et al. (2014) *British Journal of Cancer* 111(1):85-93.31; Willems et al. (2013) *Blood* 122(20):3521-3532; Lim et al. (2014) *Cancer Research* 74(13): 3535-3545). Furthermore, while calcineurin inhibitors have efficacy in the prevention of acute rejection, such agents can block the induction of immunologic tolerance in part by preventing T cell anergy and inhibiting the generation of regulatory T cells. The metabolic reprogramming agents employed in this study promote both anergy and T regulatory cell generation (FIG. 13C; Zheng et al. (2009) *Journal of Immunology* 183(10):6095-6101). However, metabolic reprogramming metabolic reprogramming therapy alone was not sufficient to completely prevent skin allograft rejection. Further, even though 100% heart graft survival was observed (FIG. 15D) while the mice were being treated, preliminary studies indicate that stopping metabolic reprogramming therapy resulted in the eventual rejection of the hearts approximately 80 days later (data not shown). Integrating tolerance inducing metabolic reprogramming therapy, such as costimulatory blockade with, or without, rapamycin, may be a means to induce long-term tolerance in the absence of long-term immunosuppression (Oderup et al. (2006) *Transplantation* 82(11):1493-1500; Pilon et al. (2014) *American Journal of Transplantation: Official Journal of the American Society of Transplantation and the American Society of Transplant Surgeons* 14(12):2874-2882; Bestard et al. (2011) *Transplant International:Official Journal of the European Society for Organ Transplantation* 24(5):451-460).

Studies have revealed a critical role for the mammalian Target Of Rapamcyin (mTOR) in regulating T cell differentiation and function (Delgoffe et al. (2011) *Nature Immunology* 12(4):295-303; Li et al. (2011) *Immunity* 34(4):541-553). By genetically dissecting mTOR signaling in mice, TCR engagement in the absence of mTOR was demonstrated to lead to the generation of Tregs (Delgoffe et al. (2011) *Nature Immunology* 12(4):295-303; Delgoffe et al. (2009) *Immunity* 30(6):832-844). However, in spite of these revealing genetic studies, the efficacy of rapamycin and other rapalogues in preventing transplantation rejection has been somewhat pedestrian (Abdelmalek et al. (2012) *American Journal of Transplantation: Official Journal of the American Society of Transplantation and the American Society of Transplant Surgeons* 12(3):694-705). In part, it is believed that this is due to a lack of strategic integration of mTOR inhibitors into immunosuppressive protocols (Lo et al. (2014) *Current Opinion in Organ Transplantation* 19(4): 363-371). For example, combining rapamycin with calcineurin inhibitors negate the potentially tolerance inducing effects of rapamycin (Satake et al. (2014) *PloS one* 9(3): e9288854). Interestingly, what has emerged from recent studies is that mechanistically, mTOR regulates T cell differentiation and function in part by regulating metabolic programs. mTOR plays an important role in regulating glycolysis and glutamine metabolism which are critical in order to support effector T cell generation and function (Wang et al. (2011) *Immunity* 35(6): 871-882; Sengupta et al. (2010) *Molecular Cell* 40(2):310-322; Csibi et al. (2013)

*Cell* 153(4):840-854). Thus, inhibition of mTOR activity abrogates effector T cell generation (both CD4+ and CD8+) and also hinders the up-regulation of glycolysis and glutaminolysis upon T cell activation. The presently disclosed metabolic reprogramming metabolic reprogramming therapy approach directly targets these pathways.

In conclusion, the presently disclosed subject matter provides a novel approach to prevention of graft rejection by inhibiting metabolic pathways necessary for effector T cell function. The differential metabolic requirements of effector and regulatory T cells reveal a new therapeutic window to simultaneously inhibit rejection and promote tolerance. Future studies combining metabolic reprogramming metabolic reprogramming therapy with tolerance-inducing regimens, such as co-stimulatory blockade and Treg metabolic reprogramming therapy, have the potential to promote long-term graft acceptance in the absence of long-term immunosuppression.

Example 3

Mice were sensitized to House Dust Mite antigen (HDM) in the absence of drug. Upon intratracheal rechallenge the mice were treated with vehicle or 25. In this model during the acute lung rechallenge 25 inhibited pathology, the recruitment/generation of Th2 cells and reduced the levels of HDM specific IgE (FIG. 16). This data shows the unexpected effectiveness of using a DON prodrug to treat asthma.

Example 4

FIG. 17A, FIG. 17B, and FIG. 17C show targeting glutamine in a mouse model of acute respiratory distress syndrome (ARDS). Mice were challenged with Ips (FIG. 17A) to induce ARDS and treated with DON on day 2 & 4. Treatment promoted a more rapid recovery (weight gain) (FIG. 17B) and less lung damage (FIG. 17C). This data shows the effectiveness of using DON to treat ARDS.

Example 5

Mice were treated with intratracheal bleomycin to induce fibrosis. DON treated mice demonstrated markedly decreased lung damage as well as a decrease in the recruitment/generation of lung fibrocytes (FIG. 18). This data shows the unexpected effectiveness of using DON to treat pulmonary fibrosis.

Example 6

FIG. 19A and FIG. 19B show the targeting of glutamine metabolism to cure Cerebral malaria. Mice were treated on day 5 post infection and on day 6 (12 hours before subsequent death) with DON every other day. The unexpected ability of DON to prevent death at such a late stage of disease highlights the robust ability of our approach in CNS inflammation.

Example 7

FIG. 20 shows the targeting of glutamine metabolism in neuromyelitis optica. Auto-reactive T cells were adoptively transferred into mice treated with PBS or 25 and mean paralysis scores were measured. This data shows the unexpected effectiveness of using a DON prodrug to treat neuromyelitis optica.

Example 8

FIG. 21A and FIG. 21B show the targeting of glutamine metabolism in multiple sclerosis. Animals were immunized for EAE (C57BL/6+MOG35-55). Mice were treated with vehicle or 25 either q.d. from the day of immunization (day 0, left), or b.d. from the time of disease onset (EAE disease score≥1, right). This data shows the unexpected effectiveness of using a DON prodrug to prevent (FIG. 21A) and treat (FIG. 21B) multiple sclerosis.

Example 9

FIG. 22 shows screening prodrugs in vivo: Thy1.1+OT-1 cells were adoptively transferred into mice infected with vaccinia ova. The mice were treated with prodrugs or vehicle (V) and the ova-specific response was monitored. In this case prodrugs P1, P1-2 and P3 unexpectedly inhibited the T cell response.

Example 10

Compound 14b Enhanced CSF Delivery of DON in Monkey

Method

Compound: Compound 14b was dissolved in 50 mM HEPES buffered saline containing 5% ethanol and 5% tween on the date of administration.

Monkey: Monkey studies were conducted according to protocol (#PR15M298) approved by the Animal Care and Use Committee at Johns Hopkins University. Two female pigtail monkeys (approximately 3.5 kg, non-drug naive) were adjacently housed in stainless steel cages on a social interaction rack (contains 4 cages, each 32.5" wide x 28" deep x 32" high) maintaining temperature of 64-84° F., humidity of 30-70% with alternating 14-10 hour light/dark cycle as per the USDA Animal Welfare Act (9 CFR, Parts 1, 2, and 3). Food was provided daily in amounts appropriate for the size and age of the animals and RO purified water provided ad libitum through an in-cage lixit valve. Food enrichment was provided Monday through Friday.

Treatment: Prior to drug administration, macaques were sedated with ketamine given as an intramuscular injection prior to test article administration. Sedation was maintained through blood and cerebrospinal fluid (CSF) sample collections with ketamine at a starting rate of 15 mg/kg with additional doses of 20-30 mg during the first hour. At subsequent time points ketamine was given at 10-15 mg/kg. DON (50 mM HEPES buffered saline) and compound 14b (50 mM HEPES buffered saline containing 5% ethanol and 5% tween) were administered (1.6 and 3.6 mg/kg equivalent dose of DON) to the animals at a dosing volume of 1 mL/kg intravenously. CSF sample (target of 50 µL) was obtained by percutaneous puncture of the cisterna magna at 30 min post dose. Blood samples (1 mL) were collected at 15 min, 30 min, 1 h, 2 h, 4 h, and 6 h post dose by percutaneous puncture of a peripheral vein. Samples were processed for plasma (centrifuged at a temperature of 4° C., at 3,000 g, for 10 minutes). All samples were maintained chilled on ice throughout processing. Samples were collected in microcentrifuge tubes, flash frozen, and placed in a freezer set to maintain −80° C. until LC/MS analysis.

Data Analysis: DON was extracted from samples (50 mg) with 250 µL methanol containing glutamate-$d_5$ (10 µM ISTD) by vortexing in low retention tubes. Samples were centrifuged at 16,000 g for 5 minutes to precipitate proteins. Supernatants (200λ) were moved to new tubez and dried at 45° C. under vacuum for 1 hour. To each tube, 50 μL of 0.2 M sodium bicarbonate buffer (pH 9.0) and 100 μL of 10 mM dabsyl chloride in acetone was added. After vortexing, samples were incubated at 60° C. for 15 minutes to derivatize. Samples (2 μL) were injected and separated on an Agilent 1290 equipped with an Agilent Eclipse plus C18 RRHD 2.1 X100 mm column over a 2.5 minute gradient from 20-95% acetonitrile+0.1% formic acid and quantified on an Agilent 6520 QTOF mass spectrometer. Calibration curves over the range of 0.005-17.1 μg/mL in plasma and CSF for DON were constructed from the peak area ratio of the analyte to the internal standard using linear regression with a weighting factor of 1/(nominal concentration). Correlation coefficient of greater than 0.99 was obtained in all analytical runs. The mean predicted relative standard deviation for back calculated concentrations of the standards and QC's for all analytes were within the range of 85 to 115%, except for the lowest concentration which was within the range of 80 to 120% with an overall accuracy and precision of 6.7% and 6.6% respectively.

Results

The pharmacokinetics of DON and compound 14b in monkeys were evaluated. In pigtail macaques, i.v. administration of DON (1.6 mg/kg) and compound 14b (3.6 mg/kg; 1.6 mg/kg DON equivalent) demonstrated significantly different DON plasma profiles (FIG. 40A). DON administration provided high plasma exposures with AUC0-t of 42.7 nmol*h/mL. In contrast, compound 14b administration delivered ~7 fold lower plasma exposure of DON with AUC0-t of 5.71 nmol*h/mL. The opposite observation was seen in the CSF where enhanced DON levels were observed after compound 14b administration. In the CSF at 30 min post dose, DON administration resulted in 0.33 nmol/g DON while compound 14b delivered 1.43 nmol/g DON. When comparing plasma to CSF ratio at 30 min, compound 14b demonstrated unexpected 10-fold enhancement of DON CSF delivery versus DON (FIG. 40B).

Example 11

Compounds 14b and 47 Enhanced CSF Delivery of DON in Swine

Method

Compound: Compound 47 was dissolved in a sterile saline containing 5% ethanol and 5% Tween 80 on the date of administration.

Swine: Swine studies were conducted under a protocol approved by the Johns Hopkins Animal Care and Use Committee. Adult, female Gottingen×Yucutan miniature swine (Massachusetts General Hospital, MA) were housed in Johns Hopkins University facilities accredited by the Association for Assessment and Accreditation of Laboratory Animal Care International in compliance with the Animal Welfare Act, Animal Welfare Regulations, and the Public Health Service Policy on the Humane Care and Use of Laboratory Animals. Animals were maintained on a 14-h light and 10-h dark schedule, provided ad libitum water and a commercial miniswine diet (Teklad, Madison, Wis.) with environmental enrichment (fruit/vegetables) twice daily.

DON and Compounds 14b and 47 Treatment: Animals were individually housed while on study in order to monitor behavior and clinical health following drug administration. Whole blood for drug pharmacokinetic evaluation was collected from a dual lumen central venous catheter (CVC) implanted in the external jugular vein prior to study initiation. Animals were anesthetized with a combination of ketamine hydrochloride (20-30 mg/kg, i.m.) and xylazine (2 mg/kg, i.m.), intubated, and maintained under isoflurane (1-2%) inhalant anesthesia. A temporary peripheral saphenous vein catheter was placed in the hind limb to allow for anatomical separation of drug infusion and whole blood sampling via CVC. DON and compounds 14b and 47 were dissolved in a sterile saline solution containing 5% ethanol and 5% Tween 80 prior to i.v. infusion via saphenous vein catheter over 1 hour (1 ml/min) for a final dose of 1.6 mg/kg or molar equivalent administered at 1 ml/kg (n=1/dose). Blood samples (1 mL) were taken from CVC at predose, 5, 15, 30, 45, and 60 min. Plasma was separated by low speed centrifugation at 3000 g for 10 min at 4° C. CSF was obtained from the cisterna *magna* using a 3.5 in×22 gauge spinal needle (Becton Dickinson Health Care, Franklin Lakes, N.J., USA) at 60 min post-dose. All samples were flash frozen upon harvest and stored at −80 C until bioanalysis.

Data analysis: Quantitation of DON in plasma, CSF, and brain homogenate by LC-MS/MS was performed. Briefly, DON was extracted from plasma, CSF, and brain samples with methanol containing glutamate-$d_5$ (10 μM ISTD) by vortexing followed by centrifugation 16000 g for 5 min. Supernatants were aliquoted and dried at 45° C. for under vacuum for 1 h. Sodium bicarbonate buffer (0.2M, pH 9.0) and dabsyl chloride (10 mM) in acetone were added to each tube, mixed, and incubated for 15 min at 60° C. to derivatize. Samples were then injected and separated on an Agilent 1290 equipped with an Agilent Eclipse plus C18 RRHD 2.1×100 mm column over a 2.5 min gradient from 20 to 95% acetonitrile+0.1% formic acid and quantified on an Agilent 6520 QTOF mass spectrometer. Peak area ratio of the analyte to the internal standard was plotted against a 14 standard curve to yield DON concentrations for each sample.

Result

The pharmacokinetic of DON, compound 14b and compound 47 were evaluated in swine. IV administration of compounds 14b and 47 (1.6 mg/kg DON equivalent dose) resulted in 3-5-fold lower DON plasma exposures relative to an equimolar dose of DON (FIG. 41A). Plasma $AUC_{0-t}$ for DON and compounds 14b and 47 were 29.9, 8.00 and 5.70 nmol·h/mL, respectively. The opposite trend occurred in CSF, where compounds 14b and 47 delivered substantially higher amounts of DON to the CSF (FIG. 41B), resulting in unexpected increased CSF-to-plasma ratios (FIG. 41C).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating a condition, disease, or disorder in a subject, the method comprising administering to the subject in need thereof a compound having formula (I):

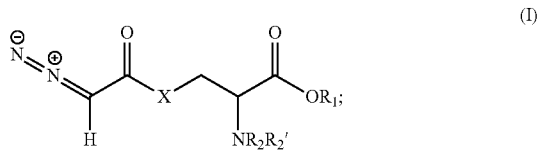

or a pharmaceutically acceptable salt thereof, wherein:
X is —$CH_2$—;
$R_1$ is selected from the group consisting of $C_{1-6}$ alkyl and substituted $C_{1-6}$ alkyl;
$R_2$ is an amino acid or an N-substituted amino acid; and
$R_2'$ is selected from the group consisting of H, $C_1$-$C_6$ alkyl, and substituted $C_1$-$C_6$ alkyl; and
a metabolic reprogramming agent selected from the group consisting of 2-deoxy-D-glucose and metformin;
wherein the condition, disease, or disorder is selected from the group consisting of acute respiratory distress syndrome, allograft rejection during cell, tissue, or organ transplantation, Alzheimer's disease, amyotrophic lateral sclerosis, arthritis, asthma, lupus, Parkinson's disease, and pulmonary fibrosis.

2. The method of claim 1, wherein $R_1$ is selected from the group consisting of methyl, ethyl, and isopropyl.

3. The method claim 1, wherein $R_2$ is an amino acid.

4. The method claim 1, wherein $R_2$ is a N-acyl amino acid.

5. The method of claim 4, wherein the amino acid is tryptophan.

6. The method of claim 1, wherein the compound having formula (I) is a compound having formula (IIA):

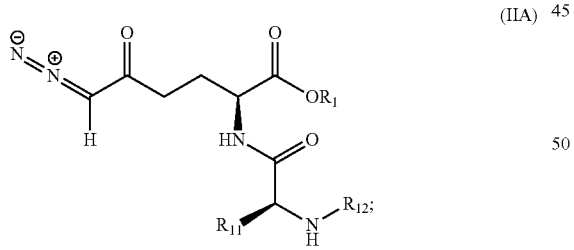

wherein:
$R_1$ is $C_{1-6}$ alkyl;
$R_{11}$ is selected from the group consisting of H, methyl, isopropyl, sec-butyl, $CH_2CH(CH_3)_2$, benzyl, p-hydroxybenzyl $CH_2OH$, $CH(OH)CH_3$, $CH_2$-3-indoyl, $CH_2COOH$, $CH_2CH_2COOH$, —$CH_2C(O)NH_2$, $CH_2CH_2C(O)NH_2$, $CH_2SH$, $CH_2CH_2SCH_3$, $(CH_2)_4NH_2$, $(CH_2)_3NHC(=NH)NH_2$, and $CH_2$-3-imidazoyl;
$R_{12}$ is selected from the group consisting of H, $C_{1-4}$ alkyl, and —$C(=O)R_{13}$; and
$R_{13}$ is $C_{1-4}$ alkyl.

7. The method of claim 6, wherein:
$R_1$ is $C_{1-4}$ alkyl;
$R_{11}$ is selected from the group consisting of isopropyl, sec-butyl, $CH_2CH(CH_3)_2$, and $CH_2$-3-indoyl;
$R_{12}$ is selected from the group consisting of H and —$C(=O)R_{13}$; and
$R_{13}$ is $C_{1-4}$ alkyl.

8. The method of claim 1, wherein the compound of formula (I) is selected from the group consisting of:

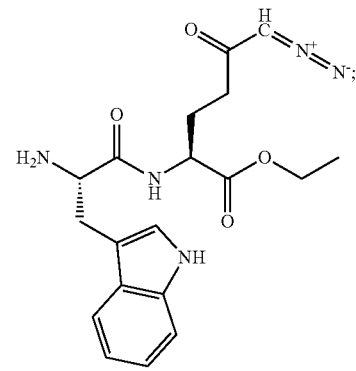

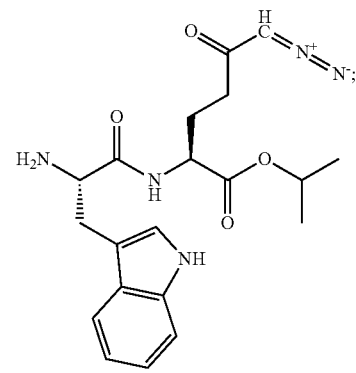

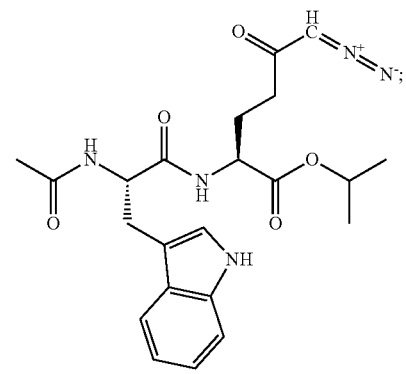

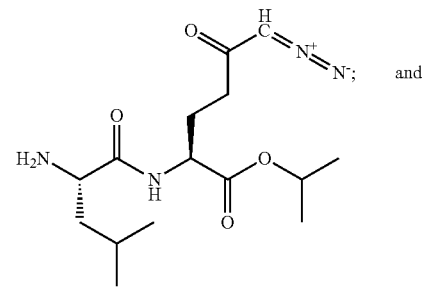

and

-continued

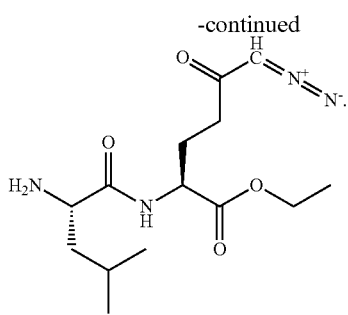

9. The method of claim 8, wherein the compound is:

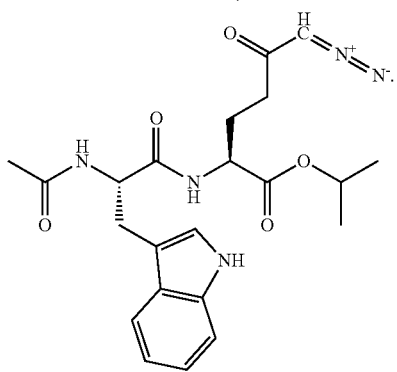

10. The method of claim 1, wherein the at least one metabolic reprogramming agent that decreases glycolysis is 2-deoxy-D-glucose.

11. The method of claim 1, wherein the condition, disease, or disorder is acute respiratory distress syndrome.

12. The method of claim 1, wherein the condition, disease, or disorder is allograft rejection during cell, tissue, or organ transplantation.

13. The method of claim 1, wherein the condition, disease, or disorder is Alzheimer's disease.

14. The method of claim 1, wherein the condition, disease, or disorder is amyotrophic lateral sclerosis.

15. The method of claim 1, wherein the condition, disease, or disorder is arthritis.

16. The method of claim 1, wherein the condition, disease, or disorder is asthma.

17. The method of claim 1, wherein the condition, disease, or disorder is lupus.

18. The method of claim 1, wherein the condition, disease, or disorder is Parkinson's disease.

19. The method of claim 1, wherein the condition, disease, or disorder is pulmonary fibrosis.

* * * * *